United States Patent
Prinz et al.

(10) Patent No.: US 12,162,941 B2
(45) Date of Patent: *Dec. 10, 2024

(54) ANTI-CD112R COMPOSITIONS AND METHODS

(71) Applicant: Surface Oncology, LLC, Cambridge, MA (US)

(72) Inventors: Bianka Prinz, Lebanon, NH (US); Nadthakarn Boland, Lebanon, NH (US); Kevin Schutz, Lebanon, NH (US); John Bukowski, Lebanon, NH (US); Jennifer Symonds, Lebanon, NH (US); James Mohan, Cambridge, MA (US); Marisella Panduro Sicheva, Cambridge, MA (US)

(73) Assignee: Surface Oncology, LLC, Cambridge, MA (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/531,380

(22) Filed: Nov. 19, 2021

(65) Prior Publication Data
US 2022/0162317 A1  May 26, 2022

Related U.S. Application Data

(63) Continuation of application No. 17/261,463, filed as application No. PCT/US2019/042545 on Jul. 19, 2019, now Pat. No. 11,214,619.

(60) Provisional application No. 62/844,958, filed on May 8, 2019, provisional application No. 62/701,065, filed on Jul. 20, 2018.

(51) Int. Cl.
*A61K 39/395* (2006.01)
*A61P 35/00* (2006.01)
*A61P 37/04* (2006.01)
*C07K 16/28* (2006.01)
*A61K 39/00* (2006.01)
*A61K 45/06* (2006.01)

(52) U.S. Cl.
CPC .......... *C07K 16/2818* (2013.01); *A61P 35/00* (2018.01); *A61P 37/04* (2018.01); *C07K 16/2803* (2013.01); *C07K 16/2827* (2013.01); *A61K 2039/505* (2013.01); *A61K 2039/507* (2013.01); *A61K 45/06* (2013.01); *C07K 2317/52* (2013.01); *C07K 2317/73* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,208,020 A | 5/1993 | Chari et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,648,237 A | 7/1997 | Carter |
| 5,648,260 A | 7/1997 | Winter et al. |
| 5,731,168 A | 3/1998 | Carter et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,207,156 B1 | 3/2001 | Kuchroo et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,737,056 B1 | 5/2004 | Presta |
| 7,125,978 B1 | 10/2006 | Vezina et al. |
| 7,332,581 B2 | 2/2008 | Presta |
| 7,521,541 B2 | 4/2009 | Eigenbrot et al. |
| 7,635,757 B2 | 12/2009 | Freeman et al. |
| 7,943,743 B2 | 5/2011 | Korman et al. |
| 8,217,149 B2 | 7/2012 | Irving et al. |
| 9,327,014 B2 | 5/2016 | Gurney et al. |
| 11,214,619 B2 | 1/2022 | Prinz et al. |
| 11,279,758 B2 | 3/2022 | Prinz et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |

(Continued)

FOREIGN PATENT DOCUMENTS

| CL | 2020003127 A1 | 10/2021 |
|---|---|---|
| EP | 0404097 B1 | 9/1996 |

(Continued)

OTHER PUBLICATIONS

Rudikoff, et al., "*Single amino acid substitution altering antigen-binding specificity*", Proceedings of the National Academy of Sciences, 79:1979-1983 (1982).

Pauken and Wherry, "Tigit and CD226: Tipping the balance between costimulatory and coinhibitory molecules to augment the cancer immunotherapy toolkit," Cancer Cell 26:785-787 (2014).

(Continued)

*Primary Examiner* — Meera Natarajan
(74) *Attorney, Agent, or Firm* — William Peter Long

(57) ABSTRACT

The invention provides anti-CD112R antibody compositions and their use in treating cancer.

19 Claims, 28 Drawing Sheets

Specification includes a Sequence Listing.

(56) References Cited

U.S. PATENT DOCUMENTS

| | | | |
|---|---|---|---|
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0014934 A1 | 1/2005 | Hinton et al. | |
| 2005/0123546 A1 | 6/2005 | Umana et al. | |
| 2005/0260186 A1 | 11/2005 | Bookbinder et al. | |
| 2006/0025576 A1 | 2/2006 | Miller et al. | |
| 2006/0104968 A1 | 5/2006 | Bookbinder et al. | |
| 2008/0069820 A1 | 3/2008 | Fuh et al. | |
| 2008/0260742 A1 | 10/2008 | Sato et al. | |
| 2009/0145493 A1 | 6/2009 | Lee | |
| 2009/0317368 A1 | 12/2009 | Chen | |
| 2011/0007023 A1 | 1/2011 | Abrahamsson et al. | |
| 2011/0150892 A1 | 6/2011 | Thudium et al. | |
| 2017/0088620 A1 | 3/2017 | Nioi et al. | |
| 2017/0240613 A1 | 8/2017 | Zhu ........................ | A61P 29/00 |
| 2017/0355752 A1 | 12/2017 | Kim et al. | |
| 2018/0169239 A1 | 6/2018 | Grogan | |
| 2020/0040081 A1 | 2/2020 | Prinz et al. | |
| 2021/0253699 A1 | 8/2021 | Prinz et al. | |
| 2022/0162317 A1 | 5/2022 | Prinz et al. | |

FOREIGN PATENT DOCUMENTS

| | | |
|---|---|---|
| EP | 2067791 A1 | 6/2009 |
| EP | 3202419 A1 | 8/2017 |
| EP | 3258951 B1 | 1/2020 |
| JP | 2021531764 | 7/2019 |
| WO | 1993001161 A1 | 1/1993 |
| WO | 1993008829 A1 | 5/1993 |
| WO | 1993016185 A2 | 8/1993 |
| WO | 1994011026 A3 | 5/1994 |
| WO | 1994029351 A2 | 12/1994 |
| WO | 1997030087 A1 | 8/1997 |
| WO | 1998042752 A1 | 10/1998 |
| WO | 1998058964 A1 | 12/1998 |
| WO | 1999022764 A1 | 5/1999 |
| WO | 1999051642 A1 | 10/1999 |
| WO | 2000037504 A2 | 6/2000 |
| WO | 2000061739 A1 | 10/2000 |
| WO | 2001029246 A1 | 4/2001 |
| WO | 2001058459 A1 | 8/2001 |
| WO | 2002031140 A1 | 4/2002 |
| WO | 2003011878 A2 | 2/2003 |
| WO | 2003084570 A1 | 10/2003 |
| WO | 2003085107 A1 | 10/2003 |
| WO | 2003085119 A1 | 10/2003 |
| WO | 2003099196 A2 | 12/2003 |
| WO | 2004056312 A2 | 7/2004 |
| WO | 2004058805 A2 | 7/2004 |
| WO | 2005035586 A1 | 4/2005 |
| WO | 2005035778 A1 | 4/2005 |
| WO | 2005053742 A1 | 6/2005 |
| WO | 2005100402 A1 | 10/2005 |
| WO | 2006029879 A2 | 3/2006 |
| WO | 2006044908 A2 | 4/2006 |
| WO | 2007005874 A2 | 1/2007 |
| WO | 2007009065 A2 | 1/2007 |
| WO | 2007146968 A2 | 12/2007 |
| WO | 2008077546 A1 | 7/2008 |
| WO | 2008132601 A1 | 11/2008 |
| WO | 2009014708 A2 | 1/2009 |
| WO | 2009036379 A2 | 3/2009 |
| WO | 2009044273 A2 | 4/2009 |
| WO | 2009089004 A1 | 7/2009 |
| WO | 2009114335 A2 | 9/2009 |
| WO | 2010019570 A2 | 2/2010 |
| WO | 2010022120 A1 | 2/2010 |
| WO | 2010105256 A1 | 9/2010 |
| WO | 2011066389 A1 | 6/2011 |
| WO | 2011161699 A2 | 12/2011 |
| WO | 2012009568 A2 | 1/2012 |
| WO | 2012145493 A1 | 10/2012 |
| WO | 2012178128 A1 | 12/2012 |
| WO | 2013059524 A2 | 4/2013 |
| WO | 2013079174 A1 | 6/2013 |
| WO | 2013173223 A1 | 11/2013 |
| WO | 2014008218 A1 | 1/2014 |
| WO | 2013184912 A4 | 4/2014 |
| WO | 2016134333 A9 | 8/2016 |
| WO | 2017221255 A1 | 12/2017 |
| WO | WO 2018/017864 A2 | 1/2018 |
| WO | 2018033798 A1 | 2/2018 |
| WO | 2019232484 A1 | 12/2019 |

OTHER PUBLICATIONS

Petkova, S.B. et al., "Enhanced half-life of genetically engineered human IgG1 antibodies in a humanized FcRn mouse model: potential application in humorally mediated autoimmune disease" Int'l. Immunol. 18(12):1759-1769 (2006). Pluckthun, "Antibodies from *Escherichia coli*" in The Pharmacology of Monoclonal Antibodies, vol. 113, Rosenburg and Moore eds., (Springer-Verlag, New York), pp. 269-315 (1994).

Portolano et al., "Lack of promiscuity in autoantigen-specific H and L chain combinations as revealed by human H and L chain roulette", J. Immunol. 150:880-887 (1993).

Ravetch and Kinet, "Fc receptors" Annu. Rev. Immunol. 9:457-492 (1991).

Remington's Pharmaceutical Sciences 16th edition, Osol, A. Ed. (1980).

Ripka et al. "Two Chinese Hamster Ovary Glycosylation Mutants Affected in the Conversion of GDP-Mannose to GDP-Fucose" Arch. Biochem. Biophys. 249:533-545 (1986).

Rotman et al., "Identification of novel immune checkpoints as targets for cancer immunotherapy," J. Immunotherapy of Cancer Biomed Central Ltd, 1(suppl. 1):p. 135 (2013).

Shields et al., "High resolution mapping of the binding site on human IgG1 for Fc gamma RI, Fc gamma RII, Fc gamma RIII, and FcRn and design of IgG1 variants with improved binding to the Fc gamma R" J. Biol. Chem. 9(2):6591-6604(2001).

Stanietsky et al., "The interaction of TIGIT with PVR and PVRL2 inhibits human NK cell cytotoxicity," PNAS 106 (42):17858-17863 (2009).

Tahara-Hanaoka et al., Functional characterization of DNAM-1 (CD226) interaction with its ligands PVR (CD155) and nectin-2 (PRR-2/CD112), Int. Immunol. 16(4)533-538 (2004).

Traunecker et al., "Bispecific single chain molecules (Janusins) target cytotoxic lymphocytes on HIV infected cells" EMBO J. 10: 3655-3659 (1991).

Tutt et al. "Trispecific F(ab')3 derivatives that use cooperative signaling via the TCR/CD3 complex and CD2 to activate and redirect resting cytotoxic T cells" J. Immunol. 147: 60-69 (1991).

UniProtKB Submission AOA1E3U6D5_9FIRM, Eisenbergiella tayi Uncharacterized protein, Jan. 18, 2017 [online]. Retrieved on Oct. 4, 2019]. Retrieved from the internet: URL: https:/lwww.uniprot. org/uniprot/AOA1 E3U6D5.

Urlaub et al., "Isolation of Chinese hamster cell mutants deficient in dihydrofolate reductase activity." Proc. Natl. Acad. Sci. USA 77:4216-4220 (1980).

Vitetta et al., "Redesigning nature's poisons to create anti-tumor reagents" Science 238:1098-1104 (1987).

Whelan et al., "PVRIG and PVRL2 are induced in cancer and inhibit CD8+ T-cell function," Cancer Immunol. Res., 7(2):257-268 (2019).

Wilson et al.,"Comparative analysis of the paired immunoglobulin-like receptor (PILR) locus in six mammalian genomes: duplication, conversion, and the birth of new genes," Physiol. Genomics 27:201-218 (2006).

Wright et al. "Effect of glycosylation on antibody function: implications for genetic engineering" TIBTECH 15:26-32 (1997).

Xu et al., "Blockade of CD112R and TIGIT signaling sensitizes human natural killer cell functions," Cancer Immunol. Immunother. 66(10):1367-1375 (2017).

Xu, et al. "Addressing polyspecificity of antibodies selected from an in vitro yeast presentation system: a FACS-based, high-throughput selection and analytical tool" PEDS 26.10, 663-70 (2013).

(56) References Cited

OTHER PUBLICATIONS

Yamane-Ohnuki et al. "Establishment of FUT8 knockout Chinese hamster ovary cells: an ideal host cell line for producing completely defucosylated antibodies with enhanced antibody-dependent cellular cytotoxicity" Biotech. Bioeng. 87: 614-622 (2004).
Yazaki and Wu, "Expression of Recombinant Antibodies in Mammalian Cell Lines" Methods in Molecular Biology, vol. 248 (B.K.C. Lo, ed., Humana Press, Totowa, NJ), pp. 255-268 (2003).
Zhu et al., "Identification of CD112R as a novel checkpoint for human T cells," J. Ex. Med. 213(2):167-76 (2016).
Tahara-Hanaoka et al., "Tumor rejection by poliovirus receptor family ligands of DNAM-1 (CD226) receptor" Blood, 107(4) 1491-1496 (2006).
Andrade et al., "DNAM-1 control of natural killer cells functions through nectin and nectin-like proteins," Immunol. and Cell Biol. 92:237-244 (2014).
Andre et al., "Anti-NKG2A mAb is checkpoint inhibitor that promotes anti-tumor immunity by unleashing both T and NK cells," Cell 175: 1731-1743 (2018).
Baessler et al., "CD137 ligand mediates opposite effects in human and mouse NK cells and impairs NK-cell reactivity against human acute myeloid leukemia cells," Blood 115 (15):3058-3069 (2010).
Beers et al., "Influence of immunoglobulin isotype on therapeutic antibody function," Blood 127(9): 1097-1101 (2016).
Brennan et al., "Preparation of bispecific antibodies by chemical recombination of monoclonal immunoglobulin G1 fragments" Science, 229: 81-83 (1985).
Bruggemann, M. et al., "Comparison of the effector functions of human immunoglobulins using a matched set of chimeric antibodies" J. Exp. Med. 166:1351-1361 (1987).
Bruhns, "Properties of mouse and human IgG receptors and their contribution to disease models," Blood 119 (24):5640-5649 (2012).
Chari et al., "Immunoconjugates containing novel maytansinoids: promising anticancer drugs" Cancer Res. 52:127-131 (1992).
Charlton, "Expression and Isolation of Recombinant Antibody Fragments in *E. coli*" Methods in Molecular Biology, vol. 248 (B.K.C. Lo, ed., Humana Press, Totowa, NJ, 2003), pp. 245-254.
Chauvin et al., "TIGIT and PD-1 impair tumor antigen-specific COB+ T cells in melanoma patients," J. Clin. Invest. 125 (5):2046-2058 (2015).
Chowdhury, "Engineering hot spots for affinity enhancement of antibodies" Methods Mol. Biol. 207:179-196 (2003).
Clynes et al. "Fc receptors are required in passive and active immunity to melanoma" Proc. Nat'l Acad. Sci. USA 95:652-656 (1998).
Cragg, M.S. and M.J. Glennie, "Antibody specificity controls in vivo effector mechanisms of anti-CD20 reagents" Blood 103:2738-2743 (2004).
Cragg, M.S. et al., "Complement-mediated lysis by anti-CD20 mAb correlates with segregation into lipid rafts" Blood 101:1045-1052 (2003).
Cunningham and Wells "High-resolution epitope mapping of hGH-receptor interactions by alanine-scanning mutagenesis" (1989) Science, 244:1081-1085.
Dahan et al., "Therapeutic activity of agonistic, human anti-CD40 monoclonal antibodies requires selective Fcγ engagement," Cancer Cell 29:820-831 (2016).
Duncan & Winter, "The binding site for C1q on IgG" Nature 322:738-40 (1988).
Estep et al, "High throughput solution-based measurement of antibody-antigen affinity and epitope binning." Mabs 5 (2) 270-278 (2013).
Flatman et al., "Process analytics for purification of monoclonal antibodies" J. Chromatogr. B 848:79-87 (2007).
Gazzano-Santoro et al., "A non-radioactive complement-dependent cytotoxicity assay for anti-CD20 monoclonal antibody" J. Immunol. Methods 202:163-71 (1997).
Gerngross, "Advances in the production of human therapeutic proteins in yeasts and filamentous fungi" Nat. Biotech. 22(11):1409-1414 (2004).
Graham et al., "Characteristics of a human cell line transformed by DNA from human adenovirus type 5" J. Gen Virol. 36:59 (1977).
Gruber et al., "Efficient tumor cell lysis mediated by a bispecific single chain antibody expressed in *Escherichia coli*" J. Immunol., 152:5368-74 (1994).
Guyer et al., "Immunoglobulin Binding by Mouse Intestinal Epithelial Cell Receptors" J. Immunol. 117:587-593 (1976).
Hellstrom, I et al., "Strong antitumor activities of IgG3 antibodies to a human melanoma-associated ganglioside" Proc. Nat'l Acad. Sci. USA 82:1499-1502 (1985).
Hellstrom, I. et al. "Antitumor effects of L6, an IgG2a antibody that reacts with most human carcinomas" Proc. Nat'l Acad. Sci. USA 83:7059-7063 (1986).
Holliger et al., "Diabodies: small bivalent and bispecific antibody fragments" Proc. Natl. Acad. Sci. USA 90:6444-6448 (1993).
Hoogenboom et al. "Overview of antibody phage-display technology and its applications" in Methods in Molecular Biology 178:1-37 (O'Brien et al., ed., Human Press, Totowa, NJ, (2002).
Hudson et al., "Engineered antibodies" Nat. Med. 9:129-134 (2003).
Hurwitz et al. "CTLA-4 Blockade Synergizes with Tumor-Derived Granulocyte-Macrophage Colony-Stimulating Factor for Treatment of an Experimental Mammary Carcinoma" (1998) Pro. Natl. Acad. Sci. USA 95(17): 10067-10071.
Idusogie et al. "Mapping of the C1q binding site on rituxan, a chimeric antibody with a human IgG1 Fc" J. Immunol. 164 (8): 4178-4184 (2000).
International Search Report and Written Opinion issued in PCT/US2019/042545 on Dec. 10, 2019.
Jain et al., "Biophysical properties of the clinical-stage antibody landscape," PNAS 114(5):944-949 (2017).
Johnston et al., "The immunoreceptor TIGIT regulates anti-tumor and anti-viral CD8+ T cell effector function," Cancer Cell 26:923-937 (2014).
Kam et al., "Carbon nanotubes as multifunctional biological transporters and near-infrared agents for selective cancer cell destruction" Proc. Natl. Acad. Sci. USA 102: 11600-11605 (2005).
Kanda, Y. et al., "Comparison of cell lines for stable production of fucose-negative antibodies with enhanced ADCC" Biotehnol. Bioeng., 94(4):680-688 (2006).
Kim et al., "Localization of the site of the murine IgG1 molecule that is involved in binding to the murine intestinal Fc receptor" Eur. J. Immunol. 24:2429-2434 (1994).
Kindt et al. Kuby Immunology, 6th ed., W.H. Freeman and Co., p. 91 (2007).
Kostelny et al., "Formation of a bispecific antibody by the use of leucine zippers" J. Immunol., 148(5):1547-1553 (1992).
Levin et al., "Vstm3 is a member of the CD28 family and an important modulator of T-cell function," Eur J. Immunol. 41:902-915 (2011).
Li et al., "Optimization of humanized IgGs in glycoengineered Pichia pastoris" Nat. Biotech. 24:210-215 (2006).
Lo et al., "Effector-attenuating substitutions that maintain antibody stability and reduce toxicity in mice," J. Biol. Chem. 292(9):3900-3908 (2017).
Martinet and Smyth, "Balancing natural killer cell activation through paired receptors," Nat. Rev. Immunol. 15:243-254 (2015).
Mather et al., "Culture of testicular cells in hormone-supplemented serum-free medium" Annals NY. Acad. Sci. 383:44-68 (1982).
Mather, "Establishment and characterization of two distinct mouse testicular epithelial cell lines" Biol. Reprod. 23:243-251 (1980).
Milstein and Cuello, "Hybrid hybridomas and their use in immunohistochemistry" Nature 305: 537-40 (1983).
Mokyr et al. "Realization of the Therapeutic Potential of CTLA-4 Blockade in Low-Dose Chemotherapy-treated Tumor-bearing Mice" (1998) Cancer Res. 58:5301-5304.
Murter et al., "Mouse PVRIG has CD8+ T cell-specific coinhibitory functions and dampens antitumor immunity," Cancer Immunol. Res. 7(2): 244-256 (2019).
Okazaki et al. "Fucose depletion from human lgG1 oligosaccharide enhances binding enthalpy and association rate between IgG1 and FcgammaRIIIa" J. Mol. Biol. 336:1239-1249 (2004).

(56) References Cited

OTHER PUBLICATIONS

Orentas et al., "Bioinformation description of immunotherapy targets for pediatric T-cell leukemia and the impact of normal gene sets used for comparison," Frontiers in Oncology, 4(134): 1-11 (2014).
De Pascalis R. et al., Grafting of "abbreviated" complementarity-determining regions containing specificity-determining residues essential for ligand contact to engineer a less immunogenic humanized monoclonal antibody, J Immunol., 2002, vol. 169, N.6, pp. 3076-3084.
Riechmann L. et al., Reshaping human antibodies for therapy, Nature. Mar. 24, 1988;332(6162):323-327.
Vajdos F.F.et al., Comprehensive Functional Maps of the Antigen binding Site of an Anti-ErbB2 Antibody Obtained with Shotgun Scanning Mutagenesis, J. Mol. Biol., 2002, vol. 320, pp. 415-428.
Wake, Hidenori, "Antibody Medicine", Department of Pharmacology, Okayama University Graduate School of Medicine, Dentistry and Pharmaceutical Sciences, Aug. 2009, pp. 119-122.
International Preliminary Report on Patentability, issued in PCT/US2020/060524, dated May 17, 2022 (6 pages).

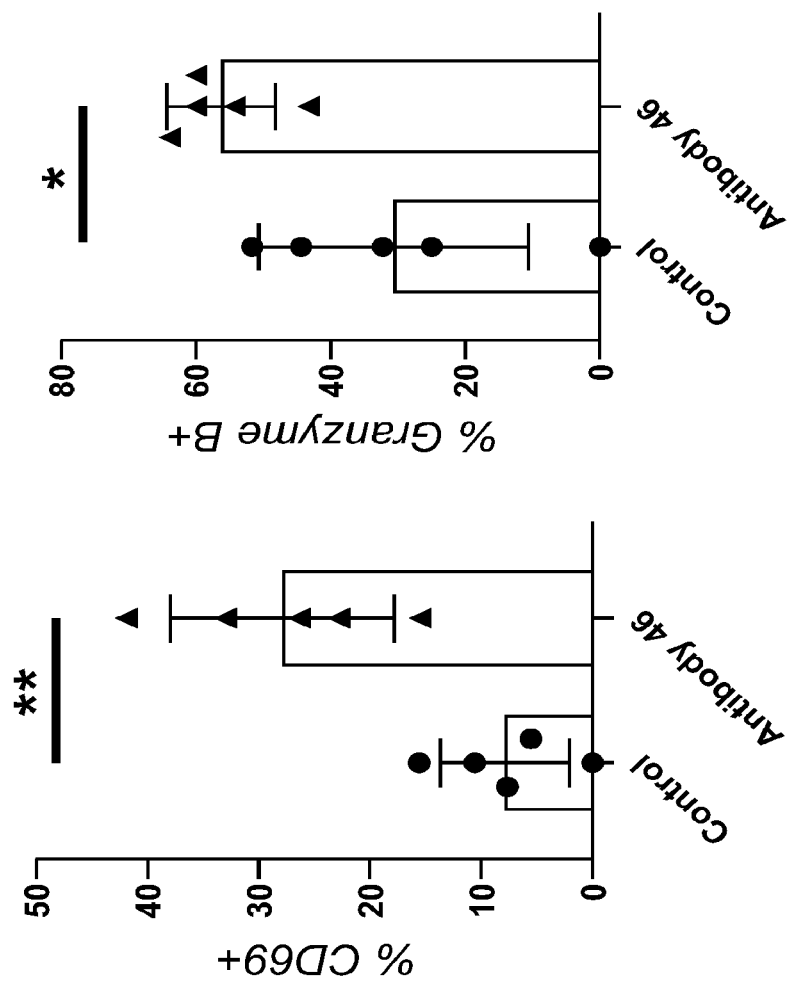

| Group | Tumor-free survivors (out of 10) |
|---|---|
| Isotype control | 0 |
| CD112R | 0 |
| PD-1 | 4 |
| CD112R + PD-1 | 8 |

*Fig. 13F*

| | | | |
|---|---|---|---|
| 36H1 | GTFATYAIS | 9 | 77.78% |
| 44H1 | GTFDNYYIS | 9 | 66.67% |
| 33H1 | GTFGNYAIS | 9 | 77.78% |
| 47H1 | GTFSNYAIS | 9 | 88.89% |
| 35H1 | GTFSSAAIS | 9 | 88.89% |
| 34H1 | GTFSSAAIS | 9 | 88.89% |
| 32H1 | GTFSSYAIS | 9 | 100% |
| 38H1 | FTFSGHLMS | 9 | 44.44% |
| 10H1 | FTFDDYAVH | 9 | 44.44% |
| 2H1 | FTFSEYTMN | 9 | 44.44% |
| 5H1 | FTFSDYAMI | 9 | 55.56% |
| 58H1 | FTFGDYAMS | 9 | 55.56% |
| 46H1 | FTFGDYAMS | 9 | 55.56% |
| 15H1 | FTFGDVAMS | 9 | 44.44% |

*Fig. 14A*

| | | | |
|---|---|---|---|
| 35H2 | --NIIPIVGIANYAQKFQG | 17 | 82.35% |
| 33H2 | --GIIPIPGIANYAQKFQG | 17 | 88.24% |
| 36H2 | --GIFPLSGTANYAQKFQG | 17 | 88.24% |
| 34H2 | --GIFPISGHANYAQKFQG | 17 | 88.24% |
| 32H2 | --GIIPISGTANYAQKFQG | 17 | 100% |
| 44H2 | --GIFPIFGTANYAQKFQG | 17 | 88.24% |
| 47H2 | --GIIPIFGTANYAQKFQG | 17 | 94.12% |
| 58H2 | FIGSKFYGGETEYTASVKG | 19 | 23.53% |
| 15H2 | YIGSKAYGGETEYTASVKG | 19 | 23.53% |
| 46H2 | FIGSKAYGGTTEYTASVKG | 19 | 29.41% |
| 10H2 | --GISWSSGLIGYADSVKG | 17 | 41.18% |
| 2H2 | --AIVGSGDSTYYADSVKG | 17 | 23.53% |
| 5H2 | --AISGGGESTYYADSVKG | 17 | 23.53% |
| 38H2 | --AISGSAGETYYADSVKG | 17 | 29.41% |

*Fig. 14B*

| | | | |
|---|---|---|---|
| 15H3 | -ARAGHSYG---SIASNWFDP | 17 | 31.25% |
| 35H3 | --ARDTGRG---YTRHFWFDP | 16 | 100% |
| 32H3 | --ARDTGRG---YTRHFWFDP | 16 | 100% |
| 33H3 | --ARDTGRG---YTRHFWFDP | 16 | 100% |
| 34H3 | --ARDTGRG---YTRHFWFDP | 16 | 100% |
| 36H3 | --ARDTGRG---YTRHFWFDP | 16 | 100% |
| 38H3 | --ARDAYYDDWSGWADWYFDL | 19 | 31.25% |
| 44H3 | AREVGHY-----SGSPYYMDV | 16 | 7.14% |
| 10H3 | AKG--PPT----YQDYFDL-- | 13 | 18.18% |
| 2H3 | --AKDYSSG---DWIDYGMDV | 16 | 25% |
| 5H3 | --AKDYSSG---DWIDYGMDV | 16 | 25% |
| 58H3 | ARG-----P---RRYTYGMDV | 13 | 9.09% |
| 46H3 | ARG-----P---RRYTYGMDV | 13 | 9.09% |
| 47H3 | ARGRGALAL---VGPYYGMDV | 18 | 12.50% |

*Fig. 14C*

| | | | |
|---|---|---|---|
| 10L1 | RASQSVS-----RYLA | 11 | 72.73% |
| 38L1 | RASQSVS-----RYLA | 11 | 72.73% |
| 44L1 | RASQSIN-----SWLA | 11 | 72.73% |
| 2L1 | QASQDIS-----NYLN | 11 | 72.73% |
| 5L1 | QASQDIS-----NYLN | 11 | 72.73% |
| 58L1 | RASQSIS-----SYLN | 11 | 100% |
| 15L1 | RASQSIS-----SYLN | 11 | 100% |
| 35L1 | RASQSIS-----SYLN | 11 | 100% |
| 46L1 | RASQSIS-----SYLN | 11 | 100% |
| 32L1 | RASQSIS-----SYLN | 11 | 100% |
| 33L1 | RASQSIS-----SYLN | 11 | 100% |
| 34L1 | RASQSIS-----SYLN | 11 | 100% |
| 36L1 | RASQSIS-----SYLN | 11 | 100% |
| 47L1 | RSSQSLLHSNGYNYLD | 16 | 54.55% |

*Fig. 14D*

| | | | |
|---|---|---|---|
| 47L2 | LGSHRAS | 7 | 28.57% |
| 2L2  | DASNLAT | 7 | 42.86% |
| 5L2  | DASNLAT | 7 | 42.86% |
| 10L2 | DASNRAT | 7 | 28.57% |
| 38L2 | DASNRAT | 7 | 28.57% |
| 44L2 | DASSLES | 7 | 71.43% |
| 58L2 | AASSLQS | 7 | 100% |
| 35L2 | AASSLQS | 7 | 100% |
| 46L2 | AASSLQS | 7 | 100% |
| 32L2 | AASSLQS | 7 | 100% |
| 33L2 | AASSLQS | 7 | 100% |
| 34L2 | AASSLQS | 7 | 100% |
| 36L2 | AASSLQS | 7 | 100% |
| 15L2 | GASSLQS | 7 | 85.71% |

*Fig. 14E*

| | | | |
|---|---|---|---|
| 47L3 | -MQALRAPT- | 8 | 0% |
| 15L3 | -QQGFYTPWT | 9 | 14.29% |
| 44L3 | QQVGPYL--T | 8 | 28.57% |
| 58L3 | QQSSTPL--T | 8 | 42.86% |
| 46L3 | QQSSTPL--T | 8 | 42.86% |
| 35L3 | QQSDILYT-- | 8 | 100% |
| 32L3 | QQSDILYT-- | 8 | 100% |
| 33L3 | QQSDILYT-- | 8 | 100% |
| 34L3 | QQSDILYT-- | 8 | 100% |
| 36L3 | QQSDILYT-- | 8 | 100% |
| 10L3 | QQVSFFPPIT | 10 | 25% |
| 2L3  | QQFDLLPPT- | 9 | 50% |
| 5L3  | QQFDLLPPT- | 9 | 50% |
| 38L3 | QQVSLLPPT- | 9 | 37.5% |

*Fig. 14F*

FR1
| | | |
|---|---|---|
| 36VH | QVQLVQSGAEVKKPGSSVKVSCKASG | 100% |
| 33VH | QVQLVQSGAEVKKPGSSVKVSCKASG | 100% |
| 35VH | QVQLVQSGAEVKKPGSSVKVSCKASG | 100% |
| 32VH | QVQLVQSGAEVKKPGSSVKVSCKASG | 100% |
| 34VH | QVQLVQSGAEVKKPGSSVKVSCKASG | 100% |
| 44VH | QVQLVQSGAEVKKPGSSVKVSCKASG | 100% |
| 47VH | EVQLVQSGAEVKKPGSSVKVSCKASG | 96.15% |
| 58VH | EVQLVESGGGLVQPGRSLRLSCTASG | 53.85% |
| 46VH | EVQLVESGGGLVQPGRSLRLSCTASG | 53.85% |
| 15VH | EVQLVESGGGLVQPGRSLRLSCTASG | 53.85% |
| 10VH | EVQLVESGGGLVQPGRSLRLSCAASG | 53.85% |
| 38VH | EVQLLESGGGLVQPGGSLRLSCAASG | 50% |
| 2VH  | EVQLVESGGGLVKPGGSLRLSCAASG | 57.69% |
| 5VH  | EVQLLESGGGLVQPGGSLRLSCAASG | 50% |

*Fig. 15A*

FR2
| | | |
|---|---|---|
| 36VH | WVRQAPGQGLEWMG | 100% |
| 33VH | WVRQAPGQGLEWMG | 100% |
| 35VH | WVRQAPGQGLEWMG | 100% |
| 32VH | WVRQAPGQGLEWMG | 100% |
| 34VH | WVRQAPGQGLEWMG | 100% |
| 44VH | WVRQAPGQGLEWMG | 100% |
| 47VH | WVRQAPGQGLEWMG | 100% |
| 58VH | WFRQAPGKGLEWVG | 78.57% |
| 46VH | WFRQAPGKGLEWVG | 78.57% |
| 15VH | WFRQAPGKGLEWVG | 78.57% |
| 10VH | WV--------WVS | 60% |
| 38VH | WVRQAPGKGLEWVS | 78.57% |
| 2VH  | WVRQAPGKGLEWVS | 78.57% |
| 5VH  | WVRQAPGKGLEWVS | 78.57% |

*Fig. 15B*

FR3
| | | |
|---|---|---|
| 36VH | RVTITADESTSTAYMELSSLRSEDTAVYYC | 100% |
| 33VH | RVTITADESTSTAYMELSSLRSEDTAVYYC | 100% |
| 35VH | RVTITADESTSTAYMELSSLRSEDTAVYYC | 100% |
| 32VH | RVTITADESTSTAYMELSSLRSEDTAVYYC | 100% |
| 34VH | RVTITADESTSTAYMELSSLRSEDTAVYYC | 100% |
| 44VH | RVTITADESTSTAYMELSSLRSEDTAVYYC | 100% |
| 47VH | RVTITADESTSTAYMELSSLRSEDTAVYYC | 100% |
| 58VH | RFTISRDGSKSIAYLQMNSLKTEDTAVYYC | 60% |
| 46VH | RFTISRDGSKSIAYLQMNSLKTEDTAVYYC | 60% |
| 15VH | RFTISRDGSKSIAYLQMNSLKTEDTAVYYC | 60% |
| 10VH | RFTISRDNAKNSLYLQMNSLRAEDTAVYYC | 53.33% |
| 38VH | RFTISRDNSKNTLYLQMNSLRAEDTAVYYC | 60% |
| 2VH | RFTISRDNSKNTLYLQMNSLRAEDTAVYYC | 60% |
| 5VH | RFTISRDNSKNTLYLQMNSLRAEDTAVYYC | 60% |

*Fig. 15C*

FR4
| | | |
|---|---|---|
| 36VH | WGQGTLVTVSS | 100% |
| 33VH | WGQGTLVTVSS | 100% |
| 35VH | WGQGTLVTVSS | 100% |
| 32VH | WGQGTLVTVSS | 100% |
| 34VH | WGQGTLVTVSS | 100% |
| 44VH | WGKGTTVTVSS | 81.82% |
| 47VH | WGQGTTVTVSS | 90.91% |
| 58VH | WGQGTTVTVSS | 90.91% |
| 46VH | WGQGTTVTVSS | 90.91% |
| 15VH | WGQGTLVTVSS | 100% |
| 10VH | WGRGTLVTVSS | 90.91% |
| 38VH | WGRGTLVTVSS | 90.91% |
| 2VH | WGQGTTVTVSS | 90.91% |
| 5VH | WGQGTTVTVSS | 90.91% |

*Fig. 15D*

FR1
| | | |
|---|---|---|
| 47VL | DIVMTQSPLSLPVTPGEPASISC | 52.17% |
| 10VL | EIVLTQSPATLSLSPGERATLSC | 52.17% |
| 38VL | EIVLTQSPATLSLSPGERATLSC | 52.17% |
| 2VL | DIQMTQSPSSLSASVGDRVTITC | 100% |
| 5VL | DIQMTQSPSSLSASVGDRVTITC | 100% |
| 44VL | DIQMTQSPSTLSASVGDRVTITC | 95.65% |
| 15VL | DIQMTQSPSSLSASVGDRVTITC | 100% |
| 58VL | DIQMTQSPSSLSASVGDRVTITC | 100% |
| 46VL | DIQMTQSPSSLSASVGDRVTITC | 100% |
| 35VL | DIQMTQSPSSLSASVGDRVTITC | 100% |
| 32VL | DIQMTQSPSSLSASVGDRVTITC | 100% |
| 33VL | DIQMTQSPSSLSASVGDRVTITC | 100% |
| 34VL | DIQMTQSPSSLSASVGDRVTITC | 100% |
| 36VL | DIQMTQSPSSLSASVGDRVTITC | 100% |

*Fig. 15E*

FR2
| | | |
|---|---|---|
| 47VL | WYLQKPGQSPQLLIY | 76.33% |
| 10VL | WYQQKPGQAPRLLIY | 86.67% |
| 38VL | WYQQKPGQAPRLLIY | 86.67% |
| 2VL | WYQQKPGKAPKLLIY | 100% |
| 5VL | WYQQKPGKAPKLLIY | 100% |
| 44VL | WYQQKPGKAPKLLIS | 93.33% |
| 15VL | WYQQKPGKAPKLLIY | 100% |
| 58VL | WYQQKPGKAPKLLIY | 100% |
| 46VL | WYQQKPGKAPKLLIY | 100% |
| 35VL | WYQQKPGKAPKLLIY | 100% |
| 32VL | WYQQKPGKAPKLLIY | 100% |
| 33VL | WYQQKPGKAPKLLIY | 100% |
| 34VL | WYQQKPGKAPKLLIY | 100% |
| 36VL | WYQQKPGKAPKLLIY | 100% |

*Fig. 15F*

FR3
| | | |
|---|---|---|
| 47VL | GVPDRFSGSGSGTDFTLKISRVEAEDVGVYYC | 71.88% |
| 10VL | GIPARFSGSGSGTDFTLTISSLEPEDFAVYYC | 87.5% |
| 38VL | GIPARFSGSGSGTDFTLTISSLEPEDFAVYYC | 87.5% |
| 2VL | GVPSRFSGSGSGTDFTFTISSLQPEDIATYYC | 93.75% |
| 5VL | GVPSRFSGSGSGTDFTFTISSLQPEDIATYYC | 93.75% |
| 44VL | GVPSRFSGSGSGTEFTLTISSLQPDDFATYYC | 93.75% |
| 15VL | GVPSRFSGSGSGTDFTLTISSLQPEDFATYYC | 100% |
| 58VL | GVPSRFSGSGSGTDFTLTISSLQPEDFATYYC | 100% |
| 46VL | GVPSRFSGSGSGTDFTLTISSLQPEDFATYYC | 100% |
| 35VL | GVPSRFSGSGSGTDFTLTISSLQPEDFATYYC | 100% |
| 32VL | GVPSRFSGSGSGTDFTLTISSLQPEDFATYYC | 100% |
| 33VL | GVPSRFSGSGSGTDFTLTISSLQPEDFATYYC | 100% |
| 34VL | GVPSRFSGSGSGTDFTLTISSLQPEDFATYYC | 100% |
| 36VL | GVPSRFSGSGSGTDFTLTISSLQPEDFATYYC | 100% |

*Fig. 15G*

FR4
| | | |
|---|---|---|
| 47VL | FGGGTKVEIK | 100% |
| 10VL | FGGGTKVEIK | 100% |
| 38VL | FGGGTKVEIK | 100% |
| 2VL | FGGGTKVEIK | 100% |
| 5VL | FGGGTKVEIK | 100% |
| 44VL | FGGGTKVEIK | 100% |
| 15VL | FGGGTKVEIK | 100% |
| 58VL | FGGGTKVEIK | 100% |
| 46VL | FGGGTKVEIK | 100% |
| 35VL | FGGGTKVEIK | 100% |
| 32VL | FGGGTKVEIK | 100% |
| 33VL | FGGGTKVEIK | 100% |
| 34VL | FGGGTKVEIK | 100% |
| 36VL | FGGGTKVEIK | 100% |

*Fig. 15H*

Variable Region Sequences

```
36VH    QVQLVQSGAEVKKPGSSVKVSCKASGGTFATYAISWVRQAPGQGLEWMGGIF--PLSGTA
33VH    QVQLVQSGAEVKKPGSSVKVSCKASGGTFGNYAISWVRQAPGQGLEWMGGII--PIPGIA
35VH    QVQLVQSGAEVKKPGSSVKVSCKASGGTFSSAAISWVRQAPGQGLEWMGNII--PIVGIA
32VH    QVQLVQSGAEVKKPGSSVKVSCKASGGTFSSYAISWVRQAPGQGLEWMGGII--PISGTA
34VH    QVQLVQSGAEVKKPGSSVKVSCKASGGTFSSAAISWVRQAPGQGLEWMGGIF--PISGHA
44VH    QVQLVQSGAEVKKPGSSVKVSCKASGGTFDNYYISWVRQAPGQGLEWMGGIF--PIFGTA
47VH    EVQLVQSGAEVKKPGSSVKVSCKASGGTFSNYAISWVRQAPGQGLEWMGGII--PIFGTA
58VH    EVQLVESGGGLVQPGRSLRLSCTASGFTFGDYAMSWFRQAPGKGLEWVGFIGSKFYGGET
46VH    EVQLVESGGGLVQPGRSLRLSCTASGFTFGDYAMSWFRQAPGKGLEWVGFIGSKAYGGTT
15VH    EVQLVESGGGLVQPGRSLRLSCTASGFTFGDVAMSWFRQAPGKGLEWVGYIGSKAYGGET
10VH    EVQLVESGGGLVQPGRSLRLSCAASGFTFDDYAVHWVRQAPGKGLEWVSGIS--WSSGLI
38VH    EVQLLESGGGLVQPGGSLRLSCAASGFTFSGHLMSWVRQAPGKGLEWVSAIS--GSAGET
2VH     EVQLVESGGGLVKPGGSLRLSCAASGFTFSEYTMNWVRQAPGKGLEWVSAIV--GSGDST
5VH     EVQLLESGGGLVQPGGSLRLSCAASGFTFSDYAMIWVRQAPGKGLEWVSAIS--GGGEST

36VH    NYAQKFQGRVTITADESTSTAYMELSSLRSEDTAVYYCARDTGRG--YT-RHFWFDPWGQ
33VH    NYAQKFQGRVTITADESTSTAYMELSSLRSEDTAVYYCARDTGRG--YT-RHFWFDPWGQ
35VH    NYAQKFQGRVTITADESTSTAYMELSSLRSEDTAVYYCARDTGRG--YT-RHFWFDPWGQ
32VH    NYAQKFQGRVTITADESTSTAYMELSSLRSEDTAVYYCARDTGRG--YT-RHFWFDPWGQ
34VH    NYAQKFQGRVTITADESTSTAYMELSSLRSEDTAVYYCARDTGRG--YT-RHFWFDPWGQ
44VH    NYAQKFQGRVTITADESTSTAYMELSSLRSEDTAVYYCAREVGHY--SG-SPYYMDVWGK
47VH    NYAQKFQGRVTITADESTSTAYMELSSLRSEDTAVYYCARGRGALALVG-PYYGMDVWGQ
58VH    EYTASVKGRFTISRDGSKSIAYLQMNSLKTEDTAVYYCARGPRRY--TY----GMDVWGQ
46VH    EYTASVKGRFTISRDGSKSIAYLQMNSLKTEDTAVYYCARGPRRY--TY----GMDVWGQ
15VH    EYTASVKGRFTISRDGSKSIAYLQMNSLKTEDTAVYYCARAGHSY--GSIASNWFDPWGQ
10VH    GYADSVKGRFTISRDNAKNSLYLQMNSLRAEDTAVYYCAKGPPT------YQDYFDLWGR
38VH    YYADSVKGRFTISRDNSKNTLYLQMNSLRAEDTAVYYCARDAYYDDWSGWADWYFDLWGR
2VH     YYADSVKGRFTISRDNSKNTLYLQMNSLRAEDTAVYYCAKDYSSGD---WIDYGMDVWGQ
5VH     YYADSVKGRFTISRDNSKNTLYLQMNSLRAEDTAVYYCAKDYSSGD---WIDYGMDVWGQ

36VH    GTLVTVSS    123    96.75%
33VH    GTLVTVSS    123    96.75%
35VH    GTLVTVSS    123    96.75%
32VH    GTLVTVSS    123    100%
34VH    GTLVTVSS    123    97.56%
44VH    GTTVTVSS    123    84.55%
47VH    GTTVTVSS    125    86.99%
58VH    GTTVTVSS    122    55.00%
46VH    GTTVTVSS    122    55.83%
15VH    GTLVTVSS    126    55.28%
10VH    GTLVTVSS    120    54.17%
38VH    GTLVTVSS    126    53.66%
2VH     GTTVTVSS    123    54.55%
5VH     GTTVTVSS    123    53.72%
```

*Fig. 16A*

```
47VL    DIVMTQSPLSLPVTPGEPASISCRSSQSLLHSNGYNYLDWYLQKPGQSPQLLIYLGSHRA
10VL    EIVLTQSPATLSLSPGERATLSCRASQSV-----SRYLAWYQQKPGQAPRLLIYDASNRA
38VL    EIVLTQSPATLSLSPGERATLSCRASQSV-----SRYLAWYQQKPGQAPRLLIYDASNRA
2VL     DIQMTQSPSSLSASVGDRVTITCQASQDI-----SNYLNWYQQKPGKAPKLLIYDASNLA
5VL     DIQMTQSPSSLSASVGDRVTITCQASQDI-----SNYLNWYQQKPGKAPKLLIYDASNLA
44VL    DIQMTQSPSTLSASVGDRVTITCRASQSI-----NSWLAWYQQKPGKAPKLLISDASSLE
15VL    DIQMTQSPSSLSASVGDRVTITCRASQSI-----SSYLNWYQQKPGKAPKLLIYGASSLQ
58VL    DIQMTQSPSSLSASVGDRVTITCRASQSI-----SSYLNWYQQKPGKAPKLLIYAASSLQ
46VL    DIQMTQSPSSLSASVGDRVTITCRASQSI-----SSYLNWYQQKPGKAPKLLIYAASSLQ
35VL    DIQMTQSPSSLSASVGDRVTITCRASQSI-----SSYLNWYQQKPGKAPKLLIYAASSLQ
32VL    DIQMTQSPSSLSASVGDRVTITCRASQSI-----SSYLNWYQQKPGKAPKLLIYAASSLQ
33VL    DIQMTQSPSSLSASVGDRVTITCRASQSI-----SSYLNWYQQKPGKAPKLLIYAASSLQ
34VL    DIQMTQSPSSLSASVGDRVTITCRASQSI-----SSYLNWYQQKPGKAPKLLIYAASSLQ
36VL    DIQMTQSPSSLSASVGDRVTITCRASQSI-----SSYLNWYQQKPGKAPKLLIYAASSLQ

47VL    SGVPDRFSGSGSGTDFTLKISRVEAEDVGVYYCMQA--LRAPTFGGGTKVEIK  111  62.26%
10VL    TGIPARFSGSGSGTDFTLTISSLEPEDFAVYYCQQVSFFPPITFGGGTKVEIK  108  71.7%
38VL    TGIPARFSGSGSGTDFTLTISSLEPEDFAVYYCQQVSLLPP-TFGGGTKVEIK  107  72.38%
2VL     TGVPSRFSGSGSGTDFTFTISSLQPEDIATYYCQQF-DLLPPTFGGGTKVEIK  107  86.79%
5VL     TGVPSRFSGSGSGTDFTFTISSLQPEDIATYYCQQF-DLLPPTFGGGTKVEIK  107  86.79%
44VL    SGVPSRFSGSGSGTEFTLTISSLQPDDFATYYCQQV--GPYLTFGGGTKVEIK  106  86.79%
15VL    SGVPSRFSGSGSGTDFTLTISSLQPEDFATYYCQQG-FYTPWTFGGGTKVEIK  107  94.34%
58VL    SGVPSRFSGSGSGTDFTLTISSLQPEDFATYYCQQS--STPLTFGGGTKVEIK  106  96.23%
46VL    SGVPSRFSGSGSGTDFTLTISSLQPEDFATYYCQQS--STPLTFGGGTKVEIK  106  96.23%
35VL    SGVPSRFSGSGSGTDFTLTISSLQPEDFATYYCQQS--DILYTFGGGTKVEIK  106  100%
32VL    SGVPSRFSGSGSGTDFTLTISSLQPEDFATYYCQQS--DILYTFGGGTKVEIK  106  100%
33VL    SGVPSRFSGSGSGTDFTLTISSLQPEDFATYYCQQS--DILYTFGGGTKVEIK  106  100%
34VL    SGVPSRFSGSGSGTDFTLTISSLQPEDFATYYCQQS--DILYTFGGGTKVEIK  106  100%
36VL    SGVPSRFSGSGSGTDFTLTISSLQPEDFATYYCQQS--DILYTFGGGTKVEIK  106  100%
```

*Fig. 16B*

SEQUENCE LISTING

<160> NUMBER OF SEQ ID NOS: 4018

<210> SEQ ID NO 1
<211> LENGTH: 9
<212> TYPE: PRT
<213> ORGANISM: Artificial Sequence
<220> FEATURE:

<223> OTHER INFORMATION: Synthetic: 2 - VH CDR1

<400> SEQUENCE: 1

Phe Thr Phe Ser Glu Tyr Thr Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic: 2 - VH CDR2

<400> SEQUENCE: 2

Ala Ile Val Gly Ser Gly Asp Ser Thr Tyr Tyr Ala Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Synthetic: 2 - VH CDR3

<400> SEQUENCE: 3

Ala Lys Asp Tyr Ser Ser Gly Asp Trp Ile Asp Tyr Gly Met Asp Val
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic: 2 - VL CDR1

<400> SEQUENCE: 4

Gln Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic: 2 - VL CDR2

<400> SEQUENCE: 5

Asp Ala Ser Asn Leu Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic: 2 - VL CDR3

<400> SEQUENCE: 6

Gln Gln Phe Asp Leu Leu Pro Pro Thr
1               5

<210> SEQ ID NO 7
<211> LENGTH: 26
<212> TYPE: PRT
<213> ORGANISM: Artificial Sequence

```
<220> FEATURE:
<223> OTHER INFORMATION: Synthetic: 2 - VH FR1

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly
            20                  25

<210> SEQ ID NO 8
<211> LENGTH: 14
<212> TYPE: PRT
<213> ORGANISM: Artificial Sequence
<220> FEATURE:
<223> OTHER INFORMATION: Synthetic: 2 - VH FR2

<400> SEQUENCE: 8

Trp Val Arg Gln Ala Pro Gly Lys Gly Leu Glu Trp Val Ser
1               5                   10

<210> SEQ ID NO 9
<211> LENGTH: 30
<212> TYPE: PRT
<213> ORGANISM: Artificial Sequence
<220> FEATURE:
<223> OTHER INFORMATION: Synthetic: 2 - VH FR3

<400> SEQUENCE: 9

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Synthetic: 2 - VH FR4

<400> SEQUENCE: 10

Trp Gly Gln Gly Thr Thr Val Thr Val Ser Ser
1               5                   10

<210> SEQ ID NO 11
<211> LENGTH: 369
<212> TYPE: PRT
<213> ORGANISM: Artificial Sequence
<220> FEATURE:
<223> OTHER INFORMATION: Synthetic: 2 - VH DNA

<400> SEQUENCE: 11

Gly Ala Gly Gly Thr Gly Cys Ala Gly Cys Thr Gly Thr Gly Gly
1               5                   10                  15

Ala Gly Thr Cys Thr Gly Gly Gly Gly Ala Gly Gly Cys Cys Thr
                20                  25                  30

Gly Gly Thr Cys Ala Ala Gly Cys Cys Thr Gly Gly Gly Gly Gly
            35                  40                  45

Thr Cys Cys Cys Thr Gly Ala Gly Ala Cys Thr Cys Thr Cys Thr
    50                  55                  60

Gly Thr Gly Cys Ala Gly Cys Cys Thr Cys Thr Gly Gly Ala Thr Thr
65                  70                  75                  80
```

Cys Ala Cys Cys Thr Thr Cys Ala Gly Thr Gly Ala Ala Thr Ala Thr
                    85                  90                  95

Ala Cys Cys Ala Thr Gly Ala Ala Cys Thr Gly Gly Thr Cys Cys
                100                 105                 110

Gly Cys Cys Ala Gly Gly Cys Thr Cys Cys Ala Gly Gly Ala Ala
                115                 120                 125

Gly Gly Gly Gly Cys Thr Gly Ala Gly Thr Gly Gly Thr Cys
            130                 135                 140

Thr Cys Ala Gly Cys Thr Ala Thr Thr Gly Thr Ala Gly Gly Thr Ala
145                 150                 155                 160

Gly Thr Gly Gly Thr Gly Ala Cys Ala Gly Cys Ala Cys Ala Thr Ala
                165                 170                 175

Cys Thr Ala Cys Gly Cys Ala Gly Ala Cys Thr Cys Cys Gly Thr Gly
                180                 185                 190

Ala Ala Gly Gly Gly Cys Cys Gly Gly Thr Thr Cys Ala Cys Cys Ala
                195                 200                 205

Thr Cys Thr Cys Cys Ala Gly Ala Gly Ala Cys Ala Ala Thr Thr Cys
210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
                245                 250                 255

Thr Gly Ala Gly Ala Gly Cys Cys Gly Ala Gly Gly Ala Cys Ala Cys
                260                 265                 270

Gly Gly Cys Gly Gly Thr Gly Thr Ala Cys Thr Ala Cys Thr Gly Cys
            275                 280                 285

Gly Cys Cys Ala Ala Gly Gly Ala Cys Thr Ala Cys Ala Gly Cys Thr
290                 295                 300

Cys Cys Gly Gly Ala Gly Ala Cys Thr Gly Gly Ala Thr Cys Gly Ala
305                 310                 315                 320

Thr Thr Ala Thr Gly Gly Ala Ala Thr Gly Gly Ala Cys Gly Thr Ala
                325                 330                 335

Thr Gly Gly Gly Gly Cys Cys Ala Gly Gly Ala Ala Cys Ala Ala
            340                 345                 350

Cys Thr Gly Thr Cys Ala Cys Cys Gly Thr Cys Thr Cys Thr Cys
            355                 360                 365

Ala

<210> SEQ ID NO 12
<211> LENGTH: 123
<212> TYPE: PRT
<213> ORGANISM: Artificial Sequence
<220> FEATURE:
<223> OTHER INFORMATION: Synthetic: 2 - VH Protein

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Glu Tyr
                20                  25                  30

Thr Met Asn Trp Val Arg Gln Ala Pro Gly Lys Gly Leu Glu Trp Val
            35                  40                  45

Ser Ala Ile Val Gly Ser Gly Asp Ser Thr Tyr Tyr Ala Asp Ser Val
        50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Tyr Ser Ser Gly Asp Trp Ile Asp Tyr Gly Met Asp Val
            100                 105                 110

Trp Gly Gln Gly Thr Thr Val Thr Val Ser Ser
        115                 120

<210> SEQ ID NO 13
<211> LENGTH: 23
<212> TYPE: PRT
<213> ORGANISM: Artificial Sequence
<220> FEATURE:
<223> OTHER INFORMATION: Synthetic: 2 - VL FR1

<400> SEQUENCE: 13

Asp Ile Gln Met Thr Gln Ser Pro Ser Ser Leu Ser Ala Ser Val Gly
  1               5                  10                  15

Asp Arg Val Thr Ile Thr Cys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic: 2 - VL FR2

<400> SEQUENCE: 14

Trp Tyr Gln Gln Lys Pro Gly Lys Ala Pro Lys Leu Leu Ile Tyr
  1               5                  10                  15

<210> SEQ ID NO 15
<211> LENGTH: 32
<212> TYPE: PRT
<213> ORGANISM: Artificial Sequence
<220> FEATURE:
<223> OTHER INFORMATION: Synthetic: 2 - VL FR3

<400> SEQUENCE: 15

Gly Val Pro Ser Arg Phe Ser Gly Ser Gly Ser Gly Thr Asp Phe Thr
  1               5                  10                  15

Phe Thr Ile Ser Ser Leu Gln Pro Glu Asp Ile Ala Thr Tyr Tyr Cys
             20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Synthetic: 2 - VL FR4

<400> SEQUENCE: 16

Phe Gly Gly Gly Thr Lys Val Glu Ile Lys
  1               5                  10

<210> SEQ ID NO 17
<211> LENGTH: 321
<212> TYPE: PRT
<213> ORGANISM: Artificial Sequence
<220> FEATURE:
<223> OTHER INFORMATION: Synthetic: 2 - VL DNA
```

<400> SEQUENCE: 17

Gly Ala Cys Ala Thr Cys Cys Ala Gly Ala Thr Gly Cys Cys Cys
1               5                   10                  15

Ala Gly Thr Cys Thr Cys Cys Ala Thr Cys Cys Thr Cys Cys Thr
                20                  25                  30

Gly Thr Cys Thr Gly Cys Ala Thr Cys Thr Gly Thr Ala Gly Gly Ala
            35                  40                  45

Gly Ala Cys Ala Gly Ala Gly Thr Cys Ala Cys Cys Ala Thr Cys Ala
        50                  55                  60

Cys Thr Thr Gly Cys Cys Ala Gly Gly Cys Gly Ala Gly Thr Cys Ala
65                  70                  75                  80

Gly Gly Ala Cys Ala Thr Thr Ala Gly Cys Ala Ala Cys Thr Ala Thr
                85                  90                  95

Thr Thr Ala Ala Ala Thr Thr Gly Gly Thr Ala Thr Cys Ala Gly Cys
                100                 105                 110

Ala Gly Ala Ala Ala Cys Cys Ala Gly Gly Gly Ala Ala Ala Gly Cys
                115                 120                 125

Cys Cys Cys Thr Ala Ala Gly Cys Thr Cys Cys Thr Gly Ala Thr Cys
130                 135                 140

Thr Ala Cys Gly Ala Thr Gly Cys Ala Thr Cys Cys Ala Ala Thr Thr
145                 150                 155                 160

Thr Gly Gly Cys Ala Ala Cys Ala Gly Gly Gly Thr Cys Cys Cys
                165                 170                 175

Ala Thr Cys Ala Ala Gly Gly Thr Thr Cys Ala Gly Thr Gly Gly Ala
                180                 185                 190

Ala Gly Thr Gly Gly Ala Thr Cys Thr Gly Gly Gly Ala Cys Ala Gly
                195                 200                 205

Ala Thr Thr Thr Thr Ala Cys Thr Thr Thr Cys Ala Cys Cys Ala Thr
                210                 215                 220

Cys Ala Gly Cys Ala Gly Cys Cys Thr Gly Cys Ala Gly Cys Cys Thr
225                 230                 235                 240

Gly Ala Ala Gly Ala Thr Ala Thr Thr Gly Cys Ala Ala Cys Ala Thr
                245                 250                 255

Ala Thr Thr Ala Cys Thr Gly Thr Cys Ala Gly Cys Ala Gly Thr Thr
                260                 265                 270

Cys Gly Ala Thr Cys Thr Cys Cys Thr Cys Cys Cys Thr Cys Cys Thr
        275                 280                 285

Ala Cys Thr Thr Thr Thr Gly Gly Cys Gly Gly Ala Gly Gly Gly Ala
    290                 295                 300

Cys Cys Ala Ala Gly Gly Thr Thr Gly Ala Gly Ala Thr Cys Ala Ala
305                 310                 315                 320

Ala

<210> SEQ ID NO 18
<211> LENGTH: 107
<212> TYPE: PRT
<213> ORGANISM: Artificial Sequence
<220> FEATURE:
<223> OTHER INFORMATION: Synthetic: 2 - VL Protein

<400> SEQUENCE: 18

Asp Ile Gln Met Thr Gln Ser Pro Ser Ser Leu Ser Ala Ser Val Gly
1               5                   10                  15

```
Asp Arg Val Thr Ile Thr Cys Gln Ala Ser Gln Asp Ile Ser Asn Tyr
                20              25                  30
Leu Asn Trp Tyr Gln Gln Lys Pro Gly Lys Ala Pro Lys Leu Leu Ile
            35                  40                  45
Tyr Asp Ala Ser Asn Leu Ala Thr Gly Val Pro Ser Arg Phe Ser Gly
        50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Phe Asp Leu Leu Pro Pro
                85                  90                  95
Thr Phe Gly Gly Gly Thr Lys Val Glu Ile Lys
            100                 105
```

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

```
<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
```

-continued

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

-continued

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 9
<212> TYPE: PRT
<213> ORGANISM: Artificial Sequence
<220> FEATURE:
<223> OTHER INFORMATION: Synthetic: 5 - VH CDR1

<400> SEQUENCE: 101

Phe Thr Phe Ser Asp Tyr Ala Met Ile
1               5

<210> SEQ ID NO 102
<211> LENGTH: 17
<212> TYPE: PRT
<213> ORGANISM: Artificial Sequence
<220> FEATURE:
<223> OTHER INFORMATION: Synthetic: 5 - VH CDR2

<400> SEQUENCE: 102

Ala Ile Ser Gly Gly Gly Glu Ser Thr Tyr Tyr Ala Asp Ser Val Lys
1               5                   10                  15

Gly

<210> SEQ ID NO 103
<211> LENGTH: 16
<212> TYPE: PRT
<213> ORGANISM: Artificial Sequence
<220> FEATURE:
<223> OTHER INFORMATION: Synthetic: 5 - VH CDR3

```
<400> SEQUENCE: 103

Ala Lys Asp Tyr Ser Ser Gly Asp Trp Ile Asp Tyr Gly Met Asp Val
1               5                   10                  15

<210> SEQ ID NO 104
<211> LENGTH: 11
<212> TYPE: PRT
<213> ORGANISM: Artificial Sequence
<220> FEATURE:
<223> OTHER INFORMATION: Synthetic: 5 - VL CDR1

<400> SEQUENCE: 104

Gln Ala Ser Gln Asp Ile Ser Asn Tyr Leu Asn
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Synthetic: 5 - VL CDR2

<400> SEQUENCE: 105

Asp Ala Ser Asn Leu Ala Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic: 5 - VL CDR3

<400> SEQUENCE: 106

Gln Gln Phe Asp Leu Leu Pro Pro Thr
1               5

<210> SEQ ID NO 107
<211> LENGTH: 26
<212> TYPE: PRT
<213> ORGANISM: Artificial Sequence
<220> FEATURE:
<223> OTHER INFORMATION: Synthetic: 5 - VH FR1

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 108
<211> LENGTH: 14
<212> TYPE: PRT
<213> ORGANISM: Artificial Sequence
<220> FEATURE:
<223> OTHER INFORMATION: Synthetic: 5 - VH FR2

<400> SEQUENCE: 108

Trp Val Arg Gln Ala Pro Gly Lys Gly Leu Glu Trp Val Ser
1               5                   10

<210> SEQ ID NO 109
<211> LENGTH: 30
<212> TYPE: PRT
<213> ORGANISM: Artificial Sequence
```

```
<220> FEATURE:
<223> OTHER INFORMATION: Synthetic: 5 - VH FR3

<400> SEQUENCE: 109

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 110
<211> LENGTH: 11
<212> TYPE: PRT
<213> ORGANISM: Artificial Sequence
<220> FEATURE:
<223> OTHER INFORMATION: Synthetic: 5 - VH FR4

<400> SEQUENCE: 110

Trp Gly Gln Gly Thr Thr Val Thr Val Ser Ser
1               5                   10

<210> SEQ ID NO 111
<211> LENGTH: 369
<212> TYPE: DNA
<213> ORGANISM: Artificial Sequence
<220> FEATURE:
<223> OTHER INFORMATION: Synthetic: 5 - VH DNA

<400> SEQUENCE: 111
```

| | |
|---|---:|
| gaggtgcagc tgttggagtc tgggggaggc ttggtacagc ctggggggtc cctgagactc | 60 |
| tcctgtgcag cctctggatt caccttagc gactatgcca tgatatgggt ccgccaggct | 120 |
| ccagggaagg ggctggagtg ggtctcagct attagtggtg gaggtgaaag cacatactac | 180 |
| gcagactccg tgaagggccg gttcaccatc tccagagaca attccaagaa cacgctgtat | 240 |
| ctgcaaatga acagcctgag agccgaggac acggcggtgt actactgcgc caaggactac | 300 |
| agctccggag actggatcga ttatggaatg gacgtatggg gccagggaac aactgtcacc | 360 |
| gtctcctca | 369 |

```
<210> SEQ ID NO 112
<211> LENGTH: 123
<212> TYPE: PRT
<213> ORGANISM: Artificial Sequence
<220> FEATURE:
<223> OTHER INFORMATION: Synthetic: 5 - VH Protein

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ile Trp Val Arg Gln Ala Pro Gly Lys Gly Leu Glu Trp Val
        35                  40                  45

Ser Ala Ile Ser Gly Gly Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Ser Ser Gly Asp Trp Ile Asp Tyr Gly Met Asp Val
            100                 105                 110
```

```
Trp Gly Gln Gly Thr Thr Val Thr Val Ser Ser
        115                 120
```

<210> SEQ ID NO 113
<211> LENGTH: 23
<212> TYPE: PRT
<213> ORGANISM: Artificial Sequence
<220> FEATURE:
<223> OTHER INFORMATION: Synthetic: 5 - VL FR1

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 114
<211> LENGTH: 15
<212> TYPE: PRT
<213> ORGANISM: Artificial Sequence
<220> FEATURE:
<223> OTHER INFORMATION: Synthetic: 5 - VL FR2

<400> SEQUENCE: 114

```
Trp Tyr Gln Gln Lys Pro Gly Lys Ala Pro Lys Leu Leu Ile Tyr
1               5                   10                  15
```

<210> SEQ ID NO 115
<211> LENGTH: 32
<212> TYPE: PRT
<213> ORGANISM: Artificial Sequence
<220> FEATURE:
<223> OTHER INFORMATION: Synthetic: 5 - VL FR3

<400> SEQUENCE: 115

```
Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30
```

<210> SEQ ID NO 116
<211> LENGTH: 10
<212> TYPE: PRT
<213> ORGANISM: Artificial Sequence
<220> FEATURE:
<223> OTHER INFORMATION: Synthetic: 5 - VL FR4

<400> SEQUENCE: 116

```
Phe Gly Gly Gly Thr Lys Val Glu Ile Lys
1               5                   10
```

<210> SEQ ID NO 117
<211> LENGTH: 321
<212> TYPE: DNA
<213> ORGANISM: Artificial Sequence
<220> FEATURE:
<223> OTHER INFORMATION: Synthetic: 5 - VL DNA

<400> SEQUENCE: 117

```
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg gaagtggatc tgggacagat tttactttca ccatcagcag cctgcagcct    240
```

```
gaagatattg caacatatta ctgtcagcag ttcgatctcc tccctcctac ttttggcgga      300
gggaccaagg ttgagatcaa a                                                321
```

<210> SEQ ID NO 118
<211> LENGTH: 107
<212> TYPE: PRT
<213> ORGANISM: Artificial Sequence
<220> FEATURE:
<223> OTHER INFORMATION: Synthetic: 5 - VL Protein

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asp Leu Leu Pro Pro
                85                  90                  95

Thr Phe Gly Gly Gly Thr Lys Val Glu Ile Lys
            100                 105
```

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

-continued

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

```
<210> SEQ ID NO 201
<211> LENGTH: 9
<212> TYPE: PRT
<213> ORGANISM: Artificial Sequence
<220> FEATURE:
<223> OTHER INFORMATION: Synthetic: 44 - VH CDR1

<400> SEQUENCE: 201

Gly Thr Phe Asp Asn Tyr Tyr Ile Ser
1               5

<210> SEQ ID NO 202
<211> LENGTH: 17
<212> TYPE: PRT
<213> ORGANISM: Artificial Sequence
<220> FEATURE:
<223> OTHER INFORMATION: Synthetic: 44 - VH CDR2
```

<210> SEQ ID NO 202

Gly Ile Phe Pro Ile Phe Gly Thr Ala Asn Tyr Ala Gln Lys Phe Gln
1               5                   10                  15

Gly

<210> SEQ ID NO 203
<211> LENGTH: 16
<212> TYPE: PRT
<213> ORGANISM: Artificial Sequence
<220> FEATURE:
<223> OTHER INFORMATION: Synthetic: 44 - VH CDR3

<400> SEQUENCE: 203

Ala Arg Glu Val Gly His Tyr Ser Gly Ser Pro Tyr Tyr Met Asp Val
1               5                   10                  15

<210> SEQ ID NO 204
<211> LENGTH: 11
<212> TYPE: PRT
<213> ORGANISM: Artificial Sequence
<220> FEATURE:
<223> OTHER INFORMATION: Synthetic: 44 - VL CDR1

<400> SEQUENCE: 204

Arg Ala Ser Gln Ser Ile Asn Ser Trp Leu Ala
1               5                   10

<210> SEQ ID NO 205
<211> LENGTH: 7
<212> TYPE: PRT
<213> ORGANISM: Artificial Sequence
<220> FEATURE:
<223> OTHER INFORMATION: Synthetic: 44 - VL CDR2

<400> SEQUENCE: 205

Asp Ala Ser Ser Leu Glu Ser
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic: 44 - VL CDR3

<400> SEQUENCE: 206

Gln Gln Val Gly Pro Tyr Leu Thr
1               5

<210> SEQ ID NO 207
<211> LENGTH: 26
<212> TYPE: PRT
<213> ORGANISM: Artificial Sequence
<220> FEATURE:
<223> OTHER INFORMATION: Synthetic: 44 - VH FR1

<400> SEQUENCE: 207

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 208
<211> LENGTH: 14

```
<212> TYPE: PRT
<213> ORGANISM: Artificial Sequence
<220> FEATURE:
<223> OTHER INFORMATION: Synthetic: 44 - VH FR2

<400> SEQUENCE: 208

Trp Val Arg Gln Ala Pro Gly Gln Gly Leu Glu Trp Met Gly
1               5                   10

<210> SEQ ID NO 209
<211> LENGTH: 30
<212> TYPE: PRT
<213> ORGANISM: Artificial Sequence
<220> FEATURE:
<223> OTHER INFORMATION: Synthetic: 44 - VH FR3

<400> SEQUENCE: 209

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 210
<211> LENGTH: 11
<212> TYPE: PRT
<213> ORGANISM: Artificial Sequence
<220> FEATURE:
<223> OTHER INFORMATION: Synthetic: 44 - VH FR4

<400> SEQUENCE: 210

Trp Gly Lys Gly Thr Thr Val Thr Val Ser Ser
1               5                   10

<210> SEQ ID NO 211
<211> LENGTH: 369
<212> TYPE: DNA
<213> ORGANISM: Artificial Sequence
<220> FEATURE:
<223> OTHER INFORMATION: Synthetic: 44 - VH DNA

<400> SEQUENCE: 211
caggtgcagc tggtgcagtc tggggctgag gtgaagaagc ctgggtcctc ggtgaaggtc      60
tcctgcaagg cttctggagg caccttcgac aactattaca tcagctgggt gcgacaggcc     120
cctggacaag ggcttgagtg gatgggaggg atcttcccta tcttcggtac cgcaaactac     180
gcacagaagt tccagggcag agtcacgatt accgcggacg aatccacgag cacagcctac     240
atggagctga gcagcctgag atctgaggac acggcggtgt actactgcgc cagagaagtc     300
ggacactact ccggcagccc atactacatg gacgtatggg gcaagggtac aactgtcacc     360
gtctcctca                                                             369

<210> SEQ ID NO 212
<211> LENGTH: 123
<212> TYPE: PRT
<213> ORGANISM: Artificial Sequence
<220> FEATURE:
<223> OTHER INFORMATION: Synthetic: 44 - VH Protein

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asp Asn Tyr
            20                  25                  30
```

```
Tyr Ile Ser Trp Val Arg Gln Ala Pro Gly Gln Gly Leu Glu Trp Met
             35                  40                  45

Gly Gly Ile Phe Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Val Gly His Tyr Ser Gly Ser Pro Tyr Tyr Met Asp Val
                100                 105                 110

Trp Gly Lys Gly Thr Thr Val Thr Val Ser Ser
            115                 120
```

<210> SEQ ID NO 213
<211> LENGTH: 23
<212> TYPE: PRT
<213> ORGANISM: Artificial Sequence
<220> FEATURE:
<223> OTHER INFORMATION: Synthetic: 44 - VL FR1

<400> SEQUENCE: 213

```
Asp Ile Gln Met Thr Gln Ser Pro Ser Thr Leu Ser Ala Ser Val Gly
 1               5                  10                  15

Asp Arg Val Thr Ile Thr Cys
             20
```

<210> SEQ ID NO 214
<211> LENGTH: 15
<212> TYPE: PRT
<213> ORGANISM: Artificial Sequence
<220> FEATURE:
<223> OTHER INFORMATION: Synthetic: 44 - VL FR2

<400> SEQUENCE: 214

```
Trp Tyr Gln Gln Lys Pro Gly Lys Ala Pro Lys Leu Leu Ile Ser
 1               5                  10                  15
```

<210> SEQ ID NO 215
<211> LENGTH: 32
<212> TYPE: PRT
<213> ORGANISM: Artificial Sequence
<220> FEATURE:
<223> OTHER INFORMATION: Synthetic: 44 - VL FR3

<400> SEQUENCE: 215

```
Gly Val Pro Ser Arg Phe Ser Gly Ser Gly Ser Gly Thr Glu Phe Thr
 1               5                  10                  15

Leu Thr Ile Ser Ser Leu Gln Pro Asp Asp Phe Ala Thr Tyr Tyr Cys
             20                  25                  30
```

<210> SEQ ID NO 216
<211> LENGTH: 10
<212> TYPE: PRT
<213> ORGANISM: Artificial Sequence
<220> FEATURE:
<223> OTHER INFORMATION: Synthetic: 44 - VL FR4

<400> SEQUENCE: 216

```
Phe Gly Gly Gly Thr Lys Val Glu Ile Lys
 1               5                  10
```

<210> SEQ ID NO 217
<211> LENGTH: 318

<212> TYPE: DNA
<213> ORGANISM: Artificial Sequence
<220> FEATURE:
<223> OTHER INFORMATION: Synthetic: 44 - VL DNA

<400> SEQUENCE: 217

```
gacatccaga tgacccagtc tccttccacc ctgtctgcat ctgtaggaga cagagtcacc    60
atcacttgcc gggccagtca gagtattaat agctggttgg cctggtatca gcagaaacca   120
gggaaagccc ctaagctcct gatctccgat gcctccagtt tggaaagtgg ggtcccatca   180
aggttcagcg gcagtggatc tgggacagaa ttcactctca ccatcagcag cctgcagcct   240
gatgattttg caacttatta ctgccagcag gtcggcccct acctcacttt tggcggaggg   300
accaaggttg agatcaaa                                                  318
```

<210> SEQ ID NO 218
<211> LENGTH: 106
<212> TYPE: PRT
<213> ORGANISM: Artificial Sequence
<220> FEATURE:
<223> OTHER INFORMATION: Synthetic: 44 - VL Protein

<400> SEQUENCE: 218

```
Asp Ile Gln Met Thr Gln Ser Pro Ser Thr Leu Ser Ala Ser Val Gly
  1               5                  10                  15
Asp Arg Val Thr Ile Thr Cys Arg Ala Ser Gln Ser Ile Asn Ser Trp
             20                  25                  30
Leu Ala Trp Tyr Gln Gln Lys Pro Gly Lys Ala Pro Lys Leu Leu Ile
         35                  40                  45
Ser Asp Ala Ser Ser Leu Glu Ser Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Val Gly Pro Tyr Leu Thr
                 85                  90                  95
Phe Gly Gly Gly Thr Lys Val Glu Ile Lys
            100                 105
```

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

```
<210> SEQ ID NO 223
<400> SEQUENCE: 223
000

<210> SEQ ID NO 224
<400> SEQUENCE: 224
000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234
```

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

```
<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
```

```
<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279
```

-continued

000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
<211> LENGTH: 9
<212> TYPE: PRT
<213> ORGANISM: Artificial Sequence
<220> FEATURE:
<223> OTHER INFORMATION: Synthetic: 58 - VH CDR1

```
<400> SEQUENCE: 301

Phe Thr Phe Gly Asp Tyr Ala Met Ser
1               5

<210> SEQ ID NO 302
<211> LENGTH: 19
<212> TYPE: PRT
<213> ORGANISM: Artificial Sequence
<220> FEATURE:
<223> OTHER INFORMATION: Synthetic: 58 - VH CDR2

<400> SEQUENCE: 302

Phe Ile Gly Ser Lys Phe Tyr Gly Gly Glu Thr Glu Tyr Thr Ala Ser
1               5                   10                  15

Val Lys Gly

<210> SEQ ID NO 303
<211> LENGTH: 13
<212> TYPE: PRT
<213> ORGANISM: Artificial Sequence
<220> FEATURE:
<223> OTHER INFORMATION: Synthetic: 58 - VH CDR3

<400> SEQUENCE: 303

Ala Arg Gly Pro Arg Arg Tyr Thr Tyr Gly Met Asp Val
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Synthetic: 58 - VL CDR1

<400> SEQUENCE: 304

Arg Ala Ser Gln Ser Ile Ser Ser Tyr Leu Asn
1               5                   10

<210> SEQ ID NO 305
<211> LENGTH: 7
<212> TYPE: PRT
<213> ORGANISM: Artificial Sequence
<220> FEATURE:
<223> OTHER INFORMATION: Synthetic: 58 - VL CDR2

<400> SEQUENCE: 305

Ala Ala Ser Ser Leu Gln Ser
1               5

<210> SEQ ID NO 306
<211> LENGTH: 8
<212> TYPE: PRT
<213> ORGANISM: Artificial Sequence
<220> FEATURE:
<223> OTHER INFORMATION: Synthetic: 58 - VL CDR3

<400> SEQUENCE: 306

Gln Gln Ser Ser Thr Pro Leu Thr
1               5

<210> SEQ ID NO 307
<211> LENGTH: 26
<212> TYPE: PRT
<213> ORGANISM: Artificial Sequence
<220> FEATURE:
<223> OTHER INFORMATION: Synthetic: 58 - VH FR1
```

-continued

<400> SEQUENCE: 307

Glu Val Gln Leu Val Glu Ser Gly Gly Gly Leu Val Gln Pro Gly Arg
1               5                   10                  15

Ser Leu Arg Leu Ser Cys Thr Ala Ser Gly
            20                  25

<210> SEQ ID NO 308
<211> LENGTH: 14
<212> TYPE: PRT
<213> ORGANISM: Artificial Sequence
<220> FEATURE:
<223> OTHER INFORMATION: Synthetic: 58 - VH FR2

<400> SEQUENCE: 308

Trp Phe Arg Gln Ala Pro Gly Lys Gly Leu Glu Trp Val Gly
1               5                   10

<210> SEQ ID NO 309
<211> LENGTH: 30
<212> TYPE: PRT
<213> ORGANISM: Artificial Sequence
<220> FEATURE:
<223> OTHER INFORMATION: Synthetic: 58 - VH FR3

<400> SEQUENCE: 309

Arg Phe Thr Ile Ser Arg Asp Gly Ser Lys Ser Ile Ala Tyr Leu Gln
1               5                   10                  15

Met Asn Ser Leu Lys Thr Glu Asp Thr Ala Val Tyr Tyr Cys
            20                  25                  30

<210> SEQ ID NO 310
<211> LENGTH: 11
<212> TYPE: PRT
<213> ORGANISM: Artificial Sequence
<220> FEATURE:
<223> OTHER INFORMATION: Synthetic: 58 - VH FR4

<400> SEQUENCE: 310

Trp Gly Gln Gly Thr Thr Val Thr Val Ser Ser
1               5                   10

<210> SEQ ID NO 311
<211> LENGTH: 366
<212> TYPE: DNA
<213> ORGANISM: Artificial Sequence
<220> FEATURE:
<223> OTHER INFORMATION: Synthetic: 58 - VH DNA

<400> SEQUENCE: 311
gaggtgcagc tggtggagtc tgggggaggc ttggtacagc cagggcggtc cctgagactc      60
tcctgtacag cttctggatt cacctttggt gattatgcta tgagctggtt ccgccaggct     120
ccagggaagg gctggagtg gtaggtttc attggaagca aattctatgg tgggaaaca       180 gaatacaccg cgtctgtgaa aggcagattc accatctcaa gagatggttc aaaaagcatc     240
gcctatctgc aaatgaacag cctgaaaacc gaggacacgg cggtgtacta ctgcgccaga     300
ggaccaagac gctacacata cggaatggac gtatggggcc agggaacaac tgtcaccgtc     360
tcctca                                                                366

<210> SEQ ID NO 312
<211> LENGTH: 122
<212> TYPE: PRT

```
<213> ORGANISM: Artificial Sequence
<220> FEATURE:
<223> OTHER INFORMATION: Synthetic: 58 - VH Protein

<400> SEQUENCE: 312

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Gly Ser Lys Phe Tyr Gly Gly Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Gly Pro Arg Arg Tyr Thr Tyr Gly Met Asp Val Trp
            100                 105                 110

Gly Gln Gly Thr Thr Val Thr Val Ser Ser
        115                 120

<210> SEQ ID NO 313
<211> LENGTH: 23
<212> TYPE: PRT
<213> ORGANISM: Artificial Sequence
<220> FEATURE:
<223> OTHER INFORMATION: Synthetic: 58 - VL FR1

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 314
<211> LENGTH: 15
<212> TYPE: PRT
<213> ORGANISM: Artificial Sequence
<220> FEATURE:
<223> OTHER INFORMATION: Synthetic: 58 - VL FR2

<400> SEQUENCE: 314

Trp Tyr Gln Gln Lys Pro Gly Lys Ala Pro Lys Leu Leu Ile Tyr
1               5                   10                  15

<210> SEQ ID NO 315
<211> LENGTH: 32
<212> TYPE: PRT
<213> ORGANISM: Artificial Sequence
<220> FEATURE:
<223> OTHER INFORMATION: Synthetic: 58 - VL FR3

<400> SEQUENCE: 315

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 316
<211> LENGTH: 10
<212> TYPE: PRT
```

```
<213> ORGANISM: Artificial Sequence
<220> FEATURE:
<223> OTHER INFORMATION: Synthetic: 58 - VL FR4

<400> SEQUENCE: 316

Phe Gly Gly Gly Thr Lys Val Glu Ile Lys
 1               5                  10

<210> SEQ ID NO 317
<211> LENGTH: 318
<212> TYPE: DNA
<213> ORGANISM: Artificial Sequence
<220> FEATURE:
<223> OTHER INFORMATION: Synthetic: 58 - VL DNA

<400> SEQUENCE: 317
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agctccaccc ccctcacttt tggcggaggg     300
accaaggttg agatcaaa                                                   318

<210> SEQ ID NO 318
<211> LENGTH: 106
<212> TYPE: PRT
<213> ORGANISM: Artificial Sequence
<220> FEATURE:
<223> OTHER INFORMATION: Synthetic: 58 - VL Protein

<400> SEQUENCE: 318

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Pro Leu Thr
                85                  90                  95

Phe Gly Gly Gly Thr Lys Val Glu Ile Lys
            100                 105

<210> SEQ ID NO 319

<400> SEQUENCE: 319

000

<210> SEQ ID NO 320

<400> SEQUENCE: 320

000

<210> SEQ ID NO 321
```

```
<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332
```

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

```
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
```

000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

-continued

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

```
<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396
<400> SEQUENCE: 396
000

<210> SEQ ID NO 397
<400> SEQUENCE: 397
000

<210> SEQ ID NO 398
<400> SEQUENCE: 398
000

<210> SEQ ID NO 399
<400> SEQUENCE: 399
000

<210> SEQ ID NO 400
```

```
<400> SEQUENCE: 400

000

<210> SEQ ID NO 401
<211> LENGTH: 9
<212> TYPE: PRT
<213> ORGANISM: Artificial Sequence
<220> FEATURE:
<223> OTHER INFORMATION: Synthetic: 10 - VH CDR1

<400> SEQUENCE: 401

Phe Thr Phe Asp Asp Tyr Ala Val His
1               5

<210> SEQ ID NO 402
<211> LENGTH: 17
<212> TYPE: PRT
<213> ORGANISM: Artificial Sequence
<220> FEATURE:
<223> OTHER INFORMATION: Synthetic: 10 - VH CDR2

<400> SEQUENCE: 402

Gly Ile Ser Trp Ser Ser Gly Leu Ile Gly Tyr Ala Asp Ser Val Lys
1               5                   10                  15

Gly

<210> SEQ ID NO 403
<211> LENGTH: 13
<212> TYPE: PRT
<213> ORGANISM: Artificial Sequence
<220> FEATURE:
<223> OTHER INFORMATION: Synthetic: 10 - VH CDR3

<400> SEQUENCE: 403

Ala Lys Gly Pro Pro Thr Tyr Gln Asp Tyr Phe Asp Leu
1               5                   10

<210> SEQ ID NO 404
<211> LENGTH: 11
<212> TYPE: PRT
<213> ORGANISM: Artificial Sequence
<220> FEATURE:
<223> OTHER INFORMATION: Synthetic: 10 - VL CDR1

<400> SEQUENCE: 404

Arg Ala Ser Gln Ser Val Ser Arg Tyr Leu Ala
1               5                   10

<210> SEQ ID NO 405
<211> LENGTH: 7
<212> TYPE: PRT
<213> ORGANISM: Artificial Sequence
<220> FEATURE:
<223> OTHER INFORMATION: Synthetic: 10 - VL CDR2

<400> SEQUENCE: 405

Asp Ala Ser Asn Arg Ala Thr
1               5

<210> SEQ ID NO 406
<211> LENGTH: 10
<212> TYPE: PRT
<213> ORGANISM: Artificial Sequence
<220> FEATURE:
<223> OTHER INFORMATION: Synthetic: 10 - VL CDR3
```

<400> SEQUENCE: 406

Gln Gln Val Ser Phe Phe Pro Pro Ile Thr
1               5                   10

<210> SEQ ID NO 407
<211> LENGTH: 26
<212> TYPE: PRT
<213> ORGANISM: Artificial Sequence
<220> FEATURE:
<223> OTHER INFORMATION: Synthetic: 10 - VH FR1

<400> SEQUENCE: 407

Glu Val Gln Leu Val Glu Ser Gly Gly Gly Leu Val Gln Pro Gly Arg
1               5                   10                  15

Ser Leu Arg Leu Ser Cys Ala Ala Ser Gly
            20                  25

<210> SEQ ID NO 408
<211> LENGTH: 14
<212> TYPE: PRT
<213> ORGANISM: Artificial Sequence
<220> FEATURE:
<223> OTHER INFORMATION: Synthetic: 10 - VH FR2

<400> SEQUENCE: 408

Trp Val Arg Gln Ala Pro Gly Lys Gly Leu Glu Trp Val Ser
1               5                   10

<210> SEQ ID NO 409
<211> LENGTH: 30
<212> TYPE: PRT
<213> ORGANISM: Artificial Sequence
<220> FEATURE:
<223> OTHER INFORMATION: Synthetic: 10 - VH FR3

<400> SEQUENCE: 409

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 410
<211> LENGTH: 11
<212> TYPE: PRT
<213> ORGANISM: Artificial Sequence
<220> FEATURE:
<223> OTHER INFORMATION: Synthetic: 10 - VH FR4

<400> SEQUENCE: 410

Trp Gly Arg Gly Thr Leu Val Thr Val Ser Ser
1               5                   10

<210> SEQ ID NO 411
<211> LENGTH: 360
<212> TYPE: DNA
<213> ORGANISM: Artificial Sequence
<220> FEATURE:
<223> OTHER INFORMATION: Synthetic: 10 - VH DNA

<400> SEQUENCE: 411
gaagtgcagc tggtggagtc tgggggaggc ttggtacagc ctggcaggtc cctgagactc    60
tcctgtgcag cctctggatt cacctttgat gattatgccg tgcactgggt ccggcaagct   120
ccagggaagg gcctggagtg gtctcaggt attagttgga gtagtggact aataggctat    180

```
gcggactctg tgaagggccg attcaccatc tccagagaca acgccaagaa ctccctgtat    240
ctgcaaatga acagtctgag agctgaggac acggcggtgt actactgcgc caagggccct    300
cctacctacc aagactactt cgacctatgg gggagaggta ccttggtcac cgtctcctca    360
```

<210> SEQ ID NO 412
<211> LENGTH: 120
<212> TYPE: PRT
<213> ORGANISM: Artificial Sequence
<220> FEATURE:
<223> OTHER INFORMATION: Synthetic: 10 - VH Protein

<400> SEQUENCE: 412

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Val His Trp Val Arg Gln Ala Pro Gly Lys Gly Leu Glu Trp Val
        35                  40                  45

Ser Gly Ile Ser Trp Ser Ser Gly Leu Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Pro Thr Tyr Gln Asp Tyr Phe Asp Leu Trp Gly Arg
            100                 105                 110

Gly Thr Leu Val Thr Val Ser Ser
        115                 120

<210> SEQ ID NO 413
<211> LENGTH: 23
<212> TYPE: PRT
<213> ORGANISM: Artificial Sequence
<220> FEATURE:
<223> OTHER INFORMATION: Synthetic: 10 - VL FR1

<400> SEQUENCE: 413

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 414
<211> LENGTH: 15
<212> TYPE: PRT
<213> ORGANISM: Artificial Sequence
<220> FEATURE:
<223> OTHER INFORMATION: Synthetic: 10 - VL FR2

<400> SEQUENCE: 414

Trp Tyr Gln Gln Lys Pro Gly Gln Ala Pro Arg Leu Leu Ile Tyr
1               5                   10                  15

<210> SEQ ID NO 415
<211> LENGTH: 32
<212> TYPE: PRT
<213> ORGANISM: Artificial Sequence
<220> FEATURE:
<223> OTHER INFORMATION: Synthetic: 10 - VL FR3

<400> SEQUENCE: 415

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 416
<211> LENGTH: 10
<212> TYPE: PRT
<213> ORGANISM: Artificial Sequence
<220> FEATURE:
<223> OTHER INFORMATION: Synthetic: 10 - VL FR4

<400> SEQUENCE: 416

Phe Gly Gly Gly Thr Lys Val Glu Ile Lys
1               5                   10

<210> SEQ ID NO 417
<211> LENGTH: 324
<212> TYPE: DNA
<213> ORGANISM: Artificial Sequence
<220> FEATURE:
<223> OTHER INFORMATION: Synthetic: 10 - VL DNA

<400> SEQUENCE: 417
gaaattgtgt tgacacagtc tccagccacc ctgtctttgt ctccagggga agagccacc      60 ctctcctgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag gtcagtttct ccctcctat cacttttggc    300 ggagggacca aggttgagat caaa                                           324

<210> SEQ ID NO 418
<211> LENGTH: 108
<212> TYPE: PRT
<213> ORGANISM: Artificial Sequence
<220> FEATURE:
<223> OTHER INFORMATION: Synthetic: 10 - VL Protein

<400> SEQUENCE: 418

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Ser Phe Ser Pro Pro
                85                  90                  95

Ile Thr Phe Gly Gly Gly Thr Lys Val Glu Ile Lys
            100                 105

<210> SEQ ID NO 419

<400> SEQUENCE: 419

000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430
<400> SEQUENCE: 430
000

```
<210> SEQ ID NO 431
<400> SEQUENCE: 431
000

<210> SEQ ID NO 432
<400> SEQUENCE: 432
000

<210> SEQ ID NO 433
<400> SEQUENCE: 433
000

<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000

<210> SEQ ID NO 438
<400> SEQUENCE: 438
000

<210> SEQ ID NO 439
<400> SEQUENCE: 439
000

<210> SEQ ID NO 440
<400> SEQUENCE: 440
000

<210> SEQ ID NO 441
<400> SEQUENCE: 441
000
```

-continued

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

-continued

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

-continued

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499
<400> SEQUENCE: 499

000

<210> SEQ ID NO 500
<400> SEQUENCE: 500

000

<210> SEQ ID NO 501
<211> LENGTH: 9
<212> TYPE: PRT
<213> ORGANISM: Artificial Sequence
<220> FEATURE:
<223> OTHER INFORMATION: Synthetic: 38 - VH CDR1

<400> SEQUENCE: 501

Phe Thr Phe Ser Gly His Leu Met Ser
1               5

<210> SEQ ID NO 502
<211> LENGTH: 17
<212> TYPE: PRT
<213> ORGANISM: Artificial Sequence
<220> FEATURE:
<223> OTHER INFORMATION: Synthetic: 38 - VH CDR2

<400> SEQUENCE: 502

Ala Ile Ser Gly Ser Ala Gly Glu Thr Tyr Tyr Ala Asp Ser Val Lys
1               5                   10                  15

Gly

<210> SEQ ID NO 503
<211> LENGTH: 19
<212> TYPE: PRT
<213> ORGANISM: Artificial Sequence
<220> FEATURE:
<223> OTHER INFORMATION: Synthetic: 38 - VH CDR3

<400> SEQUENCE: 503

Ala Arg Asp Ala Tyr Tyr Asp Asp Trp Ser Gly Trp Ala Asp Trp Tyr
1               5                   10                  15

Phe Asp Leu

<210> SEQ ID NO 504
<211> LENGTH: 11
<212> TYPE: PRT
<213> ORGANISM: Artificial Sequence
<220> FEATURE:
<223> OTHER INFORMATION: Synthetic: 38 - VL CDR1

<400> SEQUENCE: 504

Arg Ala Ser Gln Ser Val Ser Arg Tyr Leu Ala
1               5                   10

<210> SEQ ID NO 505
<211> LENGTH: 7
<212> TYPE: PRT
<213> ORGANISM: Artificial Sequence
<220> FEATURE:

```
<223> OTHER INFORMATION: Synthetic: 38 - VL CDR2

<400> SEQUENCE: 505

Asp Ala Ser Asn Arg Ala Thr
1               5

<210> SEQ ID NO 506
<211> LENGTH: 9
<212> TYPE: PRT
<213> ORGANISM: Artificial Sequence
<220> FEATURE:
<223> OTHER INFORMATION: Synthetic: 38 - VL CDR3

<400> SEQUENCE: 506

Gln Gln Val Ser Leu Leu Pro Pro Thr
1               5

<210> SEQ ID NO 507
<211> LENGTH: 26
<212> TYPE: PRT
<213> ORGANISM: Artificial Sequence
<220> FEATURE:
<223> OTHER INFORMATION: Synthetic: 38 - VH FR1

<400> SEQUENCE: 507

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 508
<211> LENGTH: 14
<212> TYPE: PRT
<213> ORGANISM: Artificial Sequence
<220> FEATURE:
<223> OTHER INFORMATION: Synthetic: 38 - VH FR2

<400> SEQUENCE: 508

Trp Val Arg Gln Ala Pro Gly Lys Gly Leu Glu Trp Val Ser
1               5                   10

<210> SEQ ID NO 509
<211> LENGTH: 30
<212> TYPE: PRT
<213> ORGANISM: Artificial Sequence
<220> FEATURE:
<223> OTHER INFORMATION: Synthetic: 38 - VH FR3

<400> SEQUENCE: 509

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 510
<211> LENGTH: 11
<212> TYPE: PRT
<213> ORGANISM: Artificial Sequence
<220> FEATURE:
<223> OTHER INFORMATION: Synthetic: 38 - VH FR4

<400> SEQUENCE: 510

Trp Gly Arg Gly Thr Leu Val Thr Val Ser Ser
1               5                   10
```

<210> SEQ ID NO 511
<211> LENGTH: 378
<212> TYPE: DNA
<213> ORGANISM: Artificial Sequence
<220> FEATURE:
<223> OTHER INFORMATION: Synthetic: 38 - VH DNA

<400> SEQUENCE: 511

```
gaggtgcagc tgttggagtc tgggggaggc ttggtacagc ctgggggtc cctgagactc      60
tcctgtgcag cctctggatt cacctttagc ggacacctaa tgagctgggt ccgccaggct    120
ccagggaagg ggctggagtg ggtctcagct attagtggat ccgcaggtga acatactac    180
gcagactccg tgaagggccg gttcaccatc tccagagaca attccaagaa cacgctgtat    240
ctgcaaatga acagcctgag agccgaggac acggcggtgt actactgcgc cagagatgcg    300
tactacgacg actggagcgg atgggccgat tggtacttcg atttatgggg gagaggtacc    360
ttggtcaccg tctcctca                                                  378
```

<210> SEQ ID NO 512
<211> LENGTH: 126
<212> TYPE: PRT
<213> ORGANISM: Artificial Sequence
<220> FEATURE:
<223> OTHER INFORMATION: Synthetic: 38 - VH Protein

<400> SEQUENCE: 512

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly His
            20                  25                  30

Leu Met Ser Trp Val Arg Gln Ala Pro Gly Lys Gly Leu Glu Trp Val
        35                  40                  45

Ser Ala Ile Ser Gly Ser Ala Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Tyr Tyr Asp Asp Trp Ser Gly Trp Ala Asp Trp Tyr
            100                 105                 110

Phe Asp Leu Trp Gly Arg Gly Thr Leu Val Thr Val Ser Ser
        115                 120                 125

<210> SEQ ID NO 513
<211> LENGTH: 23
<212> TYPE: PRT
<213> ORGANISM: Artificial Sequence
<220> FEATURE:
<223> OTHER INFORMATION: Synthetic: 38 - VL FR1

<400> SEQUENCE: 513

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 514
<211> LENGTH: 15
<212> TYPE: PRT
<213> ORGANISM: Artificial Sequence
<220> FEATURE:

-continued

<223> OTHER INFORMATION: Synthetic: 38 - VL FR2

<400> SEQUENCE: 514

Trp Tyr Gln Gln Lys Pro Gly Gln Ala Pro Arg Leu Leu Ile Tyr
1               5                   10                  15

<210> SEQ ID NO 515
<211> LENGTH: 32
<212> TYPE: PRT
<213> ORGANISM: Artificial Sequence
<220> FEATURE:
<223> OTHER INFORMATION: Synthetic: 38 - VL FR3

<400> SEQUENCE: 515

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 516
<211> LENGTH: 10
<212> TYPE: PRT
<213> ORGANISM: Artificial Sequence
<220> FEATURE:
<223> OTHER INFORMATION: Synthetic: 38 - VL FR4

<400> SEQUENCE: 516

Phe Gly Gly Gly Thr Lys Val Glu Ile Lys
1               5                   10

<210> SEQ ID NO 517
<211> LENGTH: 321
<212> TYPE: DNA
<213> ORGANISM: Artificial Sequence
<220> FEATURE:
<223> OTHER INFORMATION: Synthetic: 38 - VL DNA

<400> SEQUENCE: 517
gaaattgtgt tgacacagtc tccagccacc ctgtctttgt ctccagggga aagagccacc      60
ctctcctgca gggccagtca gagtgttagc aggtacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag gtcagtctcc tccctcctac ttttggcgga     300
gggaccaagg ttgagatcaa a                                                321

<210> SEQ ID NO 518
<211> LENGTH: 107
<212> TYPE: PRT
<213> ORGANISM: Artificial Sequence
<220> FEATURE:
<223> OTHER INFORMATION: Synthetic: 38 - VL Protein

<400> SEQUENCE: 518

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Val Ser Leu Leu Pro Pro
                 85                  90                  95

Thr Phe Gly Gly Gly Thr Lys Val Glu Ile Lys
            100                 105

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597
<400> SEQUENCE: 597

000

<210> SEQ ID NO 598
<400> SEQUENCE: 598

000

<210> SEQ ID NO 599
<400> SEQUENCE: 599

000

<210> SEQ ID NO 600
<400> SEQUENCE: 600

000

<210> SEQ ID NO 601
<211> LENGTH: 9
<212> TYPE: PRT
<213> ORGANISM: Artificial Sequence
<220> FEATURE:
<223> OTHER INFORMATION: Synthetic: 15 - VH CDR1

<400> SEQUENCE: 601

Phe Thr Phe Gly Asp Val Ala Met Ser
1               5

<210> SEQ ID NO 602
<211> LENGTH: 19
<212> TYPE: PRT
<213> ORGANISM: Artificial Sequence
<220> FEATURE:
<223> OTHER INFORMATION: Synthetic: 15 - VH CDR2

<400> SEQUENCE: 602

Tyr Ile Gly Ser Lys Ala Tyr Gly Gly Glu Thr Glu Tyr Thr Ala Ser
1               5                   10                  15

Val Lys Gly

<210> SEQ ID NO 603
<211> LENGTH: 17
<212> TYPE: PRT
<213> ORGANISM: Artificial Sequence
<220> FEATURE:
<223> OTHER INFORMATION: Synthetic: 15 - VH CDR3

<400> SEQUENCE: 603

Ala Arg Ala Gly His Ser Tyr Gly Ser Ile Ala Ser Asn Trp Phe Asp
1               5                   10                  15

Pro

<210> SEQ ID NO 604
<211> LENGTH: 11
<212> TYPE: PRT
<213> ORGANISM: Artificial Sequence

```
<220> FEATURE:
<223> OTHER INFORMATION: Synthetic: 15 - VL CDR1

<400> SEQUENCE: 604

Arg Ala Ser Gln Ser Ile Ser Ser Tyr Leu Asn
1               5                   10

<210> SEQ ID NO 605
<211> LENGTH: 7
<212> TYPE: PRT
<213> ORGANISM: Artificial Sequence
<220> FEATURE:
<223> OTHER INFORMATION: Synthetic: 15 - VL CDR2

<400> SEQUENCE: 605

Gly Ala Ser Ser Leu Gln Ser
1               5

<210> SEQ ID NO 606
<211> LENGTH: 9
<212> TYPE: PRT
<213> ORGANISM: Artificial Sequence
<220> FEATURE:
<223> OTHER INFORMATION: Synthetic: 15 - VL CDR3

<400> SEQUENCE: 606

Gln Gln Gly Phe Tyr Thr Pro Trp Thr
1               5

<210> SEQ ID NO 607
<211> LENGTH: 26
<212> TYPE: PRT
<213> ORGANISM: Artificial Sequence
<220> FEATURE:
<223> OTHER INFORMATION: Synthetic: 15 - VH FR1

<400> SEQUENCE: 607

Glu Val Gln Leu Val Glu Ser Gly Gly Gly Leu Val Gln Pro Gly Arg
1               5                   10                  15

Ser Leu Arg Leu Ser Cys Thr Ala Ser Gly
            20                  25

<210> SEQ ID NO 608
<211> LENGTH: 14
<212> TYPE: PRT
<213> ORGANISM: Artificial Sequence
<220> FEATURE:
<223> OTHER INFORMATION: Synthetic: 15 - VH FR2

<400> SEQUENCE: 608

Trp Phe Arg Gln Ala Pro Gly Lys Gly Leu Glu Trp Val Gly
1               5                   10

<210> SEQ ID NO 609
<211> LENGTH: 30
<212> TYPE: PRT
<213> ORGANISM: Artificial Sequence
<220> FEATURE:
<223> OTHER INFORMATION: Synthetic: 15 - VH FR3

<400> SEQUENCE: 609

Arg Phe Thr Ile Ser Arg Asp Gly Ser Lys Ser Ile Ala Tyr Leu Gln
1               5                   10                  15

Met Asn Ser Leu Lys Thr Glu Asp Thr Ala Val Tyr Tyr Cys
            20                  25                  30
```

<210> SEQ ID NO 610
<211> LENGTH: 11
<212> TYPE: PRT
<213> ORGANISM: Artificial Sequence
<220> FEATURE:
<223> OTHER INFORMATION: Synthetic: 15 - VH FR4

<400> SEQUENCE: 610

Trp Gly Gln Gly Thr Leu Val Thr Val Ser Ser
1               5                   10

<210> SEQ ID NO 611
<211> LENGTH: 378
<212> TYPE: DNA
<213> ORGANISM: Artificial Sequence
<220> FEATURE:
<223> OTHER INFORMATION: Synthetic: 15 - VH DNA

<400> SEQUENCE: 611
gaggtgcagc tggtggagtc tgggggaggc ttggtacagc cagggcggtc cctgagactc      60
tcctgtacag cttctggatt cacctttggt gatgtcgcta tgtcctggtt ccgccaggct     120
ccagggaagg ggctggagtg ggtaggttac attggaagca aagcttatgg tggggaaaca     180
gaatacaccg cgtctgtgaa aggcagattc accatctcaa gagatggttc aaaagcatc     240 gcctatctgc aaatgaacag cctgaaaacc gaggacacgg cggtgtacta ctgcgccaga     300
gctggacaca gctacggatc catcgccagc aactggttcg acccatgggg acagggtaca     360
ttggtcaccg tctcctca                                                   378

<210> SEQ ID NO 612
<211> LENGTH: 126
<212> TYPE: PRT
<213> ORGANISM: Artificial Sequence
<220> FEATURE:
<223> OTHER INFORMATION: Synthetic: 15 - VH Protein

<400> SEQUENCE: 612

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Val
            20                  25                  30

Ala Met Ser Trp Phe Arg Gln Ala Pro Gly Lys Gly Leu Glu Trp Val
        35                  40                  45

Gly Tyr Ile Gly Ser Lys Ala Tyr Gly Gly Glu Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Ala Gly His Ser Tyr Gly Ser Ile Ala Ser Asn Trp
            100                 105                 110

Phe Asp Pro Trp Gly Gln Gly Thr Leu Val Thr Val Ser Ser
        115                 120                 125

<210> SEQ ID NO 613
<211> LENGTH: 23
<212> TYPE: PRT
<213> ORGANISM: Artificial Sequence
<220> FEATURE:
<223> OTHER INFORMATION: Synthetic: 15 - VL FR1

<400> SEQUENCE: 613

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 614
<211> LENGTH: 15
<212> TYPE: PRT
<213> ORGANISM: Artificial Sequence
<220> FEATURE:
<223> OTHER INFORMATION: Synthetic: 15 - VL FR2

<400> SEQUENCE: 614

Trp Tyr Gln Gln Lys Pro Gly Lys Ala Pro Lys Leu Leu Ile Tyr
1               5                   10                  15

<210> SEQ ID NO 615
<211> LENGTH: 32
<212> TYPE: PRT
<213> ORGANISM: Artificial Sequence
<220> FEATURE:
<223> OTHER INFORMATION: Synthetic: 15 - VL FR3

<400> SEQUENCE: 615

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 616
<211> LENGTH: 10
<212> TYPE: PRT
<213> ORGANISM: Artificial Sequence
<220> FEATURE:
<223> OTHER INFORMATION: Synthetic: 15 - VL FR4

<400> SEQUENCE: 616

Phe Gly Gly Gly Thr Lys Val Glu Ile Lys
1               5                   10

<210> SEQ ID NO 617
<211> LENGTH: 321
<212> TYPE: DNA
<213> ORGANISM: Artificial Sequence
<220> FEATURE:
<223> OTHER INFORMATION: Synthetic: 15 - VL DNA

<400> SEQUENCE: 617
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatggt gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggattctaca ctccttggac ttttggcgga     300
gggaccaagg ttgagatcaa a                                               321

<210> SEQ ID NO 618
<211> LENGTH: 107
<212> TYPE: PRT
<213> ORGANISM: Artificial Sequence
<220> FEATURE:
<223> OTHER INFORMATION: Synthetic: 15 - VL Protein

<400> SEQUENCE: 618

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Tyr Thr Pro Trp
                85                  90                  95

Thr Phe Gly Gly Gly Thr Lys Val Glu Ile Lys
            100                 105

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

-continued

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661
<400> SEQUENCE: 661
000

<210> SEQ ID NO 662
<400> SEQUENCE: 662
000

<210> SEQ ID NO 663
<400> SEQUENCE: 663
000

<210> SEQ ID NO 664
<400> SEQUENCE: 664
000

<210> SEQ ID NO 665
<400> SEQUENCE: 665
000

<210> SEQ ID NO 666
<400> SEQUENCE: 666
000

<210> SEQ ID NO 667
<400> SEQUENCE: 667
000

<210> SEQ ID NO 668
<400> SEQUENCE: 668
000

<210> SEQ ID NO 669
<400> SEQUENCE: 669
000

<210> SEQ ID NO 670
<400> SEQUENCE: 670
000

<210> SEQ ID NO 671
<400> SEQUENCE: 671
000

-continued

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

```
<400> SEQUENCE: 683
000

<210> SEQ ID NO 684
<400> SEQUENCE: 684
000

<210> SEQ ID NO 685
<400> SEQUENCE: 685
000

<210> SEQ ID NO 686
<400> SEQUENCE: 686
000

<210> SEQ ID NO 687
<400> SEQUENCE: 687
000

<210> SEQ ID NO 688
<400> SEQUENCE: 688
000

<210> SEQ ID NO 689
<400> SEQUENCE: 689
000

<210> SEQ ID NO 690
<400> SEQUENCE: 690
000

<210> SEQ ID NO 691
<400> SEQUENCE: 691
000

<210> SEQ ID NO 692
<400> SEQUENCE: 692
000

<210> SEQ ID NO 693
<400> SEQUENCE: 693
000

<210> SEQ ID NO 694
<400> SEQUENCE: 694
```

```
<210> SEQ ID NO 695
<400> SEQUENCE: 695

000

<210> SEQ ID NO 696
<400> SEQUENCE: 696

000

<210> SEQ ID NO 697
<400> SEQUENCE: 697

000

<210> SEQ ID NO 698
<400> SEQUENCE: 698

000

<210> SEQ ID NO 699
<400> SEQUENCE: 699

000

<210> SEQ ID NO 700
<400> SEQUENCE: 700

000

<210> SEQ ID NO 701
<211> LENGTH: 9
<212> TYPE: PRT
<213> ORGANISM: Artificial Sequence
<220> FEATURE:
<223> OTHER INFORMATION: Synthetic: 35 - VH CDR1

<400> SEQUENCE: 701

Gly Thr Phe Ser Ser Ala Ala Ile Ser
1               5

<210> SEQ ID NO 702
<211> LENGTH: 17
<212> TYPE: PRT
<213> ORGANISM: Artificial Sequence
<220> FEATURE:
<223> OTHER INFORMATION: Synthetic: 35 - VH CDR2

<400> SEQUENCE: 702

Asn Ile Ile Pro Ile Val Gly Ile Ala Asn Tyr Ala Gln Lys Phe Gln
1               5                   10                  15

Gly

<210> SEQ ID NO 703
<211> LENGTH: 16
<212> TYPE: PRT
<213> ORGANISM: Artificial Sequence
<220> FEATURE:
```

<223> OTHER INFORMATION: Synthetic: 35 - VH CDR3

<400> SEQUENCE: 703

Ala Arg Asp Thr Gly Arg Gly Tyr Thr Arg His Phe Trp Phe Asp Pro
1               5                   10                  15

<210> SEQ ID NO 704
<211> LENGTH: 11
<212> TYPE: PRT
<213> ORGANISM: Artificial Sequence
<220> FEATURE:
<223> OTHER INFORMATION: Synthetic: 35 - VL CDR1

<400> SEQUENCE: 704

Arg Ala Ser Gln Ser Ile Ser Ser Tyr Leu Asn
1               5                   10

<210> SEQ ID NO 705
<211> LENGTH: 7
<212> TYPE: PRT
<213> ORGANISM: Artificial Sequence
<220> FEATURE:
<223> OTHER INFORMATION: Synthetic: 35 - VL CDR2

<400> SEQUENCE: 705

Ala Ala Ser Ser Leu Gln Ser
1               5

<210> SEQ ID NO 706
<211> LENGTH: 8
<212> TYPE: PRT
<213> ORGANISM: Artificial Sequence
<220> FEATURE:
<223> OTHER INFORMATION: Synthetic: 35 - VL CDR3

<400> SEQUENCE: 706

Gln Gln Ser Asp Ile Leu Tyr Thr
1               5

<210> SEQ ID NO 707
<211> LENGTH: 26
<212> TYPE: PRT
<213> ORGANISM: Artificial Sequence
<220> FEATURE:
<223> OTHER INFORMATION: Synthetic: 35 - VH FR1

<400> SEQUENCE: 707

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 708
<211> LENGTH: 14
<212> TYPE: PRT
<213> ORGANISM: Artificial Sequence
<220> FEATURE:
<223> OTHER INFORMATION: Synthetic: 35 - VH FR2

<400> SEQUENCE: 708

Trp Val Arg Gln Ala Pro Gly Gln Gly Leu Glu Trp Met Gly
1               5                   10

<210> SEQ ID NO 709
<211> LENGTH: 30
<212> TYPE: PRT

```
<213> ORGANISM: Artificial Sequence
<220> FEATURE:
<223> OTHER INFORMATION: Synthetic: 35 - VH FR3

<400> SEQUENCE: 709

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 710
<211> LENGTH: 11
<212> TYPE: PRT
<213> ORGANISM: Artificial Sequence
<220> FEATURE:
<223> OTHER INFORMATION: Synthetic: 35 - VH FR4

<400> SEQUENCE: 710

Trp Gly Gln Gly Thr Leu Val Thr Val Ser Ser
1               5                   10

<210> SEQ ID NO 711
<211> LENGTH: 369
<212> TYPE: DNA
<213> ORGANISM: Artificial Sequence
<220> FEATURE:
<223> OTHER INFORMATION: Synthetic: 35 - VH DNA

<400> SEQUENCE: 711
caggtgcagc tggtgcagtc tggggctgag gtgaagaagc ctgggtcctc ggtgaaggtc      60
tcctgcaagg cttctggagg caccttcagc tccgccgcta tcagctgggt gcgacaggcc     120
cctggacaag gcttgagtg gatgggaaac atcatccta tcgtaggtat agcaaactac       180
gcacagaagt tccagggcag agtcacgatt accgcggacg aatccacgag cacagcctac     240
atggagctga gcagcctgag atctgaggac acggcggtgt actactgcgc cagagacacg     300
ggacggggat acaccagaca cttctggttt gaccctgggg acagggtac attggtcacc      360 gtctcctca                                                             369

<210> SEQ ID NO 712
<211> LENGTH: 123
<212> TYPE: PRT
<213> ORGANISM: Artificial Sequence
<220> FEATURE:
<223> OTHER INFORMATION: Synthetic: 35 - VH Protein

<400> SEQUENCE: 712

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ala
            20                  25                  30

Ala Ile Ser Trp Val Arg Gln Ala Pro Gly Gln Gly Leu Glu Trp Met
        35                  40                  45

Gly Asn Ile Ile Pro Ile Val Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Arg Gly Tyr Thr Arg His Phe Trp Phe Asp Pro
            100                 105                 110
```

Trp Gly Gln Gly Thr Leu Val Thr Val Ser Ser
        115                 120

<210> SEQ ID NO 713
<211> LENGTH: 23
<212> TYPE: PRT
<213> ORGANISM: Artificial Sequence
<220> FEATURE:
<223> OTHER INFORMATION: Synthetic: 35 - VL FR1

<400> SEQUENCE: 713

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 714
<211> LENGTH: 15
<212> TYPE: PRT
<213> ORGANISM: Artificial Sequence
<220> FEATURE:
<223> OTHER INFORMATION: Synthetic: 35 - VL FR2

<400> SEQUENCE: 714

Trp Tyr Gln Gln Lys Pro Gly Lys Ala Pro Lys Leu Leu Ile Tyr
1               5                   10                  15

<210> SEQ ID NO 715
<211> LENGTH: 32
<212> TYPE: PRT
<213> ORGANISM: Artificial Sequence
<220> FEATURE:
<223> OTHER INFORMATION: Synthetic: 35 - VL FR3

<400> SEQUENCE: 715

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 716
<211> LENGTH: 10
<212> TYPE: PRT
<213> ORGANISM: Artificial Sequence
<220> FEATURE:
<223> OTHER INFORMATION: Synthetic: 35 - VL FR4

<400> SEQUENCE: 716

Phe Gly Gly Gly Thr Lys Val Glu Ile Lys
1               5                   10

<210> SEQ ID NO 717
<211> LENGTH: 318
<212> TYPE: DNA
<213> ORGANISM: Artificial Sequence
<220> FEATURE:
<223> OTHER INFORMATION: Synthetic: 35 - VL DNA

<400> SEQUENCE: 717
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240

```
gaagattttg caacttacta ctgtcagcaa agcgacatcc tctacacttt tggcggaggg    300
accaaggttg agatcaaa                                                   318
```

<210> SEQ ID NO 718
<211> LENGTH: 106
<212> TYPE: PRT
<213> ORGANISM: Artificial Sequence
<220> FEATURE:
<223> OTHER INFORMATION: Synthetic: 35 - VL Protein

<400> SEQUENCE: 718

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Tyr Thr
                85                  90                  95

Phe Gly Gly Gly Thr Lys Val Glu Ile Lys
            100                 105

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

```
<400> SEQUENCE: 736
000

<210> SEQ ID NO 737
<400> SEQUENCE: 737
000

<210> SEQ ID NO 738
<400> SEQUENCE: 738
000

<210> SEQ ID NO 739
<400> SEQUENCE: 739
000

<210> SEQ ID NO 740
<400> SEQUENCE: 740
000

<210> SEQ ID NO 741
<400> SEQUENCE: 741
000

<210> SEQ ID NO 742
<400> SEQUENCE: 742
000

<210> SEQ ID NO 743
<400> SEQUENCE: 743
000

<210> SEQ ID NO 744
<400> SEQUENCE: 744
000

<210> SEQ ID NO 745
<400> SEQUENCE: 745
000

<210> SEQ ID NO 746
<400> SEQUENCE: 746
000

<210> SEQ ID NO 747
<400> SEQUENCE: 747
```

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770

-continued

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801
<211> LENGTH: 9
<212> TYPE: PRT
<213> ORGANISM: Artificial Sequence
<220> FEATURE:
<223> OTHER INFORMATION: Synthetic: 47 - VH CDR1

<400> SEQUENCE: 801

Gly Thr Phe Ser Asn Tyr Ala Ile Ser
1               5

<210> SEQ ID NO 802
<211> LENGTH: 17
<212> TYPE: PRT
<213> ORGANISM: Artificial Sequence
<220> FEATURE:
<223> OTHER INFORMATION: Synthetic: 47 - VH CDR2

-continued

<400> SEQUENCE: 802

Gly Ile Ile Pro Ile Phe Gly Thr Ala Asn Tyr Ala Gln Lys Phe Gln
1               5                   10                  15

Gly

<210> SEQ ID NO 803
<211> LENGTH: 18
<212> TYPE: PRT
<213> ORGANISM: Artificial Sequence
<220> FEATURE:
<223> OTHER INFORMATION: Synthetic: 47 - VH CDR3

<400> SEQUENCE: 803

Ala Arg Gly Arg Gly Ala Leu Ala Leu Val Gly Pro Tyr Tyr Gly Met
1               5                   10                  15

Asp Val

<210> SEQ ID NO 804
<211> LENGTH: 16
<212> TYPE: PRT
<213> ORGANISM: Artificial Sequence
<220> FEATURE:
<223> OTHER INFORMATION: Synthetic: 47 - VL CDR1

<400> SEQUENCE: 804

Arg Ser Ser Gln Ser Leu Leu His Ser Asn Gly Tyr Asn Tyr Leu Asp
1               5                   10                  15

<210> SEQ ID NO 805
<211> LENGTH: 7
<212> TYPE: PRT
<213> ORGANISM: Artificial Sequence
<220> FEATURE:
<223> OTHER INFORMATION: Synthetic: 47 - VL CDR2

<400> SEQUENCE: 805

Leu Gly Ser His Arg Ala Ser
1               5

<210> SEQ ID NO 806
<211> LENGTH: 8
<212> TYPE: PRT
<213> ORGANISM: Artificial Sequence
<220> FEATURE:
<223> OTHER INFORMATION: Synthetic: 47 - VL CDR3

<400> SEQUENCE: 806

Met Gln Ala Leu Arg Ala Pro Thr
1               5

<210> SEQ ID NO 807
<211> LENGTH: 26
<212> TYPE: PRT
<213> ORGANISM: Artificial Sequence
<220> FEATURE:
<223> OTHER INFORMATION: Synthetic: 47 - VH FR1

<400> SEQUENCE: 807

Glu Val Gln Leu Val Gln Ser Gly Ala Glu Val Lys Lys Pro Gly Ser
1               5                   10                  15

Ser Val Lys Val Ser Cys Lys Ala Ser Gly
            20                  25

```
<210> SEQ ID NO 808
<211> LENGTH: 14
<212> TYPE: PRT
<213> ORGANISM: Artificial Sequence
<220> FEATURE:
<223> OTHER INFORMATION: Synthetic: 47 - VH FR2

<400> SEQUENCE: 808

Trp Val Arg Gln Ala Pro Gly Gln Gly Leu Glu Trp Met Gly
1               5                   10

<210> SEQ ID NO 809
<211> LENGTH: 30
<212> TYPE: PRT
<213> ORGANISM: Artificial Sequence
<220> FEATURE:
<223> OTHER INFORMATION: Synthetic: 47 - VH FR3

<400> SEQUENCE: 809

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 810
<211> LENGTH: 11
<212> TYPE: PRT
<213> ORGANISM: Artificial Sequence
<220> FEATURE:
<223> OTHER INFORMATION: Synthetic: 47 - VH FR4

<400> SEQUENCE: 810

Trp Gly Gln Gly Thr Thr Val Thr Val Ser Ser
1               5                   10

<210> SEQ ID NO 811
<211> LENGTH: 375
<212> TYPE: DNA
<213> ORGANISM: Artificial Sequence
<220> FEATURE:
<223> OTHER INFORMATION: Synthetic: 47 - VH DNA

<400> SEQUENCE: 811
gaggtgcagc tggtgcagtc tggggctgag gtgaagaagc ctgggtcctc ggtgaaggtc      60
tcctgcaagg cttctggagg caccttcagc aactatgcta tcagctgggt gcgacaggcc     120
cctggacaag gcttgagtg gatgggaggg atcatccta tctttggtac agcaaactac      180
gcacagaagt tccagggcag agtcacgatt accgcggacg aatccacgag cacagcctac     240
atggagctga gcagcctgag atctgaggac acggcggtgt actactgcgc cagaggcaga     300
ggcgctctgg cactcgtcgg accatactac ggaatggacg tatggggcca gggaacaact     360
gtcaccgtct cctca                                                     375

<210> SEQ ID NO 812
<211> LENGTH: 125
<212> TYPE: PRT
<213> ORGANISM: Artificial Sequence
<220> FEATURE:
<223> OTHER INFORMATION: Synthetic: 47 - VH Protein

<400> SEQUENCE: 812

Glu Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Ala Leu Ala Leu Val Gly Pro Tyr Gly Met
            100                 105                 110

Asp Val Trp Gly Gln Gly Thr Thr Val Thr Val Ser Ser
        115                 120                 125

<210> SEQ ID NO 813
<211> LENGTH: 23
<212> TYPE: PRT
<213> ORGANISM: Artificial Sequence
<220> FEATURE:
<223> OTHER INFORMATION: Synthetic: 47 - VL FR1

<400> SEQUENCE: 813

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 814
<211> LENGTH: 15
<212> TYPE: PRT
<213> ORGANISM: Artificial Sequence
<220> FEATURE:
<223> OTHER INFORMATION: Synthetic: 47 - VL FR2

<400> SEQUENCE: 814

Trp Tyr Leu Gln Lys Pro Gly Gln Ser Pro Gln Leu Leu Ile Tyr
1               5                   10                  15

<210> SEQ ID NO 815
<211> LENGTH: 32
<212> TYPE: PRT
<213> ORGANISM: Artificial Sequence
<220> FEATURE:
<223> OTHER INFORMATION: Synthetic: 47 - VL FR3

<400> SEQUENCE: 815

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 816
<211> LENGTH: 10
<212> TYPE: PRT
<213> ORGANISM: Artificial Sequence
<220> FEATURE:
<223> OTHER INFORMATION: Synthetic: 47 - VL FR4

<400> SEQUENCE: 816

Phe Gly Gly Gly Thr Lys Val Glu Ile Lys
1               5                   10

<210> SEQ ID NO 817
<211> LENGTH: 333
<212> TYPE: DNA
<213> ORGANISM: Artificial Sequence
<220> FEATURE:
<223> OTHER INFORMATION: Synthetic: 47 - VL DNA

<400> SEQUENCE: 817

```
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc tcatcgggcc    180
tccggggtcc ctgacaggtt cagtggcagt ggatcaggca cagattttac actgaaaatc    240
agcagagtgg aggctgagga tgttggggtt tattactgca tgcaggcact ccgagcccct    300
acttttggcg gagggaccaa ggttgagatc aaa                                 333
```

<210> SEQ ID NO 818
<211> LENGTH: 111
<212> TYPE: PRT
<213> ORGANISM: Artificial Sequence
<220> FEATURE:
<223> OTHER INFORMATION: Synthetic: 47 - VL Protein

<400> SEQUENCE: 818

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser His Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Arg Ala Pro Thr Phe Gly Gly Gly Thr Lys Val Glu Ile Lys
            100                 105                 110
```

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823
<400> SEQUENCE: 823
000

<210> SEQ ID NO 824
<400> SEQUENCE: 824
000

<210> SEQ ID NO 825
<400> SEQUENCE: 825
000

<210> SEQ ID NO 826
<400> SEQUENCE: 826
000

<210> SEQ ID NO 827
<400> SEQUENCE: 827
000

<210> SEQ ID NO 828
<400> SEQUENCE: 828
000

<210> SEQ ID NO 829
<400> SEQUENCE: 829
000

<210> SEQ ID NO 830
<400> SEQUENCE: 830
000

<210> SEQ ID NO 831
<400> SEQUENCE: 831
000

<210> SEQ ID NO 832
<400> SEQUENCE: 832
000

<210> SEQ ID NO 833
<400> SEQUENCE: 833
000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

-continued

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868
<400> SEQUENCE: 868
000

<210> SEQ ID NO 869
<400> SEQUENCE: 869
000

<210> SEQ ID NO 870
<400> SEQUENCE: 870
000

<210> SEQ ID NO 871
<400> SEQUENCE: 871
000

<210> SEQ ID NO 872
<400> SEQUENCE: 872
000

<210> SEQ ID NO 873
<400> SEQUENCE: 873
000

<210> SEQ ID NO 874
<400> SEQUENCE: 874
000

<210> SEQ ID NO 875
<400> SEQUENCE: 875
000

<210> SEQ ID NO 876
<400> SEQUENCE: 876
000

<210> SEQ ID NO 877
<400> SEQUENCE: 877
000

<210> SEQ ID NO 878
<400> SEQUENCE: 878
000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

```
<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901
<211> LENGTH: 9
<212> TYPE: PRT
```

<213> ORGANISM: Artificial Sequence
<220> FEATURE:
<223> OTHER INFORMATION: Synthetic: 46 - VH CDR1

<400> SEQUENCE: 901

Phe Thr Phe Gly Asp Tyr Ala Met Ser
1               5

<210> SEQ ID NO 902
<211> LENGTH: 19
<212> TYPE: PRT
<213> ORGANISM: Artificial Sequence
<220> FEATURE:
<223> OTHER INFORMATION: Synthetic: 46 - VH CDR2

<400> SEQUENCE: 902

Phe Ile Gly Ser Lys Ala Tyr Gly Gly Thr Thr Glu Tyr Thr Ala Ser
1               5                   10                  15

Val Lys Gly

<210> SEQ ID NO 903
<211> LENGTH: 13
<212> TYPE: PRT
<213> ORGANISM: Artificial Sequence
<220> FEATURE:
<223> OTHER INFORMATION: Synthetic: 46 - VH CDR3

<400> SEQUENCE: 903

Ala Arg Gly Pro Arg Arg Tyr Thr Tyr Gly Met Asp Val
1               5                   10

<210> SEQ ID NO 904
<211> LENGTH: 11
<212> TYPE: PRT
<213> ORGANISM: Artificial Sequence
<220> FEATURE:
<223> OTHER INFORMATION: Synthetic: 46 - VL CDR1

<400> SEQUENCE: 904

Arg Ala Ser Gln Ser Ile Ser Ser Tyr Leu Asn
1               5                   10

<210> SEQ ID NO 905
<211> LENGTH: 7
<212> TYPE: PRT
<213> ORGANISM: Artificial Sequence
<220> FEATURE:
<223> OTHER INFORMATION: Synthetic: 46 - VL CDR2

<400> SEQUENCE: 905

Ala Ala Ser Ser Leu Gln Ser
1               5

<210> SEQ ID NO 906
<211> LENGTH: 8
<212> TYPE: PRT
<213> ORGANISM: Artificial Sequence
<220> FEATURE:
<223> OTHER INFORMATION: Synthetic: 46 - VL CDR3

<400> SEQUENCE: 906

Gln Gln Ser Ser Thr Pro Leu Thr
1               5

<210> SEQ ID NO 907
<211> LENGTH: 26

```
<212> TYPE: PRT
<213> ORGANISM: Artificial Sequence
<220> FEATURE:
<223> OTHER INFORMATION: Synthetic: 46 - VH FR1

<400> SEQUENCE: 907

Glu Val Gln Leu Val Glu Ser Gly Gly Gly Leu Val Gln Pro Gly Arg
1               5                   10                  15

Ser Leu Arg Leu Ser Cys Thr Ala Ser Gly
            20                  25

<210> SEQ ID NO 908
<211> LENGTH: 14
<212> TYPE: PRT
<213> ORGANISM: Artificial Sequence
<220> FEATURE:
<223> OTHER INFORMATION: Synthetic: 46 - VH FR2

<400> SEQUENCE: 908

Trp Phe Arg Gln Ala Pro Gly Lys Gly Leu Glu Trp Val Gly
1               5                   10

<210> SEQ ID NO 909
<211> LENGTH: 30
<212> TYPE: PRT
<213> ORGANISM: Artificial Sequence
<220> FEATURE:
<223> OTHER INFORMATION: Synthetic: 46 - VH FR3

<400> SEQUENCE: 909

Arg Phe Thr Ile Ser Arg Asp Gly Ser Lys Ser Ile Ala Tyr Leu Gln
1               5                   10                  15

Met Asn Ser Leu Lys Thr Glu Asp Thr Ala Val Tyr Tyr Cys
            20                  25                  30

<210> SEQ ID NO 910
<211> LENGTH: 11
<212> TYPE: PRT
<213> ORGANISM: Artificial Sequence
<220> FEATURE:
<223> OTHER INFORMATION: Synthetic: 46 - VH FR4

<400> SEQUENCE: 910

Trp Gly Gln Gly Thr Thr Val Thr Val Ser Ser
1               5                   10

<210> SEQ ID NO 911
<211> LENGTH: 366
<212> TYPE: DNA
<213> ORGANISM: Artificial Sequence
<220> FEATURE:
<223> OTHER INFORMATION: Synthetic: 46 - VH DNA

<400> SEQUENCE: 911
gaggtgcagc tggtggagtc tgggggaggc ttggtacagc cagggcggtc cctgagactc      60
tcctgtacag cttctggatt cacctttggt gattatgcta tgagctggtt ccgccaggct     120
ccagggaagg ggctggagtg ggtaggtttc attggaagca aagcttatgg tgggacaaca     180
gaatacaccg cgtctgtgaa aggcagattc accatctcaa gagatggttc caaaagcatc     240
gcctatctgc aaatgaacag cctgaaaacc gaggacacgg cggtgtacta ctgcgccaga     300
ggaccaagac gctacacata cggaatggac gtatggggcc agggaacaac tgtcaccgtc     360
tcctca                                                                366
```

<210> SEQ ID NO 912
<211> LENGTH: 122
<212> TYPE: PRT
<213> ORGANISM: Artificial Sequence
<220> FEATURE:
<223> OTHER INFORMATION: Synthetic: 46 - VH Protein

<400> SEQUENCE: 912

Glu Val Gln Leu Val Glu Ser Gly Gly Leu Val Gln Pro Gly Arg
1               5                   10                  15

Ser Leu Arg Leu Ser Cys Thr Ala Ser Gly Phe Thr Phe Gly Asp Tyr
                20                  25                  30

Ala Met Ser Trp Phe Arg Gln Ala Pro Gly Lys Gly Leu Glu Trp Val
            35                  40                  45

Gly Phe Ile Gly Ser Lys Ala Tyr Gly Gly Thr Thr Glu Tyr Thr Ala
        50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Gly Pro Arg Arg Tyr Thr Tyr Gly Met Asp Val Trp
            100                 105                 110

Gly Gln Gly Thr Thr Val Thr Val Ser Ser
        115                 120

<210> SEQ ID NO 913
<211> LENGTH: 23
<212> TYPE: PRT
<213> ORGANISM: Artificial Sequence
<220> FEATURE:
<223> OTHER INFORMATION: Synthetic: 46 - VL FR1

<400> SEQUENCE: 913

Asp Ile Gln Met Thr Gln Ser Pro Ser Ser Leu Ser Ala Ser Val Gly
1               5                   10                  15

Asp Arg Val Thr Ile Thr Cys
                20

<210> SEQ ID NO 914
<211> LENGTH: 15
<212> TYPE: PRT
<213> ORGANISM: Artificial Sequence
<220> FEATURE:
<223> OTHER INFORMATION: Synthetic: 46 - VL FR2

<400> SEQUENCE: 914

Trp Tyr Gln Gln Lys Pro Gly Lys Ala Pro Lys Leu Leu Ile Tyr
1               5                   10                  15

<210> SEQ ID NO 915
<211> LENGTH: 32
<212> TYPE: PRT
<213> ORGANISM: Artificial Sequence
<220> FEATURE:
<223> OTHER INFORMATION: Synthetic: 46 - VL FR3

<400> SEQUENCE: 915

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 916
<211> LENGTH: 10
<212> TYPE: PRT
<213> ORGANISM: Artificial Sequence
<220> FEATURE:
<223> OTHER INFORMATION: Synthetic: 46 - VL FR4

<400> SEQUENCE: 916

Phe Gly Gly Gly Thr Lys Val Glu Ile Lys
1               5                   10

<210> SEQ ID NO 917
<211> LENGTH: 318
<212> TYPE: DNA
<213> ORGANISM: Artificial Sequence
<220> FEATURE:
<223> OTHER INFORMATION: Synthetic: 46 - VL DNA

<400> SEQUENCE: 917
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agctccaccc ccctcacttt tggcggaggg     300
accaaggttg agatcaaa                                                   318

<210> SEQ ID NO 918
<211> LENGTH: 106
<212> TYPE: PRT
<213> ORGANISM: Artificial Sequence
<220> FEATURE:
<223> OTHER INFORMATION: Synthetic: 46 - VL Protein

<400> SEQUENCE: 918

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Pro Leu Thr
                85                  90                  95

Phe Gly Gly Gly Thr Lys Val Glu Ile Lys
            100                 105

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

-continued

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

-continued

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001
<211> LENGTH: 9
<212> TYPE: PRT
<213> ORGANISM: Artificial Sequence
<220> FEATURE:
<223> OTHER INFORMATION: Synthetic: 32 - VH CDR1

<400> SEQUENCE: 1001

Gly Thr Phe Ser Ser Tyr Ala Ile Ser
1               5

<210> SEQ ID NO 1002
<211> LENGTH: 17
<212> TYPE: PRT
<213> ORGANISM: Artificial Sequence
<220> FEATURE:
<223> OTHER INFORMATION: Synthetic: 32 - VH CDR2

<400> SEQUENCE: 1002

Gly Ile Ile Pro Ile Ser Gly Thr Ala Asn Tyr Ala Gln Lys Phe Gln
1               5                   10                  15

Gly

<210> SEQ ID NO 1003
<211> LENGTH: 16
<212> TYPE: PRT
<213> ORGANISM: Artificial Sequence
<220> FEATURE:
<223> OTHER INFORMATION: Synthetic: 32 - VH CDR3

<400> SEQUENCE: 1003

Ala Arg Asp Thr Gly Arg Gly Tyr Thr Arg His Phe Trp Phe Asp Pro
1               5                   10                  15

<210> SEQ ID NO 1004
<211> LENGTH: 11
<212> TYPE: PRT
<213> ORGANISM: Artificial Sequence
<220> FEATURE:
<223> OTHER INFORMATION: Synthetic: 32 - VL CDR1

<400> SEQUENCE: 1004

Arg Ala Ser Gln Ser Ile Ser Ser Tyr Leu Asn
1               5                   10

<210> SEQ ID NO 1005
<211> LENGTH: 7
<212> TYPE: PRT
<213> ORGANISM: Artificial Sequence
<220> FEATURE:
<223> OTHER INFORMATION: Synthetic: 32 - VL CDR2

<400> SEQUENCE: 1005

Ala Ala Ser Ser Leu Gln Ser
1               5

<210> SEQ ID NO 1006
<211> LENGTH: 8
<212> TYPE: PRT

```
<213> ORGANISM: Artificial Sequence
<220> FEATURE:
<223> OTHER INFORMATION: Synthetic: 32 - VL CDR3

<400> SEQUENCE: 1006

Gln Gln Ser Asp Ile Leu Tyr Thr
1               5

<210> SEQ ID NO 1007
<211> LENGTH: 26
<212> TYPE: PRT
<213> ORGANISM: Artificial Sequence
<220> FEATURE:
<223> OTHER INFORMATION: Synthetic: 32 - VH FR1

<400> SEQUENCE: 1007

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 1008
<211> LENGTH: 14
<212> TYPE: PRT
<213> ORGANISM: Artificial Sequence
<220> FEATURE:
<223> OTHER INFORMATION: Synthetic: 32 - VH FR2

<400> SEQUENCE: 1008

Trp Val Arg Gln Ala Pro Gly Gln Gly Leu Glu Trp Met Gly
1               5                   10

<210> SEQ ID NO 1009
<211> LENGTH: 30
<212> TYPE: PRT
<213> ORGANISM: Artificial Sequence
<220> FEATURE:
<223> OTHER INFORMATION: Synthetic: 32 - VH FR3

<400> SEQUENCE: 1009

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 1010
<211> LENGTH: 11
<212> TYPE: PRT
<213> ORGANISM: Artificial Sequence
<220> FEATURE:
<223> OTHER INFORMATION: Synthetic: 32 - VH FR4

<400> SEQUENCE: 1010

Trp Gly Gln Gly Thr Leu Val Thr Val Ser Ser
1               5                   10

<210> SEQ ID NO 1011
<211> LENGTH: 369
<212> TYPE: DNA
<213> ORGANISM: Artificial Sequence
<220> FEATURE:
<223> OTHER INFORMATION: Synthetic: 32 - VH DNA
```

<400> SEQUENCE: 1011

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctctggtac agcaaactac     180
gcacagaagt tccagggcag agtcacgatt accgcggacg aatccacgag cacagcctac     240
atggagctga gcagcctgag atctgaggac acggcggtgt actactgcgc cagagacacg     300
ggacggggat acaccagaca cttctggttt gacccctggg gacagggtac attggtcacc     360
gtctcctca                                                             369
```

<210> SEQ ID NO 1012
<211> LENGTH: 123
<212> TYPE: PRT
<213> ORGANISM: Artificial Sequence
<220> FEATURE:
<223> OTHER INFORMATION: Synthetic: 32 - VH Protein

<400> SEQUENCE: 1012

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Ser Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Arg Gly Tyr Thr Arg His Phe Trp Phe Asp Pro
            100                 105                 110

Trp Gly Gln Gly Thr Leu Val Thr Val Ser Ser
        115                 120
```

<210> SEQ ID NO 1013
<211> LENGTH: 23
<212> TYPE: PRT
<213> ORGANISM: Artificial Sequence
<220> FEATURE:
<223> OTHER INFORMATION: Synthetic: 32 - VL FR1

<400> SEQUENCE: 1013

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 1014
<211> LENGTH: 15
<212> TYPE: PRT
<213> ORGANISM: Artificial Sequence
<220> FEATURE:
<223> OTHER INFORMATION: Synthetic: 32 - VL FR2

<400> SEQUENCE: 1014

```
Trp Tyr Gln Gln Lys Pro Gly Lys Ala Pro Lys Leu Leu Ile Tyr
1               5                   10                  15
```

<210> SEQ ID NO 1015
<211> LENGTH: 32
<212> TYPE: PRT
<213> ORGANISM: Artificial Sequence
<220> FEATURE:
<223> OTHER INFORMATION: Synthetic: 32 - VL FR3

<400> SEQUENCE: 1015

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 1016
<211> LENGTH: 10
<212> TYPE: PRT
<213> ORGANISM: Artificial Sequence
<220> FEATURE:
<223> OTHER INFORMATION: Synthetic: 32 - VL FR4

<400> SEQUENCE: 1016

Phe Gly Gly Gly Thr Lys Val Glu Ile Lys
1               5                   10

<210> SEQ ID NO 1017
<211> LENGTH: 318
<212> TYPE: DNA
<213> ORGANISM: Artificial Sequence
<220> FEATURE:
<223> OTHER INFORMATION: Synthetic: 32 - VL DNA

<400> SEQUENCE: 1017
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agcgacatcc tctacacttt tggcggaggg     300
accaaggttg agatcaaa                                                    318

<210> SEQ ID NO 1018
<211> LENGTH: 106
<212> TYPE: PRT
<213> ORGANISM: Artificial Sequence
<220> FEATURE:
<223> OTHER INFORMATION: Synthetic: 32 - VL Protein

<400> SEQUENCE: 1018

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Tyr Thr
                85                  90                  95

```
Phe Gly Gly Gly Thr Lys Val Glu Ile Lys
         100                 105
```

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

```
<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063
```

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

```
<210> SEQ ID NO 1086
<400> SEQUENCE: 1086
000

<210> SEQ ID NO 1087
<400> SEQUENCE: 1087
000

<210> SEQ ID NO 1088
<400> SEQUENCE: 1088
000

<210> SEQ ID NO 1089
<400> SEQUENCE: 1089
000

<210> SEQ ID NO 1090
<400> SEQUENCE: 1090
000

<210> SEQ ID NO 1091
<400> SEQUENCE: 1091
000

<210> SEQ ID NO 1092
<400> SEQUENCE: 1092
000

<210> SEQ ID NO 1093
<400> SEQUENCE: 1093
000

<210> SEQ ID NO 1094
<400> SEQUENCE: 1094
000

<210> SEQ ID NO 1095
<400> SEQUENCE: 1095
000

<210> SEQ ID NO 1096
<400> SEQUENCE: 1096
000

<210> SEQ ID NO 1097
```

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109
<400> SEQUENCE: 1109
000

<210> SEQ ID NO 1110
<400> SEQUENCE: 1110
000

<210> SEQ ID NO 1111
<400> SEQUENCE: 1111
000

<210> SEQ ID NO 1112
<400> SEQUENCE: 1112
000

<210> SEQ ID NO 1113
<400> SEQUENCE: 1113
000

<210> SEQ ID NO 1114
<400> SEQUENCE: 1114
000

<210> SEQ ID NO 1115
<400> SEQUENCE: 1115
000

<210> SEQ ID NO 1116
<400> SEQUENCE: 1116
000

<210> SEQ ID NO 1117
<400> SEQUENCE: 1117
000

<210> SEQ ID NO 1118
<400> SEQUENCE: 1118
000

<210> SEQ ID NO 1119
<400> SEQUENCE: 1119
000

```
<210> SEQ ID NO 1120
<400> SEQUENCE: 1120
000

<210> SEQ ID NO 1121
<400> SEQUENCE: 1121
000

<210> SEQ ID NO 1122
<400> SEQUENCE: 1122
000

<210> SEQ ID NO 1123
<400> SEQUENCE: 1123
000

<210> SEQ ID NO 1124
<400> SEQUENCE: 1124
000

<210> SEQ ID NO 1125
<400> SEQUENCE: 1125
000

<210> SEQ ID NO 1126
<400> SEQUENCE: 1126
000

<210> SEQ ID NO 1127
<400> SEQUENCE: 1127
000

<210> SEQ ID NO 1128
<400> SEQUENCE: 1128
000

<210> SEQ ID NO 1129
<400> SEQUENCE: 1129
000

<210> SEQ ID NO 1130
<400> SEQUENCE: 1130
000

<210> SEQ ID NO 1131
```

<210> SEQ ID NO 1131

<400> SEQUENCE: 1131

000

<210> SEQ ID NO 1132

<400> SEQUENCE: 1132

000

<210> SEQ ID NO 1133

<400> SEQUENCE: 1133

000

<210> SEQ ID NO 1134

<400> SEQUENCE: 1134

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

<210> SEQ ID NO 1140

<400> SEQUENCE: 1140

000

<210> SEQ ID NO 1141

<400> SEQUENCE: 1141

000

<210> SEQ ID NO 1142

<400> SEQUENCE: 1142

000

<210> SEQ ID NO 1143

<400> SEQUENCE: 1143

000

<210> SEQ ID NO 1144

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153

<400> SEQUENCE: 1153

000

-continued

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199
<400> SEQUENCE: 1199
000

<210> SEQ ID NO 1200
<400> SEQUENCE: 1200
000

<210> SEQ ID NO 1201
<400> SEQUENCE: 1201
000

<210> SEQ ID NO 1202
<400> SEQUENCE: 1202
000

<210> SEQ ID NO 1203
<400> SEQUENCE: 1203
000

<210> SEQ ID NO 1204
<400> SEQUENCE: 1204
000

<210> SEQ ID NO 1205
<400> SEQUENCE: 1205
000

<210> SEQ ID NO 1206
<400> SEQUENCE: 1206
000

<210> SEQ ID NO 1207
<400> SEQUENCE: 1207
000

<210> SEQ ID NO 1208
<400> SEQUENCE: 1208
000

<210> SEQ ID NO 1209
<400> SEQUENCE: 1209
000

<210> SEQ ID NO 1210

```
<400> SEQUENCE: 1210
000

<210> SEQ ID NO 1211
<400> SEQUENCE: 1211
000

<210> SEQ ID NO 1212
<400> SEQUENCE: 1212
000

<210> SEQ ID NO 1213
<400> SEQUENCE: 1213
000

<210> SEQ ID NO 1214
<400> SEQUENCE: 1214
000

<210> SEQ ID NO 1215
<400> SEQUENCE: 1215
000

<210> SEQ ID NO 1216
<400> SEQUENCE: 1216
000

<210> SEQ ID NO 1217
<400> SEQUENCE: 1217
000

<210> SEQ ID NO 1218
<400> SEQUENCE: 1218
000

<210> SEQ ID NO 1219
<400> SEQUENCE: 1219
000

<210> SEQ ID NO 1220
<400> SEQUENCE: 1220
000

<210> SEQ ID NO 1221
<400> SEQUENCE: 1221
```

000

<210> SEQ ID NO 1222

<400> SEQUENCE: 1222

000

<210> SEQ ID NO 1223

<400> SEQUENCE: 1223

000

<210> SEQ ID NO 1224

<400> SEQUENCE: 1224

000

<210> SEQ ID NO 1225

<400> SEQUENCE: 1225

000

<210> SEQ ID NO 1226

<400> SEQUENCE: 1226

000

<210> SEQ ID NO 1227

<400> SEQUENCE: 1227

000

<210> SEQ ID NO 1228

<400> SEQUENCE: 1228

000

<210> SEQ ID NO 1229

<400> SEQUENCE: 1229

000

<210> SEQ ID NO 1230

<400> SEQUENCE: 1230

000

<210> SEQ ID NO 1231

<400> SEQUENCE: 1231

000

<210> SEQ ID NO 1232

<400> SEQUENCE: 1232

000

```
<210> SEQ ID NO 1233
<400> SEQUENCE: 1233
000

<210> SEQ ID NO 1234
<400> SEQUENCE: 1234
000

<210> SEQ ID NO 1235
<400> SEQUENCE: 1235
000

<210> SEQ ID NO 1236
<400> SEQUENCE: 1236
000

<210> SEQ ID NO 1237
<400> SEQUENCE: 1237
000

<210> SEQ ID NO 1238
<400> SEQUENCE: 1238
000

<210> SEQ ID NO 1239
<400> SEQUENCE: 1239
000

<210> SEQ ID NO 1240
<400> SEQUENCE: 1240
000

<210> SEQ ID NO 1241
<400> SEQUENCE: 1241
000

<210> SEQ ID NO 1242
<400> SEQUENCE: 1242
000

<210> SEQ ID NO 1243
<400> SEQUENCE: 1243
000
```

-continued

```
<210> SEQ ID NO 1244
<400> SEQUENCE: 1244
000

<210> SEQ ID NO 1245
<400> SEQUENCE: 1245
000

<210> SEQ ID NO 1246
<400> SEQUENCE: 1246
000

<210> SEQ ID NO 1247
<400> SEQUENCE: 1247
000

<210> SEQ ID NO 1248
<400> SEQUENCE: 1248
000

<210> SEQ ID NO 1249
<400> SEQUENCE: 1249
000

<210> SEQ ID NO 1250
<400> SEQUENCE: 1250
000

<210> SEQ ID NO 1251
<400> SEQUENCE: 1251
000

<210> SEQ ID NO 1252
<400> SEQUENCE: 1252
000

<210> SEQ ID NO 1253
<400> SEQUENCE: 1253
000

<210> SEQ ID NO 1254
<400> SEQUENCE: 1254
000

<210> SEQ ID NO 1255
```

<400> SEQUENCE: 1255

000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264

<400> SEQUENCE: 1264

000

<210> SEQ ID NO 1265

<400> SEQUENCE: 1265

000

<210> SEQ ID NO 1266

<400> SEQUENCE: 1266

000

<210> SEQ ID NO 1267
<400> SEQUENCE: 1267
000

<210> SEQ ID NO 1268
<400> SEQUENCE: 1268
000

<210> SEQ ID NO 1269
<400> SEQUENCE: 1269
000

<210> SEQ ID NO 1270
<400> SEQUENCE: 1270
000

<210> SEQ ID NO 1271
<400> SEQUENCE: 1271
000

<210> SEQ ID NO 1272
<400> SEQUENCE: 1272
000

<210> SEQ ID NO 1273
<400> SEQUENCE: 1273
000

<210> SEQ ID NO 1274
<400> SEQUENCE: 1274
000

<210> SEQ ID NO 1275
<400> SEQUENCE: 1275
000

<210> SEQ ID NO 1276
<400> SEQUENCE: 1276
000

<210> SEQ ID NO 1277
<400> SEQUENCE: 1277
000

<210> SEQ ID NO 1278
<400> SEQUENCE: 1278
000

<210> SEQ ID NO 1279
<400> SEQUENCE: 1279
000

<210> SEQ ID NO 1280
<400> SEQUENCE: 1280
000

<210> SEQ ID NO 1281
<400> SEQUENCE: 1281
000

<210> SEQ ID NO 1282
<400> SEQUENCE: 1282
000

<210> SEQ ID NO 1283
<400> SEQUENCE: 1283
000

<210> SEQ ID NO 1284
<400> SEQUENCE: 1284
000

<210> SEQ ID NO 1285
<400> SEQUENCE: 1285
000

<210> SEQ ID NO 1286
<400> SEQUENCE: 1286
000

<210> SEQ ID NO 1287
<400> SEQUENCE: 1287
000

<210> SEQ ID NO 1288
<400> SEQUENCE: 1288
000

<210> SEQ ID NO 1289

```
<400> SEQUENCE: 1289
000

<210> SEQ ID NO 1290
<400> SEQUENCE: 1290
000

<210> SEQ ID NO 1291
<400> SEQUENCE: 1291
000

<210> SEQ ID NO 1292
<400> SEQUENCE: 1292
000

<210> SEQ ID NO 1293
<400> SEQUENCE: 1293
000

<210> SEQ ID NO 1294
<400> SEQUENCE: 1294
000

<210> SEQ ID NO 1295
<400> SEQUENCE: 1295
000

<210> SEQ ID NO 1296
<400> SEQUENCE: 1296
000

<210> SEQ ID NO 1297
<400> SEQUENCE: 1297
000

<210> SEQ ID NO 1298
<400> SEQUENCE: 1298
000

<210> SEQ ID NO 1299
<400> SEQUENCE: 1299
000

<210> SEQ ID NO 1300
<400> SEQUENCE: 1300
```

000

<210> SEQ ID NO 1301

<400> SEQUENCE: 1301

000

<210> SEQ ID NO 1302

<400> SEQUENCE: 1302

000

<210> SEQ ID NO 1303

<400> SEQUENCE: 1303

000

<210> SEQ ID NO 1304

<400> SEQUENCE: 1304

000

<210> SEQ ID NO 1305

<400> SEQUENCE: 1305

000

<210> SEQ ID NO 1306

<400> SEQUENCE: 1306

000

<210> SEQ ID NO 1307

<400> SEQUENCE: 1307

000

<210> SEQ ID NO 1308

<400> SEQUENCE: 1308

000

<210> SEQ ID NO 1309

<400> SEQUENCE: 1309

000

<210> SEQ ID NO 1310

<400> SEQUENCE: 1310

000

<210> SEQ ID NO 1311

<400> SEQUENCE: 1311

000

<210> SEQ ID NO 1312

<400> SEQUENCE: 1312

000

<210> SEQ ID NO 1313

<400> SEQUENCE: 1313

000

<210> SEQ ID NO 1314

<400> SEQUENCE: 1314

000

<210> SEQ ID NO 1315

<400> SEQUENCE: 1315

000

<210> SEQ ID NO 1316

<400> SEQUENCE: 1316

000

<210> SEQ ID NO 1317

<400> SEQUENCE: 1317

000

<210> SEQ ID NO 1318

<400> SEQUENCE: 1318

000

<210> SEQ ID NO 1319

<400> SEQUENCE: 1319

000

<210> SEQ ID NO 1320

<400> SEQUENCE: 1320

000

<210> SEQ ID NO 1321

<400> SEQUENCE: 1321

000

<210> SEQ ID NO 1322

<400> SEQUENCE: 1322

000

<210> SEQ ID NO 1323

<400> SEQUENCE: 1323

000

<210> SEQ ID NO 1324

<400> SEQUENCE: 1324

000

<210> SEQ ID NO 1325

<400> SEQUENCE: 1325

000

<210> SEQ ID NO 1326

<400> SEQUENCE: 1326

000

<210> SEQ ID NO 1327

<400> SEQUENCE: 1327

000

<210> SEQ ID NO 1328

<400> SEQUENCE: 1328

000

<210> SEQ ID NO 1329

<400> SEQUENCE: 1329

000

<210> SEQ ID NO 1330

<400> SEQUENCE: 1330

000

<210> SEQ ID NO 1331

<400> SEQUENCE: 1331

000

<210> SEQ ID NO 1332

<400> SEQUENCE: 1332

000

<210> SEQ ID NO 1333

<400> SEQUENCE: 1333

000

<210> SEQ ID NO 1334

<400> SEQUENCE: 1334

000

<210> SEQ ID NO 1335

<400> SEQUENCE: 1335

000

<210> SEQ ID NO 1336

<400> SEQUENCE: 1336

000

<210> SEQ ID NO 1337

<400> SEQUENCE: 1337

000

<210> SEQ ID NO 1338

<400> SEQUENCE: 1338

000

<210> SEQ ID NO 1339

<400> SEQUENCE: 1339

000

<210> SEQ ID NO 1340

<400> SEQUENCE: 1340

000

<210> SEQ ID NO 1341

<400> SEQUENCE: 1341

000

<210> SEQ ID NO 1342

<400> SEQUENCE: 1342

000

<210> SEQ ID NO 1343

<400> SEQUENCE: 1343

000

<210> SEQ ID NO 1344

<400> SEQUENCE: 1344

000

<210> SEQ ID NO 1345

<400> SEQUENCE: 1345

000

<210> SEQ ID NO 1346

<400> SEQUENCE: 1346

000

<210> SEQ ID NO 1347

<400> SEQUENCE: 1347

000

<210> SEQ ID NO 1348

<400> SEQUENCE: 1348

000

<210> SEQ ID NO 1349

<400> SEQUENCE: 1349

000

<210> SEQ ID NO 1350

<400> SEQUENCE: 1350

000

<210> SEQ ID NO 1351

<400> SEQUENCE: 1351

000

<210> SEQ ID NO 1352

<400> SEQUENCE: 1352

000

<210> SEQ ID NO 1353

<400> SEQUENCE: 1353

000

<210> SEQ ID NO 1354

<400> SEQUENCE: 1354

000

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

<210> SEQ ID NO 1359

<400> SEQUENCE: 1359

000

<210> SEQ ID NO 1360

<400> SEQUENCE: 1360

000

<210> SEQ ID NO 1361

<400> SEQUENCE: 1361

000

<210> SEQ ID NO 1362

<400> SEQUENCE: 1362

000

<210> SEQ ID NO 1363

<400> SEQUENCE: 1363

000

<210> SEQ ID NO 1364

<400> SEQUENCE: 1364

000

<210> SEQ ID NO 1365

<400> SEQUENCE: 1365

000

<210> SEQ ID NO 1366

<400> SEQUENCE: 1366

000

<210> SEQ ID NO 1367

<400> SEQUENCE: 1367

000

<210> SEQ ID NO 1368

```
<400> SEQUENCE: 1368

000

<210> SEQ ID NO 1369

<400> SEQUENCE: 1369

000

<210> SEQ ID NO 1370

<400> SEQUENCE: 1370

000

<210> SEQ ID NO 1371

<400> SEQUENCE: 1371

000

<210> SEQ ID NO 1372

<400> SEQUENCE: 1372

000

<210> SEQ ID NO 1373

<400> SEQUENCE: 1373

000

<210> SEQ ID NO 1374

<400> SEQUENCE: 1374

000

<210> SEQ ID NO 1375

<400> SEQUENCE: 1375

000

<210> SEQ ID NO 1376

<400> SEQUENCE: 1376

000

<210> SEQ ID NO 1377

<400> SEQUENCE: 1377

000

<210> SEQ ID NO 1378

<400> SEQUENCE: 1378

000

<210> SEQ ID NO 1379

<400> SEQUENCE: 1379
```

000

<210> SEQ ID NO 1380

<400> SEQUENCE: 1380

000

<210> SEQ ID NO 1381

<400> SEQUENCE: 1381

000

<210> SEQ ID NO 1382

<400> SEQUENCE: 1382

000

<210> SEQ ID NO 1383

<400> SEQUENCE: 1383

000

<210> SEQ ID NO 1384

<400> SEQUENCE: 1384

000

<210> SEQ ID NO 1385

<400> SEQUENCE: 1385

000

<210> SEQ ID NO 1386

<400> SEQUENCE: 1386

000

<210> SEQ ID NO 1387

<400> SEQUENCE: 1387

000

<210> SEQ ID NO 1388

<400> SEQUENCE: 1388

000

<210> SEQ ID NO 1389

<400> SEQUENCE: 1389

000

<210> SEQ ID NO 1390

<400> SEQUENCE: 1390

000

<210> SEQ ID NO 1391

<400> SEQUENCE: 1391

000

<210> SEQ ID NO 1392

<400> SEQUENCE: 1392

000

<210> SEQ ID NO 1393

<400> SEQUENCE: 1393

000

<210> SEQ ID NO 1394

<400> SEQUENCE: 1394

000

<210> SEQ ID NO 1395

<400> SEQUENCE: 1395

000

<210> SEQ ID NO 1396

<400> SEQUENCE: 1396

000

<210> SEQ ID NO 1397

<400> SEQUENCE: 1397

000

<210> SEQ ID NO 1398

<400> SEQUENCE: 1398

000

<210> SEQ ID NO 1399

<400> SEQUENCE: 1399

000

<210> SEQ ID NO 1400

<400> SEQUENCE: 1400

000

<210> SEQ ID NO 1401

<400> SEQUENCE: 1401

000

```
<210> SEQ ID NO 1402
<400> SEQUENCE: 1402
000

<210> SEQ ID NO 1403
<400> SEQUENCE: 1403
000

<210> SEQ ID NO 1404
<400> SEQUENCE: 1404
000

<210> SEQ ID NO 1405
<400> SEQUENCE: 1405
000

<210> SEQ ID NO 1406
<400> SEQUENCE: 1406
000

<210> SEQ ID NO 1407
<400> SEQUENCE: 1407
000

<210> SEQ ID NO 1408
<400> SEQUENCE: 1408
000

<210> SEQ ID NO 1409
<400> SEQUENCE: 1409
000

<210> SEQ ID NO 1410
<400> SEQUENCE: 1410
000

<210> SEQ ID NO 1411
<400> SEQUENCE: 1411
000

<210> SEQ ID NO 1412
<400> SEQUENCE: 1412
000

<210> SEQ ID NO 1413
```

-continued

```
<400> SEQUENCE: 1413
000

<210> SEQ ID NO 1414
<400> SEQUENCE: 1414
000

<210> SEQ ID NO 1415
<400> SEQUENCE: 1415
000

<210> SEQ ID NO 1416
<400> SEQUENCE: 1416
000

<210> SEQ ID NO 1417
<400> SEQUENCE: 1417
000

<210> SEQ ID NO 1418
<400> SEQUENCE: 1418
000

<210> SEQ ID NO 1419
<400> SEQUENCE: 1419
000

<210> SEQ ID NO 1420
<400> SEQUENCE: 1420
000

<210> SEQ ID NO 1421
<400> SEQUENCE: 1421
000

<210> SEQ ID NO 1422
<400> SEQUENCE: 1422
000

<210> SEQ ID NO 1423
<400> SEQUENCE: 1423
000

<210> SEQ ID NO 1424
<400> SEQUENCE: 1424
```

000

<210> SEQ ID NO 1425

<400> SEQUENCE: 1425

000

<210> SEQ ID NO 1426

<400> SEQUENCE: 1426

000

<210> SEQ ID NO 1427

<400> SEQUENCE: 1427

000

<210> SEQ ID NO 1428

<400> SEQUENCE: 1428

000

<210> SEQ ID NO 1429

<400> SEQUENCE: 1429

000

<210> SEQ ID NO 1430

<400> SEQUENCE: 1430

000

<210> SEQ ID NO 1431

<400> SEQUENCE: 1431

000

<210> SEQ ID NO 1432

<400> SEQUENCE: 1432

000

<210> SEQ ID NO 1433

<400> SEQUENCE: 1433

000

<210> SEQ ID NO 1434

<400> SEQUENCE: 1434

000

<210> SEQ ID NO 1435

<400> SEQUENCE: 1435

000

<210> SEQ ID NO 1436

<400> SEQUENCE: 1436

000

<210> SEQ ID NO 1437

<400> SEQUENCE: 1437

000

<210> SEQ ID NO 1438

<400> SEQUENCE: 1438

000

<210> SEQ ID NO 1439

<400> SEQUENCE: 1439

000

<210> SEQ ID NO 1440

<400> SEQUENCE: 1440

000

<210> SEQ ID NO 1441

<400> SEQUENCE: 1441

000

<210> SEQ ID NO 1442

<400> SEQUENCE: 1442

000

<210> SEQ ID NO 1443

<400> SEQUENCE: 1443

000

<210> SEQ ID NO 1444

<400> SEQUENCE: 1444

000

<210> SEQ ID NO 1445

<400> SEQUENCE: 1445

000

<210> SEQ ID NO 1446

<400> SEQUENCE: 1446

000

<210> SEQ ID NO 1447

<400> SEQUENCE: 1447

000

<210> SEQ ID NO 1448

<400> SEQUENCE: 1448

000

<210> SEQ ID NO 1449

<400> SEQUENCE: 1449

000

<210> SEQ ID NO 1450

<400> SEQUENCE: 1450

000

<210> SEQ ID NO 1451

<400> SEQUENCE: 1451

000

<210> SEQ ID NO 1452

<400> SEQUENCE: 1452

000

<210> SEQ ID NO 1453

<400> SEQUENCE: 1453

000

<210> SEQ ID NO 1454

<400> SEQUENCE: 1454

000

<210> SEQ ID NO 1455

<400> SEQUENCE: 1455

000

<210> SEQ ID NO 1456

<400> SEQUENCE: 1456

000

<210> SEQ ID NO 1457

<400> SEQUENCE: 1457

000

<210> SEQ ID NO 1458

<400> SEQUENCE: 1458

000

<210> SEQ ID NO 1459
<400> SEQUENCE: 1459
000

<210> SEQ ID NO 1460
<400> SEQUENCE: 1460
000

<210> SEQ ID NO 1461
<400> SEQUENCE: 1461
000

<210> SEQ ID NO 1462
<400> SEQUENCE: 1462
000

<210> SEQ ID NO 1463
<400> SEQUENCE: 1463
000

<210> SEQ ID NO 1464
<400> SEQUENCE: 1464
000

<210> SEQ ID NO 1465
<400> SEQUENCE: 1465
000

<210> SEQ ID NO 1466
<400> SEQUENCE: 1466
000

<210> SEQ ID NO 1467
<400> SEQUENCE: 1467
000

<210> SEQ ID NO 1468
<400> SEQUENCE: 1468
000

<210> SEQ ID NO 1469
<400> SEQUENCE: 1469
000

<210> SEQ ID NO 1470

<400> SEQUENCE: 1470

000

<210> SEQ ID NO 1471

<400> SEQUENCE: 1471

000

<210> SEQ ID NO 1472

<400> SEQUENCE: 1472

000

<210> SEQ ID NO 1473

<400> SEQUENCE: 1473

000

<210> SEQ ID NO 1474

<400> SEQUENCE: 1474

000

<210> SEQ ID NO 1475

<400> SEQUENCE: 1475

000

<210> SEQ ID NO 1476

<400> SEQUENCE: 1476

000

<210> SEQ ID NO 1477

<400> SEQUENCE: 1477

000

<210> SEQ ID NO 1478

<400> SEQUENCE: 1478

000

<210> SEQ ID NO 1479

<400> SEQUENCE: 1479

000

<210> SEQ ID NO 1480

<400> SEQUENCE: 1480

000

<210> SEQ ID NO 1481

<400> SEQUENCE: 1481

000

<210> SEQ ID NO 1482

<400> SEQUENCE: 1482

000

<210> SEQ ID NO 1483

<400> SEQUENCE: 1483

000

<210> SEQ ID NO 1484

<400> SEQUENCE: 1484

000

<210> SEQ ID NO 1485

<400> SEQUENCE: 1485

000

<210> SEQ ID NO 1486

<400> SEQUENCE: 1486

000

<210> SEQ ID NO 1487

<400> SEQUENCE: 1487

000

<210> SEQ ID NO 1488

<400> SEQUENCE: 1488

000

<210> SEQ ID NO 1489

<400> SEQUENCE: 1489

000

<210> SEQ ID NO 1490

<400> SEQUENCE: 1490

000

<210> SEQ ID NO 1491

<400> SEQUENCE: 1491

000

<210> SEQ ID NO 1492

<400> SEQUENCE: 1492

000

<210> SEQ ID NO 1493

<400> SEQUENCE: 1493

000

<210> SEQ ID NO 1494

<400> SEQUENCE: 1494

000

<210> SEQ ID NO 1495

<400> SEQUENCE: 1495

000

<210> SEQ ID NO 1496

<400> SEQUENCE: 1496

000

<210> SEQ ID NO 1497

<400> SEQUENCE: 1497

000

<210> SEQ ID NO 1498

<400> SEQUENCE: 1498

000

<210> SEQ ID NO 1499

<400> SEQUENCE: 1499

000

<210> SEQ ID NO 1500

<400> SEQUENCE: 1500

000

<210> SEQ ID NO 1501

<400> SEQUENCE: 1501

000

<210> SEQ ID NO 1502

<400> SEQUENCE: 1502

000

<210> SEQ ID NO 1503

<400> SEQUENCE: 1503

000

<210> SEQ ID NO 1504

<400> SEQUENCE: 1504

000

<210> SEQ ID NO 1505

<400> SEQUENCE: 1505

000

<210> SEQ ID NO 1506

<400> SEQUENCE: 1506

000

<210> SEQ ID NO 1507

<400> SEQUENCE: 1507

000

<210> SEQ ID NO 1508

<400> SEQUENCE: 1508

000

<210> SEQ ID NO 1509

<400> SEQUENCE: 1509

000

<210> SEQ ID NO 1510

<400> SEQUENCE: 1510

000

<210> SEQ ID NO 1511

<400> SEQUENCE: 1511

000

<210> SEQ ID NO 1512

<400> SEQUENCE: 1512

000

<210> SEQ ID NO 1513

<400> SEQUENCE: 1513

000

<210> SEQ ID NO 1514

<400> SEQUENCE: 1514

000

```
<210> SEQ ID NO 1515
<400> SEQUENCE: 1515
000

<210> SEQ ID NO 1516
<400> SEQUENCE: 1516
000

<210> SEQ ID NO 1517
<400> SEQUENCE: 1517
000

<210> SEQ ID NO 1518
<400> SEQUENCE: 1518
000

<210> SEQ ID NO 1519
<400> SEQUENCE: 1519
000

<210> SEQ ID NO 1520
<400> SEQUENCE: 1520
000

<210> SEQ ID NO 1521
<400> SEQUENCE: 1521
000

<210> SEQ ID NO 1522
<400> SEQUENCE: 1522
000

<210> SEQ ID NO 1523
<400> SEQUENCE: 1523
000

<210> SEQ ID NO 1524
<400> SEQUENCE: 1524
000

<210> SEQ ID NO 1525
<400> SEQUENCE: 1525
000

<210> SEQ ID NO 1526
```

<400> SEQUENCE: 1526

000

<210> SEQ ID NO 1527

<400> SEQUENCE: 1527

000

<210> SEQ ID NO 1528

<400> SEQUENCE: 1528

000

<210> SEQ ID NO 1529

<400> SEQUENCE: 1529

000

<210> SEQ ID NO 1530

<400> SEQUENCE: 1530

000

<210> SEQ ID NO 1531

<400> SEQUENCE: 1531

000

<210> SEQ ID NO 1532

<400> SEQUENCE: 1532

000

<210> SEQ ID NO 1533

<400> SEQUENCE: 1533

000

<210> SEQ ID NO 1534

<400> SEQUENCE: 1534

000

<210> SEQ ID NO 1535

<400> SEQUENCE: 1535

000

<210> SEQ ID NO 1536

<400> SEQUENCE: 1536

000

<210> SEQ ID NO 1537

<400> SEQUENCE: 1537

000

<210> SEQ ID NO 1538

<400> SEQUENCE: 1538

000

<210> SEQ ID NO 1539

<400> SEQUENCE: 1539

000

<210> SEQ ID NO 1540

<400> SEQUENCE: 1540

000

<210> SEQ ID NO 1541

<400> SEQUENCE: 1541

000

<210> SEQ ID NO 1542

<400> SEQUENCE: 1542

000

<210> SEQ ID NO 1543

<400> SEQUENCE: 1543

000

<210> SEQ ID NO 1544

<400> SEQUENCE: 1544

000

<210> SEQ ID NO 1545

<400> SEQUENCE: 1545

000

<210> SEQ ID NO 1546

<400> SEQUENCE: 1546

000

<210> SEQ ID NO 1547

<400> SEQUENCE: 1547

000

<210> SEQ ID NO 1548

<400> SEQUENCE: 1548

000

<210> SEQ ID NO 1549

<400> SEQUENCE: 1549

000

<210> SEQ ID NO 1550

<400> SEQUENCE: 1550

000

<210> SEQ ID NO 1551

<400> SEQUENCE: 1551

000

<210> SEQ ID NO 1552

<400> SEQUENCE: 1552

000

<210> SEQ ID NO 1553

<400> SEQUENCE: 1553

000

<210> SEQ ID NO 1554

<400> SEQUENCE: 1554

000

<210> SEQ ID NO 1555

<400> SEQUENCE: 1555

000

<210> SEQ ID NO 1556

<400> SEQUENCE: 1556

000

<210> SEQ ID NO 1557

<400> SEQUENCE: 1557

000

<210> SEQ ID NO 1558

<400> SEQUENCE: 1558

000

<210> SEQ ID NO 1559

<400> SEQUENCE: 1559

000

```
<210> SEQ ID NO 1560
<400> SEQUENCE: 1560
000

<210> SEQ ID NO 1561
<400> SEQUENCE: 1561
000

<210> SEQ ID NO 1562
<400> SEQUENCE: 1562
000

<210> SEQ ID NO 1563
<400> SEQUENCE: 1563
000

<210> SEQ ID NO 1564
<400> SEQUENCE: 1564
000

<210> SEQ ID NO 1565
<400> SEQUENCE: 1565
000

<210> SEQ ID NO 1566
<400> SEQUENCE: 1566
000

<210> SEQ ID NO 1567
<400> SEQUENCE: 1567
000

<210> SEQ ID NO 1568
<400> SEQUENCE: 1568
000

<210> SEQ ID NO 1569
<400> SEQUENCE: 1569
000

<210> SEQ ID NO 1570
<400> SEQUENCE: 1570
000

<210> SEQ ID NO 1571
```

<400> SEQUENCE: 1571

000

<210> SEQ ID NO 1572

<400> SEQUENCE: 1572

000

<210> SEQ ID NO 1573

<400> SEQUENCE: 1573

000

<210> SEQ ID NO 1574

<400> SEQUENCE: 1574

000

<210> SEQ ID NO 1575

<400> SEQUENCE: 1575

000

<210> SEQ ID NO 1576

<400> SEQUENCE: 1576

000

<210> SEQ ID NO 1577

<400> SEQUENCE: 1577

000

<210> SEQ ID NO 1578

<400> SEQUENCE: 1578

000

<210> SEQ ID NO 1579

<400> SEQUENCE: 1579

000

<210> SEQ ID NO 1580

<400> SEQUENCE: 1580

000

<210> SEQ ID NO 1581

<400> SEQUENCE: 1581

000

<210> SEQ ID NO 1582

<400> SEQUENCE: 1582

000

<210> SEQ ID NO 1583

<400> SEQUENCE: 1583

000

<210> SEQ ID NO 1584

<400> SEQUENCE: 1584

000

<210> SEQ ID NO 1585

<400> SEQUENCE: 1585

000

<210> SEQ ID NO 1586

<400> SEQUENCE: 1586

000

<210> SEQ ID NO 1587

<400> SEQUENCE: 1587

000

<210> SEQ ID NO 1588

<400> SEQUENCE: 1588

000

<210> SEQ ID NO 1589

<400> SEQUENCE: 1589

000

<210> SEQ ID NO 1590

<400> SEQUENCE: 1590

000

<210> SEQ ID NO 1591

<400> SEQUENCE: 1591

000

<210> SEQ ID NO 1592

<400> SEQUENCE: 1592

000

<210> SEQ ID NO 1593

<400> SEQUENCE: 1593

000

```
<210> SEQ ID NO 1594
<400> SEQUENCE: 1594
000

<210> SEQ ID NO 1595
<400> SEQUENCE: 1595
000

<210> SEQ ID NO 1596
<400> SEQUENCE: 1596
000

<210> SEQ ID NO 1597
<400> SEQUENCE: 1597
000

<210> SEQ ID NO 1598
<400> SEQUENCE: 1598
000

<210> SEQ ID NO 1599
<400> SEQUENCE: 1599
000

<210> SEQ ID NO 1600
<400> SEQUENCE: 1600
000

<210> SEQ ID NO 1601
<400> SEQUENCE: 1601
000

<210> SEQ ID NO 1602
<400> SEQUENCE: 1602
000

<210> SEQ ID NO 1603
<400> SEQUENCE: 1603
000

<210> SEQ ID NO 1604
<400> SEQUENCE: 1604
000

<210> SEQ ID NO 1605
```

```
<400> SEQUENCE: 1605
000

<210> SEQ ID NO 1606
<400> SEQUENCE: 1606
000

<210> SEQ ID NO 1607
<400> SEQUENCE: 1607
000

<210> SEQ ID NO 1608
<400> SEQUENCE: 1608
000

<210> SEQ ID NO 1609
<400> SEQUENCE: 1609
000

<210> SEQ ID NO 1610
<400> SEQUENCE: 1610
000

<210> SEQ ID NO 1611
<400> SEQUENCE: 1611
000

<210> SEQ ID NO 1612
<400> SEQUENCE: 1612
000

<210> SEQ ID NO 1613
<400> SEQUENCE: 1613
000

<210> SEQ ID NO 1614
<400> SEQUENCE: 1614
000

<210> SEQ ID NO 1615
<400> SEQUENCE: 1615
000

<210> SEQ ID NO 1616
<400> SEQUENCE: 1616
```

000

<210> SEQ ID NO 1617

<400> SEQUENCE: 1617

000

<210> SEQ ID NO 1618

<400> SEQUENCE: 1618

000

<210> SEQ ID NO 1619

<400> SEQUENCE: 1619

000

<210> SEQ ID NO 1620

<400> SEQUENCE: 1620

000

<210> SEQ ID NO 1621

<400> SEQUENCE: 1621

000

<210> SEQ ID NO 1622

<400> SEQUENCE: 1622

000

<210> SEQ ID NO 1623

<400> SEQUENCE: 1623

000

<210> SEQ ID NO 1624

<400> SEQUENCE: 1624

000

<210> SEQ ID NO 1625

<400> SEQUENCE: 1625

000

<210> SEQ ID NO 1626

<400> SEQUENCE: 1626

000

<210> SEQ ID NO 1627

<400> SEQUENCE: 1627

000

<210> SEQ ID NO 1628

<400> SEQUENCE: 1628

000

<210> SEQ ID NO 1629

<400> SEQUENCE: 1629

000

<210> SEQ ID NO 1630

<400> SEQUENCE: 1630

000

<210> SEQ ID NO 1631

<400> SEQUENCE: 1631

000

<210> SEQ ID NO 1632

<400> SEQUENCE: 1632

000

<210> SEQ ID NO 1633

<400> SEQUENCE: 1633

000

<210> SEQ ID NO 1634

<400> SEQUENCE: 1634

000

<210> SEQ ID NO 1635

<400> SEQUENCE: 1635

000

<210> SEQ ID NO 1636

<400> SEQUENCE: 1636

000

<210> SEQ ID NO 1637

<400> SEQUENCE: 1637

000

<210> SEQ ID NO 1638

<400> SEQUENCE: 1638

000

<210> SEQ ID NO 1639

<400> SEQUENCE: 1639

000

<210> SEQ ID NO 1640

<400> SEQUENCE: 1640

000

<210> SEQ ID NO 1641

<400> SEQUENCE: 1641

000

<210> SEQ ID NO 1642

<400> SEQUENCE: 1642

000

<210> SEQ ID NO 1643

<400> SEQUENCE: 1643

000

<210> SEQ ID NO 1644

<400> SEQUENCE: 1644

000

<210> SEQ ID NO 1645

<400> SEQUENCE: 1645

000

<210> SEQ ID NO 1646

<400> SEQUENCE: 1646

000

<210> SEQ ID NO 1647

<400> SEQUENCE: 1647

000

<210> SEQ ID NO 1648

<400> SEQUENCE: 1648

000

<210> SEQ ID NO 1649

<400> SEQUENCE: 1649

000

<210> SEQ ID NO 1650

<400> SEQUENCE: 1650

000

<210> SEQ ID NO 1651

<400> SEQUENCE: 1651

000

<210> SEQ ID NO 1652

<400> SEQUENCE: 1652

000

<210> SEQ ID NO 1653

<400> SEQUENCE: 1653

000

<210> SEQ ID NO 1654

<400> SEQUENCE: 1654

000

<210> SEQ ID NO 1655

<400> SEQUENCE: 1655

000

<210> SEQ ID NO 1656

<400> SEQUENCE: 1656

000

<210> SEQ ID NO 1657

<400> SEQUENCE: 1657

000

<210> SEQ ID NO 1658

<400> SEQUENCE: 1658

000

<210> SEQ ID NO 1659

<400> SEQUENCE: 1659

000

<210> SEQ ID NO 1660

<400> SEQUENCE: 1660

000

<210> SEQ ID NO 1661

<400> SEQUENCE: 1661

000

<210> SEQ ID NO 1662
<400> SEQUENCE: 1662
000

<210> SEQ ID NO 1663
<400> SEQUENCE: 1663
000

<210> SEQ ID NO 1664
<400> SEQUENCE: 1664
000

<210> SEQ ID NO 1665
<400> SEQUENCE: 1665
000

<210> SEQ ID NO 1666
<400> SEQUENCE: 1666
000

<210> SEQ ID NO 1667
<400> SEQUENCE: 1667
000

<210> SEQ ID NO 1668
<400> SEQUENCE: 1668
000

<210> SEQ ID NO 1669
<400> SEQUENCE: 1669
000

<210> SEQ ID NO 1670
<400> SEQUENCE: 1670
000

<210> SEQ ID NO 1671
<400> SEQUENCE: 1671
000

<210> SEQ ID NO 1672
<400> SEQUENCE: 1672
000

```
<210> SEQ ID NO 1673
<400> SEQUENCE: 1673
000

<210> SEQ ID NO 1674
<400> SEQUENCE: 1674
000

<210> SEQ ID NO 1675
<400> SEQUENCE: 1675
000

<210> SEQ ID NO 1676
<400> SEQUENCE: 1676
000

<210> SEQ ID NO 1677
<400> SEQUENCE: 1677
000

<210> SEQ ID NO 1678
<400> SEQUENCE: 1678
000

<210> SEQ ID NO 1679
<400> SEQUENCE: 1679
000

<210> SEQ ID NO 1680
<400> SEQUENCE: 1680
000

<210> SEQ ID NO 1681
<400> SEQUENCE: 1681
000

<210> SEQ ID NO 1682
<400> SEQUENCE: 1682
000

<210> SEQ ID NO 1683
<400> SEQUENCE: 1683
000

<210> SEQ ID NO 1684
```

<400> SEQUENCE: 1684

000

<210> SEQ ID NO 1685

<400> SEQUENCE: 1685

000

<210> SEQ ID NO 1686

<400> SEQUENCE: 1686

000

<210> SEQ ID NO 1687

<400> SEQUENCE: 1687

000

<210> SEQ ID NO 1688

<400> SEQUENCE: 1688

000

<210> SEQ ID NO 1689

<400> SEQUENCE: 1689

000

<210> SEQ ID NO 1690

<400> SEQUENCE: 1690

000

<210> SEQ ID NO 1691

<400> SEQUENCE: 1691

000

<210> SEQ ID NO 1692

<400> SEQUENCE: 1692

000

<210> SEQ ID NO 1693

<400> SEQUENCE: 1693

000

<210> SEQ ID NO 1694

<400> SEQUENCE: 1694

000

<210> SEQ ID NO 1695

<400> SEQUENCE: 1695

000

<210> SEQ ID NO 1696
<400> SEQUENCE: 1696
000

<210> SEQ ID NO 1697
<400> SEQUENCE: 1697
000

<210> SEQ ID NO 1698
<400> SEQUENCE: 1698
000

<210> SEQ ID NO 1699
<400> SEQUENCE: 1699
000

<210> SEQ ID NO 1700
<400> SEQUENCE: 1700
000

<210> SEQ ID NO 1701
<400> SEQUENCE: 1701
000

<210> SEQ ID NO 1702
<400> SEQUENCE: 1702
000

<210> SEQ ID NO 1703
<400> SEQUENCE: 1703
000

<210> SEQ ID NO 1704
<400> SEQUENCE: 1704
000

<210> SEQ ID NO 1705
<400> SEQUENCE: 1705
000

<210> SEQ ID NO 1706
<400> SEQUENCE: 1706
000

-continued

<210> SEQ ID NO 1707

<400> SEQUENCE: 1707

000

<210> SEQ ID NO 1708

<400> SEQUENCE: 1708

000

<210> SEQ ID NO 1709

<400> SEQUENCE: 1709

000

<210> SEQ ID NO 1710

<400> SEQUENCE: 1710

000

<210> SEQ ID NO 1711

<400> SEQUENCE: 1711

000

<210> SEQ ID NO 1712

<400> SEQUENCE: 1712

000

<210> SEQ ID NO 1713

<400> SEQUENCE: 1713

000

<210> SEQ ID NO 1714

<400> SEQUENCE: 1714

000

<210> SEQ ID NO 1715

<400> SEQUENCE: 1715

000

<210> SEQ ID NO 1716

<400> SEQUENCE: 1716

000

<210> SEQ ID NO 1717

<400> SEQUENCE: 1717

000

<210> SEQ ID NO 1718

<400> SEQUENCE: 1718

000

<210> SEQ ID NO 1719

<400> SEQUENCE: 1719

000

<210> SEQ ID NO 1720

<400> SEQUENCE: 1720

000

<210> SEQ ID NO 1721

<400> SEQUENCE: 1721

000

<210> SEQ ID NO 1722

<400> SEQUENCE: 1722

000

<210> SEQ ID NO 1723

<400> SEQUENCE: 1723

000

<210> SEQ ID NO 1724

<400> SEQUENCE: 1724

000

<210> SEQ ID NO 1725

<400> SEQUENCE: 1725

000

<210> SEQ ID NO 1726

<400> SEQUENCE: 1726

000

<210> SEQ ID NO 1727

<400> SEQUENCE: 1727

000

<210> SEQ ID NO 1728

<400> SEQUENCE: 1728

000

<210> SEQ ID NO 1729

<400> SEQUENCE: 1729

000

<210> SEQ ID NO 1730

<400> SEQUENCE: 1730

000

<210> SEQ ID NO 1731

<400> SEQUENCE: 1731

000

<210> SEQ ID NO 1732

<400> SEQUENCE: 1732

000

<210> SEQ ID NO 1733

<400> SEQUENCE: 1733

000

<210> SEQ ID NO 1734

<400> SEQUENCE: 1734

000

<210> SEQ ID NO 1735

<400> SEQUENCE: 1735

000

<210> SEQ ID NO 1736

<400> SEQUENCE: 1736

000

<210> SEQ ID NO 1737

<400> SEQUENCE: 1737

000

<210> SEQ ID NO 1738

<400> SEQUENCE: 1738

000

<210> SEQ ID NO 1739

<400> SEQUENCE: 1739

000

<210> SEQ ID NO 1740

<400> SEQUENCE: 1740

000

<210> SEQ ID NO 1741

<400> SEQUENCE: 1741

000

<210> SEQ ID NO 1742

<400> SEQUENCE: 1742

000

<210> SEQ ID NO 1743

<400> SEQUENCE: 1743

000

<210> SEQ ID NO 1744

<400> SEQUENCE: 1744

000

<210> SEQ ID NO 1745

<400> SEQUENCE: 1745

000

<210> SEQ ID NO 1746

<400> SEQUENCE: 1746

000

<210> SEQ ID NO 1747

<400> SEQUENCE: 1747

000

<210> SEQ ID NO 1748

<400> SEQUENCE: 1748

000

<210> SEQ ID NO 1749

<400> SEQUENCE: 1749

000

<210> SEQ ID NO 1750

<400> SEQUENCE: 1750

000

<210> SEQ ID NO 1751

<400> SEQUENCE: 1751

000

```
<210> SEQ ID NO 1752
<400> SEQUENCE: 1752
000

<210> SEQ ID NO 1753
<400> SEQUENCE: 1753
000

<210> SEQ ID NO 1754
<400> SEQUENCE: 1754
000

<210> SEQ ID NO 1755
<400> SEQUENCE: 1755
000

<210> SEQ ID NO 1756
<400> SEQUENCE: 1756
000

<210> SEQ ID NO 1757
<400> SEQUENCE: 1757
000

<210> SEQ ID NO 1758
<400> SEQUENCE: 1758
000

<210> SEQ ID NO 1759
<400> SEQUENCE: 1759
000

<210> SEQ ID NO 1760
<400> SEQUENCE: 1760
000

<210> SEQ ID NO 1761
<400> SEQUENCE: 1761
000

<210> SEQ ID NO 1762
<400> SEQUENCE: 1762
000

<210> SEQ ID NO 1763
```

<400> SEQUENCE: 1763

000

<210> SEQ ID NO 1764

<400> SEQUENCE: 1764

000

<210> SEQ ID NO 1765

<400> SEQUENCE: 1765

000

<210> SEQ ID NO 1766

<400> SEQUENCE: 1766

000

<210> SEQ ID NO 1767

<400> SEQUENCE: 1767

000

<210> SEQ ID NO 1768

<400> SEQUENCE: 1768

000

<210> SEQ ID NO 1769

<400> SEQUENCE: 1769

000

<210> SEQ ID NO 1770

<400> SEQUENCE: 1770

000

<210> SEQ ID NO 1771

<400> SEQUENCE: 1771

000

<210> SEQ ID NO 1772

<400> SEQUENCE: 1772

000

<210> SEQ ID NO 1773

<400> SEQUENCE: 1773

000

<210> SEQ ID NO 1774

<400> SEQUENCE: 1774

000

<210> SEQ ID NO 1775

<400> SEQUENCE: 1775

000

<210> SEQ ID NO 1776

<400> SEQUENCE: 1776

000

<210> SEQ ID NO 1777

<400> SEQUENCE: 1777

000

<210> SEQ ID NO 1778

<400> SEQUENCE: 1778

000

<210> SEQ ID NO 1779

<400> SEQUENCE: 1779

000

<210> SEQ ID NO 1780

<400> SEQUENCE: 1780

000

<210> SEQ ID NO 1781

<400> SEQUENCE: 1781

000

<210> SEQ ID NO 1782

<400> SEQUENCE: 1782

000

<210> SEQ ID NO 1783

<400> SEQUENCE: 1783

000

<210> SEQ ID NO 1784

<400> SEQUENCE: 1784

000

<210> SEQ ID NO 1785

<400> SEQUENCE: 1785

000

-continued

<210> SEQ ID NO 1786

<400> SEQUENCE: 1786

000

<210> SEQ ID NO 1787

<400> SEQUENCE: 1787

000

<210> SEQ ID NO 1788

<400> SEQUENCE: 1788

000

<210> SEQ ID NO 1789

<400> SEQUENCE: 1789

000

<210> SEQ ID NO 1790

<400> SEQUENCE: 1790

000

<210> SEQ ID NO 1791

<400> SEQUENCE: 1791

000

<210> SEQ ID NO 1792

<400> SEQUENCE: 1792

000

<210> SEQ ID NO 1793

<400> SEQUENCE: 1793

000

<210> SEQ ID NO 1794

<400> SEQUENCE: 1794

000

<210> SEQ ID NO 1795

<400> SEQUENCE: 1795

000

<210> SEQ ID NO 1796

<400> SEQUENCE: 1796

000

```
<210> SEQ ID NO 1797
<400> SEQUENCE: 1797
000

<210> SEQ ID NO 1798
<400> SEQUENCE: 1798
000

<210> SEQ ID NO 1799
<400> SEQUENCE: 1799
000

<210> SEQ ID NO 1800
<400> SEQUENCE: 1800
000

<210> SEQ ID NO 1801
<400> SEQUENCE: 1801
000

<210> SEQ ID NO 1802
<400> SEQUENCE: 1802
000

<210> SEQ ID NO 1803
<400> SEQUENCE: 1803
000

<210> SEQ ID NO 1804
<400> SEQUENCE: 1804
000

<210> SEQ ID NO 1805
<400> SEQUENCE: 1805
000

<210> SEQ ID NO 1806
<400> SEQUENCE: 1806
000

<210> SEQ ID NO 1807
<400> SEQUENCE: 1807
000

<210> SEQ ID NO 1808
```

```
<400> SEQUENCE: 1808

000

<210> SEQ ID NO 1809

<400> SEQUENCE: 1809

000

<210> SEQ ID NO 1810

<400> SEQUENCE: 1810

000

<210> SEQ ID NO 1811

<400> SEQUENCE: 1811

000

<210> SEQ ID NO 1812

<400> SEQUENCE: 1812

000

<210> SEQ ID NO 1813

<400> SEQUENCE: 1813

000

<210> SEQ ID NO 1814

<400> SEQUENCE: 1814

000

<210> SEQ ID NO 1815

<400> SEQUENCE: 1815

000

<210> SEQ ID NO 1816

<400> SEQUENCE: 1816

000

<210> SEQ ID NO 1817

<400> SEQUENCE: 1817

000

<210> SEQ ID NO 1818

<400> SEQUENCE: 1818

000

<210> SEQ ID NO 1819

<400> SEQUENCE: 1819
```

000

<210> SEQ ID NO 1820

<400> SEQUENCE: 1820

000

<210> SEQ ID NO 1821

<400> SEQUENCE: 1821

000

<210> SEQ ID NO 1822

<400> SEQUENCE: 1822

000

<210> SEQ ID NO 1823

<400> SEQUENCE: 1823

000

<210> SEQ ID NO 1824

<400> SEQUENCE: 1824

000

<210> SEQ ID NO 1825

<400> SEQUENCE: 1825

000

<210> SEQ ID NO 1826

<400> SEQUENCE: 1826

000

<210> SEQ ID NO 1827

<400> SEQUENCE: 1827

000

<210> SEQ ID NO 1828

<400> SEQUENCE: 1828

000

<210> SEQ ID NO 1829

<400> SEQUENCE: 1829

000

<210> SEQ ID NO 1830

<400> SEQUENCE: 1830

000

<210> SEQ ID NO 1831

<400> SEQUENCE: 1831

000

<210> SEQ ID NO 1832

<400> SEQUENCE: 1832

000

<210> SEQ ID NO 1833

<400> SEQUENCE: 1833

000

<210> SEQ ID NO 1834

<400> SEQUENCE: 1834

000

<210> SEQ ID NO 1835

<400> SEQUENCE: 1835

000

<210> SEQ ID NO 1836

<400> SEQUENCE: 1836

000

<210> SEQ ID NO 1837

<400> SEQUENCE: 1837

000

<210> SEQ ID NO 1838

<400> SEQUENCE: 1838

000

<210> SEQ ID NO 1839

<400> SEQUENCE: 1839

000

<210> SEQ ID NO 1840

<400> SEQUENCE: 1840

000

<210> SEQ ID NO 1841

<400> SEQUENCE: 1841

000

<210> SEQ ID NO 1842

```
<400> SEQUENCE: 1842
000

<210> SEQ ID NO 1843
<400> SEQUENCE: 1843
000

<210> SEQ ID NO 1844
<400> SEQUENCE: 1844
000

<210> SEQ ID NO 1845
<400> SEQUENCE: 1845
000

<210> SEQ ID NO 1846
<400> SEQUENCE: 1846
000

<210> SEQ ID NO 1847
<400> SEQUENCE: 1847
000

<210> SEQ ID NO 1848
<400> SEQUENCE: 1848
000

<210> SEQ ID NO 1849
<400> SEQUENCE: 1849
000

<210> SEQ ID NO 1850
<400> SEQUENCE: 1850
000

<210> SEQ ID NO 1851
<400> SEQUENCE: 1851
000

<210> SEQ ID NO 1852
<400> SEQUENCE: 1852
000

<210> SEQ ID NO 1853
<400> SEQUENCE: 1853
```

000

<210> SEQ ID NO 1854

<400> SEQUENCE: 1854

000

<210> SEQ ID NO 1855

<400> SEQUENCE: 1855

000

<210> SEQ ID NO 1856

<400> SEQUENCE: 1856

000

<210> SEQ ID NO 1857

<400> SEQUENCE: 1857

000

<210> SEQ ID NO 1858

<400> SEQUENCE: 1858

000

<210> SEQ ID NO 1859

<400> SEQUENCE: 1859

000

<210> SEQ ID NO 1860

<400> SEQUENCE: 1860

000

<210> SEQ ID NO 1861

<400> SEQUENCE: 1861

000

<210> SEQ ID NO 1862

<400> SEQUENCE: 1862

000

<210> SEQ ID NO 1863

<400> SEQUENCE: 1863

000

<210> SEQ ID NO 1864

<400> SEQUENCE: 1864

000

<210> SEQ ID NO 1865

<400> SEQUENCE: 1865

000

<210> SEQ ID NO 1866

<400> SEQUENCE: 1866

000

<210> SEQ ID NO 1867

<400> SEQUENCE: 1867

000

<210> SEQ ID NO 1868

<400> SEQUENCE: 1868

000

<210> SEQ ID NO 1869

<400> SEQUENCE: 1869

000

<210> SEQ ID NO 1870

<400> SEQUENCE: 1870

000

<210> SEQ ID NO 1871

<400> SEQUENCE: 1871

000

<210> SEQ ID NO 1872

<400> SEQUENCE: 1872

000

<210> SEQ ID NO 1873

<400> SEQUENCE: 1873

000

<210> SEQ ID NO 1874

<400> SEQUENCE: 1874

000

<210> SEQ ID NO 1875

<400> SEQUENCE: 1875

000

<210> SEQ ID NO 1876

<400> SEQUENCE: 1876

000

<210> SEQ ID NO 1877

<400> SEQUENCE: 1877

000

<210> SEQ ID NO 1878

<400> SEQUENCE: 1878

000

<210> SEQ ID NO 1879

<400> SEQUENCE: 1879

000

<210> SEQ ID NO 1880

<400> SEQUENCE: 1880

000

<210> SEQ ID NO 1881

<400> SEQUENCE: 1881

000

<210> SEQ ID NO 1882

<400> SEQUENCE: 1882

000

<210> SEQ ID NO 1883

<400> SEQUENCE: 1883

000

<210> SEQ ID NO 1884

<400> SEQUENCE: 1884

000

<210> SEQ ID NO 1885

<400> SEQUENCE: 1885

000

<210> SEQ ID NO 1886

<400> SEQUENCE: 1886

000

<210> SEQ ID NO 1887

<400> SEQUENCE: 1887

000

<210> SEQ ID NO 1888

<400> SEQUENCE: 1888

000

<210> SEQ ID NO 1889

<400> SEQUENCE: 1889

000

<210> SEQ ID NO 1890

<400> SEQUENCE: 1890

000

<210> SEQ ID NO 1891

<400> SEQUENCE: 1891

000

<210> SEQ ID NO 1892

<400> SEQUENCE: 1892

000

<210> SEQ ID NO 1893

<400> SEQUENCE: 1893

000

<210> SEQ ID NO 1894

<400> SEQUENCE: 1894

000

<210> SEQ ID NO 1895

<400> SEQUENCE: 1895

000

<210> SEQ ID NO 1896

<400> SEQUENCE: 1896

000

<210> SEQ ID NO 1897

<400> SEQUENCE: 1897

000

<210> SEQ ID NO 1898

<400> SEQUENCE: 1898

000

<210> SEQ ID NO 1899

<400> SEQUENCE: 1899

000

<210> SEQ ID NO 1900

<400> SEQUENCE: 1900

000

<210> SEQ ID NO 1901

<400> SEQUENCE: 1901

000

<210> SEQ ID NO 1902

<400> SEQUENCE: 1902

000

<210> SEQ ID NO 1903

<400> SEQUENCE: 1903

000

<210> SEQ ID NO 1904

<400> SEQUENCE: 1904

000

<210> SEQ ID NO 1905

<400> SEQUENCE: 1905

000

<210> SEQ ID NO 1906

<400> SEQUENCE: 1906

000

<210> SEQ ID NO 1907

<400> SEQUENCE: 1907

000

<210> SEQ ID NO 1908

<400> SEQUENCE: 1908

000

<210> SEQ ID NO 1909

<400> SEQUENCE: 1909

000

<210> SEQ ID NO 1910

<400> SEQUENCE: 1910

000

<210> SEQ ID NO 1911

<400> SEQUENCE: 1911

000

<210> SEQ ID NO 1912

<400> SEQUENCE: 1912

000

<210> SEQ ID NO 1913

<400> SEQUENCE: 1913

000

<210> SEQ ID NO 1914

<400> SEQUENCE: 1914

000

<210> SEQ ID NO 1915

<400> SEQUENCE: 1915

000

<210> SEQ ID NO 1916

<400> SEQUENCE: 1916

000

<210> SEQ ID NO 1917

<400> SEQUENCE: 1917

000

<210> SEQ ID NO 1918

<400> SEQUENCE: 1918

000

<210> SEQ ID NO 1919

<400> SEQUENCE: 1919

000

<210> SEQ ID NO 1920

<400> SEQUENCE: 1920

000

<210> SEQ ID NO 1921

```
<400> SEQUENCE: 1921

000

<210> SEQ ID NO 1922

<400> SEQUENCE: 1922

000

<210> SEQ ID NO 1923

<400> SEQUENCE: 1923

000

<210> SEQ ID NO 1924

<400> SEQUENCE: 1924

000

<210> SEQ ID NO 1925

<400> SEQUENCE: 1925

000

<210> SEQ ID NO 1926

<400> SEQUENCE: 1926

000

<210> SEQ ID NO 1927

<400> SEQUENCE: 1927

000

<210> SEQ ID NO 1928

<400> SEQUENCE: 1928

000

<210> SEQ ID NO 1929

<400> SEQUENCE: 1929

000

<210> SEQ ID NO 1930

<400> SEQUENCE: 1930

000

<210> SEQ ID NO 1931

<400> SEQUENCE: 1931

000

<210> SEQ ID NO 1932

<400> SEQUENCE: 1932
```

-continued

000

<210> SEQ ID NO 1933

<400> SEQUENCE: 1933

000

<210> SEQ ID NO 1934

<400> SEQUENCE: 1934

000

<210> SEQ ID NO 1935

<400> SEQUENCE: 1935

000

<210> SEQ ID NO 1936

<400> SEQUENCE: 1936

000

<210> SEQ ID NO 1937

<400> SEQUENCE: 1937

000

<210> SEQ ID NO 1938

<400> SEQUENCE: 1938

000

<210> SEQ ID NO 1939

<400> SEQUENCE: 1939

000

<210> SEQ ID NO 1940

<400> SEQUENCE: 1940

000

<210> SEQ ID NO 1941

<400> SEQUENCE: 1941

000

<210> SEQ ID NO 1942

<400> SEQUENCE: 1942

000

<210> SEQ ID NO 1943

<400> SEQUENCE: 1943

000

<210> SEQ ID NO 1944

<400> SEQUENCE: 1944

000

<210> SEQ ID NO 1945

<400> SEQUENCE: 1945

000

<210> SEQ ID NO 1946

<400> SEQUENCE: 1946

000

<210> SEQ ID NO 1947

<400> SEQUENCE: 1947

000

<210> SEQ ID NO 1948

<400> SEQUENCE: 1948

000

<210> SEQ ID NO 1949

<400> SEQUENCE: 1949

000

<210> SEQ ID NO 1950

<400> SEQUENCE: 1950

000

<210> SEQ ID NO 1951

<400> SEQUENCE: 1951

000

<210> SEQ ID NO 1952

<400> SEQUENCE: 1952

000

<210> SEQ ID NO 1953

<400> SEQUENCE: 1953

000

<210> SEQ ID NO 1954

<400> SEQUENCE: 1954

000

<210> SEQ ID NO 1955

<400> SEQUENCE: 1955

000

<210> SEQ ID NO 1956

<400> SEQUENCE: 1956

000

<210> SEQ ID NO 1957

<400> SEQUENCE: 1957

000

<210> SEQ ID NO 1958

<400> SEQUENCE: 1958

000

<210> SEQ ID NO 1959

<400> SEQUENCE: 1959

000

<210> SEQ ID NO 1960

<400> SEQUENCE: 1960

000

<210> SEQ ID NO 1961

<400> SEQUENCE: 1961

000

<210> SEQ ID NO 1962

<400> SEQUENCE: 1962

000

<210> SEQ ID NO 1963

<400> SEQUENCE: 1963

000

<210> SEQ ID NO 1964

<400> SEQUENCE: 1964

000

<210> SEQ ID NO 1965

<400> SEQUENCE: 1965

000

<210> SEQ ID NO 1966

<400> SEQUENCE: 1966

000

<210> SEQ ID NO 1967

<400> SEQUENCE: 1967

000

<210> SEQ ID NO 1968

<400> SEQUENCE: 1968

000

<210> SEQ ID NO 1969

<400> SEQUENCE: 1969

000

<210> SEQ ID NO 1970

<400> SEQUENCE: 1970

000

<210> SEQ ID NO 1971

<400> SEQUENCE: 1971

000

<210> SEQ ID NO 1972

<400> SEQUENCE: 1972

000

<210> SEQ ID NO 1973

<400> SEQUENCE: 1973

000

<210> SEQ ID NO 1974

<400> SEQUENCE: 1974

000

<210> SEQ ID NO 1975

<400> SEQUENCE: 1975

000

<210> SEQ ID NO 1976

<400> SEQUENCE: 1976

000

<210> SEQ ID NO 1977

<400> SEQUENCE: 1977

000

<210> SEQ ID NO 1978

<400> SEQUENCE: 1978

000

<210> SEQ ID NO 1979

<400> SEQUENCE: 1979

000

<210> SEQ ID NO 1980

<400> SEQUENCE: 1980

000

<210> SEQ ID NO 1981

<400> SEQUENCE: 1981

000

<210> SEQ ID NO 1982

<400> SEQUENCE: 1982

000

<210> SEQ ID NO 1983

<400> SEQUENCE: 1983

000

<210> SEQ ID NO 1984

<400> SEQUENCE: 1984

000

<210> SEQ ID NO 1985

<400> SEQUENCE: 1985

000

<210> SEQ ID NO 1986

<400> SEQUENCE: 1986

000

<210> SEQ ID NO 1987

<400> SEQUENCE: 1987

000

<210> SEQ ID NO 1988

<400> SEQUENCE: 1988

000

-continued

<210> SEQ ID NO 1989
<400> SEQUENCE: 1989
000

<210> SEQ ID NO 1990
<400> SEQUENCE: 1990
000

<210> SEQ ID NO 1991
<400> SEQUENCE: 1991
000

<210> SEQ ID NO 1992
<400> SEQUENCE: 1992
000

<210> SEQ ID NO 1993
<400> SEQUENCE: 1993
000

<210> SEQ ID NO 1994
<400> SEQUENCE: 1994
000

<210> SEQ ID NO 1995
<400> SEQUENCE: 1995
000

<210> SEQ ID NO 1996
<400> SEQUENCE: 1996
000

<210> SEQ ID NO 1997
<400> SEQUENCE: 1997
000

<210> SEQ ID NO 1998
<400> SEQUENCE: 1998
000

<210> SEQ ID NO 1999
<400> SEQUENCE: 1999
000

<210> SEQ ID NO 2000

```
<400> SEQUENCE: 2000

000

<210> SEQ ID NO 2001
<211> LENGTH: 9
<212> TYPE: PRT
<213> ORGANISM: Artificial Sequence
<220> FEATURE:
<223> OTHER INFORMATION: Synthetic: 33 - VH CDR1

<400> SEQUENCE: 2001

Gly Thr Phe Gly Asn Tyr Ala Ile Ser
1               5

<210> SEQ ID NO 2002
<211> LENGTH: 17
<212> TYPE: PRT
<213> ORGANISM: Artificial Sequence
<220> FEATURE:
<223> OTHER INFORMATION: Synthetic: 33 - VH CDR2

<400> SEQUENCE: 2002

Gly Ile Ile Pro Ile Pro Gly Ile Ala Asn Tyr Ala Gln Lys Phe Gln
1               5                   10                  15

Gly

<210> SEQ ID NO 2003
<211> LENGTH: 16
<212> TYPE: PRT
<213> ORGANISM: Artificial Sequence
<220> FEATURE:
<223> OTHER INFORMATION: Synthetic: 33 - VH CDR3

<400> SEQUENCE: 2003

Ala Arg Asp Thr Gly Arg Gly Tyr Thr Arg His Phe Trp Phe Asp Pro
1               5                   10                  15

<210> SEQ ID NO 2004
<211> LENGTH: 11
<212> TYPE: PRT
<213> ORGANISM: Artificial Sequence
<220> FEATURE:
<223> OTHER INFORMATION: Synthetic: 33 - VL CDR1

<400> SEQUENCE: 2004

Arg Ala Ser Gln Ser Ile Ser Ser Tyr Leu Asn
1               5                   10

<210> SEQ ID NO 2005
<211> LENGTH: 7
<212> TYPE: PRT
<213> ORGANISM: Artificial Sequence
<220> FEATURE:
<223> OTHER INFORMATION: Synthetic: 33 - VL CDR2

<400> SEQUENCE: 2005

Ala Ala Ser Ser Leu Gln Ser
1               5

<210> SEQ ID NO 2006
<211> LENGTH: 8
<212> TYPE: PRT
<213> ORGANISM: Artificial Sequence
<220> FEATURE:
<223> OTHER INFORMATION: Synthetic: 33 - VL CDR3
```

```
<400> SEQUENCE: 2006

Gln Gln Ser Asp Ile Leu Tyr Thr
1               5

<210> SEQ ID NO 2007
<211> LENGTH: 26
<212> TYPE: PRT
<213> ORGANISM: Artificial Sequence
<220> FEATURE:
<223> OTHER INFORMATION: Synthetic: 33 - VH FR1

<400> SEQUENCE: 2007

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 2008
<211> LENGTH: 14
<212> TYPE: PRT
<213> ORGANISM: Artificial Sequence
<220> FEATURE:
<223> OTHER INFORMATION: Synthetic: 33 - VH FR2

<400> SEQUENCE: 2008

Trp Val Arg Gln Ala Pro Gly Gln Gly Leu Glu Trp Met Gly
1               5                   10

<210> SEQ ID NO 2009
<211> LENGTH: 30
<212> TYPE: PRT
<213> ORGANISM: Artificial Sequence
<220> FEATURE:
<223> OTHER INFORMATION: Synthetic: 33 - VH FR3

<400> SEQUENCE: 2009

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 2010
<211> LENGTH: 11
<212> TYPE: PRT
<213> ORGANISM: Artificial Sequence
<220> FEATURE:
<223> OTHER INFORMATION: Synthetic: 33 - VH FR4

<400> SEQUENCE: 2010

Trp Gly Gln Gly Thr Leu Val Thr Val Ser Ser
1               5                   10

<210> SEQ ID NO 2011
<211> LENGTH: 369
<212> TYPE: DNA
<213> ORGANISM: Artificial Sequence
<220> FEATURE:
<223> OTHER INFORMATION: Synthetic: 33 - VH DNA

<400> SEQUENCE: 2011
caggtgcagc tggtgcagtc tggggctgag gtgaagaagc ctgggtcctc ggtgaaggtc      60
tcctgcaagg cttctggagg caccttcgga aactatgcta tcagctgggt gcgacaggcc     120
cctggacaag ggcttgagtg gatgggaggg atcatcccta tcccaggtat cgcaaactac     180
```

```
gcacagaagt tccagggcag agtcacgatt accgcggacg aatccacgag cacagcctac    240
atggagctga gcagcctgag atctgaggac acggcggtgt actactgcgc cagagacacg    300
ggacggggat acaccagaca cttctggttt gaccctgggg acagggtac attggtcacc     360 gtctcctca                                                            369
```

```
<210> SEQ ID NO 2012
<211> LENGTH: 123
<212> TYPE: PRT
<213> ORGANISM: Artificial Sequence
<220> FEATURE:
<223> OTHER INFORMATION: Synthetic: 33 - VH Protein

<400> SEQUENCE: 2012
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Pro Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Arg Gly Tyr Thr Arg His Phe Trp Phe Asp Pro
            100                 105                 110

Trp Gly Gln Gly Thr Leu Val Thr Val Ser Ser
        115                 120

```
<210> SEQ ID NO 2013
<211> LENGTH: 23
<212> TYPE: PRT
<213> ORGANISM: Artificial Sequence
<220> FEATURE:
<223> OTHER INFORMATION: Synthetic: 33 - VL FR1

<400> SEQUENCE: 2013
```

Asp Ile Gln Met Thr Gln Ser Pro Ser Ser Leu Ser Ala Ser Val Gly
1               5                   10                  15

Asp Arg Val Thr Ile Thr Cys
            20

```
<210> SEQ ID NO 2014
<211> LENGTH: 15
<212> TYPE: PRT
<213> ORGANISM: Artificial Sequence
<220> FEATURE:
<223> OTHER INFORMATION: Synthetic: 33 - VL FR2

<400> SEQUENCE: 2014
```

Trp Tyr Gln Gln Lys Pro Gly Lys Ala Pro Lys Leu Leu Ile Tyr
1               5                   10                  15

```
<210> SEQ ID NO 2015
<211> LENGTH: 32
<212> TYPE: PRT
<213> ORGANISM: Artificial Sequence
<220> FEATURE:
<223> OTHER INFORMATION: Synthetic: 33 - VL FR3
```

<400> SEQUENCE: 2015

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 2016
<211> LENGTH: 10
<212> TYPE: PRT
<213> ORGANISM: Artificial Sequence
<220> FEATURE:
<223> OTHER INFORMATION: Synthetic: 33 - VL FR4

<400> SEQUENCE: 2016

Phe Gly Gly Gly Thr Lys Val Glu Ile Lys
1               5                   10

<210> SEQ ID NO 2017
<211> LENGTH: 318
<212> TYPE: DNA
<213> ORGANISM: Artificial Sequence
<220> FEATURE:
<223> OTHER INFORMATION: Synthetic: 33 - VL DNA

<400> SEQUENCE: 2017

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agcgacatcc tctacacttt tggcggaggg   300
accaaggttg agatcaaa                                                 318
```

<210> SEQ ID NO 2018
<211> LENGTH: 106
<212> TYPE: PRT
<213> ORGANISM: Artificial Sequence
<220> FEATURE:
<223> OTHER INFORMATION: Synthetic: 33 - VL Protein

<400> SEQUENCE: 2018

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Tyr Thr
                85                  90                  95

Phe Gly Gly Gly Thr Lys Val Glu Ile Lys
            100                 105

<210> SEQ ID NO 2019

<400> SEQUENCE: 2019

000

<210> SEQ ID NO 2020

<400> SEQUENCE: 2020

000

<210> SEQ ID NO 2021

<400> SEQUENCE: 2021

000

<210> SEQ ID NO 2022

<400> SEQUENCE: 2022

000

<210> SEQ ID NO 2023

<400> SEQUENCE: 2023

000

<210> SEQ ID NO 2024

<400> SEQUENCE: 2024

000

<210> SEQ ID NO 2025

<400> SEQUENCE: 2025

000

<210> SEQ ID NO 2026

<400> SEQUENCE: 2026

000

<210> SEQ ID NO 2027

<400> SEQUENCE: 2027

000

<210> SEQ ID NO 2028

<400> SEQUENCE: 2028

000

<210> SEQ ID NO 2029

<400> SEQUENCE: 2029

000

<210> SEQ ID NO 2030

<400> SEQUENCE: 2030

000

<210> SEQ ID NO 2031

<400> SEQUENCE: 2031

000

<210> SEQ ID NO 2032

<400> SEQUENCE: 2032

000

<210> SEQ ID NO 2033

<400> SEQUENCE: 2033

000

<210> SEQ ID NO 2034

<400> SEQUENCE: 2034

000

<210> SEQ ID NO 2035

<400> SEQUENCE: 2035

000

<210> SEQ ID NO 2036

<400> SEQUENCE: 2036

000

<210> SEQ ID NO 2037

<400> SEQUENCE: 2037

000

<210> SEQ ID NO 2038

<400> SEQUENCE: 2038

000

<210> SEQ ID NO 2039

<400> SEQUENCE: 2039

000

<210> SEQ ID NO 2040

<400> SEQUENCE: 2040

000

<210> SEQ ID NO 2041

<400> SEQUENCE: 2041

000

-continued

<210> SEQ ID NO 2042

<400> SEQUENCE: 2042

000

<210> SEQ ID NO 2043

<400> SEQUENCE: 2043

000

<210> SEQ ID NO 2044

<400> SEQUENCE: 2044

000

<210> SEQ ID NO 2045

<400> SEQUENCE: 2045

000

<210> SEQ ID NO 2046

<400> SEQUENCE: 2046

000

<210> SEQ ID NO 2047

<400> SEQUENCE: 2047

000

<210> SEQ ID NO 2048

<400> SEQUENCE: 2048

000

<210> SEQ ID NO 2049

<400> SEQUENCE: 2049

000

<210> SEQ ID NO 2050

<400> SEQUENCE: 2050

000

<210> SEQ ID NO 2051

<400> SEQUENCE: 2051

000

<210> SEQ ID NO 2052

<400> SEQUENCE: 2052

000

<210> SEQ ID NO 2053

<400> SEQUENCE: 2053

000

<210> SEQ ID NO 2054

<400> SEQUENCE: 2054

000

<210> SEQ ID NO 2055

<400> SEQUENCE: 2055

000

<210> SEQ ID NO 2056

<400> SEQUENCE: 2056

000

<210> SEQ ID NO 2057

<400> SEQUENCE: 2057

000

<210> SEQ ID NO 2058

<400> SEQUENCE: 2058

000

<210> SEQ ID NO 2059

<400> SEQUENCE: 2059

000

<210> SEQ ID NO 2060

<400> SEQUENCE: 2060

000

<210> SEQ ID NO 2061

<400> SEQUENCE: 2061

000

<210> SEQ ID NO 2062

<400> SEQUENCE: 2062

000

<210> SEQ ID NO 2063

<400> SEQUENCE: 2063

000

<210> SEQ ID NO 2064

<400> SEQUENCE: 2064

000

<210> SEQ ID NO 2065

<400> SEQUENCE: 2065

000

<210> SEQ ID NO 2066

<400> SEQUENCE: 2066

000

<210> SEQ ID NO 2067

<400> SEQUENCE: 2067

000

<210> SEQ ID NO 2068

<400> SEQUENCE: 2068

000

<210> SEQ ID NO 2069

<400> SEQUENCE: 2069

000

<210> SEQ ID NO 2070

<400> SEQUENCE: 2070

000

<210> SEQ ID NO 2071

<400> SEQUENCE: 2071

000

<210> SEQ ID NO 2072

<400> SEQUENCE: 2072

000

<210> SEQ ID NO 2073

<400> SEQUENCE: 2073

000

<210> SEQ ID NO 2074

<400> SEQUENCE: 2074

000

<210> SEQ ID NO 2075

<400> SEQUENCE: 2075

000

<210> SEQ ID NO 2076

<400> SEQUENCE: 2076

000

<210> SEQ ID NO 2077

<400> SEQUENCE: 2077

000

<210> SEQ ID NO 2078

<400> SEQUENCE: 2078

000

<210> SEQ ID NO 2079

<400> SEQUENCE: 2079

000

<210> SEQ ID NO 2080

<400> SEQUENCE: 2080

000

<210> SEQ ID NO 2081

<400> SEQUENCE: 2081

000

<210> SEQ ID NO 2082

<400> SEQUENCE: 2082

000

<210> SEQ ID NO 2083

<400> SEQUENCE: 2083

000

<210> SEQ ID NO 2084

<400> SEQUENCE: 2084

000

<210> SEQ ID NO 2085

<400> SEQUENCE: 2085

000

<210> SEQ ID NO 2086

<400> SEQUENCE: 2086

000

<210> SEQ ID NO 2087

<400> SEQUENCE: 2087

000

<210> SEQ ID NO 2088

<400> SEQUENCE: 2088

000

<210> SEQ ID NO 2089

<400> SEQUENCE: 2089

000

<210> SEQ ID NO 2090

<400> SEQUENCE: 2090

000

<210> SEQ ID NO 2091

<400> SEQUENCE: 2091

000

<210> SEQ ID NO 2092

<400> SEQUENCE: 2092

000

<210> SEQ ID NO 2093

<400> SEQUENCE: 2093

000

<210> SEQ ID NO 2094

<400> SEQUENCE: 2094

000

<210> SEQ ID NO 2095

<400> SEQUENCE: 2095

000

<210> SEQ ID NO 2096

<400> SEQUENCE: 2096

000

<210> SEQ ID NO 2097

<400> SEQUENCE: 2097

000

<210> SEQ ID NO 2098

<400> SEQUENCE: 2098

000

<210> SEQ ID NO 2099

<400> SEQUENCE: 2099

000

<210> SEQ ID NO 2100

<400> SEQUENCE: 2100

000

<210> SEQ ID NO 2101

<400> SEQUENCE: 2101

000

<210> SEQ ID NO 2102

<400> SEQUENCE: 2102

000

<210> SEQ ID NO 2103

<400> SEQUENCE: 2103

000

<210> SEQ ID NO 2104

<400> SEQUENCE: 2104

000

<210> SEQ ID NO 2105

<400> SEQUENCE: 2105

000

<210> SEQ ID NO 2106

<400> SEQUENCE: 2106

000

<210> SEQ ID NO 2107

<400> SEQUENCE: 2107

000

<210> SEQ ID NO 2108

<400> SEQUENCE: 2108

000

<210> SEQ ID NO 2109

<400> SEQUENCE: 2109

000

<210> SEQ ID NO 2110

<400> SEQUENCE: 2110

000

<210> SEQ ID NO 2111

<400> SEQUENCE: 2111

000

<210> SEQ ID NO 2112

<400> SEQUENCE: 2112

000

<210> SEQ ID NO 2113

<400> SEQUENCE: 2113

000

<210> SEQ ID NO 2114

<400> SEQUENCE: 2114

000

<210> SEQ ID NO 2115

<400> SEQUENCE: 2115

000

<210> SEQ ID NO 2116

<400> SEQUENCE: 2116

000

<210> SEQ ID NO 2117

<400> SEQUENCE: 2117

000

<210> SEQ ID NO 2118

<400> SEQUENCE: 2118

000

<210> SEQ ID NO 2119

<400> SEQUENCE: 2119

000

<210> SEQ ID NO 2120

<400> SEQUENCE: 2120

000

```
<210> SEQ ID NO 2121
<400> SEQUENCE: 2121
000

<210> SEQ ID NO 2122
<400> SEQUENCE: 2122
000

<210> SEQ ID NO 2123
<400> SEQUENCE: 2123
000

<210> SEQ ID NO 2124
<400> SEQUENCE: 2124
000

<210> SEQ ID NO 2125
<400> SEQUENCE: 2125
000

<210> SEQ ID NO 2126
<400> SEQUENCE: 2126
000

<210> SEQ ID NO 2127
<400> SEQUENCE: 2127
000

<210> SEQ ID NO 2128
<400> SEQUENCE: 2128
000

<210> SEQ ID NO 2129
<400> SEQUENCE: 2129
000

<210> SEQ ID NO 2130
<400> SEQUENCE: 2130
000

<210> SEQ ID NO 2131
<400> SEQUENCE: 2131
000

<210> SEQ ID NO 2132
```

```
<400> SEQUENCE: 2132
000

<210> SEQ ID NO 2133
<400> SEQUENCE: 2133
000

<210> SEQ ID NO 2134
<400> SEQUENCE: 2134
000

<210> SEQ ID NO 2135
<400> SEQUENCE: 2135
000

<210> SEQ ID NO 2136
<400> SEQUENCE: 2136
000

<210> SEQ ID NO 2137
<400> SEQUENCE: 2137
000

<210> SEQ ID NO 2138
<400> SEQUENCE: 2138
000

<210> SEQ ID NO 2139
<400> SEQUENCE: 2139
000

<210> SEQ ID NO 2140
<400> SEQUENCE: 2140
000

<210> SEQ ID NO 2141
<400> SEQUENCE: 2141
000

<210> SEQ ID NO 2142
<400> SEQUENCE: 2142
000

<210> SEQ ID NO 2143
<400> SEQUENCE: 2143
```

000

<210> SEQ ID NO 2144

<400> SEQUENCE: 2144

000

<210> SEQ ID NO 2145

<400> SEQUENCE: 2145

000

<210> SEQ ID NO 2146

<400> SEQUENCE: 2146

000

<210> SEQ ID NO 2147

<400> SEQUENCE: 2147

000

<210> SEQ ID NO 2148

<400> SEQUENCE: 2148

000

<210> SEQ ID NO 2149

<400> SEQUENCE: 2149

000

<210> SEQ ID NO 2150

<400> SEQUENCE: 2150

000

<210> SEQ ID NO 2151

<400> SEQUENCE: 2151

000

<210> SEQ ID NO 2152

<400> SEQUENCE: 2152

000

<210> SEQ ID NO 2153

<400> SEQUENCE: 2153

000

<210> SEQ ID NO 2154

<400> SEQUENCE: 2154

000

<210> SEQ ID NO 2155

<400> SEQUENCE: 2155

000

<210> SEQ ID NO 2156

<400> SEQUENCE: 2156

000

<210> SEQ ID NO 2157

<400> SEQUENCE: 2157

000

<210> SEQ ID NO 2158

<400> SEQUENCE: 2158

000

<210> SEQ ID NO 2159

<400> SEQUENCE: 2159

000

<210> SEQ ID NO 2160

<400> SEQUENCE: 2160

000

<210> SEQ ID NO 2161

<400> SEQUENCE: 2161

000

<210> SEQ ID NO 2162

<400> SEQUENCE: 2162

000

<210> SEQ ID NO 2163

<400> SEQUENCE: 2163

000

<210> SEQ ID NO 2164

<400> SEQUENCE: 2164

000

<210> SEQ ID NO 2165

<400> SEQUENCE: 2165

000

<210> SEQ ID NO 2166

-continued

<400> SEQUENCE: 2166

000

<210> SEQ ID NO 2167

<400> SEQUENCE: 2167

000

<210> SEQ ID NO 2168

<400> SEQUENCE: 2168

000

<210> SEQ ID NO 2169

<400> SEQUENCE: 2169

000

<210> SEQ ID NO 2170

<400> SEQUENCE: 2170

000

<210> SEQ ID NO 2171

<400> SEQUENCE: 2171

000

<210> SEQ ID NO 2172

<400> SEQUENCE: 2172

000

<210> SEQ ID NO 2173

<400> SEQUENCE: 2173

000

<210> SEQ ID NO 2174

<400> SEQUENCE: 2174

000

<210> SEQ ID NO 2175

<400> SEQUENCE: 2175

000

<210> SEQ ID NO 2176

<400> SEQUENCE: 2176

000

<210> SEQ ID NO 2177

<400> SEQUENCE: 2177

000

<210> SEQ ID NO 2178

<400> SEQUENCE: 2178

000

<210> SEQ ID NO 2179

<400> SEQUENCE: 2179

000

<210> SEQ ID NO 2180

<400> SEQUENCE: 2180

000

<210> SEQ ID NO 2181

<400> SEQUENCE: 2181

000

<210> SEQ ID NO 2182

<400> SEQUENCE: 2182

000

<210> SEQ ID NO 2183

<400> SEQUENCE: 2183

000

<210> SEQ ID NO 2184

<400> SEQUENCE: 2184

000

<210> SEQ ID NO 2185

<400> SEQUENCE: 2185

000

<210> SEQ ID NO 2186

<400> SEQUENCE: 2186

000

<210> SEQ ID NO 2187

<400> SEQUENCE: 2187

000

<210> SEQ ID NO 2188

<400> SEQUENCE: 2188

000

<210> SEQ ID NO 2189

<400> SEQUENCE: 2189

000

<210> SEQ ID NO 2190

<400> SEQUENCE: 2190

000

<210> SEQ ID NO 2191

<400> SEQUENCE: 2191

000

<210> SEQ ID NO 2192

<400> SEQUENCE: 2192

000

<210> SEQ ID NO 2193

<400> SEQUENCE: 2193

000

<210> SEQ ID NO 2194

<400> SEQUENCE: 2194

000

<210> SEQ ID NO 2195

<400> SEQUENCE: 2195

000

<210> SEQ ID NO 2196

<400> SEQUENCE: 2196

000

<210> SEQ ID NO 2197

<400> SEQUENCE: 2197

000

<210> SEQ ID NO 2198

<400> SEQUENCE: 2198

000

<210> SEQ ID NO 2199

<400> SEQUENCE: 2199

000

<210> SEQ ID NO 2200

<400> SEQUENCE: 2200

000

<210> SEQ ID NO 2201

<400> SEQUENCE: 2201

000

<210> SEQ ID NO 2202

<400> SEQUENCE: 2202

000

<210> SEQ ID NO 2203

<400> SEQUENCE: 2203

000

<210> SEQ ID NO 2204

<400> SEQUENCE: 2204

000

<210> SEQ ID NO 2205

<400> SEQUENCE: 2205

000

<210> SEQ ID NO 2206

<400> SEQUENCE: 2206

000

<210> SEQ ID NO 2207

<400> SEQUENCE: 2207

000

<210> SEQ ID NO 2208

<400> SEQUENCE: 2208

000

<210> SEQ ID NO 2209

<400> SEQUENCE: 2209

000

<210> SEQ ID NO 2210

<400> SEQUENCE: 2210

000

<210> SEQ ID NO 2211

```
<400> SEQUENCE: 2211
000

<210> SEQ ID NO 2212
<400> SEQUENCE: 2212
000

<210> SEQ ID NO 2213
<400> SEQUENCE: 2213
000

<210> SEQ ID NO 2214
<400> SEQUENCE: 2214
000

<210> SEQ ID NO 2215
<400> SEQUENCE: 2215
000

<210> SEQ ID NO 2216
<400> SEQUENCE: 2216
000

<210> SEQ ID NO 2217
<400> SEQUENCE: 2217
000

<210> SEQ ID NO 2218
<400> SEQUENCE: 2218
000

<210> SEQ ID NO 2219
<400> SEQUENCE: 2219
000

<210> SEQ ID NO 2220
<400> SEQUENCE: 2220
000

<210> SEQ ID NO 2221
<400> SEQUENCE: 2221
000

<210> SEQ ID NO 2222
<400> SEQUENCE: 2222
```

000

<210> SEQ ID NO 2223

<400> SEQUENCE: 2223

000

<210> SEQ ID NO 2224

<400> SEQUENCE: 2224

000

<210> SEQ ID NO 2225

<400> SEQUENCE: 2225

000

<210> SEQ ID NO 2226

<400> SEQUENCE: 2226

000

<210> SEQ ID NO 2227

<400> SEQUENCE: 2227

000

<210> SEQ ID NO 2228

<400> SEQUENCE: 2228

000

<210> SEQ ID NO 2229

<400> SEQUENCE: 2229

000

<210> SEQ ID NO 2230

<400> SEQUENCE: 2230

000

<210> SEQ ID NO 2231

<400> SEQUENCE: 2231

000

<210> SEQ ID NO 2232

<400> SEQUENCE: 2232

000

<210> SEQ ID NO 2233

<400> SEQUENCE: 2233

000

<210> SEQ ID NO 2234

<400> SEQUENCE: 2234

000

<210> SEQ ID NO 2235

<400> SEQUENCE: 2235

000

<210> SEQ ID NO 2236

<400> SEQUENCE: 2236

000

<210> SEQ ID NO 2237

<400> SEQUENCE: 2237

000

<210> SEQ ID NO 2238

<400> SEQUENCE: 2238

000

<210> SEQ ID NO 2239

<400> SEQUENCE: 2239

000

<210> SEQ ID NO 2240

<400> SEQUENCE: 2240

000

<210> SEQ ID NO 2241

<400> SEQUENCE: 2241

000

<210> SEQ ID NO 2242

<400> SEQUENCE: 2242

000

<210> SEQ ID NO 2243

<400> SEQUENCE: 2243

000

<210> SEQ ID NO 2244

<400> SEQUENCE: 2244

000

<210> SEQ ID NO 2245

```
<400> SEQUENCE: 2245
000

<210> SEQ ID NO 2246
<400> SEQUENCE: 2246
000

<210> SEQ ID NO 2247
<400> SEQUENCE: 2247
000

<210> SEQ ID NO 2248
<400> SEQUENCE: 2248
000

<210> SEQ ID NO 2249
<400> SEQUENCE: 2249
000

<210> SEQ ID NO 2250
<400> SEQUENCE: 2250
000

<210> SEQ ID NO 2251
<400> SEQUENCE: 2251
000

<210> SEQ ID NO 2252
<400> SEQUENCE: 2252
000

<210> SEQ ID NO 2253
<400> SEQUENCE: 2253
000

<210> SEQ ID NO 2254
<400> SEQUENCE: 2254
000

<210> SEQ ID NO 2255
<400> SEQUENCE: 2255
000

<210> SEQ ID NO 2256
<400> SEQUENCE: 2256
```

000

<210> SEQ ID NO 2257

<400> SEQUENCE: 2257

000

<210> SEQ ID NO 2258

<400> SEQUENCE: 2258

000

<210> SEQ ID NO 2259

<400> SEQUENCE: 2259

000

<210> SEQ ID NO 2260

<400> SEQUENCE: 2260

000

<210> SEQ ID NO 2261

<400> SEQUENCE: 2261

000

<210> SEQ ID NO 2262

<400> SEQUENCE: 2262

000

<210> SEQ ID NO 2263

<400> SEQUENCE: 2263

000

<210> SEQ ID NO 2264

<400> SEQUENCE: 2264

000

<210> SEQ ID NO 2265

<400> SEQUENCE: 2265

000

<210> SEQ ID NO 2266

<400> SEQUENCE: 2266

000

<210> SEQ ID NO 2267

<400> SEQUENCE: 2267

000

<210> SEQ ID NO 2268

<400> SEQUENCE: 2268

000

<210> SEQ ID NO 2269

<400> SEQUENCE: 2269

000

<210> SEQ ID NO 2270

<400> SEQUENCE: 2270

000

<210> SEQ ID NO 2271

<400> SEQUENCE: 2271

000

<210> SEQ ID NO 2272

<400> SEQUENCE: 2272

000

<210> SEQ ID NO 2273

<400> SEQUENCE: 2273

000

<210> SEQ ID NO 2274

<400> SEQUENCE: 2274

000

<210> SEQ ID NO 2275

<400> SEQUENCE: 2275

000

<210> SEQ ID NO 2276

<400> SEQUENCE: 2276

000

<210> SEQ ID NO 2277

<400> SEQUENCE: 2277

000

<210> SEQ ID NO 2278

<400> SEQUENCE: 2278

000

-continued

<210> SEQ ID NO 2279

<400> SEQUENCE: 2279

000

<210> SEQ ID NO 2280

<400> SEQUENCE: 2280

000

<210> SEQ ID NO 2281

<400> SEQUENCE: 2281

000

<210> SEQ ID NO 2282

<400> SEQUENCE: 2282

000

<210> SEQ ID NO 2283

<400> SEQUENCE: 2283

000

<210> SEQ ID NO 2284

<400> SEQUENCE: 2284

000

<210> SEQ ID NO 2285

<400> SEQUENCE: 2285

000

<210> SEQ ID NO 2286

<400> SEQUENCE: 2286

000

<210> SEQ ID NO 2287

<400> SEQUENCE: 2287

000

<210> SEQ ID NO 2288

<400> SEQUENCE: 2288

000

<210> SEQ ID NO 2289

<400> SEQUENCE: 2289

000

<210> SEQ ID NO 2290

```
<400> SEQUENCE: 2290

000

<210> SEQ ID NO 2291

<400> SEQUENCE: 2291

000

<210> SEQ ID NO 2292

<400> SEQUENCE: 2292

000

<210> SEQ ID NO 2293

<400> SEQUENCE: 2293

000

<210> SEQ ID NO 2294

<400> SEQUENCE: 2294

000

<210> SEQ ID NO 2295

<400> SEQUENCE: 2295

000

<210> SEQ ID NO 2296

<400> SEQUENCE: 2296

000

<210> SEQ ID NO 2297

<400> SEQUENCE: 2297

000

<210> SEQ ID NO 2298

<400> SEQUENCE: 2298

000

<210> SEQ ID NO 2299

<400> SEQUENCE: 2299

000

<210> SEQ ID NO 2300

<400> SEQUENCE: 2300

000

<210> SEQ ID NO 2301

<400> SEQUENCE: 2301
```

000

<210> SEQ ID NO 2302

<400> SEQUENCE: 2302

000

<210> SEQ ID NO 2303

<400> SEQUENCE: 2303

000

<210> SEQ ID NO 2304

<400> SEQUENCE: 2304

000

<210> SEQ ID NO 2305

<400> SEQUENCE: 2305

000

<210> SEQ ID NO 2306

<400> SEQUENCE: 2306

000

<210> SEQ ID NO 2307

<400> SEQUENCE: 2307

000

<210> SEQ ID NO 2308

<400> SEQUENCE: 2308

000

<210> SEQ ID NO 2309

<400> SEQUENCE: 2309

000

<210> SEQ ID NO 2310

<400> SEQUENCE: 2310

000

<210> SEQ ID NO 2311

<400> SEQUENCE: 2311

000

<210> SEQ ID NO 2312

<400> SEQUENCE: 2312

000

-continued

<210> SEQ ID NO 2313

<400> SEQUENCE: 2313

000

<210> SEQ ID NO 2314

<400> SEQUENCE: 2314

000

<210> SEQ ID NO 2315

<400> SEQUENCE: 2315

000

<210> SEQ ID NO 2316

<400> SEQUENCE: 2316

000

<210> SEQ ID NO 2317

<400> SEQUENCE: 2317

000

<210> SEQ ID NO 2318

<400> SEQUENCE: 2318

000

<210> SEQ ID NO 2319

<400> SEQUENCE: 2319

000

<210> SEQ ID NO 2320

<400> SEQUENCE: 2320

000

<210> SEQ ID NO 2321

<400> SEQUENCE: 2321

000

<210> SEQ ID NO 2322

<400> SEQUENCE: 2322

000

<210> SEQ ID NO 2323

<400> SEQUENCE: 2323

000

<210> SEQ ID NO 2324

<400> SEQUENCE: 2324

000

<210> SEQ ID NO 2325

<400> SEQUENCE: 2325

000

<210> SEQ ID NO 2326

<400> SEQUENCE: 2326

000

<210> SEQ ID NO 2327

<400> SEQUENCE: 2327

000

<210> SEQ ID NO 2328

<400> SEQUENCE: 2328

000

<210> SEQ ID NO 2329

<400> SEQUENCE: 2329

000

<210> SEQ ID NO 2330

<400> SEQUENCE: 2330

000

<210> SEQ ID NO 2331

<400> SEQUENCE: 2331

000

<210> SEQ ID NO 2332

<400> SEQUENCE: 2332

000

<210> SEQ ID NO 2333

<400> SEQUENCE: 2333

000

<210> SEQ ID NO 2334

<400> SEQUENCE: 2334

000

<210> SEQ ID NO 2335

<400> SEQUENCE: 2335

000

<210> SEQ ID NO 2336

<400> SEQUENCE: 2336

000

<210> SEQ ID NO 2337

<400> SEQUENCE: 2337

000

<210> SEQ ID NO 2338

<400> SEQUENCE: 2338

000

<210> SEQ ID NO 2339

<400> SEQUENCE: 2339

000

<210> SEQ ID NO 2340

<400> SEQUENCE: 2340

000

<210> SEQ ID NO 2341

<400> SEQUENCE: 2341

000

<210> SEQ ID NO 2342

<400> SEQUENCE: 2342

000

<210> SEQ ID NO 2343

<400> SEQUENCE: 2343

000

<210> SEQ ID NO 2344

<400> SEQUENCE: 2344

000

<210> SEQ ID NO 2345

<400> SEQUENCE: 2345

000

<210> SEQ ID NO 2346

<400> SEQUENCE: 2346

000

<210> SEQ ID NO 2347

<400> SEQUENCE: 2347

000

<210> SEQ ID NO 2348

<400> SEQUENCE: 2348

000

<210> SEQ ID NO 2349

<400> SEQUENCE: 2349

000

<210> SEQ ID NO 2350

<400> SEQUENCE: 2350

000

<210> SEQ ID NO 2351

<400> SEQUENCE: 2351

000

<210> SEQ ID NO 2352

<400> SEQUENCE: 2352

000

<210> SEQ ID NO 2353

<400> SEQUENCE: 2353

000

<210> SEQ ID NO 2354

<400> SEQUENCE: 2354

000

<210> SEQ ID NO 2355

<400> SEQUENCE: 2355

000

<210> SEQ ID NO 2356

<400> SEQUENCE: 2356

000

<210> SEQ ID NO 2357

<400> SEQUENCE: 2357

000

```
<210> SEQ ID NO 2358
<400> SEQUENCE: 2358
000

<210> SEQ ID NO 2359
<400> SEQUENCE: 2359
000

<210> SEQ ID NO 2360
<400> SEQUENCE: 2360
000

<210> SEQ ID NO 2361
<400> SEQUENCE: 2361
000

<210> SEQ ID NO 2362
<400> SEQUENCE: 2362
000

<210> SEQ ID NO 2363
<400> SEQUENCE: 2363
000

<210> SEQ ID NO 2364
<400> SEQUENCE: 2364
000

<210> SEQ ID NO 2365
<400> SEQUENCE: 2365
000

<210> SEQ ID NO 2366
<400> SEQUENCE: 2366
000

<210> SEQ ID NO 2367
<400> SEQUENCE: 2367
000

<210> SEQ ID NO 2368
<400> SEQUENCE: 2368
000

<210> SEQ ID NO 2369
```

<400> SEQUENCE: 2369

000

<210> SEQ ID NO 2370

<400> SEQUENCE: 2370

000

<210> SEQ ID NO 2371

<400> SEQUENCE: 2371

000

<210> SEQ ID NO 2372

<400> SEQUENCE: 2372

000

<210> SEQ ID NO 2373

<400> SEQUENCE: 2373

000

<210> SEQ ID NO 2374

<400> SEQUENCE: 2374

000

<210> SEQ ID NO 2375

<400> SEQUENCE: 2375

000

<210> SEQ ID NO 2376

<400> SEQUENCE: 2376

000

<210> SEQ ID NO 2377

<400> SEQUENCE: 2377

000

<210> SEQ ID NO 2378

<400> SEQUENCE: 2378

000

<210> SEQ ID NO 2379

<400> SEQUENCE: 2379

000

<210> SEQ ID NO 2380

<400> SEQUENCE: 2380

000

<210> SEQ ID NO 2381

<400> SEQUENCE: 2381

000

<210> SEQ ID NO 2382

<400> SEQUENCE: 2382

000

<210> SEQ ID NO 2383

<400> SEQUENCE: 2383

000

<210> SEQ ID NO 2384

<400> SEQUENCE: 2384

000

<210> SEQ ID NO 2385

<400> SEQUENCE: 2385

000

<210> SEQ ID NO 2386

<400> SEQUENCE: 2386

000

<210> SEQ ID NO 2387

<400> SEQUENCE: 2387

000

<210> SEQ ID NO 2388

<400> SEQUENCE: 2388

000

<210> SEQ ID NO 2389

<400> SEQUENCE: 2389

000

<210> SEQ ID NO 2390

<400> SEQUENCE: 2390

000

<210> SEQ ID NO 2391

<400> SEQUENCE: 2391

000

<210> SEQ ID NO 2392

<400> SEQUENCE: 2392

000

<210> SEQ ID NO 2393

<400> SEQUENCE: 2393

000

<210> SEQ ID NO 2394

<400> SEQUENCE: 2394

000

<210> SEQ ID NO 2395

<400> SEQUENCE: 2395

000

<210> SEQ ID NO 2396

<400> SEQUENCE: 2396

000

<210> SEQ ID NO 2397

<400> SEQUENCE: 2397

000

<210> SEQ ID NO 2398

<400> SEQUENCE: 2398

000

<210> SEQ ID NO 2399

<400> SEQUENCE: 2399

000

<210> SEQ ID NO 2400

<400> SEQUENCE: 2400

000

<210> SEQ ID NO 2401

<400> SEQUENCE: 2401

000

<210> SEQ ID NO 2402

<400> SEQUENCE: 2402

000

<210> SEQ ID NO 2403

-continued

<400> SEQUENCE: 2403

000

<210> SEQ ID NO 2404

<400> SEQUENCE: 2404

000

<210> SEQ ID NO 2405

<400> SEQUENCE: 2405

000

<210> SEQ ID NO 2406

<400> SEQUENCE: 2406

000

<210> SEQ ID NO 2407

<400> SEQUENCE: 2407

000

<210> SEQ ID NO 2408

<400> SEQUENCE: 2408

000

<210> SEQ ID NO 2409

<400> SEQUENCE: 2409

000

<210> SEQ ID NO 2410

<400> SEQUENCE: 2410

000

<210> SEQ ID NO 2411

<400> SEQUENCE: 2411

000

<210> SEQ ID NO 2412

<400> SEQUENCE: 2412

000

<210> SEQ ID NO 2413

<400> SEQUENCE: 2413

000

<210> SEQ ID NO 2414

<400> SEQUENCE: 2414

000

<210> SEQ ID NO 2415

<400> SEQUENCE: 2415

000

<210> SEQ ID NO 2416

<400> SEQUENCE: 2416

000

<210> SEQ ID NO 2417

<400> SEQUENCE: 2417

000

<210> SEQ ID NO 2418

<400> SEQUENCE: 2418

000

<210> SEQ ID NO 2419

<400> SEQUENCE: 2419

000

<210> SEQ ID NO 2420

<400> SEQUENCE: 2420

000

<210> SEQ ID NO 2421

<400> SEQUENCE: 2421

000

<210> SEQ ID NO 2422

<400> SEQUENCE: 2422

000

<210> SEQ ID NO 2423

<400> SEQUENCE: 2423

000

<210> SEQ ID NO 2424

<400> SEQUENCE: 2424

000

<210> SEQ ID NO 2425

<400> SEQUENCE: 2425

000

<210> SEQ ID NO 2426

<400> SEQUENCE: 2426

000

<210> SEQ ID NO 2427

<400> SEQUENCE: 2427

000

<210> SEQ ID NO 2428

<400> SEQUENCE: 2428

000

<210> SEQ ID NO 2429

<400> SEQUENCE: 2429

000

<210> SEQ ID NO 2430

<400> SEQUENCE: 2430

000

<210> SEQ ID NO 2431

<400> SEQUENCE: 2431

000

<210> SEQ ID NO 2432

<400> SEQUENCE: 2432

000

<210> SEQ ID NO 2433

<400> SEQUENCE: 2433

000

<210> SEQ ID NO 2434

<400> SEQUENCE: 2434

000

<210> SEQ ID NO 2435

<400> SEQUENCE: 2435

000

<210> SEQ ID NO 2436

<400> SEQUENCE: 2436

000

<210> SEQ ID NO 2437

<400> SEQUENCE: 2437

000

<210> SEQ ID NO 2438

<400> SEQUENCE: 2438

000

<210> SEQ ID NO 2439

<400> SEQUENCE: 2439

000

<210> SEQ ID NO 2440

<400> SEQUENCE: 2440

000

<210> SEQ ID NO 2441

<400> SEQUENCE: 2441

000

<210> SEQ ID NO 2442

<400> SEQUENCE: 2442

000

<210> SEQ ID NO 2443

<400> SEQUENCE: 2443

000

<210> SEQ ID NO 2444

<400> SEQUENCE: 2444

000

<210> SEQ ID NO 2445

<400> SEQUENCE: 2445

000

<210> SEQ ID NO 2446

<400> SEQUENCE: 2446

000

<210> SEQ ID NO 2447

<400> SEQUENCE: 2447

000

<210> SEQ ID NO 2448

```
<400> SEQUENCE: 2448

000

<210> SEQ ID NO 2449

<400> SEQUENCE: 2449

000

<210> SEQ ID NO 2450

<400> SEQUENCE: 2450

000

<210> SEQ ID NO 2451

<400> SEQUENCE: 2451

000

<210> SEQ ID NO 2452

<400> SEQUENCE: 2452

000

<210> SEQ ID NO 2453

<400> SEQUENCE: 2453

000

<210> SEQ ID NO 2454

<400> SEQUENCE: 2454

000

<210> SEQ ID NO 2455

<400> SEQUENCE: 2455

000

<210> SEQ ID NO 2456

<400> SEQUENCE: 2456

000

<210> SEQ ID NO 2457

<400> SEQUENCE: 2457

000

<210> SEQ ID NO 2458

<400> SEQUENCE: 2458

000

<210> SEQ ID NO 2459

<400> SEQUENCE: 2459
```

000

<210> SEQ ID NO 2460
<400> SEQUENCE: 2460
000

<210> SEQ ID NO 2461
<400> SEQUENCE: 2461
000

<210> SEQ ID NO 2462
<400> SEQUENCE: 2462
000

<210> SEQ ID NO 2463
<400> SEQUENCE: 2463
000

<210> SEQ ID NO 2464
<400> SEQUENCE: 2464
000

<210> SEQ ID NO 2465
<400> SEQUENCE: 2465
000

<210> SEQ ID NO 2466
<400> SEQUENCE: 2466
000

<210> SEQ ID NO 2467
<400> SEQUENCE: 2467
000

<210> SEQ ID NO 2468
<400> SEQUENCE: 2468
000

<210> SEQ ID NO 2469
<400> SEQUENCE: 2469
000

<210> SEQ ID NO 2470
<400> SEQUENCE: 2470
000

<210> SEQ ID NO 2471

<400> SEQUENCE: 2471

000

<210> SEQ ID NO 2472

<400> SEQUENCE: 2472

000

<210> SEQ ID NO 2473

<400> SEQUENCE: 2473

000

<210> SEQ ID NO 2474

<400> SEQUENCE: 2474

000

<210> SEQ ID NO 2475

<400> SEQUENCE: 2475

000

<210> SEQ ID NO 2476

<400> SEQUENCE: 2476

000

<210> SEQ ID NO 2477

<400> SEQUENCE: 2477

000

<210> SEQ ID NO 2478

<400> SEQUENCE: 2478

000

<210> SEQ ID NO 2479

<400> SEQUENCE: 2479

000

<210> SEQ ID NO 2480

<400> SEQUENCE: 2480

000

<210> SEQ ID NO 2481

<400> SEQUENCE: 2481

000

<210> SEQ ID NO 2482

-continued

<400> SEQUENCE: 2482

000

<210> SEQ ID NO 2483

<400> SEQUENCE: 2483

000

<210> SEQ ID NO 2484

<400> SEQUENCE: 2484

000

<210> SEQ ID NO 2485

<400> SEQUENCE: 2485

000

<210> SEQ ID NO 2486

<400> SEQUENCE: 2486

000

<210> SEQ ID NO 2487

<400> SEQUENCE: 2487

000

<210> SEQ ID NO 2488

<400> SEQUENCE: 2488

000

<210> SEQ ID NO 2489

<400> SEQUENCE: 2489

000

<210> SEQ ID NO 2490

<400> SEQUENCE: 2490

000

<210> SEQ ID NO 2491

<400> SEQUENCE: 2491

000

<210> SEQ ID NO 2492

<400> SEQUENCE: 2492

000

<210> SEQ ID NO 2493

<400> SEQUENCE: 2493

000

<210> SEQ ID NO 2494

<400> SEQUENCE: 2494

000

<210> SEQ ID NO 2495

<400> SEQUENCE: 2495

000

<210> SEQ ID NO 2496

<400> SEQUENCE: 2496

000

<210> SEQ ID NO 2497

<400> SEQUENCE: 2497

000

<210> SEQ ID NO 2498

<400> SEQUENCE: 2498

000

<210> SEQ ID NO 2499

<400> SEQUENCE: 2499

000

<210> SEQ ID NO 2500

<400> SEQUENCE: 2500

000

<210> SEQ ID NO 2501

<400> SEQUENCE: 2501

000

<210> SEQ ID NO 2502

<400> SEQUENCE: 2502

000

<210> SEQ ID NO 2503

<400> SEQUENCE: 2503

000

<210> SEQ ID NO 2504

<400> SEQUENCE: 2504

000

<210> SEQ ID NO 2505

<400> SEQUENCE: 2505

000

<210> SEQ ID NO 2506

<400> SEQUENCE: 2506

000

<210> SEQ ID NO 2507

<400> SEQUENCE: 2507

000

<210> SEQ ID NO 2508

<400> SEQUENCE: 2508

000

<210> SEQ ID NO 2509

<400> SEQUENCE: 2509

000

<210> SEQ ID NO 2510

<400> SEQUENCE: 2510

000

<210> SEQ ID NO 2511

<400> SEQUENCE: 2511

000

<210> SEQ ID NO 2512

<400> SEQUENCE: 2512

000

<210> SEQ ID NO 2513

<400> SEQUENCE: 2513

000

<210> SEQ ID NO 2514

<400> SEQUENCE: 2514

000

<210> SEQ ID NO 2515

<400> SEQUENCE: 2515

000

<210> SEQ ID NO 2516

<400> SEQUENCE: 2516

000

<210> SEQ ID NO 2517

<400> SEQUENCE: 2517

000

<210> SEQ ID NO 2518

<400> SEQUENCE: 2518

000

<210> SEQ ID NO 2519

<400> SEQUENCE: 2519

000

<210> SEQ ID NO 2520

<400> SEQUENCE: 2520

000

<210> SEQ ID NO 2521

<400> SEQUENCE: 2521

000

<210> SEQ ID NO 2522

<400> SEQUENCE: 2522

000

<210> SEQ ID NO 2523

<400> SEQUENCE: 2523

000

<210> SEQ ID NO 2524

<400> SEQUENCE: 2524

000

<210> SEQ ID NO 2525

<400> SEQUENCE: 2525

000

<210> SEQ ID NO 2526

<400> SEQUENCE: 2526

000

<210> SEQ ID NO 2527

```
<400> SEQUENCE: 2527
000

<210> SEQ ID NO 2528
<400> SEQUENCE: 2528
000

<210> SEQ ID NO 2529
<400> SEQUENCE: 2529
000

<210> SEQ ID NO 2530
<400> SEQUENCE: 2530
000

<210> SEQ ID NO 2531
<400> SEQUENCE: 2531
000

<210> SEQ ID NO 2532
<400> SEQUENCE: 2532
000

<210> SEQ ID NO 2533
<400> SEQUENCE: 2533
000

<210> SEQ ID NO 2534
<400> SEQUENCE: 2534
000

<210> SEQ ID NO 2535
<400> SEQUENCE: 2535
000

<210> SEQ ID NO 2536
<400> SEQUENCE: 2536
000

<210> SEQ ID NO 2537
<400> SEQUENCE: 2537
000

<210> SEQ ID NO 2538
<400> SEQUENCE: 2538
```

000

<210> SEQ ID NO 2539

<400> SEQUENCE: 2539

000

<210> SEQ ID NO 2540

<400> SEQUENCE: 2540

000

<210> SEQ ID NO 2541

<400> SEQUENCE: 2541

000

<210> SEQ ID NO 2542

<400> SEQUENCE: 2542

000

<210> SEQ ID NO 2543

<400> SEQUENCE: 2543

000

<210> SEQ ID NO 2544

<400> SEQUENCE: 2544

000

<210> SEQ ID NO 2545

<400> SEQUENCE: 2545

000

<210> SEQ ID NO 2546

<400> SEQUENCE: 2546

000

<210> SEQ ID NO 2547

<400> SEQUENCE: 2547

000

<210> SEQ ID NO 2548

<400> SEQUENCE: 2548

000

<210> SEQ ID NO 2549

<400> SEQUENCE: 2549

000

```
<210> SEQ ID NO 2550
<400> SEQUENCE: 2550
000

<210> SEQ ID NO 2551
<400> SEQUENCE: 2551
000

<210> SEQ ID NO 2552
<400> SEQUENCE: 2552
000

<210> SEQ ID NO 2553
<400> SEQUENCE: 2553
000

<210> SEQ ID NO 2554
<400> SEQUENCE: 2554
000

<210> SEQ ID NO 2555
<400> SEQUENCE: 2555
000

<210> SEQ ID NO 2556
<400> SEQUENCE: 2556
000

<210> SEQ ID NO 2557
<400> SEQUENCE: 2557
000

<210> SEQ ID NO 2558
<400> SEQUENCE: 2558
000

<210> SEQ ID NO 2559
<400> SEQUENCE: 2559
000

<210> SEQ ID NO 2560
<400> SEQUENCE: 2560
000

<210> SEQ ID NO 2561
```

<400> SEQUENCE: 2561

000

<210> SEQ ID NO 2562

<400> SEQUENCE: 2562

000

<210> SEQ ID NO 2563

<400> SEQUENCE: 2563

000

<210> SEQ ID NO 2564

<400> SEQUENCE: 2564

000

<210> SEQ ID NO 2565

<400> SEQUENCE: 2565

000

<210> SEQ ID NO 2566

<400> SEQUENCE: 2566

000

<210> SEQ ID NO 2567

<400> SEQUENCE: 2567

000

<210> SEQ ID NO 2568

<400> SEQUENCE: 2568

000

<210> SEQ ID NO 2569

<400> SEQUENCE: 2569

000

<210> SEQ ID NO 2570

<400> SEQUENCE: 2570

000

<210> SEQ ID NO 2571

<400> SEQUENCE: 2571

000

<210> SEQ ID NO 2572

<400> SEQUENCE: 2572

000

<210> SEQ ID NO 2573

<400> SEQUENCE: 2573

000

<210> SEQ ID NO 2574

<400> SEQUENCE: 2574

000

<210> SEQ ID NO 2575

<400> SEQUENCE: 2575

000

<210> SEQ ID NO 2576

<400> SEQUENCE: 2576

000

<210> SEQ ID NO 2577

<400> SEQUENCE: 2577

000

<210> SEQ ID NO 2578

<400> SEQUENCE: 2578

000

<210> SEQ ID NO 2579

<400> SEQUENCE: 2579

000

<210> SEQ ID NO 2580

<400> SEQUENCE: 2580

000

<210> SEQ ID NO 2581

<400> SEQUENCE: 2581

000

<210> SEQ ID NO 2582

<400> SEQUENCE: 2582

000

<210> SEQ ID NO 2583

<400> SEQUENCE: 2583

000

<210> SEQ ID NO 2584

<400> SEQUENCE: 2584

000

<210> SEQ ID NO 2585

<400> SEQUENCE: 2585

000

<210> SEQ ID NO 2586

<400> SEQUENCE: 2586

000

<210> SEQ ID NO 2587

<400> SEQUENCE: 2587

000

<210> SEQ ID NO 2588

<400> SEQUENCE: 2588

000

<210> SEQ ID NO 2589

<400> SEQUENCE: 2589

000

<210> SEQ ID NO 2590

<400> SEQUENCE: 2590

000

<210> SEQ ID NO 2591

<400> SEQUENCE: 2591

000

<210> SEQ ID NO 2592

<400> SEQUENCE: 2592

000

<210> SEQ ID NO 2593

<400> SEQUENCE: 2593

000

<210> SEQ ID NO 2594

<400> SEQUENCE: 2594

000

<210> SEQ ID NO 2595

<400> SEQUENCE: 2595

000

<210> SEQ ID NO 2596

<400> SEQUENCE: 2596

000

<210> SEQ ID NO 2597

<400> SEQUENCE: 2597

000

<210> SEQ ID NO 2598

<400> SEQUENCE: 2598

000

<210> SEQ ID NO 2599

<400> SEQUENCE: 2599

000

<210> SEQ ID NO 2600

<400> SEQUENCE: 2600

000

<210> SEQ ID NO 2601

<400> SEQUENCE: 2601

000

<210> SEQ ID NO 2602

<400> SEQUENCE: 2602

000

<210> SEQ ID NO 2603

<400> SEQUENCE: 2603

000

<210> SEQ ID NO 2604

<400> SEQUENCE: 2604

000

<210> SEQ ID NO 2605

<400> SEQUENCE: 2605

000

<210> SEQ ID NO 2606

```
<400> SEQUENCE: 2606
000

<210> SEQ ID NO 2607
<400> SEQUENCE: 2607
000

<210> SEQ ID NO 2608
<400> SEQUENCE: 2608
000

<210> SEQ ID NO 2609
<400> SEQUENCE: 2609
000

<210> SEQ ID NO 2610
<400> SEQUENCE: 2610
000

<210> SEQ ID NO 2611
<400> SEQUENCE: 2611
000

<210> SEQ ID NO 2612
<400> SEQUENCE: 2612
000

<210> SEQ ID NO 2613
<400> SEQUENCE: 2613
000

<210> SEQ ID NO 2614
<400> SEQUENCE: 2614
000

<210> SEQ ID NO 2615
<400> SEQUENCE: 2615
000

<210> SEQ ID NO 2616
<400> SEQUENCE: 2616
000

<210> SEQ ID NO 2617
<400> SEQUENCE: 2617
```

000

<210> SEQ ID NO 2618

<400> SEQUENCE: 2618

000

<210> SEQ ID NO 2619

<400> SEQUENCE: 2619

000

<210> SEQ ID NO 2620

<400> SEQUENCE: 2620

000

<210> SEQ ID NO 2621

<400> SEQUENCE: 2621

000

<210> SEQ ID NO 2622

<400> SEQUENCE: 2622

000

<210> SEQ ID NO 2623

<400> SEQUENCE: 2623

000

<210> SEQ ID NO 2624

<400> SEQUENCE: 2624

000

<210> SEQ ID NO 2625

<400> SEQUENCE: 2625

000

<210> SEQ ID NO 2626

<400> SEQUENCE: 2626

000

<210> SEQ ID NO 2627

<400> SEQUENCE: 2627

000

<210> SEQ ID NO 2628

<400> SEQUENCE: 2628

000

<210> SEQ ID NO 2629

<400> SEQUENCE: 2629

000

<210> SEQ ID NO 2630

<400> SEQUENCE: 2630

000

<210> SEQ ID NO 2631

<400> SEQUENCE: 2631

000

<210> SEQ ID NO 2632

<400> SEQUENCE: 2632

000

<210> SEQ ID NO 2633

<400> SEQUENCE: 2633

000

<210> SEQ ID NO 2634

<400> SEQUENCE: 2634

000

<210> SEQ ID NO 2635

<400> SEQUENCE: 2635

000

<210> SEQ ID NO 2636

<400> SEQUENCE: 2636

000

<210> SEQ ID NO 2637

<400> SEQUENCE: 2637

000

<210> SEQ ID NO 2638

<400> SEQUENCE: 2638

000

<210> SEQ ID NO 2639

<400> SEQUENCE: 2639

000

<210> SEQ ID NO 2640

<400> SEQUENCE: 2640

000

<210> SEQ ID NO 2641

<400> SEQUENCE: 2641

000

<210> SEQ ID NO 2642

<400> SEQUENCE: 2642

000

<210> SEQ ID NO 2643

<400> SEQUENCE: 2643

000

<210> SEQ ID NO 2644

<400> SEQUENCE: 2644

000

<210> SEQ ID NO 2645

<400> SEQUENCE: 2645

000

<210> SEQ ID NO 2646

<400> SEQUENCE: 2646

000

<210> SEQ ID NO 2647

<400> SEQUENCE: 2647

000

<210> SEQ ID NO 2648

<400> SEQUENCE: 2648

000

<210> SEQ ID NO 2649

<400> SEQUENCE: 2649

000

<210> SEQ ID NO 2650

<400> SEQUENCE: 2650

000

<210> SEQ ID NO 2651

<400> SEQUENCE: 2651

000

<210> SEQ ID NO 2652

<400> SEQUENCE: 2652

000

<210> SEQ ID NO 2653

<400> SEQUENCE: 2653

000

<210> SEQ ID NO 2654

<400> SEQUENCE: 2654

000

<210> SEQ ID NO 2655

<400> SEQUENCE: 2655

000

<210> SEQ ID NO 2656

<400> SEQUENCE: 2656

000

<210> SEQ ID NO 2657

<400> SEQUENCE: 2657

000

<210> SEQ ID NO 2658

<400> SEQUENCE: 2658

000

<210> SEQ ID NO 2659

<400> SEQUENCE: 2659

000

<210> SEQ ID NO 2660

<400> SEQUENCE: 2660

000

<210> SEQ ID NO 2661

<400> SEQUENCE: 2661

000

<210> SEQ ID NO 2662

<400> SEQUENCE: 2662

000

<210> SEQ ID NO 2663

<400> SEQUENCE: 2663

000

<210> SEQ ID NO 2664

<400> SEQUENCE: 2664

000

<210> SEQ ID NO 2665

<400> SEQUENCE: 2665

000

<210> SEQ ID NO 2666

<400> SEQUENCE: 2666

000

<210> SEQ ID NO 2667

<400> SEQUENCE: 2667

000

<210> SEQ ID NO 2668

<400> SEQUENCE: 2668

000

<210> SEQ ID NO 2669

<400> SEQUENCE: 2669

000

<210> SEQ ID NO 2670

<400> SEQUENCE: 2670

000

<210> SEQ ID NO 2671

<400> SEQUENCE: 2671

000

<210> SEQ ID NO 2672

<400> SEQUENCE: 2672

000

<210> SEQ ID NO 2673

<400> SEQUENCE: 2673

000

```
<210> SEQ ID NO 2674
<400> SEQUENCE: 2674
000

<210> SEQ ID NO 2675
<400> SEQUENCE: 2675
000

<210> SEQ ID NO 2676
<400> SEQUENCE: 2676
000

<210> SEQ ID NO 2677
<400> SEQUENCE: 2677
000

<210> SEQ ID NO 2678
<400> SEQUENCE: 2678
000

<210> SEQ ID NO 2679
<400> SEQUENCE: 2679
000

<210> SEQ ID NO 2680
<400> SEQUENCE: 2680
000

<210> SEQ ID NO 2681
<400> SEQUENCE: 2681
000

<210> SEQ ID NO 2682
<400> SEQUENCE: 2682
000

<210> SEQ ID NO 2683
<400> SEQUENCE: 2683
000

<210> SEQ ID NO 2684
<400> SEQUENCE: 2684
000

<210> SEQ ID NO 2685
```

<400> SEQUENCE: 2685

000

<210> SEQ ID NO 2686

<400> SEQUENCE: 2686

000

<210> SEQ ID NO 2687

<400> SEQUENCE: 2687

000

<210> SEQ ID NO 2688

<400> SEQUENCE: 2688

000

<210> SEQ ID NO 2689

<400> SEQUENCE: 2689

000

<210> SEQ ID NO 2690

<400> SEQUENCE: 2690

000

<210> SEQ ID NO 2691

<400> SEQUENCE: 2691

000

<210> SEQ ID NO 2692

<400> SEQUENCE: 2692

000

<210> SEQ ID NO 2693

<400> SEQUENCE: 2693

000

<210> SEQ ID NO 2694

<400> SEQUENCE: 2694

000

<210> SEQ ID NO 2695

<400> SEQUENCE: 2695

000

<210> SEQ ID NO 2696

<400> SEQUENCE: 2696

000

<210> SEQ ID NO 2697

<400> SEQUENCE: 2697

000

<210> SEQ ID NO 2698

<400> SEQUENCE: 2698

000

<210> SEQ ID NO 2699

<400> SEQUENCE: 2699

000

<210> SEQ ID NO 2700

<400> SEQUENCE: 2700

000

<210> SEQ ID NO 2701

<400> SEQUENCE: 2701

000

<210> SEQ ID NO 2702

<400> SEQUENCE: 2702

000

<210> SEQ ID NO 2703

<400> SEQUENCE: 2703

000

<210> SEQ ID NO 2704

<400> SEQUENCE: 2704

000

<210> SEQ ID NO 2705

<400> SEQUENCE: 2705

000

<210> SEQ ID NO 2706

<400> SEQUENCE: 2706

000

<210> SEQ ID NO 2707

<400> SEQUENCE: 2707

000

```
<210> SEQ ID NO 2708
<400> SEQUENCE: 2708
000

<210> SEQ ID NO 2709
<400> SEQUENCE: 2709
000

<210> SEQ ID NO 2710
<400> SEQUENCE: 2710
000

<210> SEQ ID NO 2711
<400> SEQUENCE: 2711
000

<210> SEQ ID NO 2712
<400> SEQUENCE: 2712
000

<210> SEQ ID NO 2713
<400> SEQUENCE: 2713
000

<210> SEQ ID NO 2714
<400> SEQUENCE: 2714
000

<210> SEQ ID NO 2715
<400> SEQUENCE: 2715
000

<210> SEQ ID NO 2716
<400> SEQUENCE: 2716
000

<210> SEQ ID NO 2717
<400> SEQUENCE: 2717
000

<210> SEQ ID NO 2718
<400> SEQUENCE: 2718
000

<210> SEQ ID NO 2719
```

```
<400> SEQUENCE: 2719

000

<210> SEQ ID NO 2720

<400> SEQUENCE: 2720

000

<210> SEQ ID NO 2721

<400> SEQUENCE: 2721

000

<210> SEQ ID NO 2722

<400> SEQUENCE: 2722

000

<210> SEQ ID NO 2723

<400> SEQUENCE: 2723

000

<210> SEQ ID NO 2724

<400> SEQUENCE: 2724

000

<210> SEQ ID NO 2725

<400> SEQUENCE: 2725

000

<210> SEQ ID NO 2726

<400> SEQUENCE: 2726

000

<210> SEQ ID NO 2727

<400> SEQUENCE: 2727

000

<210> SEQ ID NO 2728

<400> SEQUENCE: 2728

000

<210> SEQ ID NO 2729

<400> SEQUENCE: 2729

000

<210> SEQ ID NO 2730

<400> SEQUENCE: 2730
```

000

<210> SEQ ID NO 2731

<400> SEQUENCE: 2731

000

<210> SEQ ID NO 2732

<400> SEQUENCE: 2732

000

<210> SEQ ID NO 2733

<400> SEQUENCE: 2733

000

<210> SEQ ID NO 2734

<400> SEQUENCE: 2734

000

<210> SEQ ID NO 2735

<400> SEQUENCE: 2735

000

<210> SEQ ID NO 2736

<400> SEQUENCE: 2736

000

<210> SEQ ID NO 2737

<400> SEQUENCE: 2737

000

<210> SEQ ID NO 2738

<400> SEQUENCE: 2738

000

<210> SEQ ID NO 2739

<400> SEQUENCE: 2739

000

<210> SEQ ID NO 2740

<400> SEQUENCE: 2740

000

<210> SEQ ID NO 2741

<400> SEQUENCE: 2741

000

<210> SEQ ID NO 2742

<400> SEQUENCE: 2742

000

<210> SEQ ID NO 2743

<400> SEQUENCE: 2743

000

<210> SEQ ID NO 2744

<400> SEQUENCE: 2744

000

<210> SEQ ID NO 2745

<400> SEQUENCE: 2745

000

<210> SEQ ID NO 2746

<400> SEQUENCE: 2746

000

<210> SEQ ID NO 2747

<400> SEQUENCE: 2747

000

<210> SEQ ID NO 2748

<400> SEQUENCE: 2748

000

<210> SEQ ID NO 2749

<400> SEQUENCE: 2749

000

<210> SEQ ID NO 2750

<400> SEQUENCE: 2750

000

<210> SEQ ID NO 2751

<400> SEQUENCE: 2751

000

<210> SEQ ID NO 2752

<400> SEQUENCE: 2752

000

```
<210> SEQ ID NO 2753
<400> SEQUENCE: 2753
000

<210> SEQ ID NO 2754
<400> SEQUENCE: 2754
000

<210> SEQ ID NO 2755
<400> SEQUENCE: 2755
000

<210> SEQ ID NO 2756
<400> SEQUENCE: 2756
000

<210> SEQ ID NO 2757
<400> SEQUENCE: 2757
000

<210> SEQ ID NO 2758
<400> SEQUENCE: 2758
000

<210> SEQ ID NO 2759
<400> SEQUENCE: 2759
000

<210> SEQ ID NO 2760
<400> SEQUENCE: 2760
000

<210> SEQ ID NO 2761
<400> SEQUENCE: 2761
000

<210> SEQ ID NO 2762
<400> SEQUENCE: 2762
000

<210> SEQ ID NO 2763
<400> SEQUENCE: 2763
000

<210> SEQ ID NO 2764
```

<400> SEQUENCE: 2764

000

<210> SEQ ID NO 2765

<400> SEQUENCE: 2765

000

<210> SEQ ID NO 2766

<400> SEQUENCE: 2766

000

<210> SEQ ID NO 2767

<400> SEQUENCE: 2767

000

<210> SEQ ID NO 2768

<400> SEQUENCE: 2768

000

<210> SEQ ID NO 2769

<400> SEQUENCE: 2769

000

<210> SEQ ID NO 2770

<400> SEQUENCE: 2770

000

<210> SEQ ID NO 2771

<400> SEQUENCE: 2771

000

<210> SEQ ID NO 2772

<400> SEQUENCE: 2772

000

<210> SEQ ID NO 2773

<400> SEQUENCE: 2773

000

<210> SEQ ID NO 2774

<400> SEQUENCE: 2774

000

<210> SEQ ID NO 2775

<400> SEQUENCE: 2775

-continued

000

<210> SEQ ID NO 2776
<400> SEQUENCE: 2776
000

<210> SEQ ID NO 2777
<400> SEQUENCE: 2777
000

<210> SEQ ID NO 2778
<400> SEQUENCE: 2778
000

<210> SEQ ID NO 2779
<400> SEQUENCE: 2779
000

<210> SEQ ID NO 2780
<400> SEQUENCE: 2780
000

<210> SEQ ID NO 2781
<400> SEQUENCE: 2781
000

<210> SEQ ID NO 2782
<400> SEQUENCE: 2782
000

<210> SEQ ID NO 2783
<400> SEQUENCE: 2783
000

<210> SEQ ID NO 2784
<400> SEQUENCE: 2784
000

<210> SEQ ID NO 2785
<400> SEQUENCE: 2785
000

<210> SEQ ID NO 2786
<400> SEQUENCE: 2786
000

<210> SEQ ID NO 2787

<400> SEQUENCE: 2787

000

<210> SEQ ID NO 2788

<400> SEQUENCE: 2788

000

<210> SEQ ID NO 2789

<400> SEQUENCE: 2789

000

<210> SEQ ID NO 2790

<400> SEQUENCE: 2790

000

<210> SEQ ID NO 2791

<400> SEQUENCE: 2791

000

<210> SEQ ID NO 2792

<400> SEQUENCE: 2792

000

<210> SEQ ID NO 2793

<400> SEQUENCE: 2793

000

<210> SEQ ID NO 2794

<400> SEQUENCE: 2794

000

<210> SEQ ID NO 2795

<400> SEQUENCE: 2795

000

<210> SEQ ID NO 2796

<400> SEQUENCE: 2796

000

<210> SEQ ID NO 2797

<400> SEQUENCE: 2797

000

<210> SEQ ID NO 2798

-continued

<400> SEQUENCE: 2798

000

<210> SEQ ID NO 2799

<400> SEQUENCE: 2799

000

<210> SEQ ID NO 2800

<400> SEQUENCE: 2800

000

<210> SEQ ID NO 2801

<400> SEQUENCE: 2801

000

<210> SEQ ID NO 2802

<400> SEQUENCE: 2802

000

<210> SEQ ID NO 2803

<400> SEQUENCE: 2803

000

<210> SEQ ID NO 2804

<400> SEQUENCE: 2804

000

<210> SEQ ID NO 2805

<400> SEQUENCE: 2805

000

<210> SEQ ID NO 2806

<400> SEQUENCE: 2806

000

<210> SEQ ID NO 2807

<400> SEQUENCE: 2807

000

<210> SEQ ID NO 2808

<400> SEQUENCE: 2808

000

<210> SEQ ID NO 2809

<400> SEQUENCE: 2809

000

<210> SEQ ID NO 2810
<400> SEQUENCE: 2810
000

<210> SEQ ID NO 2811
<400> SEQUENCE: 2811
000

<210> SEQ ID NO 2812
<400> SEQUENCE: 2812
000

<210> SEQ ID NO 2813
<400> SEQUENCE: 2813
000

<210> SEQ ID NO 2814
<400> SEQUENCE: 2814
000

<210> SEQ ID NO 2815
<400> SEQUENCE: 2815
000

<210> SEQ ID NO 2816
<400> SEQUENCE: 2816
000

<210> SEQ ID NO 2817
<400> SEQUENCE: 2817
000

<210> SEQ ID NO 2818
<400> SEQUENCE: 2818
000

<210> SEQ ID NO 2819
<400> SEQUENCE: 2819
000

<210> SEQ ID NO 2820
<400> SEQUENCE: 2820
000

-continued

<210> SEQ ID NO 2821

<400> SEQUENCE: 2821

000

<210> SEQ ID NO 2822

<400> SEQUENCE: 2822

000

<210> SEQ ID NO 2823

<400> SEQUENCE: 2823

000

<210> SEQ ID NO 2824

<400> SEQUENCE: 2824

000

<210> SEQ ID NO 2825

<400> SEQUENCE: 2825

000

<210> SEQ ID NO 2826

<400> SEQUENCE: 2826

000

<210> SEQ ID NO 2827

<400> SEQUENCE: 2827

000

<210> SEQ ID NO 2828

<400> SEQUENCE: 2828

000

<210> SEQ ID NO 2829

<400> SEQUENCE: 2829

000

<210> SEQ ID NO 2830

<400> SEQUENCE: 2830

000

<210> SEQ ID NO 2831

<400> SEQUENCE: 2831

000

<210> SEQ ID NO 2832

<400> SEQUENCE: 2832

000

<210> SEQ ID NO 2833

<400> SEQUENCE: 2833

000

<210> SEQ ID NO 2834

<400> SEQUENCE: 2834

000

<210> SEQ ID NO 2835

<400> SEQUENCE: 2835

000

<210> SEQ ID NO 2836

<400> SEQUENCE: 2836

000

<210> SEQ ID NO 2837

<400> SEQUENCE: 2837

000

<210> SEQ ID NO 2838

<400> SEQUENCE: 2838

000

<210> SEQ ID NO 2839

<400> SEQUENCE: 2839

000

<210> SEQ ID NO 2840

<400> SEQUENCE: 2840

000

<210> SEQ ID NO 2841

<400> SEQUENCE: 2841

000

<210> SEQ ID NO 2842

<400> SEQUENCE: 2842

000

<210> SEQ ID NO 2843

-continued

<400> SEQUENCE: 2843

000

<210> SEQ ID NO 2844

<400> SEQUENCE: 2844

000

<210> SEQ ID NO 2845

<400> SEQUENCE: 2845

000

<210> SEQ ID NO 2846

<400> SEQUENCE: 2846

000

<210> SEQ ID NO 2847

<400> SEQUENCE: 2847

000

<210> SEQ ID NO 2848

<400> SEQUENCE: 2848

000

<210> SEQ ID NO 2849

<400> SEQUENCE: 2849

000

<210> SEQ ID NO 2850

<400> SEQUENCE: 2850

000

<210> SEQ ID NO 2851

<400> SEQUENCE: 2851

000

<210> SEQ ID NO 2852

<400> SEQUENCE: 2852

000

<210> SEQ ID NO 2853

<400> SEQUENCE: 2853

000

<210> SEQ ID NO 2854

<400> SEQUENCE: 2854

000

<210> SEQ ID NO 2855

<400> SEQUENCE: 2855

000

<210> SEQ ID NO 2856

<400> SEQUENCE: 2856

000

<210> SEQ ID NO 2857

<400> SEQUENCE: 2857

000

<210> SEQ ID NO 2858

<400> SEQUENCE: 2858

000

<210> SEQ ID NO 2859

<400> SEQUENCE: 2859

000

<210> SEQ ID NO 2860

<400> SEQUENCE: 2860

000

<210> SEQ ID NO 2861

<400> SEQUENCE: 2861

000

<210> SEQ ID NO 2862

<400> SEQUENCE: 2862

000

<210> SEQ ID NO 2863

<400> SEQUENCE: 2863

000

<210> SEQ ID NO 2864

<400> SEQUENCE: 2864

000

<210> SEQ ID NO 2865

<400> SEQUENCE: 2865

000

<210> SEQ ID NO 2866

<400> SEQUENCE: 2866

000

<210> SEQ ID NO 2867

<400> SEQUENCE: 2867

000

<210> SEQ ID NO 2868

<400> SEQUENCE: 2868

000

<210> SEQ ID NO 2869

<400> SEQUENCE: 2869

000

<210> SEQ ID NO 2870

<400> SEQUENCE: 2870

000

<210> SEQ ID NO 2871

<400> SEQUENCE: 2871

000

<210> SEQ ID NO 2872

<400> SEQUENCE: 2872

000

<210> SEQ ID NO 2873

<400> SEQUENCE: 2873

000

<210> SEQ ID NO 2874

<400> SEQUENCE: 2874

000

<210> SEQ ID NO 2875

<400> SEQUENCE: 2875

000

<210> SEQ ID NO 2876

<400> SEQUENCE: 2876

000

<210> SEQ ID NO 2877

```
<400> SEQUENCE: 2877

000

<210> SEQ ID NO 2878

<400> SEQUENCE: 2878

000

<210> SEQ ID NO 2879

<400> SEQUENCE: 2879

000

<210> SEQ ID NO 2880

<400> SEQUENCE: 2880

000

<210> SEQ ID NO 2881

<400> SEQUENCE: 2881

000

<210> SEQ ID NO 2882

<400> SEQUENCE: 2882

000

<210> SEQ ID NO 2883

<400> SEQUENCE: 2883

000

<210> SEQ ID NO 2884

<400> SEQUENCE: 2884

000

<210> SEQ ID NO 2885

<400> SEQUENCE: 2885

000

<210> SEQ ID NO 2886

<400> SEQUENCE: 2886

000

<210> SEQ ID NO 2887

<400> SEQUENCE: 2887

000

<210> SEQ ID NO 2888

<400> SEQUENCE: 2888
```

000

<210> SEQ ID NO 2889

<400> SEQUENCE: 2889

000

<210> SEQ ID NO 2890

<400> SEQUENCE: 2890

000

<210> SEQ ID NO 2891

<400> SEQUENCE: 2891

000

<210> SEQ ID NO 2892

<400> SEQUENCE: 2892

000

<210> SEQ ID NO 2893

<400> SEQUENCE: 2893

000

<210> SEQ ID NO 2894

<400> SEQUENCE: 2894

000

<210> SEQ ID NO 2895

<400> SEQUENCE: 2895

000

<210> SEQ ID NO 2896

<400> SEQUENCE: 2896

000

<210> SEQ ID NO 2897

<400> SEQUENCE: 2897

000

<210> SEQ ID NO 2898

<400> SEQUENCE: 2898

000

<210> SEQ ID NO 2899

<400> SEQUENCE: 2899

000

```
<210> SEQ ID NO 2900
<400> SEQUENCE: 2900
000

<210> SEQ ID NO 2901
<400> SEQUENCE: 2901
000

<210> SEQ ID NO 2902
<400> SEQUENCE: 2902
000

<210> SEQ ID NO 2903
<400> SEQUENCE: 2903
000

<210> SEQ ID NO 2904
<400> SEQUENCE: 2904
000

<210> SEQ ID NO 2905
<400> SEQUENCE: 2905
000

<210> SEQ ID NO 2906
<400> SEQUENCE: 2906
000

<210> SEQ ID NO 2907
<400> SEQUENCE: 2907
000

<210> SEQ ID NO 2908
<400> SEQUENCE: 2908
000

<210> SEQ ID NO 2909
<400> SEQUENCE: 2909
000

<210> SEQ ID NO 2910
<400> SEQUENCE: 2910
000
```

<210> SEQ ID NO 2911

<400> SEQUENCE: 2911

000

<210> SEQ ID NO 2912

<400> SEQUENCE: 2912

000

<210> SEQ ID NO 2913

<400> SEQUENCE: 2913

000

<210> SEQ ID NO 2914

<400> SEQUENCE: 2914

000

<210> SEQ ID NO 2915

<400> SEQUENCE: 2915

000

<210> SEQ ID NO 2916

<400> SEQUENCE: 2916

000

<210> SEQ ID NO 2917

<400> SEQUENCE: 2917

000

<210> SEQ ID NO 2918

<400> SEQUENCE: 2918

000

<210> SEQ ID NO 2919

<400> SEQUENCE: 2919

000

<210> SEQ ID NO 2920

<400> SEQUENCE: 2920

000

<210> SEQ ID NO 2921

<400> SEQUENCE: 2921

000

<210> SEQ ID NO 2922

```
<400> SEQUENCE: 2922
000

<210> SEQ ID NO 2923
<400> SEQUENCE: 2923
000

<210> SEQ ID NO 2924
<400> SEQUENCE: 2924
000

<210> SEQ ID NO 2925
<400> SEQUENCE: 2925
000

<210> SEQ ID NO 2926
<400> SEQUENCE: 2926
000

<210> SEQ ID NO 2927
<400> SEQUENCE: 2927
000

<210> SEQ ID NO 2928
<400> SEQUENCE: 2928
000

<210> SEQ ID NO 2929
<400> SEQUENCE: 2929
000

<210> SEQ ID NO 2930
<400> SEQUENCE: 2930
000

<210> SEQ ID NO 2931
<400> SEQUENCE: 2931
000

<210> SEQ ID NO 2932
<400> SEQUENCE: 2932
000

<210> SEQ ID NO 2933
<400> SEQUENCE: 2933
```

000

<210> SEQ ID NO 2934

<400> SEQUENCE: 2934

000

<210> SEQ ID NO 2935

<400> SEQUENCE: 2935

000

<210> SEQ ID NO 2936

<400> SEQUENCE: 2936

000

<210> SEQ ID NO 2937

<400> SEQUENCE: 2937

000

<210> SEQ ID NO 2938

<400> SEQUENCE: 2938

000

<210> SEQ ID NO 2939

<400> SEQUENCE: 2939

000

<210> SEQ ID NO 2940

<400> SEQUENCE: 2940

000

<210> SEQ ID NO 2941

<400> SEQUENCE: 2941

000

<210> SEQ ID NO 2942

<400> SEQUENCE: 2942

000

<210> SEQ ID NO 2943

<400> SEQUENCE: 2943

000

<210> SEQ ID NO 2944

<400> SEQUENCE: 2944

000

```
<210> SEQ ID NO 2945
<400> SEQUENCE: 2945
000

<210> SEQ ID NO 2946
<400> SEQUENCE: 2946
000

<210> SEQ ID NO 2947
<400> SEQUENCE: 2947
000

<210> SEQ ID NO 2948
<400> SEQUENCE: 2948
000

<210> SEQ ID NO 2949
<400> SEQUENCE: 2949
000

<210> SEQ ID NO 2950
<400> SEQUENCE: 2950
000

<210> SEQ ID NO 2951
<400> SEQUENCE: 2951
000

<210> SEQ ID NO 2952
<400> SEQUENCE: 2952
000

<210> SEQ ID NO 2953
<400> SEQUENCE: 2953
000

<210> SEQ ID NO 2954
<400> SEQUENCE: 2954
000

<210> SEQ ID NO 2955
<400> SEQUENCE: 2955
000

<210> SEQ ID NO 2956
```

<400> SEQUENCE: 2956

000

<210> SEQ ID NO 2957

<400> SEQUENCE: 2957

000

<210> SEQ ID NO 2958

<400> SEQUENCE: 2958

000

<210> SEQ ID NO 2959

<400> SEQUENCE: 2959

000

<210> SEQ ID NO 2960

<400> SEQUENCE: 2960

000

<210> SEQ ID NO 2961

<400> SEQUENCE: 2961

000

<210> SEQ ID NO 2962

<400> SEQUENCE: 2962

000

<210> SEQ ID NO 2963

<400> SEQUENCE: 2963

000

<210> SEQ ID NO 2964

<400> SEQUENCE: 2964

000

<210> SEQ ID NO 2965

<400> SEQUENCE: 2965

000

<210> SEQ ID NO 2966

<400> SEQUENCE: 2966

000

<210> SEQ ID NO 2967

<400> SEQUENCE: 2967

000

<210> SEQ ID NO 2968

<400> SEQUENCE: 2968

000

<210> SEQ ID NO 2969

<400> SEQUENCE: 2969

000

<210> SEQ ID NO 2970

<400> SEQUENCE: 2970

000

<210> SEQ ID NO 2971

<400> SEQUENCE: 2971

000

<210> SEQ ID NO 2972

<400> SEQUENCE: 2972

000

<210> SEQ ID NO 2973

<400> SEQUENCE: 2973

000

<210> SEQ ID NO 2974

<400> SEQUENCE: 2974

000

<210> SEQ ID NO 2975

<400> SEQUENCE: 2975

000

<210> SEQ ID NO 2976

<400> SEQUENCE: 2976

000

<210> SEQ ID NO 2977

<400> SEQUENCE: 2977

000

<210> SEQ ID NO 2978

<400> SEQUENCE: 2978

000

<210> SEQ ID NO 2979

<400> SEQUENCE: 2979

000

<210> SEQ ID NO 2980

<400> SEQUENCE: 2980

000

<210> SEQ ID NO 2981

<400> SEQUENCE: 2981

000

<210> SEQ ID NO 2982

<400> SEQUENCE: 2982

000

<210> SEQ ID NO 2983

<400> SEQUENCE: 2983

000

<210> SEQ ID NO 2984

<400> SEQUENCE: 2984

000

<210> SEQ ID NO 2985

<400> SEQUENCE: 2985

000

<210> SEQ ID NO 2986

<400> SEQUENCE: 2986

000

<210> SEQ ID NO 2987

<400> SEQUENCE: 2987

000

<210> SEQ ID NO 2988

<400> SEQUENCE: 2988

000

<210> SEQ ID NO 2989

<400> SEQUENCE: 2989

000

```
<210> SEQ ID NO 2990
<400> SEQUENCE: 2990
000

<210> SEQ ID NO 2991
<400> SEQUENCE: 2991
000

<210> SEQ ID NO 2992
<400> SEQUENCE: 2992
000

<210> SEQ ID NO 2993
<400> SEQUENCE: 2993
000

<210> SEQ ID NO 2994
<400> SEQUENCE: 2994
000

<210> SEQ ID NO 2995
<400> SEQUENCE: 2995
000

<210> SEQ ID NO 2996
<400> SEQUENCE: 2996
000

<210> SEQ ID NO 2997
<400> SEQUENCE: 2997
000

<210> SEQ ID NO 2998
<400> SEQUENCE: 2998
000

<210> SEQ ID NO 2999
<400> SEQUENCE: 2999
000

<210> SEQ ID NO 3000
<400> SEQUENCE: 3000
000

<210> SEQ ID NO 3001
<211> LENGTH: 9
```

```
<212> TYPE: PRT
<213> ORGANISM: Artificial Sequence
<220> FEATURE:
<223> OTHER INFORMATION: Synthetic: 34 - VH CDR1

<400> SEQUENCE: 3001

Gly Thr Phe Ser Ser Ala Ala Ile Ser
1               5

<210> SEQ ID NO 3002
<211> LENGTH: 17
<212> TYPE: PRT
<213> ORGANISM: Artificial Sequence
<220> FEATURE:
<223> OTHER INFORMATION: Synthetic: 34 - VH CDR2

<400> SEQUENCE: 3002

Gly Ile Phe Pro Ile Ser Gly His Ala Asn Tyr Ala Gln Lys Phe Gln
1               5                   10                  15

Gly

<210> SEQ ID NO 3003
<211> LENGTH: 16
<212> TYPE: PRT
<213> ORGANISM: Artificial Sequence
<220> FEATURE:
<223> OTHER INFORMATION: Synthetic: 34 - VH CDR3

<400> SEQUENCE: 3003

Ala Arg Asp Thr Gly Arg Gly Tyr Thr Arg His Phe Trp Phe Asp Pro
1               5                   10                  15

<210> SEQ ID NO 3004
<211> LENGTH: 11
<212> TYPE: PRT
<213> ORGANISM: Artificial Sequence
<220> FEATURE:
<223> OTHER INFORMATION: Synthetic: 34 - VL CDR1

<400> SEQUENCE: 3004

Arg Ala Ser Gln Ser Ile Ser Ser Tyr Leu Asn
1               5                   10

<210> SEQ ID NO 3005
<211> LENGTH: 7
<212> TYPE: PRT
<213> ORGANISM: Artificial Sequence
<220> FEATURE:
<223> OTHER INFORMATION: Synthetic: 34 - VL CDR2

<400> SEQUENCE: 3005

Ala Ala Ser Ser Leu Gln Ser
1               5

<210> SEQ ID NO 3006
<211> LENGTH: 8
<212> TYPE: PRT
<213> ORGANISM: Artificial Sequence
<220> FEATURE:
<223> OTHER INFORMATION: Synthetic: 34 - VL CDR3

<400> SEQUENCE: 3006

Gln Gln Ser Asp Ile Leu Tyr Thr
1               5

<210> SEQ ID NO 3007
```

<211> LENGTH: 26
<212> TYPE: PRT
<213> ORGANISM: Artificial Sequence
<220> FEATURE:
<223> OTHER INFORMATION: Synthetic: 34 - VH FR1

<400> SEQUENCE: 3007

Gln Val Gln Leu Val Gln Ser Gly Ala Glu Val Lys Lys Pro Gly Ser
1               5                   10                  15
Ser Val Lys Val Ser Cys Lys Ala Ser Gly
            20                  25

<210> SEQ ID NO 3008
<211> LENGTH: 14
<212> TYPE: PRT
<213> ORGANISM: Artificial Sequence
<220> FEATURE:
<223> OTHER INFORMATION: Synthetic: 34 - VH FR2

<400> SEQUENCE: 3008

Trp Val Arg Gln Ala Pro Gly Gln Gly Leu Glu Trp Met Gly
1               5                   10

<210> SEQ ID NO 3009
<211> LENGTH: 30
<212> TYPE: PRT
<213> ORGANISM: Artificial Sequence
<220> FEATURE:
<223> OTHER INFORMATION: Synthetic: 34 - VH FR3

<400> SEQUENCE: 3009

Arg Val Thr Ile Thr Ala Asp Glu Ser Thr Ser Thr Ala Tyr Met Glu
1               5                   10                  15
Leu Ser Ser Leu Arg Ser Glu Asp Thr Ala Val Tyr Tyr Cys
            20                  25                  30

<210> SEQ ID NO 3010
<211> LENGTH: 11
<212> TYPE: PRT
<213> ORGANISM: Artificial Sequence
<220> FEATURE:
<223> OTHER INFORMATION: Synthetic: 34 - VH FR4

<400> SEQUENCE: 3010

Trp Gly Gln Gly Thr Leu Val Thr Val Ser Ser
1               5                   10

<210> SEQ ID NO 3011
<211> LENGTH: 369
<212> TYPE: DNA
<213> ORGANISM: Artificial Sequence
<220> FEATURE:
<223> OTHER INFORMATION: Synthetic: 34 - VH DNA

<400> SEQUENCE: 3011
caggtgcagc tggtgcagtc tggggctgag gtgaagaagc ctgggtcctc ggtgaaggtc      60
tcctgcaagg cttctggagg caccttcagc agcgccgcta tcagctgggt gcgacaggcc     120
cctggacaag gctcgagtg atgggaggg atcttcccta tctccggtca cgcaaactac       180
gcacagaagt tccagggcag agtcacgatt accgcggacg aatccacgag cacagcctac     240
atggagctga gcagcctgag atctgaggac acggcggtgt actactgcgc cagagacacg     300
ggacggggat acaccagaca cttctggttt gaccctggg gacagggtac attggtcacc      360
gtctcctca                                                             369

<210> SEQ ID NO 3012
<211> LENGTH: 123
<212> TYPE: PRT
<213> ORGANISM: Artificial Sequence
<220> FEATURE:
<223> OTHER INFORMATION: Synthetic: 34 - VH Protein

<400> SEQUENCE: 3012

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ala
            20                  25                  30

Ala Ile Ser Trp Val Arg Gln Ala Pro Gly Gln Gly Leu Glu Trp Met
        35                  40                  45

Gly Gly Ile Phe Pro Ile Ser Gly His Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Arg Gly Tyr Thr Arg His Phe Trp Phe Asp Pro
            100                 105                 110

Trp Gly Gln Gly Thr Leu Val Thr Val Ser Ser
        115                 120

<210> SEQ ID NO 3013
<211> LENGTH: 23
<212> TYPE: PRT
<213> ORGANISM: Artificial Sequence
<220> FEATURE:
<223> OTHER INFORMATION: Synthetic: 34 - VL FR1

<400> SEQUENCE: 3013

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 3014
<211> LENGTH: 15
<212> TYPE: PRT
<213> ORGANISM: Artificial Sequence
<220> FEATURE:
<223> OTHER INFORMATION: Synthetic: 34 - VL FR2

<400> SEQUENCE: 3014

Trp Tyr Gln Gln Lys Pro Gly Lys Ala Pro Lys Leu Leu Ile Tyr
1               5                   10                  15

<210> SEQ ID NO 3015
<211> LENGTH: 32
<212> TYPE: PRT
<213> ORGANISM: Artificial Sequence
<220> FEATURE:
<223> OTHER INFORMATION: Synthetic: 34 - VL FR3

<400> SEQUENCE: 3015

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 3016
<211> LENGTH: 10
<212> TYPE: PRT
<213> ORGANISM: Artificial Sequence
<220> FEATURE:
<223> OTHER INFORMATION: Synthetic: 34 - VL FR4

<400> SEQUENCE: 3016

Phe Gly Gly Gly Thr Lys Val Glu Ile Lys
1               5                   10

<210> SEQ ID NO 3017
<211> LENGTH: 318
<212> TYPE: DNA
<213> ORGANISM: Artificial Sequence
<220> FEATURE:
<223> OTHER INFORMATION: Synthetic: 34 - VL DNA

<400> SEQUENCE: 3017
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agcgacatcc tctacacttt tggcggaggg     300
accaaggttg agatcaaa                                                   318

<210> SEQ ID NO 3018
<211> LENGTH: 106
<212> TYPE: PRT
<213> ORGANISM: Artificial Sequence
<220> FEATURE:
<223> OTHER INFORMATION: Synthetic: 34 - VL Protein

<400> SEQUENCE: 3018

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Tyr Thr
                85                  90                  95

Phe Gly Gly Gly Thr Lys Val Glu Ile Lys
            100                 105

<210> SEQ ID NO 3019

<400> SEQUENCE: 3019

000

<210> SEQ ID NO 3020

<400> SEQUENCE: 3020

000

<210> SEQ ID NO 3021

<400> SEQUENCE: 3021

000

<210> SEQ ID NO 3022

<400> SEQUENCE: 3022

000

<210> SEQ ID NO 3023

<400> SEQUENCE: 3023

000

<210> SEQ ID NO 3024

<400> SEQUENCE: 3024

000

<210> SEQ ID NO 3025

<400> SEQUENCE: 3025

000

<210> SEQ ID NO 3026

<400> SEQUENCE: 3026

000

<210> SEQ ID NO 3027

<400> SEQUENCE: 3027

000

<210> SEQ ID NO 3028

<400> SEQUENCE: 3028

000

<210> SEQ ID NO 3029

<400> SEQUENCE: 3029

000

<210> SEQ ID NO 3030

<400> SEQUENCE: 3030

000

<210> SEQ ID NO 3031

<400> SEQUENCE: 3031

000

-continued

<210> SEQ ID NO 3032

<400> SEQUENCE: 3032

000

<210> SEQ ID NO 3033

<400> SEQUENCE: 3033

000

<210> SEQ ID NO 3034

<400> SEQUENCE: 3034

000

<210> SEQ ID NO 3035

<400> SEQUENCE: 3035

000

<210> SEQ ID NO 3036

<400> SEQUENCE: 3036

000

<210> SEQ ID NO 3037

<400> SEQUENCE: 3037

000

<210> SEQ ID NO 3038

<400> SEQUENCE: 3038

000

<210> SEQ ID NO 3039

<400> SEQUENCE: 3039

000

<210> SEQ ID NO 3040

<400> SEQUENCE: 3040

000

<210> SEQ ID NO 3041

<400> SEQUENCE: 3041

000

<210> SEQ ID NO 3042

<400> SEQUENCE: 3042

000

<210> SEQ ID NO 3043

```
<400> SEQUENCE: 3043

000

<210> SEQ ID NO 3044

<400> SEQUENCE: 3044

000

<210> SEQ ID NO 3045

<400> SEQUENCE: 3045

000

<210> SEQ ID NO 3046

<400> SEQUENCE: 3046

000

<210> SEQ ID NO 3047

<400> SEQUENCE: 3047

000

<210> SEQ ID NO 3048

<400> SEQUENCE: 3048

000

<210> SEQ ID NO 3049

<400> SEQUENCE: 3049

000

<210> SEQ ID NO 3050

<400> SEQUENCE: 3050

000

<210> SEQ ID NO 3051

<400> SEQUENCE: 3051

000

<210> SEQ ID NO 3052

<400> SEQUENCE: 3052

000

<210> SEQ ID NO 3053

<400> SEQUENCE: 3053

000

<210> SEQ ID NO 3054

<400> SEQUENCE: 3054
```

000

<210> SEQ ID NO 3055

<400> SEQUENCE: 3055

000

<210> SEQ ID NO 3056

<400> SEQUENCE: 3056

000

<210> SEQ ID NO 3057

<400> SEQUENCE: 3057

000

<210> SEQ ID NO 3058

<400> SEQUENCE: 3058

000

<210> SEQ ID NO 3059

<400> SEQUENCE: 3059

000

<210> SEQ ID NO 3060

<400> SEQUENCE: 3060

000

<210> SEQ ID NO 3061

<400> SEQUENCE: 3061

000

<210> SEQ ID NO 3062

<400> SEQUENCE: 3062

000

<210> SEQ ID NO 3063

<400> SEQUENCE: 3063

000

<210> SEQ ID NO 3064

<400> SEQUENCE: 3064

000

<210> SEQ ID NO 3065

<400> SEQUENCE: 3065

000

<210> SEQ ID NO 3066

<400> SEQUENCE: 3066

000

<210> SEQ ID NO 3067

<400> SEQUENCE: 3067

000

<210> SEQ ID NO 3068

<400> SEQUENCE: 3068

000

<210> SEQ ID NO 3069

<400> SEQUENCE: 3069

000

<210> SEQ ID NO 3070

<400> SEQUENCE: 3070

000

<210> SEQ ID NO 3071

<400> SEQUENCE: 3071

000

<210> SEQ ID NO 3072

<400> SEQUENCE: 3072

000

<210> SEQ ID NO 3073

<400> SEQUENCE: 3073

000

<210> SEQ ID NO 3074

<400> SEQUENCE: 3074

000

<210> SEQ ID NO 3075

<400> SEQUENCE: 3075

000

<210> SEQ ID NO 3076

<400> SEQUENCE: 3076

000

-continued

<210> SEQ ID NO 3077

<400> SEQUENCE: 3077

000

<210> SEQ ID NO 3078

<400> SEQUENCE: 3078

000

<210> SEQ ID NO 3079

<400> SEQUENCE: 3079

000

<210> SEQ ID NO 3080

<400> SEQUENCE: 3080

000

<210> SEQ ID NO 3081

<400> SEQUENCE: 3081

000

<210> SEQ ID NO 3082

<400> SEQUENCE: 3082

000

<210> SEQ ID NO 3083

<400> SEQUENCE: 3083

000

<210> SEQ ID NO 3084

<400> SEQUENCE: 3084

000

<210> SEQ ID NO 3085

<400> SEQUENCE: 3085

000

<210> SEQ ID NO 3086

<400> SEQUENCE: 3086

000

<210> SEQ ID NO 3087

<400> SEQUENCE: 3087

000

<210> SEQ ID NO 3088

<400> SEQUENCE: 3088

000

<210> SEQ ID NO 3089

<400> SEQUENCE: 3089

000

<210> SEQ ID NO 3090

<400> SEQUENCE: 3090

000

<210> SEQ ID NO 3091

<400> SEQUENCE: 3091

000

<210> SEQ ID NO 3092

<400> SEQUENCE: 3092

000

<210> SEQ ID NO 3093

<400> SEQUENCE: 3093

000

<210> SEQ ID NO 3094

<400> SEQUENCE: 3094

000

<210> SEQ ID NO 3095

<400> SEQUENCE: 3095

000

<210> SEQ ID NO 3096

<400> SEQUENCE: 3096

000

<210> SEQ ID NO 3097

<400> SEQUENCE: 3097

000

<210> SEQ ID NO 3098

<400> SEQUENCE: 3098

000

<210> SEQ ID NO 3099

<400> SEQUENCE: 3099

000

<210> SEQ ID NO 3100

<400> SEQUENCE: 3100

000

<210> SEQ ID NO 3101

<400> SEQUENCE: 3101

000

<210> SEQ ID NO 3102

<400> SEQUENCE: 3102

000

<210> SEQ ID NO 3103

<400> SEQUENCE: 3103

000

<210> SEQ ID NO 3104

<400> SEQUENCE: 3104

000

<210> SEQ ID NO 3105

<400> SEQUENCE: 3105

000

<210> SEQ ID NO 3106

<400> SEQUENCE: 3106

000

<210> SEQ ID NO 3107

<400> SEQUENCE: 3107

000

<210> SEQ ID NO 3108

<400> SEQUENCE: 3108

000

<210> SEQ ID NO 3109

<400> SEQUENCE: 3109

000

<210> SEQ ID NO 3110

<400> SEQUENCE: 3110

000

<210> SEQ ID NO 3111

<400> SEQUENCE: 3111

000

<210> SEQ ID NO 3112

<400> SEQUENCE: 3112

000

<210> SEQ ID NO 3113

<400> SEQUENCE: 3113

000

<210> SEQ ID NO 3114

<400> SEQUENCE: 3114

000

<210> SEQ ID NO 3115

<400> SEQUENCE: 3115

000

<210> SEQ ID NO 3116

<400> SEQUENCE: 3116

000

<210> SEQ ID NO 3117

<400> SEQUENCE: 3117

000

<210> SEQ ID NO 3118

<400> SEQUENCE: 3118

000

<210> SEQ ID NO 3119

<400> SEQUENCE: 3119

000

<210> SEQ ID NO 3120

<400> SEQUENCE: 3120

000

<210> SEQ ID NO 3121

<400> SEQUENCE: 3121

000

<210> SEQ ID NO 3122

```
<400> SEQUENCE: 3122

000

<210> SEQ ID NO 3123

<400> SEQUENCE: 3123

000

<210> SEQ ID NO 3124

<400> SEQUENCE: 3124

000

<210> SEQ ID NO 3125

<400> SEQUENCE: 3125

000

<210> SEQ ID NO 3126

<400> SEQUENCE: 3126

000

<210> SEQ ID NO 3127

<400> SEQUENCE: 3127

000

<210> SEQ ID NO 3128

<400> SEQUENCE: 3128

000

<210> SEQ ID NO 3129

<400> SEQUENCE: 3129

000

<210> SEQ ID NO 3130

<400> SEQUENCE: 3130

000

<210> SEQ ID NO 3131

<400> SEQUENCE: 3131

000

<210> SEQ ID NO 3132

<400> SEQUENCE: 3132

000

<210> SEQ ID NO 3133

<400> SEQUENCE: 3133
```

000

<210> SEQ ID NO 3134

<400> SEQUENCE: 3134

000

<210> SEQ ID NO 3135

<400> SEQUENCE: 3135

000

<210> SEQ ID NO 3136

<400> SEQUENCE: 3136

000

<210> SEQ ID NO 3137

<400> SEQUENCE: 3137

000

<210> SEQ ID NO 3138

<400> SEQUENCE: 3138

000

<210> SEQ ID NO 3139

<400> SEQUENCE: 3139

000

<210> SEQ ID NO 3140

<400> SEQUENCE: 3140

000

<210> SEQ ID NO 3141

<400> SEQUENCE: 3141

000

<210> SEQ ID NO 3142

<400> SEQUENCE: 3142

000

<210> SEQ ID NO 3143

<400> SEQUENCE: 3143

000

<210> SEQ ID NO 3144

<400> SEQUENCE: 3144

000

<210> SEQ ID NO 3145

<400> SEQUENCE: 3145

000

<210> SEQ ID NO 3146

<400> SEQUENCE: 3146

000

<210> SEQ ID NO 3147

<400> SEQUENCE: 3147

000

<210> SEQ ID NO 3148

<400> SEQUENCE: 3148

000

<210> SEQ ID NO 3149

<400> SEQUENCE: 3149

000

<210> SEQ ID NO 3150

<400> SEQUENCE: 3150

000

<210> SEQ ID NO 3151

<400> SEQUENCE: 3151

000

<210> SEQ ID NO 3152

<400> SEQUENCE: 3152

000

<210> SEQ ID NO 3153

<400> SEQUENCE: 3153

000

<210> SEQ ID NO 3154

<400> SEQUENCE: 3154

000

<210> SEQ ID NO 3155

<400> SEQUENCE: 3155

000

-continued

<210> SEQ ID NO 3156

<400> SEQUENCE: 3156

000

<210> SEQ ID NO 3157

<400> SEQUENCE: 3157

000

<210> SEQ ID NO 3158

<400> SEQUENCE: 3158

000

<210> SEQ ID NO 3159

<400> SEQUENCE: 3159

000

<210> SEQ ID NO 3160

<400> SEQUENCE: 3160

000

<210> SEQ ID NO 3161

<400> SEQUENCE: 3161

000

<210> SEQ ID NO 3162

<400> SEQUENCE: 3162

000

<210> SEQ ID NO 3163

<400> SEQUENCE: 3163

000

<210> SEQ ID NO 3164

<400> SEQUENCE: 3164

000

<210> SEQ ID NO 3165

<400> SEQUENCE: 3165

000

<210> SEQ ID NO 3166

<400> SEQUENCE: 3166

000

<210> SEQ ID NO 3167

<400> SEQUENCE: 3167

000

<210> SEQ ID NO 3168

<400> SEQUENCE: 3168

000

<210> SEQ ID NO 3169

<400> SEQUENCE: 3169

000

<210> SEQ ID NO 3170

<400> SEQUENCE: 3170

000

<210> SEQ ID NO 3171

<400> SEQUENCE: 3171

000

<210> SEQ ID NO 3172

<400> SEQUENCE: 3172

000

<210> SEQ ID NO 3173

<400> SEQUENCE: 3173

000

<210> SEQ ID NO 3174

<400> SEQUENCE: 3174

000

<210> SEQ ID NO 3175

<400> SEQUENCE: 3175

000

<210> SEQ ID NO 3176

<400> SEQUENCE: 3176

000

<210> SEQ ID NO 3177

<400> SEQUENCE: 3177

000

<210> SEQ ID NO 3178

<400> SEQUENCE: 3178

000

<210> SEQ ID NO 3179
<400> SEQUENCE: 3179
000

<210> SEQ ID NO 3180
<400> SEQUENCE: 3180
000

<210> SEQ ID NO 3181
<400> SEQUENCE: 3181
000

<210> SEQ ID NO 3182
<400> SEQUENCE: 3182
000

<210> SEQ ID NO 3183
<400> SEQUENCE: 3183
000

<210> SEQ ID NO 3184
<400> SEQUENCE: 3184
000

<210> SEQ ID NO 3185
<400> SEQUENCE: 3185
000

<210> SEQ ID NO 3186
<400> SEQUENCE: 3186
000

<210> SEQ ID NO 3187
<400> SEQUENCE: 3187
000

<210> SEQ ID NO 3188
<400> SEQUENCE: 3188
000

<210> SEQ ID NO 3189
<400> SEQUENCE: 3189
000

-continued

<210> SEQ ID NO 3190

<400> SEQUENCE: 3190

000

<210> SEQ ID NO 3191

<400> SEQUENCE: 3191

000

<210> SEQ ID NO 3192

<400> SEQUENCE: 3192

000

<210> SEQ ID NO 3193

<400> SEQUENCE: 3193

000

<210> SEQ ID NO 3194

<400> SEQUENCE: 3194

000

<210> SEQ ID NO 3195

<400> SEQUENCE: 3195

000

<210> SEQ ID NO 3196

<400> SEQUENCE: 3196

000

<210> SEQ ID NO 3197

<400> SEQUENCE: 3197

000

<210> SEQ ID NO 3198

<400> SEQUENCE: 3198

000

<210> SEQ ID NO 3199

<400> SEQUENCE: 3199

000

<210> SEQ ID NO 3200

<400> SEQUENCE: 3200

000

<210> SEQ ID NO 3201

```
<400> SEQUENCE: 3201
000

<210> SEQ ID NO 3202
<400> SEQUENCE: 3202
000

<210> SEQ ID NO 3203
<400> SEQUENCE: 3203
000

<210> SEQ ID NO 3204
<400> SEQUENCE: 3204
000

<210> SEQ ID NO 3205
<400> SEQUENCE: 3205
000

<210> SEQ ID NO 3206
<400> SEQUENCE: 3206
000

<210> SEQ ID NO 3207
<400> SEQUENCE: 3207
000

<210> SEQ ID NO 3208
<400> SEQUENCE: 3208
000

<210> SEQ ID NO 3209
<400> SEQUENCE: 3209
000

<210> SEQ ID NO 3210
<400> SEQUENCE: 3210
000

<210> SEQ ID NO 3211
<400> SEQUENCE: 3211
000

<210> SEQ ID NO 3212
<400> SEQUENCE: 3212
```

000

<210> SEQ ID NO 3213

<400> SEQUENCE: 3213

000

<210> SEQ ID NO 3214

<400> SEQUENCE: 3214

000

<210> SEQ ID NO 3215

<400> SEQUENCE: 3215

000

<210> SEQ ID NO 3216

<400> SEQUENCE: 3216

000

<210> SEQ ID NO 3217

<400> SEQUENCE: 3217

000

<210> SEQ ID NO 3218

<400> SEQUENCE: 3218

000

<210> SEQ ID NO 3219

<400> SEQUENCE: 3219

000

<210> SEQ ID NO 3220

<400> SEQUENCE: 3220

000

<210> SEQ ID NO 3221

<400> SEQUENCE: 3221

000

<210> SEQ ID NO 3222

<400> SEQUENCE: 3222

000

<210> SEQ ID NO 3223

<400> SEQUENCE: 3223

000

<210> SEQ ID NO 3224

<400> SEQUENCE: 3224

000

<210> SEQ ID NO 3225

<400> SEQUENCE: 3225

000

<210> SEQ ID NO 3226

<400> SEQUENCE: 3226

000

<210> SEQ ID NO 3227

<400> SEQUENCE: 3227

000

<210> SEQ ID NO 3228

<400> SEQUENCE: 3228

000

<210> SEQ ID NO 3229

<400> SEQUENCE: 3229

000

<210> SEQ ID NO 3230

<400> SEQUENCE: 3230

000

<210> SEQ ID NO 3231

<400> SEQUENCE: 3231

000

<210> SEQ ID NO 3232

<400> SEQUENCE: 3232

000

<210> SEQ ID NO 3233

<400> SEQUENCE: 3233

000

<210> SEQ ID NO 3234

<400> SEQUENCE: 3234

000

```
<210> SEQ ID NO 3235
<400> SEQUENCE: 3235
000

<210> SEQ ID NO 3236
<400> SEQUENCE: 3236
000

<210> SEQ ID NO 3237
<400> SEQUENCE: 3237
000

<210> SEQ ID NO 3238
<400> SEQUENCE: 3238
000

<210> SEQ ID NO 3239
<400> SEQUENCE: 3239
000

<210> SEQ ID NO 3240
<400> SEQUENCE: 3240
000

<210> SEQ ID NO 3241
<400> SEQUENCE: 3241
000

<210> SEQ ID NO 3242
<400> SEQUENCE: 3242
000

<210> SEQ ID NO 3243
<400> SEQUENCE: 3243
000

<210> SEQ ID NO 3244
<400> SEQUENCE: 3244
000

<210> SEQ ID NO 3245
<400> SEQUENCE: 3245
000

<210> SEQ ID NO 3246
```

<400> SEQUENCE: 3246

000

<210> SEQ ID NO 3247

<400> SEQUENCE: 3247

000

<210> SEQ ID NO 3248

<400> SEQUENCE: 3248

000

<210> SEQ ID NO 3249

<400> SEQUENCE: 3249

000

<210> SEQ ID NO 3250

<400> SEQUENCE: 3250

000

<210> SEQ ID NO 3251

<400> SEQUENCE: 3251

000

<210> SEQ ID NO 3252

<400> SEQUENCE: 3252

000

<210> SEQ ID NO 3253

<400> SEQUENCE: 3253

000

<210> SEQ ID NO 3254

<400> SEQUENCE: 3254

000

<210> SEQ ID NO 3255

<400> SEQUENCE: 3255

000

<210> SEQ ID NO 3256

<400> SEQUENCE: 3256

000

<210> SEQ ID NO 3257

<400> SEQUENCE: 3257

000

<210> SEQ ID NO 3258

<400> SEQUENCE: 3258

000

<210> SEQ ID NO 3259

<400> SEQUENCE: 3259

000

<210> SEQ ID NO 3260

<400> SEQUENCE: 3260

000

<210> SEQ ID NO 3261

<400> SEQUENCE: 3261

000

<210> SEQ ID NO 3262

<400> SEQUENCE: 3262

000

<210> SEQ ID NO 3263

<400> SEQUENCE: 3263

000

<210> SEQ ID NO 3264

<400> SEQUENCE: 3264

000

<210> SEQ ID NO 3265

<400> SEQUENCE: 3265

000

<210> SEQ ID NO 3266

<400> SEQUENCE: 3266

000

<210> SEQ ID NO 3267

<400> SEQUENCE: 3267

000

<210> SEQ ID NO 3268

<400> SEQUENCE: 3268

000

```
<210> SEQ ID NO 3269
<400> SEQUENCE: 3269
000

<210> SEQ ID NO 3270
<400> SEQUENCE: 3270
000

<210> SEQ ID NO 3271
<400> SEQUENCE: 3271
000

<210> SEQ ID NO 3272
<400> SEQUENCE: 3272
000

<210> SEQ ID NO 3273
<400> SEQUENCE: 3273
000

<210> SEQ ID NO 3274
<400> SEQUENCE: 3274
000

<210> SEQ ID NO 3275
<400> SEQUENCE: 3275
000

<210> SEQ ID NO 3276
<400> SEQUENCE: 3276
000

<210> SEQ ID NO 3277
<400> SEQUENCE: 3277
000

<210> SEQ ID NO 3278
<400> SEQUENCE: 3278
000

<210> SEQ ID NO 3279
<400> SEQUENCE: 3279
000

<210> SEQ ID NO 3280
```

```
<400> SEQUENCE: 3280

000

<210> SEQ ID NO 3281

<400> SEQUENCE: 3281

000

<210> SEQ ID NO 3282

<400> SEQUENCE: 3282

000

<210> SEQ ID NO 3283

<400> SEQUENCE: 3283

000

<210> SEQ ID NO 3284

<400> SEQUENCE: 3284

000

<210> SEQ ID NO 3285

<400> SEQUENCE: 3285

000

<210> SEQ ID NO 3286

<400> SEQUENCE: 3286

000

<210> SEQ ID NO 3287

<400> SEQUENCE: 3287

000

<210> SEQ ID NO 3288

<400> SEQUENCE: 3288

000

<210> SEQ ID NO 3289

<400> SEQUENCE: 3289

000

<210> SEQ ID NO 3290

<400> SEQUENCE: 3290

000

<210> SEQ ID NO 3291

<400> SEQUENCE: 3291
```

000

<210> SEQ ID NO 3292

<400> SEQUENCE: 3292

000

<210> SEQ ID NO 3293

<400> SEQUENCE: 3293

000

<210> SEQ ID NO 3294

<400> SEQUENCE: 3294

000

<210> SEQ ID NO 3295

<400> SEQUENCE: 3295

000

<210> SEQ ID NO 3296

<400> SEQUENCE: 3296

000

<210> SEQ ID NO 3297

<400> SEQUENCE: 3297

000

<210> SEQ ID NO 3298

<400> SEQUENCE: 3298

000

<210> SEQ ID NO 3299

<400> SEQUENCE: 3299

000

<210> SEQ ID NO 3300

<400> SEQUENCE: 3300

000

<210> SEQ ID NO 3301

<400> SEQUENCE: 3301

000

<210> SEQ ID NO 3302

<400> SEQUENCE: 3302

000

<210> SEQ ID NO 3303

<400> SEQUENCE: 3303

000

<210> SEQ ID NO 3304

<400> SEQUENCE: 3304

000

<210> SEQ ID NO 3305

<400> SEQUENCE: 3305

000

<210> SEQ ID NO 3306

<400> SEQUENCE: 3306

000

<210> SEQ ID NO 3307

<400> SEQUENCE: 3307

000

<210> SEQ ID NO 3308

<400> SEQUENCE: 3308

000

<210> SEQ ID NO 3309

<400> SEQUENCE: 3309

000

<210> SEQ ID NO 3310

<400> SEQUENCE: 3310

000

<210> SEQ ID NO 3311

<400> SEQUENCE: 3311

000

<210> SEQ ID NO 3312

<400> SEQUENCE: 3312

000

<210> SEQ ID NO 3313

<400> SEQUENCE: 3313

000

-continued

<210> SEQ ID NO 3314

<400> SEQUENCE: 3314

000

<210> SEQ ID NO 3315

<400> SEQUENCE: 3315

000

<210> SEQ ID NO 3316

<400> SEQUENCE: 3316

000

<210> SEQ ID NO 3317

<400> SEQUENCE: 3317

000

<210> SEQ ID NO 3318

<400> SEQUENCE: 3318

000

<210> SEQ ID NO 3319

<400> SEQUENCE: 3319

000

<210> SEQ ID NO 3320

<400> SEQUENCE: 3320

000

<210> SEQ ID NO 3321

<400> SEQUENCE: 3321

000

<210> SEQ ID NO 3322

<400> SEQUENCE: 3322

000

<210> SEQ ID NO 3323

<400> SEQUENCE: 3323

000

<210> SEQ ID NO 3324

<400> SEQUENCE: 3324

000

<210> SEQ ID NO 3325

<400> SEQUENCE: 3325

000

<210> SEQ ID NO 3326

<400> SEQUENCE: 3326

000

<210> SEQ ID NO 3327

<400> SEQUENCE: 3327

000

<210> SEQ ID NO 3328

<400> SEQUENCE: 3328

000

<210> SEQ ID NO 3329

<400> SEQUENCE: 3329

000

<210> SEQ ID NO 3330

<400> SEQUENCE: 3330

000

<210> SEQ ID NO 3331

<400> SEQUENCE: 3331

000

<210> SEQ ID NO 3332

<400> SEQUENCE: 3332

000

<210> SEQ ID NO 3333

<400> SEQUENCE: 3333

000

<210> SEQ ID NO 3334

<400> SEQUENCE: 3334

000

<210> SEQ ID NO 3335

<400> SEQUENCE: 3335

000

<210> SEQ ID NO 3336

<400> SEQUENCE: 3336

000

<210> SEQ ID NO 3337

<400> SEQUENCE: 3337

000

<210> SEQ ID NO 3338

<400> SEQUENCE: 3338

000

<210> SEQ ID NO 3339

<400> SEQUENCE: 3339

000

<210> SEQ ID NO 3340

<400> SEQUENCE: 3340

000

<210> SEQ ID NO 3341

<400> SEQUENCE: 3341

000

<210> SEQ ID NO 3342

<400> SEQUENCE: 3342

000

<210> SEQ ID NO 3343

<400> SEQUENCE: 3343

000

<210> SEQ ID NO 3344

<400> SEQUENCE: 3344

000

<210> SEQ ID NO 3345

<400> SEQUENCE: 3345

000

<210> SEQ ID NO 3346

<400> SEQUENCE: 3346

000

<210> SEQ ID NO 3347

<400> SEQUENCE: 3347

000

<210> SEQ ID NO 3348

<400> SEQUENCE: 3348

000

<210> SEQ ID NO 3349

<400> SEQUENCE: 3349

000

<210> SEQ ID NO 3350

<400> SEQUENCE: 3350

000

<210> SEQ ID NO 3351

<400> SEQUENCE: 3351

000

<210> SEQ ID NO 3352

<400> SEQUENCE: 3352

000

<210> SEQ ID NO 3353

<400> SEQUENCE: 3353

000

<210> SEQ ID NO 3354

<400> SEQUENCE: 3354

000

<210> SEQ ID NO 3355

<400> SEQUENCE: 3355

000

<210> SEQ ID NO 3356

<400> SEQUENCE: 3356

000

<210> SEQ ID NO 3357

<400> SEQUENCE: 3357

000

<210> SEQ ID NO 3358

<400> SEQUENCE: 3358

000

<210> SEQ ID NO 3359

<400> SEQUENCE: 3359

000

<210> SEQ ID NO 3360

<400> SEQUENCE: 3360

000

<210> SEQ ID NO 3361

<400> SEQUENCE: 3361

000

<210> SEQ ID NO 3362

<400> SEQUENCE: 3362

000

<210> SEQ ID NO 3363

<400> SEQUENCE: 3363

000

<210> SEQ ID NO 3364

<400> SEQUENCE: 3364

000

<210> SEQ ID NO 3365

<400> SEQUENCE: 3365

000

<210> SEQ ID NO 3366

<400> SEQUENCE: 3366

000

<210> SEQ ID NO 3367

<400> SEQUENCE: 3367

000

<210> SEQ ID NO 3368

<400> SEQUENCE: 3368

000

<210> SEQ ID NO 3369

<400> SEQUENCE: 3369

000

<210> SEQ ID NO 3370

<400> SEQUENCE: 3370

000

<210> SEQ ID NO 3371

<400> SEQUENCE: 3371

000

<210> SEQ ID NO 3372

<400> SEQUENCE: 3372

000

<210> SEQ ID NO 3373

<400> SEQUENCE: 3373

000

<210> SEQ ID NO 3374

<400> SEQUENCE: 3374

000

<210> SEQ ID NO 3375

<400> SEQUENCE: 3375

000

<210> SEQ ID NO 3376

<400> SEQUENCE: 3376

000

<210> SEQ ID NO 3377

<400> SEQUENCE: 3377

000

<210> SEQ ID NO 3378

<400> SEQUENCE: 3378

000

<210> SEQ ID NO 3379

<400> SEQUENCE: 3379

000

<210> SEQ ID NO 3380

<400> SEQUENCE: 3380

000

<210> SEQ ID NO 3381

<400> SEQUENCE: 3381

000

<210> SEQ ID NO 3382

<400> SEQUENCE: 3382

000

<210> SEQ ID NO 3383

<400> SEQUENCE: 3383

000

<210> SEQ ID NO 3384

<400> SEQUENCE: 3384

000

<210> SEQ ID NO 3385

<400> SEQUENCE: 3385

000

<210> SEQ ID NO 3386

<400> SEQUENCE: 3386

000

<210> SEQ ID NO 3387

<400> SEQUENCE: 3387

000

<210> SEQ ID NO 3388

<400> SEQUENCE: 3388

000

<210> SEQ ID NO 3389

<400> SEQUENCE: 3389

000

<210> SEQ ID NO 3390

<400> SEQUENCE: 3390

000

<210> SEQ ID NO 3391

<400> SEQUENCE: 3391

000

<210> SEQ ID NO 3392

<400> SEQUENCE: 3392

000

<210> SEQ ID NO 3393

<400> SEQUENCE: 3393

000

<210> SEQ ID NO 3394

<400> SEQUENCE: 3394

000

<210> SEQ ID NO 3395

<400> SEQUENCE: 3395

000

<210> SEQ ID NO 3396

<400> SEQUENCE: 3396

000

<210> SEQ ID NO 3397

<400> SEQUENCE: 3397

000

<210> SEQ ID NO 3398

<400> SEQUENCE: 3398

000

<210> SEQ ID NO 3399

<400> SEQUENCE: 3399

000

<210> SEQ ID NO 3400

<400> SEQUENCE: 3400

000

<210> SEQ ID NO 3401

<400> SEQUENCE: 3401

000

<210> SEQ ID NO 3402

<400> SEQUENCE: 3402

000

<210> SEQ ID NO 3403

<400> SEQUENCE: 3403

000

<210> SEQ ID NO 3404

<400> SEQUENCE: 3404

000

<210> SEQ ID NO 3405

<400> SEQUENCE: 3405

000

<210> SEQ ID NO 3406

<400> SEQUENCE: 3406

000

<210> SEQ ID NO 3407

<400> SEQUENCE: 3407

000

<210> SEQ ID NO 3408

<400> SEQUENCE: 3408

000

<210> SEQ ID NO 3409

<400> SEQUENCE: 3409

000

<210> SEQ ID NO 3410

<400> SEQUENCE: 3410

000

<210> SEQ ID NO 3411

<400> SEQUENCE: 3411

000

<210> SEQ ID NO 3412

<400> SEQUENCE: 3412

000

<210> SEQ ID NO 3413

<400> SEQUENCE: 3413

000

<210> SEQ ID NO 3414

<400> SEQUENCE: 3414

000

<210> SEQ ID NO 3415

<400> SEQUENCE: 3415

000

<210> SEQ ID NO 3416

<400> SEQUENCE: 3416

000

<210> SEQ ID NO 3417

<400> SEQUENCE: 3417

000

<210> SEQ ID NO 3418

<400> SEQUENCE: 3418

000

<210> SEQ ID NO 3419

<400> SEQUENCE: 3419

000

<210> SEQ ID NO 3420

<400> SEQUENCE: 3420

000

<210> SEQ ID NO 3421

<400> SEQUENCE: 3421

000

<210> SEQ ID NO 3422

<400> SEQUENCE: 3422

000

<210> SEQ ID NO 3423

<400> SEQUENCE: 3423

000

<210> SEQ ID NO 3424

<400> SEQUENCE: 3424

000

<210> SEQ ID NO 3425

<400> SEQUENCE: 3425

000

<210> SEQ ID NO 3426

<400> SEQUENCE: 3426

000

<210> SEQ ID NO 3427

<400> SEQUENCE: 3427

000

<210> SEQ ID NO 3428

<400> SEQUENCE: 3428

000

<210> SEQ ID NO 3429

<400> SEQUENCE: 3429

000

<210> SEQ ID NO 3430

<400> SEQUENCE: 3430

000

<210> SEQ ID NO 3431

<400> SEQUENCE: 3431

000

<210> SEQ ID NO 3432

<400> SEQUENCE: 3432

000

<210> SEQ ID NO 3433

<400> SEQUENCE: 3433

000

<210> SEQ ID NO 3434

<400> SEQUENCE: 3434

000

<210> SEQ ID NO 3435

<400> SEQUENCE: 3435

000

<210> SEQ ID NO 3436

<400> SEQUENCE: 3436

000

<210> SEQ ID NO 3437

<400> SEQUENCE: 3437

000

<210> SEQ ID NO 3438

<400> SEQUENCE: 3438

000

<210> SEQ ID NO 3439

<400> SEQUENCE: 3439

000

<210> SEQ ID NO 3440

<400> SEQUENCE: 3440

000

<210> SEQ ID NO 3441

<400> SEQUENCE: 3441

000

<210> SEQ ID NO 3442

<400> SEQUENCE: 3442

000

<210> SEQ ID NO 3443

<400> SEQUENCE: 3443

000

<210> SEQ ID NO 3444

<400> SEQUENCE: 3444

000

<210> SEQ ID NO 3445

<400> SEQUENCE: 3445

000

<210> SEQ ID NO 3446

<400> SEQUENCE: 3446

000

<210> SEQ ID NO 3447

<400> SEQUENCE: 3447

000

<210> SEQ ID NO 3448

<400> SEQUENCE: 3448

000

<210> SEQ ID NO 3449

<400> SEQUENCE: 3449

000

<210> SEQ ID NO 3450

<400> SEQUENCE: 3450

000

<210> SEQ ID NO 3451

<400> SEQUENCE: 3451

000

<210> SEQ ID NO 3452

<400> SEQUENCE: 3452

000

<210> SEQ ID NO 3453

<400> SEQUENCE: 3453

000

<210> SEQ ID NO 3454

<400> SEQUENCE: 3454

000

<210> SEQ ID NO 3455

<400> SEQUENCE: 3455

000

<210> SEQ ID NO 3456

<400> SEQUENCE: 3456

000

<210> SEQ ID NO 3457

<400> SEQUENCE: 3457

000

<210> SEQ ID NO 3458

<400> SEQUENCE: 3458

000

<210> SEQ ID NO 3459

<400> SEQUENCE: 3459

000

<210> SEQ ID NO 3460

<400> SEQUENCE: 3460

000

<210> SEQ ID NO 3461

<400> SEQUENCE: 3461

000

<210> SEQ ID NO 3462

<400> SEQUENCE: 3462

000

<210> SEQ ID NO 3463

<400> SEQUENCE: 3463

000

<210> SEQ ID NO 3464

<400> SEQUENCE: 3464

000

<210> SEQ ID NO 3465

<400> SEQUENCE: 3465

000

<210> SEQ ID NO 3466

<400> SEQUENCE: 3466

000

<210> SEQ ID NO 3467

<400> SEQUENCE: 3467

000

<210> SEQ ID NO 3468

<400> SEQUENCE: 3468

000

<210> SEQ ID NO 3469

<400> SEQUENCE: 3469

000

<210> SEQ ID NO 3470

<400> SEQUENCE: 3470

000

<210> SEQ ID NO 3471

<400> SEQUENCE: 3471

000

-continued

<210> SEQ ID NO 3472

<400> SEQUENCE: 3472

000

<210> SEQ ID NO 3473

<400> SEQUENCE: 3473

000

<210> SEQ ID NO 3474

<400> SEQUENCE: 3474

000

<210> SEQ ID NO 3475

<400> SEQUENCE: 3475

000

<210> SEQ ID NO 3476

<400> SEQUENCE: 3476

000

<210> SEQ ID NO 3477

<400> SEQUENCE: 3477

000

<210> SEQ ID NO 3478

<400> SEQUENCE: 3478

000

<210> SEQ ID NO 3479

<400> SEQUENCE: 3479

000

<210> SEQ ID NO 3480

<400> SEQUENCE: 3480

000

<210> SEQ ID NO 3481

<400> SEQUENCE: 3481

000

<210> SEQ ID NO 3482

<400> SEQUENCE: 3482

000

<210> SEQ ID NO 3483

<400> SEQUENCE: 3483

000

<210> SEQ ID NO 3484

<400> SEQUENCE: 3484

000

<210> SEQ ID NO 3485

<400> SEQUENCE: 3485

000

<210> SEQ ID NO 3486

<400> SEQUENCE: 3486

000

<210> SEQ ID NO 3487

<400> SEQUENCE: 3487

000

<210> SEQ ID NO 3488

<400> SEQUENCE: 3488

000

<210> SEQ ID NO 3489

<400> SEQUENCE: 3489

000

<210> SEQ ID NO 3490

<400> SEQUENCE: 3490

000

<210> SEQ ID NO 3491

<400> SEQUENCE: 3491

000

<210> SEQ ID NO 3492

<400> SEQUENCE: 3492

000

<210> SEQ ID NO 3493

<400> SEQUENCE: 3493

000

<210> SEQ ID NO 3494

<400> SEQUENCE: 3494

-continued

000

<210> SEQ ID NO 3495

<400> SEQUENCE: 3495

000

<210> SEQ ID NO 3496

<400> SEQUENCE: 3496

000

<210> SEQ ID NO 3497

<400> SEQUENCE: 3497

000

<210> SEQ ID NO 3498

<400> SEQUENCE: 3498

000

<210> SEQ ID NO 3499

<400> SEQUENCE: 3499

000

<210> SEQ ID NO 3500

<400> SEQUENCE: 3500

000

<210> SEQ ID NO 3501

<400> SEQUENCE: 3501

000

<210> SEQ ID NO 3502

<400> SEQUENCE: 3502

000

<210> SEQ ID NO 3503

<400> SEQUENCE: 3503

000

<210> SEQ ID NO 3504

<400> SEQUENCE: 3504

000

<210> SEQ ID NO 3505

<400> SEQUENCE: 3505

000

<210> SEQ ID NO 3506

<400> SEQUENCE: 3506

000

<210> SEQ ID NO 3507

<400> SEQUENCE: 3507

000

<210> SEQ ID NO 3508

<400> SEQUENCE: 3508

000

<210> SEQ ID NO 3509

<400> SEQUENCE: 3509

000

<210> SEQ ID NO 3510

<400> SEQUENCE: 3510

000

<210> SEQ ID NO 3511

<400> SEQUENCE: 3511

000

<210> SEQ ID NO 3512

<400> SEQUENCE: 3512

000

<210> SEQ ID NO 3513

<400> SEQUENCE: 3513

000

<210> SEQ ID NO 3514

<400> SEQUENCE: 3514

000

<210> SEQ ID NO 3515

<400> SEQUENCE: 3515

000

<210> SEQ ID NO 3516

<400> SEQUENCE: 3516

000

<210> SEQ ID NO 3517

-continued

<400> SEQUENCE: 3517

000

<210> SEQ ID NO 3518

<400> SEQUENCE: 3518

000

<210> SEQ ID NO 3519

<400> SEQUENCE: 3519

000

<210> SEQ ID NO 3520

<400> SEQUENCE: 3520

000

<210> SEQ ID NO 3521

<400> SEQUENCE: 3521

000

<210> SEQ ID NO 3522

<400> SEQUENCE: 3522

000

<210> SEQ ID NO 3523

<400> SEQUENCE: 3523

000

<210> SEQ ID NO 3524

<400> SEQUENCE: 3524

000

<210> SEQ ID NO 3525

<400> SEQUENCE: 3525

000

<210> SEQ ID NO 3526

<400> SEQUENCE: 3526

000

<210> SEQ ID NO 3527

<400> SEQUENCE: 3527

000

<210> SEQ ID NO 3528

<400> SEQUENCE: 3528

000

<210> SEQ ID NO 3529

<400> SEQUENCE: 3529

000

<210> SEQ ID NO 3530

<400> SEQUENCE: 3530

000

<210> SEQ ID NO 3531

<400> SEQUENCE: 3531

000

<210> SEQ ID NO 3532

<400> SEQUENCE: 3532

000

<210> SEQ ID NO 3533

<400> SEQUENCE: 3533

000

<210> SEQ ID NO 3534

<400> SEQUENCE: 3534

000

<210> SEQ ID NO 3535

<400> SEQUENCE: 3535

000

<210> SEQ ID NO 3536

<400> SEQUENCE: 3536

000

<210> SEQ ID NO 3537

<400> SEQUENCE: 3537

000

<210> SEQ ID NO 3538

<400> SEQUENCE: 3538

000

<210> SEQ ID NO 3539

<400> SEQUENCE: 3539

000

<210> SEQ ID NO 3540

<400> SEQUENCE: 3540

000

<210> SEQ ID NO 3541

<400> SEQUENCE: 3541

000

<210> SEQ ID NO 3542

<400> SEQUENCE: 3542

000

<210> SEQ ID NO 3543

<400> SEQUENCE: 3543

000

<210> SEQ ID NO 3544

<400> SEQUENCE: 3544

000

<210> SEQ ID NO 3545

<400> SEQUENCE: 3545

000

<210> SEQ ID NO 3546

<400> SEQUENCE: 3546

000

<210> SEQ ID NO 3547

<400> SEQUENCE: 3547

000

<210> SEQ ID NO 3548

<400> SEQUENCE: 3548

000

<210> SEQ ID NO 3549

<400> SEQUENCE: 3549

000

<210> SEQ ID NO 3550

<400> SEQUENCE: 3550

000

<210> SEQ ID NO 3551

<400> SEQUENCE: 3551

000

<210> SEQ ID NO 3552

<400> SEQUENCE: 3552

000

<210> SEQ ID NO 3553

<400> SEQUENCE: 3553

000

<210> SEQ ID NO 3554

<400> SEQUENCE: 3554

000

<210> SEQ ID NO 3555

<400> SEQUENCE: 3555

000

<210> SEQ ID NO 3556

<400> SEQUENCE: 3556

000

<210> SEQ ID NO 3557

<400> SEQUENCE: 3557

000

<210> SEQ ID NO 3558

<400> SEQUENCE: 3558

000

<210> SEQ ID NO 3559

<400> SEQUENCE: 3559

000

<210> SEQ ID NO 3560

<400> SEQUENCE: 3560

000

<210> SEQ ID NO 3561

<400> SEQUENCE: 3561

000

<210> SEQ ID NO 3562

<400> SEQUENCE: 3562

000

<210> SEQ ID NO 3563

<400> SEQUENCE: 3563

000

<210> SEQ ID NO 3564

<400> SEQUENCE: 3564

000

<210> SEQ ID NO 3565

<400> SEQUENCE: 3565

000

<210> SEQ ID NO 3566

<400> SEQUENCE: 3566

000

<210> SEQ ID NO 3567

<400> SEQUENCE: 3567

000

<210> SEQ ID NO 3568

<400> SEQUENCE: 3568

000

<210> SEQ ID NO 3569

<400> SEQUENCE: 3569

000

<210> SEQ ID NO 3570

<400> SEQUENCE: 3570

000

<210> SEQ ID NO 3571

<400> SEQUENCE: 3571

000

<210> SEQ ID NO 3572

<400> SEQUENCE: 3572

000

<210> SEQ ID NO 3573

<400> SEQUENCE: 3573

000

<210> SEQ ID NO 3574

<400> SEQUENCE: 3574

000

<210> SEQ ID NO 3575

<400> SEQUENCE: 3575

000

<210> SEQ ID NO 3576

<400> SEQUENCE: 3576

000

<210> SEQ ID NO 3577

<400> SEQUENCE: 3577

000

<210> SEQ ID NO 3578

<400> SEQUENCE: 3578

000

<210> SEQ ID NO 3579

<400> SEQUENCE: 3579

000

<210> SEQ ID NO 3580

<400> SEQUENCE: 3580

000

<210> SEQ ID NO 3581

<400> SEQUENCE: 3581

000

<210> SEQ ID NO 3582

<400> SEQUENCE: 3582

000

<210> SEQ ID NO 3583

<400> SEQUENCE: 3583

000

<210> SEQ ID NO 3584

<400> SEQUENCE: 3584

000

<210> SEQ ID NO 3585

<400> SEQUENCE: 3585

000

<210> SEQ ID NO 3586

<400> SEQUENCE: 3586

000

<210> SEQ ID NO 3587

<400> SEQUENCE: 3587

000

<210> SEQ ID NO 3588

<400> SEQUENCE: 3588

000

<210> SEQ ID NO 3589

<400> SEQUENCE: 3589

000

<210> SEQ ID NO 3590

<400> SEQUENCE: 3590

000

<210> SEQ ID NO 3591

<400> SEQUENCE: 3591

000

<210> SEQ ID NO 3592

<400> SEQUENCE: 3592

000

<210> SEQ ID NO 3593

<400> SEQUENCE: 3593

000

<210> SEQ ID NO 3594

<400> SEQUENCE: 3594

000

<210> SEQ ID NO 3595

<400> SEQUENCE: 3595

000

<210> SEQ ID NO 3596

<400> SEQUENCE: 3596

000

<210> SEQ ID NO 3597

<400> SEQUENCE: 3597

000

<210> SEQ ID NO 3598

<400> SEQUENCE: 3598

000

<210> SEQ ID NO 3599

<400> SEQUENCE: 3599

000

<210> SEQ ID NO 3600

<400> SEQUENCE: 3600

000

<210> SEQ ID NO 3601

<400> SEQUENCE: 3601

000

<210> SEQ ID NO 3602

<400> SEQUENCE: 3602

000

<210> SEQ ID NO 3603

<400> SEQUENCE: 3603

000

<210> SEQ ID NO 3604

<400> SEQUENCE: 3604

000

<210> SEQ ID NO 3605

<400> SEQUENCE: 3605

000

<210> SEQ ID NO 3606

<400> SEQUENCE: 3606

000

<210> SEQ ID NO 3607

<400> SEQUENCE: 3607

000

<210> SEQ ID NO 3608

<400> SEQUENCE: 3608

000

<210> SEQ ID NO 3609

<400> SEQUENCE: 3609

000

<210> SEQ ID NO 3610

<400> SEQUENCE: 3610

000

<210> SEQ ID NO 3611

<400> SEQUENCE: 3611

000

<210> SEQ ID NO 3612

<400> SEQUENCE: 3612

000

<210> SEQ ID NO 3613

<400> SEQUENCE: 3613

000

<210> SEQ ID NO 3614

<400> SEQUENCE: 3614

000

<210> SEQ ID NO 3615

<400> SEQUENCE: 3615

000

<210> SEQ ID NO 3616

<400> SEQUENCE: 3616

000

<210> SEQ ID NO 3617

<400> SEQUENCE: 3617

000

<210> SEQ ID NO 3618

<400> SEQUENCE: 3618

000

<210> SEQ ID NO 3619

<400> SEQUENCE: 3619

000

<210> SEQ ID NO 3620

<400> SEQUENCE: 3620

000

<210> SEQ ID NO 3621

<400> SEQUENCE: 3621

000

<210> SEQ ID NO 3622

<400> SEQUENCE: 3622

000

<210> SEQ ID NO 3623

<400> SEQUENCE: 3623

000

<210> SEQ ID NO 3624

<400> SEQUENCE: 3624

000

<210> SEQ ID NO 3625

<400> SEQUENCE: 3625

000

<210> SEQ ID NO 3626

<400> SEQUENCE: 3626

000

<210> SEQ ID NO 3627

<400> SEQUENCE: 3627

000

<210> SEQ ID NO 3628

<400> SEQUENCE: 3628

000

<210> SEQ ID NO 3629

<400> SEQUENCE: 3629

000

```
<210> SEQ ID NO 3630
<400> SEQUENCE: 3630
000

<210> SEQ ID NO 3631
<400> SEQUENCE: 3631
000

<210> SEQ ID NO 3632
<400> SEQUENCE: 3632
000

<210> SEQ ID NO 3633
<400> SEQUENCE: 3633
000

<210> SEQ ID NO 3634
<400> SEQUENCE: 3634
000

<210> SEQ ID NO 3635
<400> SEQUENCE: 3635
000

<210> SEQ ID NO 3636
<400> SEQUENCE: 3636
000

<210> SEQ ID NO 3637
<400> SEQUENCE: 3637
000

<210> SEQ ID NO 3638
<400> SEQUENCE: 3638
000

<210> SEQ ID NO 3639
<400> SEQUENCE: 3639
000

<210> SEQ ID NO 3640
<400> SEQUENCE: 3640
000

<210> SEQ ID NO 3641
```

```
<400> SEQUENCE: 3641

000

<210> SEQ ID NO 3642

<400> SEQUENCE: 3642

000

<210> SEQ ID NO 3643

<400> SEQUENCE: 3643

000

<210> SEQ ID NO 3644

<400> SEQUENCE: 3644

000

<210> SEQ ID NO 3645

<400> SEQUENCE: 3645

000

<210> SEQ ID NO 3646

<400> SEQUENCE: 3646

000

<210> SEQ ID NO 3647

<400> SEQUENCE: 3647

000

<210> SEQ ID NO 3648

<400> SEQUENCE: 3648

000

<210> SEQ ID NO 3649

<400> SEQUENCE: 3649

000

<210> SEQ ID NO 3650

<400> SEQUENCE: 3650

000

<210> SEQ ID NO 3651

<400> SEQUENCE: 3651

000

<210> SEQ ID NO 3652

<400> SEQUENCE: 3652
```

-continued

000

<210> SEQ ID NO 3653
<400> SEQUENCE: 3653
000

<210> SEQ ID NO 3654
<400> SEQUENCE: 3654
000

<210> SEQ ID NO 3655
<400> SEQUENCE: 3655
000

<210> SEQ ID NO 3656
<400> SEQUENCE: 3656
000

<210> SEQ ID NO 3657
<400> SEQUENCE: 3657
000

<210> SEQ ID NO 3658
<400> SEQUENCE: 3658
000

<210> SEQ ID NO 3659
<400> SEQUENCE: 3659
000

<210> SEQ ID NO 3660
<400> SEQUENCE: 3660
000

<210> SEQ ID NO 3661
<400> SEQUENCE: 3661
000

<210> SEQ ID NO 3662
<400> SEQUENCE: 3662
000

<210> SEQ ID NO 3663
<400> SEQUENCE: 3663
000

<210> SEQ ID NO 3664

<400> SEQUENCE: 3664

000

<210> SEQ ID NO 3665

<400> SEQUENCE: 3665

000

<210> SEQ ID NO 3666

<400> SEQUENCE: 3666

000

<210> SEQ ID NO 3667

<400> SEQUENCE: 3667

000

<210> SEQ ID NO 3668

<400> SEQUENCE: 3668

000

<210> SEQ ID NO 3669

<400> SEQUENCE: 3669

000

<210> SEQ ID NO 3670

<400> SEQUENCE: 3670

000

<210> SEQ ID NO 3671

<400> SEQUENCE: 3671

000

<210> SEQ ID NO 3672

<400> SEQUENCE: 3672

000

<210> SEQ ID NO 3673

<400> SEQUENCE: 3673

000

<210> SEQ ID NO 3674

<400> SEQUENCE: 3674

000

<210> SEQ ID NO 3675

<400> SEQUENCE: 3675

000

<210> SEQ ID NO 3676

<400> SEQUENCE: 3676

000

<210> SEQ ID NO 3677

<400> SEQUENCE: 3677

000

<210> SEQ ID NO 3678

<400> SEQUENCE: 3678

000

<210> SEQ ID NO 3679

<400> SEQUENCE: 3679

000

<210> SEQ ID NO 3680

<400> SEQUENCE: 3680

000

<210> SEQ ID NO 3681

<400> SEQUENCE: 3681

000

<210> SEQ ID NO 3682

<400> SEQUENCE: 3682

000

<210> SEQ ID NO 3683

<400> SEQUENCE: 3683

000

<210> SEQ ID NO 3684

<400> SEQUENCE: 3684

000

<210> SEQ ID NO 3685

<400> SEQUENCE: 3685

000

<210> SEQ ID NO 3686

<400> SEQUENCE: 3686

000

<210> SEQ ID NO 3687

<400> SEQUENCE: 3687

000

<210> SEQ ID NO 3688

<400> SEQUENCE: 3688

000

<210> SEQ ID NO 3689

<400> SEQUENCE: 3689

000

<210> SEQ ID NO 3690

<400> SEQUENCE: 3690

000

<210> SEQ ID NO 3691

<400> SEQUENCE: 3691

000

<210> SEQ ID NO 3692

<400> SEQUENCE: 3692

000

<210> SEQ ID NO 3693

<400> SEQUENCE: 3693

000

<210> SEQ ID NO 3694

<400> SEQUENCE: 3694

000

<210> SEQ ID NO 3695

<400> SEQUENCE: 3695

000

<210> SEQ ID NO 3696

<400> SEQUENCE: 3696

000

<210> SEQ ID NO 3697

<400> SEQUENCE: 3697

000

-continued

<210> SEQ ID NO 3698

<400> SEQUENCE: 3698

000

<210> SEQ ID NO 3699

<400> SEQUENCE: 3699

000

<210> SEQ ID NO 3700

<400> SEQUENCE: 3700

000

<210> SEQ ID NO 3701

<400> SEQUENCE: 3701

000

<210> SEQ ID NO 3702

<400> SEQUENCE: 3702

000

<210> SEQ ID NO 3703

<400> SEQUENCE: 3703

000

<210> SEQ ID NO 3704

<400> SEQUENCE: 3704

000

<210> SEQ ID NO 3705

<400> SEQUENCE: 3705

000

<210> SEQ ID NO 3706

<400> SEQUENCE: 3706

000

<210> SEQ ID NO 3707

<400> SEQUENCE: 3707

000

<210> SEQ ID NO 3708

<400> SEQUENCE: 3708

000

<210> SEQ ID NO 3709

<400> SEQUENCE: 3709

000

<210> SEQ ID NO 3710

<400> SEQUENCE: 3710

000

<210> SEQ ID NO 3711

<400> SEQUENCE: 3711

000

<210> SEQ ID NO 3712

<400> SEQUENCE: 3712

000

<210> SEQ ID NO 3713

<400> SEQUENCE: 3713

000

<210> SEQ ID NO 3714

<400> SEQUENCE: 3714

000

<210> SEQ ID NO 3715

<400> SEQUENCE: 3715

000

<210> SEQ ID NO 3716

<400> SEQUENCE: 3716

000

<210> SEQ ID NO 3717

<400> SEQUENCE: 3717

000

<210> SEQ ID NO 3718

<400> SEQUENCE: 3718

000

<210> SEQ ID NO 3719

<400> SEQUENCE: 3719

000

<210> SEQ ID NO 3720

<400> SEQUENCE: 3720

000

<210> SEQ ID NO 3721

<400> SEQUENCE: 3721

000

<210> SEQ ID NO 3722

<400> SEQUENCE: 3722

000

<210> SEQ ID NO 3723

<400> SEQUENCE: 3723

000

<210> SEQ ID NO 3724

<400> SEQUENCE: 3724

000

<210> SEQ ID NO 3725

<400> SEQUENCE: 3725

000

<210> SEQ ID NO 3726

<400> SEQUENCE: 3726

000

<210> SEQ ID NO 3727

<400> SEQUENCE: 3727

000

<210> SEQ ID NO 3728

<400> SEQUENCE: 3728

000

<210> SEQ ID NO 3729

<400> SEQUENCE: 3729

000

<210> SEQ ID NO 3730

<400> SEQUENCE: 3730

000

<210> SEQ ID NO 3731

<400> SEQUENCE: 3731

000

<210> SEQ ID NO 3732
<400> SEQUENCE: 3732
000

<210> SEQ ID NO 3733
<400> SEQUENCE: 3733
000

<210> SEQ ID NO 3734
<400> SEQUENCE: 3734
000

<210> SEQ ID NO 3735
<400> SEQUENCE: 3735
000

<210> SEQ ID NO 3736
<400> SEQUENCE: 3736
000

<210> SEQ ID NO 3737
<400> SEQUENCE: 3737
000

<210> SEQ ID NO 3738
<400> SEQUENCE: 3738
000

<210> SEQ ID NO 3739
<400> SEQUENCE: 3739
000

<210> SEQ ID NO 3740
<400> SEQUENCE: 3740
000

<210> SEQ ID NO 3741
<400> SEQUENCE: 3741
000

<210> SEQ ID NO 3742
<400> SEQUENCE: 3742
000

-continued

<210> SEQ ID NO 3743

<400> SEQUENCE: 3743

000

<210> SEQ ID NO 3744

<400> SEQUENCE: 3744

000

<210> SEQ ID NO 3745

<400> SEQUENCE: 3745

000

<210> SEQ ID NO 3746

<400> SEQUENCE: 3746

000

<210> SEQ ID NO 3747

<400> SEQUENCE: 3747

000

<210> SEQ ID NO 3748

<400> SEQUENCE: 3748

000

<210> SEQ ID NO 3749

<400> SEQUENCE: 3749

000

<210> SEQ ID NO 3750

<400> SEQUENCE: 3750

000

<210> SEQ ID NO 3751

<400> SEQUENCE: 3751

000

<210> SEQ ID NO 3752

<400> SEQUENCE: 3752

000

<210> SEQ ID NO 3753

<400> SEQUENCE: 3753

000

<210> SEQ ID NO 3754

<400> SEQUENCE: 3754

000

<210> SEQ ID NO 3755

<400> SEQUENCE: 3755

000

<210> SEQ ID NO 3756

<400> SEQUENCE: 3756

000

<210> SEQ ID NO 3757

<400> SEQUENCE: 3757

000

<210> SEQ ID NO 3758

<400> SEQUENCE: 3758

000

<210> SEQ ID NO 3759

<400> SEQUENCE: 3759

000

<210> SEQ ID NO 3760

<400> SEQUENCE: 3760

000

<210> SEQ ID NO 3761

<400> SEQUENCE: 3761

000

<210> SEQ ID NO 3762

<400> SEQUENCE: 3762

000

<210> SEQ ID NO 3763

<400> SEQUENCE: 3763

000

<210> SEQ ID NO 3764

<400> SEQUENCE: 3764

000

<210> SEQ ID NO 3765

<400> SEQUENCE: 3765

000

<210> SEQ ID NO 3766

<400> SEQUENCE: 3766

000

<210> SEQ ID NO 3767

<400> SEQUENCE: 3767

000

<210> SEQ ID NO 3768

<400> SEQUENCE: 3768

000

<210> SEQ ID NO 3769

<400> SEQUENCE: 3769

000

<210> SEQ ID NO 3770

<400> SEQUENCE: 3770

000

<210> SEQ ID NO 3771

<400> SEQUENCE: 3771

000

<210> SEQ ID NO 3772

<400> SEQUENCE: 3772

000

<210> SEQ ID NO 3773

<400> SEQUENCE: 3773

000

<210> SEQ ID NO 3774

<400> SEQUENCE: 3774

000

<210> SEQ ID NO 3775

<400> SEQUENCE: 3775

000

<210> SEQ ID NO 3776

<400> SEQUENCE: 3776

000

<210> SEQ ID NO 3777

<400> SEQUENCE: 3777

000

<210> SEQ ID NO 3778

<400> SEQUENCE: 3778

000

<210> SEQ ID NO 3779

<400> SEQUENCE: 3779

000

<210> SEQ ID NO 3780

<400> SEQUENCE: 3780

000

<210> SEQ ID NO 3781

<400> SEQUENCE: 3781

000

<210> SEQ ID NO 3782

<400> SEQUENCE: 3782

000

<210> SEQ ID NO 3783

<400> SEQUENCE: 3783

000

<210> SEQ ID NO 3784

<400> SEQUENCE: 3784

000

<210> SEQ ID NO 3785

<400> SEQUENCE: 3785

000

<210> SEQ ID NO 3786

<400> SEQUENCE: 3786

000

<210> SEQ ID NO 3787

<400> SEQUENCE: 3787

000

```
<210> SEQ ID NO 3788
<400> SEQUENCE: 3788
000

<210> SEQ ID NO 3789
<400> SEQUENCE: 3789
000

<210> SEQ ID NO 3790
<400> SEQUENCE: 3790
000

<210> SEQ ID NO 3791
<400> SEQUENCE: 3791
000

<210> SEQ ID NO 3792
<400> SEQUENCE: 3792
000

<210> SEQ ID NO 3793
<400> SEQUENCE: 3793
000

<210> SEQ ID NO 3794
<400> SEQUENCE: 3794
000

<210> SEQ ID NO 3795
<400> SEQUENCE: 3795
000

<210> SEQ ID NO 3796
<400> SEQUENCE: 3796
000

<210> SEQ ID NO 3797
<400> SEQUENCE: 3797
000

<210> SEQ ID NO 3798
<400> SEQUENCE: 3798
000

<210> SEQ ID NO 3799
```

<400> SEQUENCE: 3799

000

<210> SEQ ID NO 3800

<400> SEQUENCE: 3800

000

<210> SEQ ID NO 3801

<400> SEQUENCE: 3801

000

<210> SEQ ID NO 3802

<400> SEQUENCE: 3802

000

<210> SEQ ID NO 3803

<400> SEQUENCE: 3803

000

<210> SEQ ID NO 3804

<400> SEQUENCE: 3804

000

<210> SEQ ID NO 3805

<400> SEQUENCE: 3805

000

<210> SEQ ID NO 3806

<400> SEQUENCE: 3806

000

<210> SEQ ID NO 3807

<400> SEQUENCE: 3807

000

<210> SEQ ID NO 3808

<400> SEQUENCE: 3808

000

<210> SEQ ID NO 3809

<400> SEQUENCE: 3809

000

<210> SEQ ID NO 3810

<400> SEQUENCE: 3810

000

<210> SEQ ID NO 3811

<400> SEQUENCE: 3811

000

<210> SEQ ID NO 3812

<400> SEQUENCE: 3812

000

<210> SEQ ID NO 3813

<400> SEQUENCE: 3813

000

<210> SEQ ID NO 3814

<400> SEQUENCE: 3814

000

<210> SEQ ID NO 3815

<400> SEQUENCE: 3815

000

<210> SEQ ID NO 3816

<400> SEQUENCE: 3816

000

<210> SEQ ID NO 3817

<400> SEQUENCE: 3817

000

<210> SEQ ID NO 3818

<400> SEQUENCE: 3818

000

<210> SEQ ID NO 3819

<400> SEQUENCE: 3819

000

<210> SEQ ID NO 3820

<400> SEQUENCE: 3820

000

<210> SEQ ID NO 3821

<400> SEQUENCE: 3821

000

-continued

<210> SEQ ID NO 3822

<400> SEQUENCE: 3822

000

<210> SEQ ID NO 3823

<400> SEQUENCE: 3823

000

<210> SEQ ID NO 3824

<400> SEQUENCE: 3824

000

<210> SEQ ID NO 3825

<400> SEQUENCE: 3825

000

<210> SEQ ID NO 3826

<400> SEQUENCE: 3826

000

<210> SEQ ID NO 3827

<400> SEQUENCE: 3827

000

<210> SEQ ID NO 3828

<400> SEQUENCE: 3828

000

<210> SEQ ID NO 3829

<400> SEQUENCE: 3829

000

<210> SEQ ID NO 3830

<400> SEQUENCE: 3830

000

<210> SEQ ID NO 3831

<400> SEQUENCE: 3831

000

<210> SEQ ID NO 3832

<400> SEQUENCE: 3832

000

<210> SEQ ID NO 3833

```
<400> SEQUENCE: 3833
000

<210> SEQ ID NO 3834
<400> SEQUENCE: 3834
000

<210> SEQ ID NO 3835
<400> SEQUENCE: 3835
000

<210> SEQ ID NO 3836
<400> SEQUENCE: 3836
000

<210> SEQ ID NO 3837
<400> SEQUENCE: 3837
000

<210> SEQ ID NO 3838
<400> SEQUENCE: 3838
000

<210> SEQ ID NO 3839
<400> SEQUENCE: 3839
000

<210> SEQ ID NO 3840
<400> SEQUENCE: 3840
000

<210> SEQ ID NO 3841
<400> SEQUENCE: 3841
000

<210> SEQ ID NO 3842
<400> SEQUENCE: 3842
000

<210> SEQ ID NO 3843
<400> SEQUENCE: 3843
000

<210> SEQ ID NO 3844
<400> SEQUENCE: 3844
```

000

<210> SEQ ID NO 3845

<400> SEQUENCE: 3845

000

<210> SEQ ID NO 3846

<400> SEQUENCE: 3846

000

<210> SEQ ID NO 3847

<400> SEQUENCE: 3847

000

<210> SEQ ID NO 3848

<400> SEQUENCE: 3848

000

<210> SEQ ID NO 3849

<400> SEQUENCE: 3849

000

<210> SEQ ID NO 3850

<400> SEQUENCE: 3850

000

<210> SEQ ID NO 3851

<400> SEQUENCE: 3851

000

<210> SEQ ID NO 3852

<400> SEQUENCE: 3852

000

<210> SEQ ID NO 3853

<400> SEQUENCE: 3853

000

<210> SEQ ID NO 3854

<400> SEQUENCE: 3854

000

<210> SEQ ID NO 3855

<400> SEQUENCE: 3855

000

<210> SEQ ID NO 3856

<400> SEQUENCE: 3856

000

<210> SEQ ID NO 3857

<400> SEQUENCE: 3857

000

<210> SEQ ID NO 3858

<400> SEQUENCE: 3858

000

<210> SEQ ID NO 3859

<400> SEQUENCE: 3859

000

<210> SEQ ID NO 3860

<400> SEQUENCE: 3860

000

<210> SEQ ID NO 3861

<400> SEQUENCE: 3861

000

<210> SEQ ID NO 3862

<400> SEQUENCE: 3862

000

<210> SEQ ID NO 3863

<400> SEQUENCE: 3863

000

<210> SEQ ID NO 3864

<400> SEQUENCE: 3864

000

<210> SEQ ID NO 3865

<400> SEQUENCE: 3865

000

<210> SEQ ID NO 3866

<400> SEQUENCE: 3866

000

-continued

<210> SEQ ID NO 3867

<400> SEQUENCE: 3867

000

<210> SEQ ID NO 3868

<400> SEQUENCE: 3868

000

<210> SEQ ID NO 3869

<400> SEQUENCE: 3869

000

<210> SEQ ID NO 3870

<400> SEQUENCE: 3870

000

<210> SEQ ID NO 3871

<400> SEQUENCE: 3871

000

<210> SEQ ID NO 3872

<400> SEQUENCE: 3872

000

<210> SEQ ID NO 3873

<400> SEQUENCE: 3873

000

<210> SEQ ID NO 3874

<400> SEQUENCE: 3874

000

<210> SEQ ID NO 3875

<400> SEQUENCE: 3875

000

<210> SEQ ID NO 3876

<400> SEQUENCE: 3876

000

<210> SEQ ID NO 3877

<400> SEQUENCE: 3877

000

<210> SEQ ID NO 3878

<400> SEQUENCE: 3878

000

<210> SEQ ID NO 3879

<400> SEQUENCE: 3879

000

<210> SEQ ID NO 3880

<400> SEQUENCE: 3880

000

<210> SEQ ID NO 3881

<400> SEQUENCE: 3881

000

<210> SEQ ID NO 3882

<400> SEQUENCE: 3882

000

<210> SEQ ID NO 3883

<400> SEQUENCE: 3883

000

<210> SEQ ID NO 3884

<400> SEQUENCE: 3884

000

<210> SEQ ID NO 3885

<400> SEQUENCE: 3885

000

<210> SEQ ID NO 3886

<400> SEQUENCE: 3886

000

<210> SEQ ID NO 3887

<400> SEQUENCE: 3887

000

<210> SEQ ID NO 3888

<400> SEQUENCE: 3888

000

<210> SEQ ID NO 3889

<400> SEQUENCE: 3889

000

<210> SEQ ID NO 3890

<400> SEQUENCE: 3890

000

<210> SEQ ID NO 3891

<400> SEQUENCE: 3891

000

<210> SEQ ID NO 3892

<400> SEQUENCE: 3892

000

<210> SEQ ID NO 3893

<400> SEQUENCE: 3893

000

<210> SEQ ID NO 3894

<400> SEQUENCE: 3894

000

<210> SEQ ID NO 3895

<400> SEQUENCE: 3895

000

<210> SEQ ID NO 3896

<400> SEQUENCE: 3896

000

<210> SEQ ID NO 3897

<400> SEQUENCE: 3897

000

<210> SEQ ID NO 3898

<400> SEQUENCE: 3898

000

<210> SEQ ID NO 3899

<400> SEQUENCE: 3899

000

<210> SEQ ID NO 3900

<400> SEQUENCE: 3900

000

```
<210> SEQ ID NO 3901
<400> SEQUENCE: 3901
000

<210> SEQ ID NO 3902
<400> SEQUENCE: 3902
000

<210> SEQ ID NO 3903
<400> SEQUENCE: 3903
000

<210> SEQ ID NO 3904
<400> SEQUENCE: 3904
000

<210> SEQ ID NO 3905
<400> SEQUENCE: 3905
000

<210> SEQ ID NO 3906
<400> SEQUENCE: 3906
000

<210> SEQ ID NO 3907
<400> SEQUENCE: 3907
000

<210> SEQ ID NO 3908
<400> SEQUENCE: 3908
000

<210> SEQ ID NO 3909
<400> SEQUENCE: 3909
000

<210> SEQ ID NO 3910
<400> SEQUENCE: 3910
000

<210> SEQ ID NO 3911
<400> SEQUENCE: 3911
000

<210> SEQ ID NO 3912
```

<400> SEQUENCE: 3912

000

<210> SEQ ID NO 3913

<400> SEQUENCE: 3913

000

<210> SEQ ID NO 3914

<400> SEQUENCE: 3914

000

<210> SEQ ID NO 3915

<400> SEQUENCE: 3915

000

<210> SEQ ID NO 3916

<400> SEQUENCE: 3916

000

<210> SEQ ID NO 3917

<400> SEQUENCE: 3917

000

<210> SEQ ID NO 3918

<400> SEQUENCE: 3918

000

<210> SEQ ID NO 3919

<400> SEQUENCE: 3919

000

<210> SEQ ID NO 3920

<400> SEQUENCE: 3920

000

<210> SEQ ID NO 3921

<400> SEQUENCE: 3921

000

<210> SEQ ID NO 3922

<400> SEQUENCE: 3922

000

<210> SEQ ID NO 3923

<400> SEQUENCE: 3923

000

<210> SEQ ID NO 3924

<400> SEQUENCE: 3924

000

<210> SEQ ID NO 3925

<400> SEQUENCE: 3925

000

<210> SEQ ID NO 3926

<400> SEQUENCE: 3926

000

<210> SEQ ID NO 3927

<400> SEQUENCE: 3927

000

<210> SEQ ID NO 3928

<400> SEQUENCE: 3928

000

<210> SEQ ID NO 3929

<400> SEQUENCE: 3929

000

<210> SEQ ID NO 3930

<400> SEQUENCE: 3930

000

<210> SEQ ID NO 3931

<400> SEQUENCE: 3931

000

<210> SEQ ID NO 3932

<400> SEQUENCE: 3932

000

<210> SEQ ID NO 3933

<400> SEQUENCE: 3933

000

<210> SEQ ID NO 3934

<400> SEQUENCE: 3934

000

<210> SEQ ID NO 3935

<400> SEQUENCE: 3935

000

<210> SEQ ID NO 3936

<400> SEQUENCE: 3936

000

<210> SEQ ID NO 3937

<400> SEQUENCE: 3937

000

<210> SEQ ID NO 3938

<400> SEQUENCE: 3938

000

<210> SEQ ID NO 3939

<400> SEQUENCE: 3939

000

<210> SEQ ID NO 3940

<400> SEQUENCE: 3940

000

<210> SEQ ID NO 3941

<400> SEQUENCE: 3941

000

<210> SEQ ID NO 3942

<400> SEQUENCE: 3942

000

<210> SEQ ID NO 3943

<400> SEQUENCE: 3943

000

<210> SEQ ID NO 3944

<400> SEQUENCE: 3944

000

<210> SEQ ID NO 3945

<400> SEQUENCE: 3945

000

```
<210> SEQ ID NO 3946
<400> SEQUENCE: 3946
000

<210> SEQ ID NO 3947
<400> SEQUENCE: 3947
000

<210> SEQ ID NO 3948
<400> SEQUENCE: 3948
000

<210> SEQ ID NO 3949
<400> SEQUENCE: 3949
000

<210> SEQ ID NO 3950
<400> SEQUENCE: 3950
000

<210> SEQ ID NO 3951
<400> SEQUENCE: 3951
000

<210> SEQ ID NO 3952
<400> SEQUENCE: 3952
000

<210> SEQ ID NO 3953
<400> SEQUENCE: 3953
000

<210> SEQ ID NO 3954
<400> SEQUENCE: 3954
000

<210> SEQ ID NO 3955
<400> SEQUENCE: 3955
000

<210> SEQ ID NO 3956
<400> SEQUENCE: 3956
000

<210> SEQ ID NO 3957
```

<400> SEQUENCE: 3957

000

<210> SEQ ID NO 3958

<400> SEQUENCE: 3958

000

<210> SEQ ID NO 3959

<400> SEQUENCE: 3959

000

<210> SEQ ID NO 3960

<400> SEQUENCE: 3960

000

<210> SEQ ID NO 3961

<400> SEQUENCE: 3961

000

<210> SEQ ID NO 3962

<400> SEQUENCE: 3962

000

<210> SEQ ID NO 3963

<400> SEQUENCE: 3963

000

<210> SEQ ID NO 3964

<400> SEQUENCE: 3964

000

<210> SEQ ID NO 3965

<400> SEQUENCE: 3965

000

<210> SEQ ID NO 3966

<400> SEQUENCE: 3966

000

<210> SEQ ID NO 3967

<400> SEQUENCE: 3967

000

<210> SEQ ID NO 3968

<400> SEQUENCE: 3968

000

<210> SEQ ID NO 3969
<400> SEQUENCE: 3969
000

<210> SEQ ID NO 3970
<400> SEQUENCE: 3970
000

<210> SEQ ID NO 3971
<400> SEQUENCE: 3971
000

<210> SEQ ID NO 3972
<400> SEQUENCE: 3972
000

<210> SEQ ID NO 3973
<400> SEQUENCE: 3973
000

<210> SEQ ID NO 3974
<400> SEQUENCE: 3974
000

<210> SEQ ID NO 3975
<400> SEQUENCE: 3975
000

<210> SEQ ID NO 3976
<400> SEQUENCE: 3976
000

<210> SEQ ID NO 3977
<400> SEQUENCE: 3977
000

<210> SEQ ID NO 3978
<400> SEQUENCE: 3978
000

<210> SEQ ID NO 3979
<400> SEQUENCE: 3979
000

<210> SEQ ID NO 3980

<400> SEQUENCE: 3980

000

<210> SEQ ID NO 3981

<400> SEQUENCE: 3981

000

<210> SEQ ID NO 3982

<400> SEQUENCE: 3982

000

<210> SEQ ID NO 3983

<400> SEQUENCE: 3983

000

<210> SEQ ID NO 3984

<400> SEQUENCE: 3984

000

<210> SEQ ID NO 3985

<400> SEQUENCE: 3985

000

<210> SEQ ID NO 3986

<400> SEQUENCE: 3986

000

<210> SEQ ID NO 3987

<400> SEQUENCE: 3987

000

<210> SEQ ID NO 3988

<400> SEQUENCE: 3988

000

<210> SEQ ID NO 3989

<400> SEQUENCE: 3989

000

<210> SEQ ID NO 3990

<400> SEQUENCE: 3990

000

<210> SEQ ID NO 3991

<400> SEQUENCE: 3991

000

<210> SEQ ID NO 3992

<400> SEQUENCE: 3992

000

<210> SEQ ID NO 3993

<400> SEQUENCE: 3993

000

<210> SEQ ID NO 3994

<400> SEQUENCE: 3994

000

<210> SEQ ID NO 3995

<400> SEQUENCE: 3995

000

<210> SEQ ID NO 3996

<400> SEQUENCE: 3996

000

<210> SEQ ID NO 3997

<400> SEQUENCE: 3997

000

<210> SEQ ID NO 3998

<400> SEQUENCE: 3998

000

<210> SEQ ID NO 3999

<400> SEQUENCE: 3999

000

<210> SEQ ID NO 4000

<400> SEQUENCE: 4000

000

<210> SEQ ID NO 4001
<211> LENGTH: 9
<212> TYPE: PRT
<213> ORGANISM: Artificial Sequence
<220> FEATURE:
<223> OTHER INFORMATION: Synthetic: 36 - VH CDR1

```
<400> SEQUENCE: 4001

Gly Thr Phe Ala Thr Tyr Ala Ile Ser
1               5

<210> SEQ ID NO 4002
<211> LENGTH: 17
<212> TYPE: PRT
<213> ORGANISM: Artificial Sequence
<220> FEATURE:
<223> OTHER INFORMATION: Synthetic: 36 - VH CDR2

<400> SEQUENCE: 4002

Gly Ile Phe Pro Leu Ser Gly Thr Ala Asn Tyr Ala Gln Lys Phe Gln
1               5                   10                  15

Gly

<210> SEQ ID NO 4003
<211> LENGTH: 16
<212> TYPE: PRT
<213> ORGANISM: Artificial Sequence
<220> FEATURE:
<223> OTHER INFORMATION: Synthetic: 36 - VH CDR3

<400> SEQUENCE: 4003

Ala Arg Asp Thr Gly Arg Gly Tyr Thr Arg His Phe Trp Phe Asp Pro
1               5                   10                  15

<210> SEQ ID NO 4004
<211> LENGTH: 11
<212> TYPE: PRT
<213> ORGANISM: Artificial Sequence
<220> FEATURE:
<223> OTHER INFORMATION: Synthetic: 36 - VL CDR1

<400> SEQUENCE: 4004

Arg Ala Ser Gln Ser Ile Ser Ser Tyr Leu Asn
1               5                   10

<210> SEQ ID NO 4005
<211> LENGTH: 7
<212> TYPE: PRT
<213> ORGANISM: Artificial Sequence
<220> FEATURE:
<223> OTHER INFORMATION: Synthetic: 36 - VL CDR2

<400> SEQUENCE: 4005

Ala Ala Ser Ser Leu Gln Ser
1               5

<210> SEQ ID NO 4006
<211> LENGTH: 8
<212> TYPE: PRT
<213> ORGANISM: Artificial Sequence
<220> FEATURE:
<223> OTHER INFORMATION: Synthetic: 36 - VL CDR3

<400> SEQUENCE: 4006

Gln Gln Ser Asp Ile Leu Tyr Thr
1               5

<210> SEQ ID NO 4007
<211> LENGTH: 26
<212> TYPE: PRT
<213> ORGANISM: Artificial Sequence
<220> FEATURE:
```

<223> OTHER INFORMATION: Synthetic: 36 - VH FR1

<400> SEQUENCE: 4007

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 4008
<211> LENGTH: 14
<212> TYPE: PRT
<213> ORGANISM: Artificial Sequence
<220> FEATURE:
<223> OTHER INFORMATION: Synthetic: 36 - VH FR2

<400> SEQUENCE: 4008

Trp Val Arg Gln Ala Pro Gly Gln Gly Leu Glu Trp Met Gly
1               5                   10

<210> SEQ ID NO 4009
<211> LENGTH: 30
<212> TYPE: PRT
<213> ORGANISM: Artificial Sequence
<220> FEATURE:
<223> OTHER INFORMATION: Synthetic: 36 - VH FR3

<400> SEQUENCE: 4009

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 4010
<211> LENGTH: 11
<212> TYPE: PRT
<213> ORGANISM: Artificial Sequence
<220> FEATURE:
<223> OTHER INFORMATION: Synthetic: 36 - VH FR4

<400> SEQUENCE: 4010

Trp Gly Gln Gly Thr Leu Val Thr Val Ser Ser
1               5                   10

<210> SEQ ID NO 4011
<211> LENGTH: 369
<212> TYPE: DNA
<213> ORGANISM: Artificial Sequence
<220> FEATURE:
<223> OTHER INFORMATION: Synthetic: 36 - VH DNA

<400> SEQUENCE: 4011
caggtgcagc tggtgcagtc tggggctgag gtgaagaagc ctgggtcctc ggtgaaggtc     60
tcctgcaagg cttctggagg caccttcgca acctatgcta tcagctgggt gcgacaggcc    120
cctggacaag ggcttgagtg gatgggaggg atcttccctc tctccggtac agcaaactac    180
gcacagaagt tccagggcag agtcacgatt accgcggacg aatccacgag cacagcctac    240
atggagctga gcagcctgag atctgaggac acggcggtgt actactgcgc cagagacacg    300
ggacggggat acaccagaca cttctggttt gaccccgggg acagggtac attggtcacc    360 gtctcctca                                                           369

<210> SEQ ID NO 4012
<211> LENGTH: 123

<212> TYPE: PRT
<213> ORGANISM: Artificial Sequence
<220> FEATURE:
<223> OTHER INFORMATION: Synthetic: 36 - VH Protein

<400> SEQUENCE: 4012

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ala Thr Tyr
            20                  25                  30

Ala Ile Ser Trp Val Arg Gln Ala Pro Gly Gln Gly Leu Glu Trp Met
        35                  40                  45

Gly Gly Ile Phe Pro Leu Ser Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Arg Gly Tyr Thr Arg His Phe Trp Phe Asp Pro
            100                 105                 110

Trp Gly Gln Gly Thr Leu Val Thr Val Ser Ser
        115                 120

<210> SEQ ID NO 4013
<211> LENGTH: 23
<212> TYPE: PRT
<213> ORGANISM: Artificial Sequence
<220> FEATURE:
<223> OTHER INFORMATION: Synthetic: 36 - VL FR1

<400> SEQUENCE: 4013

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 4014
<211> LENGTH: 15
<212> TYPE: PRT
<213> ORGANISM: Artificial Sequence
<220> FEATURE:
<223> OTHER INFORMATION: Synthetic: 36 - VL FR2

<400> SEQUENCE: 4014

Trp Tyr Gln Gln Lys Pro Gly Lys Ala Pro Lys Leu Leu Ile Tyr
1               5                   10                  15

<210> SEQ ID NO 4015
<211> LENGTH: 32
<212> TYPE: PRT
<213> ORGANISM: Artificial Sequence
<220> FEATURE:
<223> OTHER INFORMATION: Synthetic: 36 - VL FR3

<400> SEQUENCE: 4015

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 4016
<211> LENGTH: 10

```
<212> TYPE: PRT
<213> ORGANISM: Artificial Sequence
<220> FEATURE:
<223> OTHER INFORMATION: Synthetic: 36 - VL FR4

<400> SEQUENCE: 4016

Phe Gly Gly Gly Thr Lys Val Glu Ile Lys
1               5                   10

<210> SEQ ID NO 4017
<211> LENGTH: 318
<212> TYPE: DNA
<213> ORGANISM: Artificial Sequence
<220> FEATURE:
<223> OTHER INFORMATION: Synthetic: 36 - VL DNA

<400> SEQUENCE: 4017
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agcgacatcc tctacacttt tggcggaggg     300
accaaggttg agatcaaa                                                   318

<210> SEQ ID NO 4018
<211> LENGTH: 106
<212> TYPE: PRT
<213> ORGANISM: Artificial Sequence
<220> FEATURE:
<223> OTHER INFORMATION: Synthetic: 36 - VL Protein

<400> SEQUENCE: 4018

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Tyr Thr
                85                  90                  95

Phe Gly Gly Gly Thr Lys Val Glu Ile Lys
                100                 105
```

ANTI-CD112R COMPOSITIONS AND METHODS

CROSS-REFERENCE TO RELATED APPLICATIONS

This application is a continuation of U.S. patent application Ser. No. 17/261,463, filed Nov. 19, 2021, now U.S. Pat. No. 11,214,619, which is a National Stage Entry of International Application No. PCT/US19/42545, filed Jul. 19, 2019, which claims benefit of U.S. Provisional Application No. 62/701,065, filed Jul. 20, 2018, and U.S. Provisional Application No. 62/844,958, filed May 8, 2019, the contents of which are incorporated herein by reference in their entirety.

Reference to Sequence Listing Submitted Electronically

The instant application contains a Sequence Listing which has been submitted in ASCII format via EFS-Web and is hereby incorporated by reference in its entirety. Said ASCII copy, created on Feb. 15, 2022, is named "LU67075 Sequence Listing.txt" and is 229 KB in size.

FIELD OF THE INVENTION

Anti-CD112R antibodies are provided, as well as their use in enhancing, increasing, and sustaining an anti-tumor immune response, treating cancer, and enhancing CD226 interactions with CD112.

BACKGROUND

Both the innate and adaptive arms of the immune system utilize highly specialized immune cells to patrol the body, searching for signs of malignancy. Innate immunity provides the first line of defense and a rapid response using mechanisms such as barriers and destructive peptides that are non-specific and naturally present. Natural killer (NK) cells are a type of lymphocyte that is part of the innate immune system and can recognize and destroy virally infected and tumor cells using granzymes stored in their cytoplasm.

Adaptive immunity develops over time in response to antigen and provides lasting immunity. Cytotoxic lymphocytes (CTLs), also known as CD8$^+$ T cells are part of the adaptive immune response as they recognize virus and tumor derived antigens presented by antigen presenting cells (APCs). CTLs are activated by interaction with an APC such as a dendritic cell or macrophage. The APC presents the tumor antigens in the context of MHC molecules to the T cell receptor (TCR) on the T cell surface. During this cognate interaction, the APC provides a costimulatory signal which leads to T cell activation, T cell proliferation, and reduction or elimination of cells expressing the antigen via cytotoxic mechanisms.

Administration of anti-CD112R immunotherapy provides an opportunity to increase, enhance and sustain immune responses. CD112R is an inhibitory receptor primarily expressed by T cells and NK cells and competes for CD112 binding with the activating receptor CD226. The interaction of CD112 with CD112R is of higher affinity than with CD226 and thereby effectively regulates CD226 mediated cell activation. Anti-CD112R antibodies that block the interaction with CD112 limit inhibitory signaling directly downstream of CD112R while simultaneously promoting greater immune cell activation by increasing CD226 interactions with CD112. In in vitro studies, anti-CD112R antibodies have been shown to increase the proliferation, activation and cytotoxicity of immune effector cells.

CD112R mRNA expression is detected in a number of cancer tissues and based on predictive analysis using TCGA (The Cancer Genome Atlas) dataset. Its expression is strongest in tumors that are enriched for T and NK cells. In addition to being expressed on myeloid cells, the expression of the CD112R ligand, CD112, is routinely elevated on tumor cells of different cellular origins. Given these circumstances, engagement of CD112R on tumor infiltrating immune cells has a strong potential to negatively regulate local immune responses within the tumor microenvironment.

Therapeutic treatment with anti-CD112R antibodies thereby provides an opportunity to down modulate the inhibitory signaling that occurs putatively when CD112R expressing immune cells engage CD112 on tumor cells and/or myeloid cells within the tumor microenvironment and has the potential to enhance, increase and sustain anti-tumor immune responses.

SUMMARY

In some embodiments, an isolated anti-CD112R antibody is provided. Such isolated anti-CD112R antibody binds to human CD112R, wherein said antibody blocks the binding interaction between human CD112 and human CD112R and does not block the binding interaction between mouse CD112 and mouse CD112R, wherein the antibody is optionally fully human or humanized.

In some embodiments, the disclosure provides an isolated antibody comprising:
 (a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6; or
 (a) HCDR1 comprising the amino acid sequence of SEQ ID NO: 101; (b) HCDR2 comprising the amino acid sequence of SEQ ID NO: 102; (c) HCDR3 comprising the amino acid sequence of SEQ ID NO: 103; (d) LCDR1 comprising the amino acid sequence of SEQ ID NO: 104; (e) LCDR2 comprising the amino acid sequence of SEQ ID NO: 105; and (f) LCDR3 comprising the amino acid sequence of SEQ ID NO: 106; or
 (a) HCDR1 comprising the amino acid sequence of SEQ ID NO: 201; (b) HCDR2 comprising the amino acid sequence of SEQ ID NO: 202; (c) HCDR3 comprising the amino acid sequence of SEQ ID NO: 203; (d) LCDR1 comprising the amino acid sequence of SEQ ID NO: 204; (e) LCDR2 comprising the amino acid sequence of SEQ ID NO: 205; and (0 LCDR3 comprising the amino acid sequence of SEQ ID NO: 206; or
 (a) HCDR1 comprising the amino acid sequence of SEQ ID NO: 301; (b) HCDR2 comprising the amino acid sequence of SEQ ID NO: 302; (c) HCDR3 comprising the amino acid sequence of SEQ ID NO: 303; (d) LCDR1 comprising the amino acid sequence of SEQ ID NO: 304; (e) LCDR2 comprising the amino acid sequence of SEQ ID NO: 305; and (f) LCDR3 comprising the amino acid sequence of SEQ ID NO: 306; or (a) HCDR1 comprising the amino acid sequence of SEQ ID NO: 401; (b) HCDR2 comprising the amino acid sequence of SEQ ID NO: 402; (c) HCDR3 comprising the amino acid sequence of SEQ ID NO: 403; (d) LCDR1 comprising the amino acid sequence of SEQ ID NO: 404; (e) LCDR2 comprising the amino acid sequence of SEQ ID NO: 405; and (f) LCDR3 comprising the amino acid sequence of SEQ ID NO: 406; or (a) HCDR1 comprising the amino acid sequence of SEQ ID NO: 501; (b) HCDR2 comprising the amino acid sequence of SEQ ID NO: 502; (c) HCDR3 comprising the amino acid sequence of SEQ ID NO: 503; (d) LCDR1 comprising the amino acid sequence of SEQ ID NO: 504; (e) LCDR2 comprising the amino acid sequence of SEQ ID NO: 505; and (f) LCDR3 comprising the amino acid sequence of SEQ ID NO: 506; or (a) HCDR1 comprising the amino acid sequence of SEQ ID NO: 601; (b) HCDR2 comprising the amino acid sequence of SEQ ID NO: 602; (c) HCDR3 comprising the amino acid sequence of SEQ ID NO: 603; (d) LCDR1 comprising the amino acid sequence of SEQ ID NO: 604; (e) LCDR2 comprising the amino acid sequence of SEQ ID NO: 605; and (f) LCDR3 comprising the amino acid sequence of SEQ ID NO: 606; or (a) HCDR1 comprising the amino acid sequence of SEQ ID NO: 701; (b) HCDR2 comprising the amino acid sequence of SEQ ID NO: 702; (c) HCDR3 comprising the amino acid sequence of SEQ ID NO: 703; (d) LCDR1 comprising the amino acid sequence of SEQ ID NO: 704; (e) LCDR2 comprising the amino acid sequence of SEQ ID NO: 705; and (f) LCDR3 comprising the amino acid sequence of SEQ ID NO: 706; or (a) HCDR1 comprising the amino acid sequence of SEQ ID NO: 801; (b) HCDR2 comprising the amino acid sequence of SEQ ID NO: 802; (c) HCDR3 comprising the amino acid sequence of SEQ ID NO: 803; (d) LCDR1 comprising the amino acid sequence of SEQ ID NO: 804; (e) LCDR2 comprising the amino acid sequence of SEQ ID NO: 805; and (f) LCDR3 comprising the amino acid sequence of SEQ ID NO: 806; or (a) HCDR1 comprising the amino acid sequence of SEQ ID NO: 901; (b) HCDR2 comprising the amino acid sequence of SEQ ID NO: 902; (c) HCDR3 comprising the amino acid sequence of SEQ ID NO: 903; (d) LCDR1 comprising the amino acid sequence of SEQ ID NO: 904; (e) LCDR2 comprising the amino acid sequence of SEQ ID NO: 905; and (f) LCDR3 comprising the amino acid sequence of SEQ ID NO: 906; or (a) HCDR1 comprising the amino acid sequence of SEQ ID NO: 1001; (b) HCDR2 comprising the amino acid sequence of SEQ ID NO: 1002; (c) HCDR3 comprising the amino acid sequence of SEQ ID NO: 1003; (d) LCDR1 comprising the amino acid sequence of SEQ ID NO: 1004; (e) LCDR2 comprising the amino acid sequence of SEQ ID NO: 1005; and (f) LCDR3 comprising the amino acid sequence of SEQ ID NO: 1006; or (a) HCDR1 comprising the amino acid sequence of SEQ ID NO: 2001; (b) HCDR2 comprising the amino acid sequence of SEQ ID NO: 2002; (c) HCDR3 comprising the amino acid sequence of SEQ ID NO: 2003; (d) LCDR1 comprising the amino acid sequence of SEQ ID NO: 2004; (e) LCDR2 comprising the amino acid sequence of SEQ ID NO: 2005; and (f) LCDR3 comprising the amino acid sequence of SEQ ID NO: 2006; or (a) HCDR1 comprising the amino acid sequence of SEQ ID NO: 3001; (b) HCDR2 comprising the amino acid sequence of SEQ ID NO: 3002; (c) HCDR3 comprising the amino acid sequence of SEQ ID NO: 3003; (d) LCDR1 comprising the amino acid sequence of SEQ ID NO: 3004; (e) LCDR2 comprising the amino acid sequence of SEQ ID NO: 3005; and (f) LCDR3 comprising the amino acid sequence of SEQ ID NO: 3006; or (a) HCDR1 comprising the amino acid sequence of SEQ ID NO: 4001; (b) HCDR2 comprising the amino acid sequence of SEQ ID NO: 4002; (c) HCDR3 comprising the amino acid sequence of SEQ ID NO: 4003; (d) LCDR1 comprising the amino acid sequence of SEQ ID NO: 4004; (e) LCDR2 comprising the amino acid sequence of SEQ ID NO: 4005; and (f) LCDR3 comprising the amino acid sequence of SEQ ID NO: 4006.

In some embodiments, the antibody comprises a heavy chain variable region (VH) and a light chain variable region (VL), wherein:

the VH is at least 90%, 91%, 92%, 93%, 94%, 95%, 96%, 97%, 98%, 99%, or 100% identical to the amino acid sequence of SEQ ID NO: 12 and the VL is at least 90%, 91%, 92%, 93%, 94%, 95%, 96%, 97%, 98%, 99%, or 100% identical to the amino acid sequence of SEQ ID NO: 18; or the VH is at least 90%, 91%, 92%, 93%, 94%, 95%, 96%, 97%, 98%, 99%, or 100% identical to the amino acid sequence of SEQ ID NO: 112 and the VL is at least 90%, 91%, 92%, 93%, 94%, 95%, 96%, 97%, 98%, 99%, or 100% identical to the amino acid sequence of SEQ ID NO: 118; or the VH is at least 90%, 91%, 92%, 93%, 94%, 95%, 96%, 97%, 98%, 99%, or 100% identical to the amino acid sequence of SEQ ID NO: 212 and the VL is at least 90%, 91%, 92%, 93%, 94%, 95%, 96%, 97%, 98%, 99%, or 100% identical to the amino acid sequence of SEQ ID NO: 218; or the VH is at least 90%, 91%, 92%, 93%, 94%, 95%, 96%, 97%, 98%, 99%, or 100% identical to the amino acid sequence of SEQ ID NO: 312 and the VL is at least 90%, 91%, 92%, 93%, 94%, 95%, 96%, 97%, 98%, 99%, or 100% identical to the amino acid sequence of SEQ ID NO: 318; or the VH is at least 90%, 91%, 92%, 93%, 94%, 95%, 96%, 97%, 98%, 99%, or 100% identical to the amino acid sequence of SEQ ID NO: 412 and the VL is at least 90%, 91%, 92%, 93%, 94%, 95%, 96%, 97%, 98%, 99%, or 100% identical to the amino acid sequence of SEQ ID NO: 418; or the VH is at least 90%, 91%, 92%, 93%, 94%, 95%, 96%, 97%, 98%, 99%, or 100% identical to the amino acid sequence of SEQ ID NO: 512 and the VL is at least 90%, 91%, 92%, 93%, 94%, 95%, 96%, 97%, 98%, 99%, or 100% identical to the amino acid sequence of SEQ ID NO: 518; or the VH is at least 90%, 91%, 92%, 93%, 94%, 95%, 96%, 97%, 98%, 99%, or 100% identical to the amino acid sequence of SEQ ID NO: 612 and the VL is at least 90%, 91%, 92%, 93%, 94%, 95%, 96%, 97%, 98%, 99%, or 100% identical to the amino acid sequence of SEQ ID NO: 618; or the VH is at least 90%, 91%, 92%, 93%, 94%, 95%, 96%, 97%, 98%, 99%, or 100% identical to the amino acid sequence of SEQ ID NO: 712 and the VL is at least 90%, 91%, 92%, 93%, 94%, 95%, 96%, 97%, 98%, 99%, or 100% identical to the amino acid sequence of SEQ ID NO: 718; or the VH is at least 90%, 91%, 92%, 93%, 94%, 95%, 96%, 97%, 98%, 99%, or 100% identical to the amino acid sequence of SEQ ID NO: 812 and the VL is at least 90%, 91%, 92%, 93%, 94%, 95%, 96%, 97%, 98%, 99%, or 100% identical to the amino acid sequence of SEQ ID NO: 818; or the VH is at least 90%, 91%, 92%, 93%, 94%, 95%, 96%, 97%, 98%, 99%, or 100% identical to the amino acid sequence of SEQ ID NO: 912 and the VL is at least 90%, 91%, 92%, 93%, 94%, 95%, 96%, 97%, 98%, 99%, or 100% identical to the amino acid sequence of SEQ ID NO: 918; or the VH is at least 90%, 91%, 92%, 93%, 94%, 95%, 96%, 97%, 98%, 99%, or 100% identical to the amino acid sequence of SEQ ID NO: 1012 and the VL is at least 90%, 91%, 92%, 93%, 94%, 95%, 96%, 97%, 98%, 99%, or 100% identical to the amino acid sequence of SEQ ID NO: 1018; or the VH is at least 90%, 91%, 92%, 93%, 94%, 95%, 96%, 97%, 98%, 99%, or 100% identical to the amino acid sequence of SEQ ID NO: 2012 and the VL is at least 90%, 91%, 92%, 93%, 94%, 95%, 96%, 97%, 98%, 99%, or 100% identical to the amino acid sequence of SEQ ID NO: 2018; or the VH is at least 90%, 91%, 92%, 93%, 94%, 95%, 96%, 97%, 98%, 99%, or 100% identical to the amino acid sequence of SEQ ID NO: 3012 and the VL is at least 90%, 91%, 92%, 93%, 94%, 95%, 96%, 97%, 98%, 99%, or 100% identical to the amino acid sequence of SEQ ID NO: 3018; or the VH is at least 90%, 91%, 92%, 93%, 94%, 95%, 96%, 97%, 98%, 99%, or 100% identical to the amino acid sequence of SEQ ID NO: 4012 and the VL is at least 90%, 91%, 92%, 93%, 94%, 95%, 96%, 97%, 98%, 99%, or 100% identical to the amino acid sequence of SEQ ID NO: 4018.

In some embodiments, the antibody comprises six CDRs (HCDR1, HCDR2, HCDR3, LCDR1, LCDR2, and LCDR3) as described herein, and VH and/or VL sequences that are at least 90%, 91%, 92%, 93%, 94%, 95%, 96%, 97%, 98%, 99%, or 100% identical to VH and/or VL amino acid sequence described herein. In some embodiments, the VH and/or VL sequences are not 100% identical to an amino acid sequence described herein. In some embodiments, the antibody comprises HCDR1, HCDR2, HCDR3, LCDR1, LCDR2, and LCDR3 amino acid sequences described herein, and sequence variation within the VH and/or VL sequences that is outside of the CDR sequences. In such embodiments, the sequence variation of the VH and/or VL sequences is within one or more framework regions of the VH and/or VL.

In some embodiments, the antibody comprises VH and/or VL sequences that are at least 90%, 91%, 92%, 93%, 94%, 95%, 96%, 97%, 98%, 99%, or 100% identical to an amino acid sequence described herein. In some embodiments, the VH and/or VL sequences are not 100% identical to an amino acid described herein. In such embodiments, the sequence variation of the VH and/or VL sequences is within and/or outside of the CDR sequences, unless otherwise specified.

In some embodiments, the antibody comprises a heavy chain variable region (VH) and a light chain variable region (VL), wherein:

the VH comprises the amino acid sequence of SEQ ID NO: 12 and the VL comprises the amino acid sequence of SEQ ID NO: 18; or the VH comprises the amino acid sequence of SEQ ID NO: 112 and the VL comprises the amino acid sequence of SEQ ID NO: 118; or the VH comprises the amino acid sequence of SEQ ID NO: 212 and the VL comprises the amino acid sequence of SEQ ID NO: 218; or the VH comprises the amino acid sequence of SEQ ID NO: 312 and the VL comprises the amino acid sequence of SEQ ID NO: 318; or the VH comprises the amino acid sequence of SEQ ID NO: 412 and the VL comprises the amino acid sequence of SEQ ID NO: 418; or the VH comprises the amino acid sequence of SEQ ID NO: 512 and the VL comprises the amino acid sequence of SEQ ID NO: 518; or the VH comprises the amino acid sequence of SEQ ID NO: 612 and the VL comprises the amino acid sequence of SEQ ID NO: 618; or the VH comprises the amino acid sequence of SEQ ID NO: 712 and the VL comprises the amino acid sequence of SEQ ID NO: 718; or the VH comprises the amino acid sequence of SEQ ID NO: 812 and the VL comprises the amino acid sequence of SEQ ID NO: 818; or the VH comprises the amino acid sequence of SEQ ID NO: 912 and the VL comprises the amino acid sequence of SEQ ID NO: 918; or the VH comprises the amino acid sequence of SEQ ID NO: 1012 and the VL comprises the amino acid sequence of SEQ ID NO: 1018; or the VH comprises the amino acid sequence of SEQ ID NO: 2012 and the VL comprises the amino acid sequence of SEQ ID NO: 2018; or the VH comprises the amino acid sequence of SEQ ID NO: 3012 and the VL comprises the amino acid sequence of SEQ ID NO: 3018; or the VH comprises the amino acid sequence of SEQ ID NO: 4012 and the VL comprises the amino acid sequence of SEQ ID NO: 4018.

In some embodiments, anti-CD112R antibodies are provided that activate NK cells. In some embodiments, anti-CD112R antibodies are provided that upregulate CD137 on NK cells. In some embodiments, the anti-CD112R antibodies that activate NK cells and/or upregulate CD137 on NK cells are antibodies any of the antibodies described in the Table of Sequences, such as, for example, antibodies 32, 33, 34, 35, and 36. In some embodiments, the anti-CD112R antibodies that activate NK cells and/or upregulate CD137 on NK cells comprise the six CDRs of antibodies 32, 33, 34, 35, and 36 respectively (see Table of Sequences).

In some embodiments, the antibody is a monoclonal antibody. In some embodiments, the antibody is a humanized antibody. In some embodiments, the antibody is a fully human antibody. In some embodiments, the antibody is an antibody fragment selected from a Fab, Fab', Fv, scFv or (Fab')$_2$. In some embodiments, the antibody is a full-length antibody. In some embodiments, the isolated antibody comprises an IgG1, IgG2, IgG3, or IgG4 Fc region. In some embodiments, the disclosure provides a composition comprising an antibody disclosed herein and a pharmaceutically acceptable carrier.

In some embodiments, the antibody increases NK cell degranulation, increases activation of NK cells, increases activation of intra-tumoral NK cells when presented in combination with an anti-TIGIT antibody, inhibits tumor growth in vivo, and/or prevents tumor engraftment upon re-challenge with tumor. In some such embodiments, the antibody comprises a human IgG1 heavy chain constant region, and the antibody increases NK cell degranulation, increases activation of NK cells, increases activation of intra-tumoral NK cells when presented in combination with an anti-TIGIT antibody, inhibits tumor growth in vivo, and/or prevents tumor engraftment upon re-challenge with tumor relative to an otherwise identical antibody comprising a human IgG heavy chain constant region of a different isotype.

In some embodiments, the disclosure provides a method of enhancing, increasing and/or sustaining an anti-tumor immune response in a subject comprising administering the antibody or composition described herein to a subject having a tumor.

In some embodiments, the disclosure provides a method of treating cancer in a subject comprising administering the antibody or composition described herein to a subject having cancer. In some embodiments, the cancer is carcinoma, lymphoma, blastoma, sarcoma, or leukemia. In some embodiments, the cancer is squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or various types of head and neck cancer (including squamous cell carcinoma of the head and neck).

In some embodiments, the disclosure provides a method of enhancing CD226 interactions with CD112 in a subject comprising administering the antibody or the composition described herein to a subject.

In some embodiments, the disclosure provides a method of enhancing CD8 T cell activation in a subject comprising administering the antibody or the composition described herein to a subject in need of CD8 T cell activation.

In some embodiments, the disclosure provides a method of enhancing CD8 T cell interferon gamma production in a subject comprising administering the antibody or the composition described herein to a subject in need of CD8 T cell interferon gamma production.

In some embodiments, the disclosure provides a method of enhancing NK cell activation in a subject comprising administering the antibody or the composition described herein to a subject in need of NK cell activation.

In some embodiments, the disclosure provides a method of enhancing NK cell mediated cytotoxicity in a subject comprising administering the antibody or the composition described herein to a subject in need of increasing NK cell mediated cytotoxicity.

In some embodiments, the methods described herein further comprise administering a second therapy. In some embodiments, the second therapy is radiotherapy, surgery or administration of a second agent. In some embodiments, the second therapy is a second agent. In some such embodiments, the second agent is an antagonist of PD-1, PD-L1, CTLA-4, Lag-3 or TIM-3. In some embodiments, the second agent is an antagonist of TIGIT or CD96. In some embodiments, the second agent is an antagonist of PVRL1, PVRL2, PVRL3, PVRL4, or CD155. In some embodiments, the second agent an antagonist of CD47, CD39, or IL-27. In some embodiments, the second agent is a STING agonist.

In some embodiments, the disclosure provides use of the antibody or the composition described herein for enhancing, and/or increasing and/or sustaining an anti-tumor immune, and/or treating cancer, and/or enhancing CD226 interactions with CD112.

In some embodiments, the disclosure provides use of the antibody or the composition described herein in the preparation of a medicament for enhancing, and/or increasing and/or sustaining an anti-tumor immune response, and/or treating cancer, and/or enhancing CD226 interactions with CD112.

In some embodiments, the disclosure provides a nucleic acid encoding an antibody disclosed herein.

In some embodiments, the disclosure provides a host cell comprising a nucleic acid encoding an antibody disclosed herein.

In some embodiments, the disclosure provides a method of producing an antibody disclosed herein comprising culturing host cell comprising a nucleic acid encoding an antibody disclosed herein, the host cell being cultured under conditions wherein the antibody is expressed. In some embodiments, the method further comprises purifying the antibody.

Exemplary embodiments of the disclosure include the following:

Embodiment 1. An isolated anti-CD112R antibody which binds to human CD112R, wherein said antibody blocks the binding interaction between human CD112 and human CD112R and does not block the binding interaction between mouse CD112 and mouse CD112R, wherein the antibody is optionally fully human or humanized.

Embodiment 2. The isolated antibody of embodiment 1, wherein the isolated antibody comprises:
i) (a) HCDR1 comprising the amino acid sequence of SEQ ID NO: 701; (b) HCDR2 comprising the amino acid sequence of SEQ ID NO: 702; (c) HCDR3 comprising the amino acid sequence of SEQ ID NO: 703; (d) LCDR1 comprising the amino acid sequence of SEQ ID NO: 704; (e) LCDR2 comprising the amino acid sequence of SEQ ID NO: 705; and (f) LCDR3 comprising the amino acid sequence of SEQ ID NO: 706; or
ii) (a) HCDR1 comprising the amino acid sequence of SEQ ID NO: 1001; (b) HCDR2 comprising the amino acid sequence of SEQ ID NO: 1002; (c) HCDR3 comprising the amino acid sequence of SEQ ID NO: 1003; (d) LCDR1 comprising the amino acid sequence of SEQ ID NO: 1004; (e) LCDR2 comprising the amino acid sequence of SEQ ID NO: 1005; and (f) LCDR3 comprising the amino acid sequence of SEQ TD NO: 1006; or
iii) (a) HCDR1 comprising the amino acid sequence of SEQ ID NO: 2001; (b) HCDR2 comprising the amino acid sequence of SEQ ID NO: 2002; (c) HCDR3 comprising the amino acid sequence of SEQ ID NO:

2003; (d) LCDR1 comprising the amino acid sequence of SEQ ID NO: 2004; (e) LCDR2 comprising the amino acid sequence of SEQ ID NO: 2005; and (f) LCDR3 comprising the amino acid sequence of SEQ ID NO: 2006; or iv) (a) HCDR1 comprising the amino acid sequence of SEQ ID NO: 3001; (b) HCDR2 comprising the amino acid sequence of SEQ ID NO: 3002; (c) HCDR3 comprising the amino acid sequence of SEQ ID NO: 3003; (d) LCDR1 comprising the amino acid sequence of SEQ ID NO: 3004; (e) LCDR2 comprising the amino acid sequence of SEQ ID NO: 3005; and (f) LCDR3 comprising the amino acid sequence of SEQ ID NO: 3006; or v) (a) HCDR1 comprising the amino acid sequence of SEQ ID NO: 4001; (b) HCDR2 comprising the amino acid sequence of SEQ ID NO: 4002; (c) HCDR3 comprising the amino acid sequence of SEQ ID NO: 4003; (d) LCDR1 comprising the amino acid sequence of SEQ ID NO: 4004; (e) LCDR2 comprising the amino acid sequence of SEQ ID NO: 4005; and (f) LCDR3 comprising the amino acid sequence of SEQ ID NO: 4006; or vi) (a) HCDR1 comprising the amino acid sequence of SEQ ID NO: 1001 with 1, 2, or 3 amino acid changes to positions 4, 5, and/or 6 of SEQ ID NO: 1001; (b) HCDR2 comprising the amino acid sequence of SEQ ID NO: 1002 with 1, 2, 3, 4, or 5 amino acid changes to positions 1, 3, 5, 6, and/or 8 of SEQ ID NO: 1002; (c) HCDR3 comprising the amino acid sequence of SEQ ID NO: 1003; (d) LCDR1 comprising the amino acid sequence of SEQ ID NO: 1004; (e) LCDR2 comprising the amino acid sequence of SEQ ID NO: 1005; and (f) LCDR3 comprising the amino acid sequence of SEQ ID NO: 1006.

Embodiment 3. The isolated antibody of embodiment 1 or 2, wherein the antibody comprises a heavy chain variable region (VH) and a light chain variable region (VL), wherein:
i) the $V_H$ is at least 90%, 91%, 92%, 93%, 94%, 95%, 96%, 97%, 98%, 99%, or 100% identical to the amino acid sequence of SEQ ID NO: 712 and the VL is at least 90%, 91%, 92%, 93%, 94%, 95%, 96%, 97%, 98%, 99%, or 100% identical to the amino acid sequence of SEQ ID NO: 718; or
ii) the $V_H$ is at least 90%, 91%, 92%, 93%, 94%, 95%, 96%, 97%, 98%, 99%, or 100% identical to the amino acid sequence of SEQ ID NO: 1012 and the VL is at least 90%, 91%, 92%, 93%, 94%, 95%, 96%, 97%, 98%, 99%, or 100% identical to the amino acid sequence of SEQ ID NO: 1018; or
iii) the VH is at least 90%, 91%, 92%, 93%, 94%, 95%, 96%, 97%, 98%, 99%, or 100% identical to the amino acid sequence of SEQ ID NO: 2012 and the VL is at least 90%, 91%, 92%, 93%, 94%, 95%, 96%, 97%, 98%, 99%, or 100% identical to the amino acid sequence of SEQ ID NO: 2018; or
iv) the VH is at least 90%, 91%, 92%, 93%, 94%, 95%, 96%, 97%, 98%, 99%, or 100% identical to the amino acid sequence of SEQ ID NO: 3012 and the VL is at least 90%, 91%, 92%, 93%, 94%, 95%, 96%, 97%, 98%, 99%, or 100% identical to the amino acid sequence of SEQ ID NO: 3018; or
v) the VH is at least 90%, 91%, 92%, 93%, 94%, 95%, 96%, 97%, 98%, 99%, or 100% identical to the amino acid sequence of SEQ ID NO: 4012 and the VL is at least 90%, 91%, 92%, 93%, 94%, 95%, 96%, 97%, 98%, 99%, or 100% identical to the amino acid sequence of SEQ ID NO: 4018, optionally with the proviso that if any sequence variation is present in the CDRs, such sequence variation is within HCDR1 or HCDR2 with no more than 3 amino acid changes, such as no more than 2 amino acid changes to positions 4, 5, and/or 6 of HCDR1 and no more than 5 amino acids changes, such as no more than 2 amino acid changes to positions 1, 3, 5, 6, and/or 8 of HCDR2, optionally wherein the variation is not within HCDR3, LCDR1, LCDR2 and LCDR3.

Embodiment 4. The isolated antibody of any one of embodiments 1-3, wherein the antibody comprises a heavy chain variable region (VH) and a light chain variable region (VL), wherein:
i) the VH comprises the amino acid sequence of SEQ ID NO: 712 and the VL comprises the amino acid sequence of SEQ ID NO: 718; or
ii) the VH comprises the amino acid sequence of SEQ ID NO: 1012 and the VL comprises the amino acid sequence of SEQ ID NO: 1018; or
iii) the VH comprises the amino acid sequence of SEQ ID NO: 2012 and the VL comprises the amino acid sequence of SEQ ID NO: 2018; or
iv) the VH comprises the amino acid sequence of SEQ ID NO: 3012 and the VL comprises the amino acid sequence of SEQ ID NO: 3018; or
v) the VH comprises the amino acid sequence of SEQ ID NO: 4012 and the VL comprises the amino acid sequence of SEQ ID NO: 4018.

Embodiment 5. The isolated antibody of any one of the preceding embodiments, wherein the antibody is a monoclonal antibody.

Embodiment 6. The isolated antibody of any one of the preceding embodiments, wherein the antibody is a full-length antibody or is an antibody fragment, optionally a Fab, Fab', Fv, scFv or (Fab')$_2$.

Embodiment 7. The isolated antibody of any one of embodiments 1-5, wherein the antibody comprises an IgG1, IgG2, IgG3, or IgG4 Fc region, wherein the antibody optionally comprises a human IgG1 heavy chain constant region, a human IgG4 heavy chain constant region, or a mutant human IgG4 heavy chain constant region, wherein the mutant human IgG4 heavy chain constant region optionally comprises a mutation selected from a substitution at Ser228, a substitution at Leu235, a substitution at Asn297, or a combination thereof, numbering according to EU numbering or an S228P substitution and an L235E substitution, numbering according to EU numbering.

Embodiment 8. The isolated antibody of any one of embodiments 1-7, wherein the antibody
i) increases NK cell degranulation; and/or
ii) increases activation of NK cells; and/or
iii) increases activation of intra-tumoral NK cells when presented in combination with an anti-TIGIT antibody; and/or
iv) inhibits tumor growth in vivo; and/or
v) prevents tumor engraftment upon re-challenge with tumor, optionally wherein the antibody is IgG1 or IgG4.

Embodiment 9. A pharmaceutical composition comprising the antibody of any one of embodiments 1-8 and a pharmaceutically acceptable carrier, wherein the composition optionally comprises an opsonizing agent, a regulatory T cell depleting agent, chemotherapy, and/or an antagonist of PD-1, PD-L1, CTLA-4, Lag-3 or TIM-3.

Embodiment 10. The isolated antibody of any one of embodiments 1-8 or pharmaceutical composition of embodiment 9 for use in enhancing, increasing and/or sustaining an anti-tumor immune response in a subject, optionally wherein CD8 T cell activation is enhanced or CD8 T cell interferon gamma production is enhanced in the subject, or optionally wherein NK cell activation is enhanced in the subject or NK cell mediated cytotoxicity is enhanced in the subject, or optionally wherein CD226 interactions with CD112 are enhanced in a subject.

Embodiment 11. The isolated antibody of any one of embodiments 1-8 or pharmaceutical composition of embodiment 9 for use in treating cancer in a subject, wherein the cancer is optionally carcinoma, lymphoma, blastoma, sarcoma, or leukemia, or wherein the cancer is optionally squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or various types of head and neck cancer (including squamous cell carcinoma of the head and neck).

Embodiment 12. The isolated antibody or pharmaceutical composition for use of embodiment 10 or 11, wherein the use further comprises administering a second therapy, wherein the second therapy is optionally radiotherapy, surgery or administration of a second agent, wherein the second agent is optionally an antagonist of PD-1, PD-L1, CTLA-4, Lag-3 or TIM-3, or an antagonist of TIGIT or CD96, or an antagonist of PVRL1, PVRL2, PVRL3, PVRL4, and CD155, or is an antagonist of CD47, or is an antagonist of CD39, or is an antagonist of IL-27, or is a STING agonist, wherein the second agent is optionally an antagonist antibody.

Embodiment 13. A nucleic acid encoding the antibody of any one of embodiments 1-8.

Embodiment 14. A host cell comprising the nucleic acid of embodiment 13.

Embodiment 15. A method of producing the antibody of any one of embodiment 1-8 comprising culturing the host cell of embodiment 14 under conditions wherein the antibody is expressed, optionally further comprising purifying the antibody.

BRIEF DESCRIPTION OF THE FIGURES

In FIG. 2A, cells were pre-incubated with either IgG1 isotype control or anti-CD112R antibody. After washing, cells were stained with biotinylated his-labeled human CD112 and Streptavidin-PE simultaneously. The ability of anti-CD112R antibodies to block the binding of CD112 to CD112R was assessed by the geometric mean fluorescent intensity (gMFI) of the PE labeling and displayed as percent inhibition. Percent inhibition was calculated as [100−((test sample MFI/Max MFI)*100%)]. FIG. 2B shows percent inhibition as measured by ELISA of the interaction between human CD112R and CD112 by anti-CD112R antibodies described herein.

FIG. 10A shows the survival frequency of mice following primary tumor challenge with anti-CD112R treatment. Survivor mice exhibited no palpable tumors beyond day 50 of inoculation and were deemed to be complete responders. FIG. 10B shows tumor growth inhibition in survival mice upon tumor rechallenge compared to naïve control mice. Statistical analysis was performed by Mantel-Cox test on day 50 post implant (FIG. 10A) and by Mann-Whitney test on day 15 post implant (FIG. 10B).

FIG. 12A-12B show expression of CD69 (FIG. 12A) and Granzyme B (FIG. 12B) on intratumoral NK cells in CT-26 tumor model after treatment with an anti-CD112R antibody.

FIG. 13A-13F show mean (FIG. 13A) and individual (FIGS. 13B-E) tumor volume measurements as a function of time in a CT-26 tumor model after administration of anti-CD112R antibodies alone and in combination with anti-PD1 antibodies. FIG. 13F shows overall tumor-free survival on day 50 post-implantation as a fraction of tumor-free survivors per group.

FIG. 14A-14F show alignments of the CDR sequences of antibodies described herein. FIGS. 14A-14C show the CDR sequences of the heavy chain variable region, and FIGS. 14D-14F show the CDR sequences of the light chain variable region. In each of FIGS. 14A-14F, the first column shows HCDR1 (FIG. 14A), HCDR2 (FIG. 14B), and HCDR3 (FIG. 14C), LCDR1 (FIG. 14D), LCDR2 (FIG. 14E), and LCDR3 (FIG. 14F), where the antibody clone number is provided preceding H1 (for HCDR1), H2 (for HCDR2), H3 (for HCDR3), L1 (for LCDR1), L2 (for LCDR2), and L3 (for LCDR3). The second column shows the sequence, the third column shows the number of amino acids in the sequence, and the last column shows the percent identity of each sequence relative to the sequence from parent antibody clone 32. Family member clones 32, 33, 34, 35, and 36 are bolded.

FIG. 15A-15H show alignments of the framework region sequences of antibodies described herein. FIGS. 15A-15D show the framework region sequences of the heavy chain variable region, and FIGS. 15E-15H show the framework region sequences of the light chain variable region. In each of FIGS. 15A-15F, the first column shows heavy chain FR1 (FIG. 15A), FR2 (FIG. 15B), FR3 (FIG. 15C), FR4 (FIG. 15D) and light chain FR1 (FIG. 15E), FR2 (FIG. 15F), and FR3 (FIG. 15G), and FR4 (FIG. 15H), where the antibody clone number is provided preceding VH (for HFR1, HFR3, HFR3, and HFR4), and VL (for LFR1, LFR2, LFR3, and LFR4). The second column shows the sequence, and the last column shows the percent identity of each sequence relative to the sequence from parent antibody clone 32. Family member clones 32, 33, 34, 35, and 36 are bolded.

FIG. 16A-16B show alignments of the variable region sequences of antibodies described herein. FIG. 16A shows the heavy chain variable region sequences, and FIG. 16B shows the light chain variable region sequences. Each sequence is labeled with its corresponding clone number. The percent identity of each sequence relative to the sequence from antibody clone 32 is shown. Family member clones 32, 33, 34, 35, and 36 are bolded.

DETAILED DESCRIPTION OF EMBODIMENTS OF THE INVENTION

I. Definitions

Figure 1:
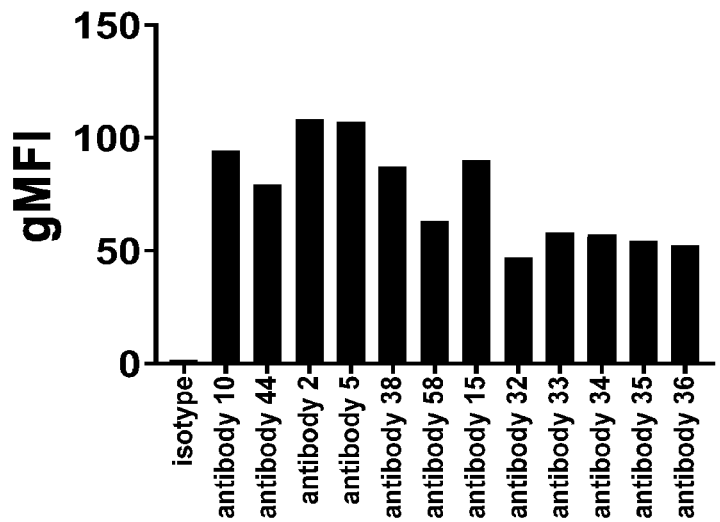
FIG. 1 depicts the ability of anti-CD112R antibodies, as compared to an IgG1 isotype control antibody, to bind to Jurkat cells engineered to overexpress human CD112R. Binding intensity was assessed by the geometric mean fluorescent intensity (gMFI) of the Alexa Fluor® 647 antibody label.

In this application, the use of "or" means "and/or" unless stated otherwise. In the context of a multiple dependent claim, the use of "or" refers back to more than one preceding independent or dependent claim in the alternative only. The terms "comprising," "including," and "having" can be used interchangeably herein.

The terms "CD112R," "PVR Related Immunoglobulin Domain Containing," "CD112 Receptor," "Poliovirus Receptor-Related Immunoglobulin Domain-Containing Protein" "Poliovirus Receptor Related Immunoglobulin Domain Containing," "Nectin-2 Receptor," "C7orf15," and "Transmembrane Protein PVRIG" are all used interchangeably and refer to a native, human CD112R, unless otherwise specifically indicated (e.g. mouse CD112R, cynomolgus CD112R, etc.). The term includes full-length, unprocessed CD112R as well as any form of CD112R that results from processing in the cell. The term encompasses naturally occurring variants of human CD112R, e.g., splice variants or allelic variants. External ID's for CD112R gene include Entrez Gene: 79037, Ensembl: ENSG00000213413, OM™: 617012, and UniProtKB: Q6DK17.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations optionally resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "block," in the context of an interaction between two or more molecules, is used herein to refer to inhibition or prevention of said interaction between the two or more molecules, wherein the inhibition or prevention of said interaction between the two or more molecules is complete or nearly complete under at least one condition. A "nearly complete" inhibition is a percent inhibition of about 70-99.9%, and a "complete" inhibition is 100%. For example, a molecule is said to "block" an interaction between two or more other molecules if it completely or nearly completely inhibits such interaction at certain concentrations in a dose dependent manner.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells. The term "tumor" is used herein to refer to a cell or cells that comprise a cancer. The term "tumor growth" is used herein to refer to proliferation or growth by a cell or cells that comprise a cancer that leads to a corresponding increase in the size or extent of the cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

Administration "in combination with" one or more further therapeutic agents includes simultaneous (concurrent) and consecutive (sequential) administration in any order.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In some embodiments, a human IgG heavy chain Fc region extends from Cys226, or from Pro230, to the carboxyl-terminus of the heavy chain. However, the C-terminal lysine (Lys447) of the Fc region may or may not be present (numbering in this paragraph is according to the EU numbering system, also called the EU index, as described in Kabat et al., *Sequences of Proteins of Immunological Interest*, 5th Ed. Public Health Service, National Institutes of Health, Bethesda, MD, 1991).

"Framework," "framework region," or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, and may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In some embodiments, for the VL, the subgroup is subgroup kappa I as in Kabat et al., supra. In some embodiments, for the VH, the subgroup is subgroup III as in Kabat et al., supra.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3).

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ) based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation or composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

Anti-CD112R antibodies, compositions comprising the described antibodies and methods of their use are provided.

A. Exemplary Anti-CD112R Antibodies

The Sequence Table below provides the sequences of certain embodiments of the antibodies disclosed and claimed herein.

In certain embodiments, antibodies are provided that bind to CD112R, and/or block binding of CD112R to CD112, and/or enhance activation of T cells and NK cells. In some embodiments, antibodies are provided that bind to CD112R. In some embodiments, antibodies are provided that block CD112R binding to CD112. In some embodiments, antibodies are provided that enhance activation of CD226, T cells, and/or NK cells.

Inhibition of binding between CD112R and CD112 such as on T and NK cells can be determined by measuring the inhibition of binding of cells to which CD112R binds in the presence and absence of the antibody.

Provided herein are antibodies that bind specifically to CD112R.

In some embodiments, the antibodies bind to human CD112R.

In some embodiments, the antibodies bind to human CD112R, and block the interaction of human CD112R to human CD112. In some embodiments, the antibodies bind to human CD112R, block the interaction of human CD112R to human CD112, but do not block the interaction of mouse CD112R to mouse CD112. In some embodiments, the antibodies that bind to human CD112R, block the interaction of human CD112R to human CD112, but do not block the interaction of mouse CD112R to mouse CD112 comprise antibodies 32, 33, 34, 35, and 36.

In certain embodiments, a CD112R antibody comprises a heavy chain variable region ("VH") comprising VH CDR1, CDR2 and/or CDR3 of any of the CD112R antibodies provided herein (i.e., antibody clone numbers 2, 5, 44, 58, 10, 38, 15, 35, 46, 47, 32, 33, 34, or 36).

In certain embodiments, a CD112R antibody comprises a VH comprising VH CDR1, CDR2 and/or CDR3 of any of the CD112R antibodies provided herein and a VL comprising CDR1, CDR2 and/or CDR3 of any of the CD112R antibodies provided herein. In certain embodiments, a CD112R antibody comprises a VH comprising VH CDR1, CDR2 and/or CDR3 of any one of antibody clone numbers 2, 5, 44, 58, 10, 38, 15, 35, 46, 47, 32, 33, 34, or 36, and a VL comprising VL CDR1, CDR2, and/or CDR3 of any one of antibody clone numbers 2, 5, 44, 58, 10, 38, 15, 35, 46, 47, 32, 33, 34, or 36, optionally wherein the VH and VL CDRs are from the same antibody clone.

In some embodiments, antibodies comprising the following are provided:

(a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; with or without (d) LCDR1 comprising the amino acid sequence of SEQ ID NO: 4; (e) LCDR2 comprising the amino acid sequence of SEQ ID NO: 5; and (0 LCDR3 comprising the amino acid sequence of SEQ ID NO: 6; or (b) HCDR1 comprising the amino acid sequence of SEQ ID NO: 101; (b) HCDR2 comprising the amino acid sequence of SEQ ID NO: 102; (c) HCDR3 comprising the amino acid sequence of SEQ ID NO: 103; with or without (d) LCDR1 comprising the amino acid sequence of SEQ ID NO: 104; (e) LCDR2 comprising the amino acid sequence of SEQ ID NO: 105; and (f) LCDR3 comprising the amino acid sequence of SEQ ID NO: 106; or (c) HCDR1 comprising the amino acid sequence of SEQ ID NO: 201; (b) HCDR2 comprising the amino acid sequence of SEQ ID NO: 202; (c) HCDR3 comprising the amino acid sequence of SEQ ID NO: 203; with or without (d) LCDR1 comprising the amino acid sequence of SEQ ID NO: 204; (e) LCDR2 comprising the amino acid sequence of SEQ ID NO: 205; and (f) LCDR3 comprising the amino acid sequence of SEQ ID NO: 206; or (d) HCDR1 comprising the amino acid sequence of SEQ ID NO: 301; (b) HCDR2 comprising the amino acid sequence of SEQ ID NO: 302; (c) HCDR3 comprising the amino acid sequence of SEQ ID NO: 303; with or without (d) LCDR1 comprising the amino acid sequence of SEQ ID NO: 304; (e) LCDR2 comprising the amino acid sequence of SEQ ID NO: 305; and (f) LCDR3 comprising the amino acid sequence of SEQ ID NO: 306; or (e) HCDR1 comprising the amino acid sequence of SEQ ID NO: 401; (b) HCDR2 comprising the amino acid sequence of SEQ ID NO: 402; (c) HCDR3 comprising the amino acid sequence of SEQ ID NO: 403; with or without (d) LCDR1 comprising the amino acid sequence of SEQ ID NO: 404; (e) LCDR2 comprising the amino acid sequence of SEQ ID NO: 405; and (f) LCDR3 comprising the amino acid sequence of SEQ ID NO: 406; or (f) HCDR1 comprising the amino acid sequence of SEQ ID NO: 501; (b) HCDR2 comprising the amino acid sequence of SEQ ID NO: 502; (c) HCDR3 comprising the amino acid sequence of SEQ ID NO: 503; with or without (d) LCDR1 comprising the amino acid sequence of SEQ ID NO: 504; (e) LCDR2 comprising the amino acid sequence of SEQ ID NO: 505; and (f) LCDR3 comprising the amino acid sequence of SEQ ID NO: 506; or (g) HCDR1 comprising the amino acid sequence of SEQ ID NO: 601; (b) HCDR2 comprising the amino acid sequence of SEQ ID NO: 602; (c) HCDR3 comprising the amino acid sequence of SEQ ID NO: 603; with or without (d) LCDR1 comprising the amino acid sequence of SEQ ID NO: 604; (e) LCDR2 comprising the amino acid sequence of SEQ ID NO: 605; and (f) LCDR3 comprising the amino acid sequence of SEQ ID NO: 606; or (h) HCDR1 comprising the amino acid sequence of SEQ ID NO: 701; (b) HCDR2 comprising the amino acid sequence of SEQ ID NO: 702; (c) HCDR3 comprising the amino acid sequence of SEQ ID NO: 703; with or without (d) LCDR1 comprising the amino acid sequence of SEQ ID NO: 704; (e) LCDR2 comprising the amino acid sequence of SEQ ID NO: 705; and (0 LCDR3 comprising the amino acid sequence of SEQ ID NO: 706; or (i) HCDR1 comprising the amino acid sequence of SEQ ID NO: 801; (b) HCDR2 comprising the amino acid sequence of SEQ ID NO: 802; (c) HCDR3 comprising the amino acid sequence of SEQ ID NO: 803; with or without (d) LCDR1 comprising the amino acid sequence of SEQ ID NO: 804; (e) LCDR2 comprising the amino acid sequence of SEQ ID NO: 805; and (0 LCDR3 comprising the amino acid sequence of SEQ ID NO: 806; or (j) (a) HCDR1 comprising the amino acid sequence of SEQ ID NO: 901; (b) HCDR2 comprising the amino acid sequence of SEQ ID NO: 902; (c) HCDR3 comprising the amino acid sequence of SEQ ID NO: 903; (d) LCDR1 comprising the amino acid sequence of SEQ ID NO: 904; (e) LCDR2 comprising the amino acid sequence of SEQ ID NO: 905; and (f) LCDR3 comprising the amino acid sequence of SEQ ID NO: 906; or (k) (a) HCDR1 comprising the amino acid sequence of SEQ ID NO: 1001; (b) HCDR2 comprising the amino acid sequence of SEQ ID NO: 1002; (c) HCDR3 comprising the amino acid sequence of SEQ ID NO: 1003; (d) LCDR1 comprising the amino acid sequence of SEQ ID NO: 1004; (e) LCDR2 comprising the amino acid sequence of SEQ ID NO: 1005; and (1) LCDR3 comprising the amino acid sequence of SEQ ID NO: 1006; or (l) (a) HCDR1 comprising the amino acid sequence of SEQ ID NO: 2001; (b) HCDR2 comprising the amino acid sequence of SEQ ID NO: 2002; (c) HCDR3 comprising the amino acid sequence of SEQ ID NO: 2003; (d) LCDR1 comprising the amino acid sequence of SEQ ID NO: 2004; (e) LCDR2 comprising the amino acid sequence of SEQ ID NO: 2005; and (f) LCDR3 comprising the amino acid sequence of SEQ ID NO: 2006; or (m) (a) HCDR1 comprising the amino acid sequence of SEQ ID NO: 3001; (b) HCDR2 comprising the amino acid sequence of SEQ ID NO: 3002; (c) HCDR3 comprising the amino acid sequence of SEQ ID NO: 3003; (d) LCDR1 comprising the amino acid sequence of SEQ ID NO: 3004; (e) LCDR2 comprising the amino acid sequence of SEQ ID NO: 3005; and (1) LCDR3 comprising the amino acid sequence of SEQ ID NO: 3006; or (n) (a) HCDR1 comprising the amino acid sequence of SEQ ID NO: 4001; (b) HCDR2 comprising the amino acid sequence of SEQ ID NO: 4002; (c) HCDR3 comprising the amino acid sequence of SEQ ID NO: 4003; (d) LCDR1 comprising the amino acid sequence of SEQ ID NO: 4004; (e) LCDR2 comprising the amino acid sequence of SEQ ID NO: 4005; and (f) LCDR3 comprising the amino acid sequence of SEQ ID NO: 4006.

In certain embodiments, a CD112R antibody comprises a VL comprising VL CDR1, CDR2 and CDR3 of any of the CD112R antibodies provided herein. In certain embodiments, a CD112R antibody comprises a VL comprising VL CDR1, CDR2 and CDR3 of any one of antibody clone numbers 2, 5, 44, 58, 10, 38, 15, 35, 46, 47, 32, 33, 34, or 36.

In some embodiments, a CD112R antibody may comprise:

(a) a VH comprising the amino acid sequence of the VH CDR1, CDR2 and CDR3 of antibody clone number 2 and a VL comprising the VL CDR1, CDR2 and CDR3 of antibody clone number 2; or (b) a VH comprising the amino acid sequence of the VH CDR1, CDR2 and CDR3 of antibody clone number 5 and a VL comprising the VL CDR1, CDR2 and CDR3 of antibody clone number 5; or (c) a VH comprising the amino acid sequence of the VH CDR1, CDR2 and CDR3 of antibody clone number 44 and a VL comprising the VL CDR1, CDR2 and CDR3 of antibody clone number 44; or (d) a VH comprising the amino acid sequence of the VH CDR1, CDR2 and CDR3 of antibody clone number 58 and a VL comprising the VL CDR1, CDR2 and CDR3 of antibody clone number 58; or (e) a VH comprising the amino acid sequence of the VH CDR1, CDR2 and CDR3 of antibody clone number 10 and a VL comprising the VL CDR1, CDR2 and CDR3 of antibody clone number 10; or (f) a VH comprising the amino acid sequence of the VH CDR1, CDR2 and CDR3 of antibody clone number 38 and a VL comprising the VL CDR1, CDR2 and CDR3 of antibody clone number 38; or (g) a VH comprising the amino acid sequence of the VH CDR1, CDR2 and CDR3 of antibody clone number 15 and a VL comprising the VL CDR1, CDR2 and CDR3 of antibody clone number 15; or (h) a VH comprising the amino acid sequence of the VH CDR1, CDR2 and CDR3 of antibody clone number 35 and a VL comprising the VL CDR1, CDR2 and CDR3 of antibody clone number 35; or (i) a VH comprising the amino acid sequence of the VH CDR1, CDR2 and CDR3 of antibody clone number 47 and a VL comprising the VL CDR1, CDR2 and CDR3 of antibody clone number 47; or (j) a VH comprising the amino acid sequence of the VH CDR1, CDR2 and CDR3 of antibody clone number 46 and a VL comprising the VL CDR1, CDR2 and CDR3 of antibody clone number 46; or (k) a VH comprising the amino acid sequence of the VH CDR1, CDR2 and CDR3 of antibody clone number 32 and a VL comprising the VL CDR1, CDR2 and CDR3 of antibody clone number 32; or (l) a VH comprising the amino acid sequence of the VH CDR1, CDR2 and CDR3 of antibody clone number 33 and a VL comprising the VL CDR1, CDR2 and CDR3 of antibody clone number 33; or (m) a VH comprising the amino acid sequence of the VH CDR1, CDR2 and CDR3 of antibody clone number 34 and a VL comprising the VL CDR1, CDR2 and CDR3 of antibody clone number 34; or (n) a VH comprising the amino acid sequence of the VH CDR1, CDR2 and CDR3 of antibody clone number 36 and a VL comprising the VL CDR1, CDR2 and CDR3 of antibody clone number 36.

The Sequence Table below provides the heavy and light chain variable region sequences of certain disclosed antibodies.

In certain embodiments, a CD112R antibody comprises a VH comprising the amino acid sequence of the VH of any of the CD112R antibodies provided herein. In certain embodiments, a CD112R antibody comprises a VH comprising the amino acid sequence of the VH of any one of the antibody clone numbers 2, 5, 44, 58, 10, 38, 15, 35, 46, 47, 32, 33, 34, or 36.

In some embodiments, a CD112R antibody comprises the VH of any one of antibody clone numbers 2, 5, 44, 58, 10, 38, 15, 35, 46, 47, 32, 33, 34, or 36 but with 1, 2, 3, 4, or 5 amino acid substitutions outside the complementarity determining regions (CDRs), such as 1, 2, 3, 4, or 5 conservative substitutions outside the CDRs. In some embodiments, a CD112R antibody comprises the VH of any one of antibody clone numbers 2, 5, 44, 58, 10, 38, 15, 35, 46, 47, 32, 33, 34, or 36 but with 1, 2, 3, 4, or 5 reversion substitutions outside the complementarity determining regions (CDRs).

In some embodiments, a CD112R antibody comprises the VH of any one of antibody clone numbers 2, 5, 44, 58, 10, 38, 15, 35, 46, 47, 32, 33, 34, or 36 but with 1, 2, 3, 4, or 5 amino acid substitutions in the framework regions of the VH sequence, such as 1, 2, 3, 4, or 5 conservative substitutions. In some embodiments, a CD112R antibody comprises the VH of any one of antibody clone numbers 2, 5, 44, 58, 10, 38, 15, 35, 46, 47, 32, 33, 34, or 36 but with 1, 2, 3, 4, or 5 reversion substitutions in the framework regions of the VH sequence.

In some embodiments, a CD112R antibody comprises the VH and VL CDRs of any of the CD112R antibodies described herein, wherein each CDR comprises 0, 1, 2 or 3 amino acid additions, substitutions (e.g., conservative substitutions), or deletions.

In certain embodiments, a CD112R antibody comprises a VH CDR1, CDR2, and CDR3 comprising the amino acid sequences of the VH CDRs of any of the CD112R antibodies provided herein and comprises a VH that is at least 90%, at least 91%, at least 92%, at least 93%, at least 94%, at least 95%, at least 96%, at least 97%, at least 98%, or at least 99% identical to the VH of any of the CD112R antibodies provided herein. In certain embodiments, a CD112R antibody comprises a VH comprising an amino acid sequence that is at least 90%, at least 91%, at least 92%, at least 93%, at least 94%, at least 95%, at least 96%, at least 97%, at least 98%, or at least 99% identical to the amino acid sequence of the VH of any one of antibody clone numbers 2, 5, 44, 58, 10, 38, 15, 35, 46, 47, 32, 33, 34, or 36. In certain embodiments, the VH of the antibody differs from that of the VH sequences shown in the Sequence Table due to 1, 2, 3, 4, or 5 amino acid substitutions in the framework regions of the VH sequence, such as 1, 2, 3, 4, or 5 conservative substitutions. In certain embodiments, the VH of the antibody differs from that of the VH sequences shown in the Sequence Table due to 1, 2, 3, 4, or 5 reversion substitutions in the framework regions of the VH sequence.

In certain embodiments, a CD112R antibody comprises a VH consisting of the amino acid sequence of the VH of any of the CD112R antibodies provided herein. In certain embodiments, a CD112R antibody comprises a VH that consists of the amino acid sequence of the VH of any one of antibody clone numbers 2, 5, 44, 58, 10, 38, 15, 35, 46, 47, 32, 33, 34, or 36.

In certain embodiments, a CD112R antibody comprises a VL comprising the amino acid sequence of the VL of any of the CD112R antibodies provided herein. In certain embodiments, a CD112R antibody comprises a VL comprising the amino acid sequence of the VL of any one of antibody clone numbers 2, 5, 44, 58, 10, 38, 15, 35, 46, 47, 32, 33, 34, or 36. In certain embodiments, a CD112R antibody comprises a VL CDR1, CDR2, and CDR3 comprising the amino acid sequences of the VL CDRs of any of the CD112R antibodies provided herein and comprises a VL that is at least 90%, at least 91%, at least 92%, at least 93%, at least 94%, at least 95%, at least 96%, at least 97%, at least 98%, or at least 99% identical to the VL of any of the CD112R antibodies provided herein. In certain embodiments, a CD112R antibody comprises a VL comprising an amino acid sequence that is at least 90%, at least 91%, at least 92%, at least 93%, at least 94%, at least 95%, at least 96%, at least 97%, at least 98%, or at least 99% identical to the amino acid sequence of the VL of any one of antibody clone numbers 2, 5, 44, 58, 10, 38, 15, 35, 46, 47, 32, 33, 34, or 36. In certain embodiments, the VL of the antibody differs from that of the VL sequences shown in the Sequence Table due to 1, 2, 3, 4, or 5 amino acid substitutions in the framework regions of the VL sequence, such as 1, 2, 3, 4, or 5 conservative substitutions. In certain embodiments, the VL of the antibody differs from that of the VL sequences shown in the Sequence Table due to 1, 2, 3, 4, or 5 reversion substitutions.

In certain embodiments, a CD112R antibody comprises a VL consisting of the amino acid sequence of the VL of any of the CD112R antibodies provided herein. In certain embodiments, a CD112R antibody comprises a VL that consists of the amino acid sequence of the VL of any one of antibody clone numbers 2, 5, 44, 58, 10, 38, 15, 35, 46, 47, 32, 33, 34, or 36.

In certain embodiments, a CD112R antibody comprises a VH comprising the amino acid sequence of the VH of any of the CD112R antibodies provided herein and comprises a VL comprising the amino acid sequence of the VL of any of the same CD112R antibodies provided herein. In certain of these embodiments, a CD112R antibody comprises a VH comprising the amino acid sequence of the VH of any one of antibody clone numbers 2, 5, 44, 58, 10, 38, 15, 35, 46, 47, 32, 33, 34, or 36 and a VL comprising the amino acid sequence of the VL of any one of antibody clone numbers 2, 5, 44, 58, 10, 38, 15, 35, 46, 47, 32, 33, 34, or 36, optionally wherein the VH and VL are from the same antibody clone number.

In certain embodiments, the VH of the antibody is that of any one of antibody clone numbers 2, 5, 44, 58, 10, 38, 15, 35, 46, 47, 32, 33, 34, or 36, but with 1, 2, 3, 4, or 5 amino acid substitutions in the framework regions of the VH sequence, such as 1, 2, 3, 4, or 5 conservative substitutions, and the VL is that of any one of the same antibody from the list above. In certain embodiments, however, the VH of the antibody is that of any one of antibody clone numbers 2, 5, 44, 58, 10, 38, 15, 35, 46, 47, 32, 33, 34, or 36, but with 1, 2, 3, 4, or 5 substitutions in the framework regions of the VH sequence.

In certain embodiments, a CD112R antibody comprises a VH and a VL comprising the amino acid sequences of the VH and VL of any one of antibody clone numbers 2, 5, 44, 58, 10, 38, 15, 35, 46, 47, 32, 33, 34, or 36.

In certain embodiments, a CD112R antibody comprises a VH CDR1, CDR2, and CDR3 comprising the amino acid sequences of the VH CDRs of any of the CD112R antibodies provided herein as well as a VL CDR1, CDR2, and CDR3 comprising the amino acid sequences of the VL CDRs of any of the CD112R antibodies provided herein, and also comprises a VH and a VL that are each at least 90%, at least 91%, at least 92%, at least 93%, at least 94%, at least 95%, at least 96%, at least 97%, at least 98%, or at least 99% identical to the corresponding VH and VL of any of the CD112R antibodies provided herein. In certain embodiments, the VH and the VL of the antibody differ from the VH and VL sequences shown in the Sequence Table due to 1, 2, 3, 4, or 5 amino acid substitutions in the framework regions of the sequences, such as 1, 2, 3, 4, or 5 conservative substitutions, or such as 1, 2, 3, 4 or 5 reversion substitutions.

In certain embodiments, a CD112R antibody comprises a VH and a VL consisting of the amino acid sequence of the VH and VL of any of the CD112R antibodies provided herein. In certain embodiments, a CD112R antibody comprises a VH and a VL that each consist of the amino acid sequences of the VH and VL of any one of antibody clone numbers 2, 5, 44, 58, 10, 38, 15, 35, 46, 47, 32, 33, 34, and 36.

A CD112R antibody may comprise:
(a) a VH comprising the amino acid sequence of the VH of antibody clone number 2 and a VL comprising the amino acid sequence of the VL of antibody clone number 2; or
(b) a VH comprising the amino acid sequence of the VH of antibody clone number 5 and a VL comprising the amino acid sequence of the VL of antibody clone number 5; or
(c) a VH comprising the amino acid sequence of the VH of antibody clone number 44 and a VL comprising the amino acid sequence of the VL of antibody clone number 44; or
(d) a VH comprising the amino acid sequence of the VH of antibody clone number 58 and a VL comprising the amino acid sequence of the VL of antibody clone number 58; or
(e) a VH comprising the amino acid sequence of the VH of antibody clone number 10 and a VL comprising the amino acid sequence of the VL of antibody clone number 10; or
(f) a VH comprising the amino acid sequence of the VH of antibody clone number 38 and a VL comprising the amino acid sequence of the VL of antibody clone number 38; or
(g) a VH comprising the amino acid sequence of the VH of antibody clone number 15 and a VL comprising the amino acid sequence of the VL of antibody clone number 15; or
(h) a VH comprising the amino acid sequence of the VH of antibody clone number 35 and a VL comprising the amino acid sequence of the VL of antibody clone number 35; or
(i) a VH comprising the amino acid sequence of the VH of antibody clone number 47 and a VL comprising the amino acid sequence of the VL of antibody clone number 47;
(j) a VH comprising the amino acid sequence of the VH of antibody clone number 46 and a VL comprising the amino acid sequence of the VL of antibody clone number 46;
(k) a VH comprising the amino acid sequence of the VH of antibody clone number 32 and a VL comprising the amino acid sequence of the VL of antibody clone number 32; or
(l) a VH comprising the amino acid sequence of the VH of antibody clone number 33 and a VL comprising the amino acid sequence of the VL of antibody clone number 33; or
(m) a VH comprising the amino acid sequence of the VH of antibody clone number 34 and a VL comprising the amino acid sequence of the VL of antibody clone number 34; or
(n) a VH comprising the amino acid sequence of the VH of antibody clone number 36 and a VL comprising the amino acid sequence of the VL of antibody clone number 36; or.

A CD112R antibody may comprise:
(a) a VH comprising the VH CDRs of the VH of antibody clone number 2, and a VL comprising the VL CDRs of antibody clone number 2, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 2; or
(b) a VH comprising the VH CDRs of the VH of antibody clone number 5, and a VL comprising the VL CDRs of antibody clone number 5, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 5; or
(c) a VH comprising the VH CDRs of the VH of antibody clone number 44, and a VL comprising the VL CDRs of antibody clone number 44, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 44; or
(d) a VH comprising the VH CDRs of the VH of antibody clone number 58, and a VL comprising the VL CDRs of antibody clone number 58, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 58; or
(e) a VH comprising the VH CDRs of the VH of antibody clone number 10, and a VL comprising the VL CDRs of antibody clone number 10, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 10; or
(f) a VH comprising the VH CDRs of the VH of antibody clone number 38, and a VL comprising the VL CDRs of antibody clone number 38, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 38; or
(g) a VH comprising the VH CDRs of the VH of antibody clone number 15, and a VL comprising the VL CDRs of antibody clone number 15, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 15; or (h) a VH comprising the VH CDRs of the VH of antibody clone number 35, and a VL comprising the VL CDRs of antibody clone number 35, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 35; or (i) a VH comprising the VH CDRs of the VH of antibody clone number 47, and a VL comprising the VL CDRs of antibody clone number 47, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 47; or (j) a VH comprising the VH CDRs of the VH of antibody clone number 46, and a VL comprising the VL CDRs of antibody clone number 46, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 46; or (k) a VH comprising the VH CDRs of the VH of antibody clone number 32, and a VL comprising the VL CDRs of antibody clone number 32, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 32; or (l) a VH comprising the VH CDRs of the VH of antibody clone number 33, and a VL comprising the VL CDRs of antibody clone number 33, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 33; or (m) a VH comprising the VH CDRs of the VH of antibody clone number 34, and a VL comprising the VL CDRs of antibody clone number 34, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 34; or (n) a VH comprising the VH CDRs of the VH of antibody clone number 36, and a VL comprising the VL CDRs of antibody clone number 36, and VH and VL amino acid sequences that are at least 90%, at least 91%, at least 92%, at least 93%, at least 94%, at least 95%, at least 96%, at least 97%, at least 98%, or at least 99% identical to the VH and VL of antibody clone number 36.

In some of the above embodiments, the VH and/or VL may differ from the sequence of each of the species by the presence of 1, 2, 3, 4, or 5 amino acid substitutions, such as 1, 2, 3, 4, or 5 conservative substitutions. In some embodiments, the VH may comprise 1, 2, 3, 4, or 5 reversion substitutions.

A CD112R antibody may comprise:

(a) a VH consisting of the amino acid sequence of the VH of antibody clone number 2 and a VL consisting of the VL of antibody clone number 2; or (b) a VH consisting of the amino acid sequence of the VH of antibody clone number 5 and a VL consisting of the VL of antibody clone number 5; or (c) a VH consisting of the amino acid sequence of the VH of antibody clone number 44 and a VL consisting of the VL of antibody clone number 44; or (d) a VH consisting of the amino acid sequence of the VH of antibody clone number 58 and a VL consisting of the VL of antibody clone number 58; or (e) a VH consisting of the amino acid sequence of the VH of antibody clone number 10 and a VL consisting of the VL of antibody clone number 10; or (f) a VH consisting of the amino acid sequence of the VH of antibody clone number 38 and a VL consisting of the VL of antibody clone number 38; or (g) a VH consisting of the amino acid sequence of the VH of antibody clone number 15 and a VL consisting of the VL of antibody clone number 15; or (h) a VH consisting of the amino acid sequence of the VH of antibody clone number 35 and a VL consisting of the VL of antibody clone number 35; or (i) a VH consisting of the amino acid sequence of the VH of antibody clone number 47 and a VL consisting of the VL of antibody clone number 47; or (j) a VH consisting of the amino acid sequence of the VH of antibody clone number 46 and a VL consisting of the VL of antibody clone number 46; or (k) a VH consisting of the amino acid sequence of the VH of antibody clone number 32 and a VL consisting of the VL of antibody clone number 32; or (l) a VH consisting of the amino acid sequence of the VH of antibody clone number 33 and a VL consisting of the VL of antibody clone number 33; or (m) a VH consisting of the amino acid sequence of the VH of antibody clone number 34 and a VL consisting of the VL of antibody clone number 34; or (n) a VH consisting of the amino acid sequence of the VH of antibody clone number 36 and a VL consisting of the VL of antibody clone number 36.

In certain embodiments, a CD112R antibody comprises any of the variable regions and/or variable region CDRs 1-3 of the antibodies described above and elsewhere herein, such as in the Sequence Table.

In some embodiments, the CD112R antibody is an IgG antibody, such as IgG1, IgG2, IgG3 or IgG4 antibody or a modified form thereof as described in the section below. In some embodiments, the constant region has effector function, and in some embodiments, the constant region is effectorless.

In certain embodiments, a CD112R antibody comprises a heavy chain (HC) comprising the amino acid sequence of the heavy chain of any of the CD antibodies provided herein. In certain embodiments, a CD112R antibody comprises a heavy chain comprising the amino acid sequence of the heavy chain of any one of antibody clone numbers 2, 5, 44, 58, 10, 38, 15, 35, 46, 47, 32, 33, 34, or 36.

In some embodiments, a CD112R antibody may comprise:

(a) a heavy chain comprising the amino acid sequence of the heavy chain of antibody clone number 2 and a light chain comprising the light chain amino acid sequence of antibody clone number 2; or
(b) a heavy chain comprising the amino acid sequence of the heavy chain of antibody clone number 5 and a light chain comprising the light chain amino acid sequence of antibody clone number 5; or
(c) a heavy chain comprising the amino acid sequence of the heavy chain of antibody clone number 44 and a light chain comprising the light chain amino acid sequence of antibody clone number 44; or
(d) a heavy chain comprising the amino acid sequence of the heavy chain of antibody clone number 58 and a light chain comprising the light chain amino acid sequence of antibody clone number 58; or
(e) a heavy chain comprising the amino acid sequence of the heavy chain of antibody clone number 10 and a light chain comprising the light chain amino acid sequence of antibody clone number 10; or
(f) a heavy chain comprising the amino acid sequence of the heavy chain of antibody clone number 38 and a light chain comprising the light chain amino acid sequence of antibody clone number 38; or
(g) a heavy chain comprising the amino acid sequence of the heavy chain of antibody clone number 15 and a light chain comprising the light chain amino acid sequence of antibody clone number 15; or
(h) a heavy chain comprising the amino acid sequence of the heavy chain of antibody clone number 35 and a light chain comprising the light chain amino acid sequence of antibody clone number 35; or
(i) a heavy chain comprising the amino acid sequence of the heavy chain of antibody clone number 47 and a light chain comprising the light chain amino acid sequence of antibody clone number 47; or
(j) a heavy chain comprising the amino acid sequence of the heavy chain of antibody clone number 46 and a light chain comprising the light chain amino acid sequence of antibody clone number 46; or
(k) a heavy chain comprising the amino acid sequence of the heavy chain of antibody clone number 32 and a light chain comprising the light chain amino acid sequence of antibody clone number 32; or
(l) a heavy chain comprising the amino acid sequence of the heavy chain of antibody clone number 33 and a light chain comprising the light chain amino acid sequence of antibody clone number 33; or
(m) a heavy chain comprising the amino acid sequence of the heavy chain of antibody clone number 34 and a light chain comprising the light chain amino acid sequence of antibody clone number 34; or
(n) a heavy chain comprising the amino acid sequence of the heavy chain of antibody clone number 36 and a light chain comprising the light chain amino acid sequence of antibody clone number 36.

A CD112R antibody may comprise:
(a) a heavy chain (HC) comprising the HC CDRs of the HC of antibody clone number 2 and a light chain (LC) comprising the LC CDRs of antibody clone number 2 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 2, respectively; or
(b) a HC comprising the HC CDRs of the HC of antibody clone number 5, and a light chain (LC) comprising the LC CDRs of antibody clone number 5 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 5, respectively; or
(c) a HC comprising the HC CDRs of the HC of antibody clone number 44, and a light chain (LC) comprising the LC CDRs of antibody clone number 44 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 44, respectively; or
(d) a HC comprising the HC CDRs of the HC of antibody clone number 58, and a light chain (LC) comprising the LC CDRs of antibody clone number 58 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 58, respectively; or
(e) a HC comprising the HC CDRs of the HC of antibody clone number 10, and a light chain (LC) comprising the LC CDRs of antibody clone number 10 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 10, respectively; or
(f) a HC comprising the HC CDRs of the HC of antibody clone number 38, and a light chain (LC) comprising the LC CDRs of antibody clone number 38 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 38, respectively; or
(g) a HC comprising the HC CDRs of the HC of antibody clone number 15, and a light chain (LC) comprising the LC CDRs of antibody clone number 15 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 15, respectively; or
(h) a HC comprising the HC CDRs of the HC of antibody clone number 35, and a light chain (LC) comprising the LC CDRs of antibody clone number 35 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 35, respectively; or
(i) a HC comprising the HC CDRs of the HC of antibody clone number 47, and a light chain (LC) comprising the LC CDRs of antibody clone number 47 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 47, respectively; or
(j) a HC comprising the HC CDRs of the HC of antibody clone number 46, and a light chain (LC) comprising the LC CDRs of antibody clone number 46 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 46, respectively; or (k) a HC comprising the HC CDRs of the HC of antibody clone number 32, and a LC comprising the LC CDRs of antibody clone number 32 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 32, respectively; or (l) a HC comprising the HC CDRs of the HC of antibody clone number 33, and a light chain (LC) comprising the LC CDRs of antibody clone number 33 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 33, respectively; or (m) a HC comprising the HC CDRs of the HC of antibody clone number 34, and a light chain (LC) comprising the LC CDRs of antibody clone number 34 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 34, respectively; or (n) a HC comprising the HC CDRs of the HC of antibody clone number 36, and a light chain (LC) comprising the LC CDRs of antibody clone number 36 and HC and LC amino acid sequences that are at least 90%, at least 91%, at least 92%, at least 93%, at least 94%, at least 95%, at least 96%, at least 97%, at least 98%, or at least 99% identical to the HC and LC of antibody clone number 36, respectively.

In some of the above embodiments, the HC and/or LC may differ from the sequence of each of the species by the presence of 1, 2, 3, 4, or 5 amino acid substitutions, such as 1, 2, 3, 4, or 5 conservative substitutions. In some of the above embodiments, the HC and/or LC may differ from the sequence of each of the species by the presence of 1, 2, 3, 4, or 5 amino acid substitutions, such as 1, 2, 3, 4, or 5 reversion substitutions.

1. Exemplary Class of Antibodies with Shared Structural and Functional Features

In some embodiments, anti-CD112R antibodies are provided. In certain embodiments, the anti-CD112 antibodies share certain structural and/or functional features. In some embodiments, the class of antibodies includes a parent antibody and affinity matured variants thereof. One exemplary class of antibodies includes, but is not limited to, parent clone 32, and affinity matured variants thereof. In some embodiments, the affinity matured variants comprise antibodies 33, 34, 35, and 36. In some embodiments, the affinity matured variants comprise antibodies with conservative substitutions as compared to antibodies 32, 33, 34, 35 and 36.

a. Structural Features of Exemplary Class of Antibodies

In some embodiments, the anti-CD112R antibodies share structural features, such as, for example, those shown in FIGS. 14 and 15. When a "class" or "members of a class" of antibodies is described herein, it is to be understood that embodiments describing a single anti-CD112R antibody or multiple anti-CD112R antibodies is encompassed/envisioned. In some embodiments, the anti-CD112R antibodies comprise identical HCDR3s. In some embodiments, the anti-CD112R antibodies comprise identical LCDR1s. In some embodiments, the anti-CD112R antibodies comprise identical LCDR2s. In some embodiments, the anti-CD112R antibodies comprise identical LCDR3s. In some embodiments, the anti-CD112R antibodies comprise identical HCDR3s and identical LCDR1s, LCDR2s, and/or LCDR3s. In some embodiments, the anti-CD112R antibodies comprise HCDR3 comprising the amino acid sequence of SEQ ID NO: 1003, and/or LCDR1 comprising the amino acid sequence of SEQ ID NO: 1004, and/or LCDR2 comprising the amino acid sequence of SEQ ID NO: 1005, and/or LCDR3 comprising the amino acid sequence of SEQ ID NO: 1006.

In some embodiments, each member of the class of antibodies comprises heavy chain framework regions comprising the amino acid sequences of SEQ ID NOs: 1007, 1008, 1009, and 1010. In some embodiments, each member of the class of antibodies comprises a heavy chain variable region amino acid sequence that is at least 90%, at least 91%, at least 92%, or at least 93% identical to the amino acid sequence of SEQ ID NO: 1012, wherein any and all of the sequence variation relative to SEQ ID NO: 1012 is in HCDR1 and/or HCDR2. In some embodiments, each member of the class of antibodies comprises light chain framework regions comprising the amino acid sequences of SEQ ID NOs: 1013, 1014, 1015, and 1016. In some embodiments, each member of the class of antibodies comprises the light chain variable region amino acid sequence of SEQ ID NO: 1018.

Members of this exemplary class of antibodies may comprise some variation in the amino acid sequences of HCDR1 and HCDR2. In some embodiments, each member of the class of antibodies comprise HCDR1 comprising the amino acid sequence of SEQ ID NO: 1001 or the amino acid sequence of SEQ ID NO: 1001 with 1, 2, or 3 amino acid changes to positions 4, 5, and/or 6 of SEQ ID NO: 1001. In some embodiments, the class of antibodies comprise HCDR1 comprising the amino acid sequence of SEQ ID NO: 1001 with 1, 2, or 3 amino acid changes to positions that vary between the amino acids of SEQ ID NO: 1001, 2001, 3001, 4001, and 701 as shown in FIG. 14. In some embodiments, one or more of the 1, 2, or 3 amino acid changes are not conservative substitutions. In some embodiments, one or more of the 1, 2, or 3 amino acid changes are conservative substitutions. In certain embodiments, a member of the class of antibodies comprises HCDR1 comprising the amino acid sequence of SEQ ID NO: 2001, 3001, 701, or 4001.

In some embodiments, each member of the class of antibodies comprise HCDR2 comprising the amino acid sequence of SEQ ID NO: 1002 or the amino acid sequence of SEQ ID NO: 1002 with 1, 2, 3, 4, or 5 amino acid changes to positions 1, 3, 5, 6, and/or 8 of SEQ ID NO: 1002. In some embodiments, the class of antibodies comprise HCDR2 comprising the amino acid sequence of SEQ ID NO: 1002 with 1, 2, 3, 4, or 5 amino acid changes to positions that vary between the amino acids of SEQ ID NO: 1002, 2002, 3002, 4002, and 702 as shown in FIG. 14. In some embodiments, one or more of the 1, 2, 3, 4, or 5 amino acid changes are not conservative substitutions. In some embodiments, one or more of the 1, 2, 3, 4, or 5 amino acid changes are conservative substitutions. In certain embodiments, a member of the class of antibodies comprises HCDR2 comprising the amino acid sequence of SEQ ID NO: 2002, 3002, 702, or 4002.

In some embodiments, each member of the class of antibodies comprise identical heavy chain and light chain framework regions.

b. Functional Features of Exemplary Class of Antibodies

In some embodiments, anti-CD112R antibodies are provided, wherein the antibodies share a special technical effect of binding to human CD112R, blocking the interaction of human CD112R to CD112, and failing to block the interaction of mouse CD112R to CD112. In some embodiments, each member of a class of antibodies binds to human CD112R and blocks the binding interaction between human CD112 and human CD112R. In some embodiments, each member of the class of antibodies does not block the binding interaction between mouse CD112 and mouse CD112R. Although the members of the class of antibodies do not block the interaction between mouse CD112 and mouse CD112R, the members of the class of antibodies either partially inhibits the binding interaction between mouse CD112 and mouse CD112R or does not inhibit the binding interaction between mouse CD112 and mouse CD112R. In some such embodiments, no member of the class of antibodies inhibits the interaction between mouse CD112R and mouse CD112 by more than 50%. In some embodiments, each member of the class of antibodies exhibits at least some binding to soluble mouse CD112R. In some embodiments, the antibody is fully human or humanized. In some embodiments, each member of the class of antibodies binds the same epitope on human CD112R.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CD112R and the other is for any other antigen. In certain embodiments, one of the binding specificities is for CD112R and the other is for selected independently from one (in the case of bispecific) or more (in the case of multispecific) of PD-1, PD-L1, CTLA-4, Lag-3, TIM-3, TIGIT, CD96, PVRL1, PVRL2, PVRL3, PVRL4, CD155, STING, CD47, CD39, and IL-27. In certain embodiments, bispecific antibodies may bind to two different epitopes of CD112R. Bispecific antibodies may also be used to localize cytotoxic agents to cells which express CD112R. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fantibody" or "DAF" comprising an antigen binding site that binds to CD112R as well as another, different antigen (see, US 2008/0069820, for example).

4. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

5. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 as are "exemplary substitutions. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu, Asn | Glu |
| Cys (C) | Ser; Ala | Ser |
| Gln (Q) | Asn; Glu | Asn |

TABLE 1-continued

| Original Residue | Exemplary Substitutions | Conservative Substitutions |
|---|---|---|
| Glu (E) | Asp; Gln | Asp |
| Gly (G) | Ala | Ala |
| His (H) | Asn; Gln; Lys; Arg | Arg |
| Ile (I) | Leu, Val, Met; Ala, Phe, Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.
Non-conservative substitutions will entail exchanging a member of one of these classes for another class.

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

6. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/

035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

7. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., *J Immunol.* 117:587 (1976) and Kim et al., *J Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (e.g., U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some embodiments, an antibody is provided according to the Table of Sequences, wherein the isotype is human IgG1. In some embodiments, an antibody is provided according to the Table of Sequences, wherein the isotype is human IgG4. In some embodiments, an antibody is provided according to the Table of Sequences, wherein the isotype is human IgG4, wherein there is a single mutation at serine 228 to proline (S228P).

8. Cysteine Engineered Antibody Variants

In certain embodiments, it may be desirable to create cysteine engineered antibodies, e.g., "thioMantibodies," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

9. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods

Antibodies may be produced using recombinant methods and compositions, e.g., as described in U.S. Pat. No. 4,816,567. In some embodiments, isolated nucleic acid encoding an anti-CD112R antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-CD112R antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD112R antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology,* Vol. 248 (B. K. C. Lo, ed., Humana Press, Totowa, NJ), pp. 255-268 (2003).

C. Immunoconjugates

The invention also provides immunoconjugates comprising an anti-CD112R antibody herein conjugated to one or more other therapeutic agents or radioactive isotopes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208, 020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

D. Pharmaceutical Formulations and Compositions

Pharmaceutical formulations or compositions of an anti-CD112R antibody as described herein are prepared by mixing such antibody having the desired degree of purity with one or more optional pharmaceutically acceptable carriers, diluents, and/or excipients (*Remington's Pharmaceutical Sciences* 16th edition, Osol, A. Ed. (1980)), in the form of lyophilized formulations or aqueous solutions. Pharmaceutically acceptable carriers, diluents, and excipients are generally nontoxic to recipients at the dosages and concentrations employed, and include, but are not limited to: sterile water, buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

The formulation or composition herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations or compositions to be used for in vivo administration are generally sterile. Sterility may be readily accomplished, e.g., by filtration through sterile filtration membranes.

E. Therapeutic Methods

Any of the anti-CD112R antibodies provided herein may be used in therapeutic methods. Throughout, where an "antibody" is discussed, it should also be appreciated that a composition comprising the antibody is also encompassed.

In one aspect, an anti-CD112R antibody for use as a medicament is provided. In some embodiments, an anti-CD112R antibody for use in enhancing, increasing and/or sustaining an anti-tumor immune response in a subject having a tumor is provided. In some embodiments, the tumor is cancerous. In some embodiments, an anti-CD112R antibody for use in treating cancer is provided. In some embodiments, an anti-CD112R antibody for use in enhancing CD226 interactions with CD112 is provided.

In a further aspect, the invention provides for the use of an anti-CD112R antibody in the manufacture or preparation of a medicament. In some embodiments, the medicament is for use in enhancing, increasing and/or sustaining an anti-tumor immune response in a subject having a tumor. In some embodiments, the tumor is cancerous. In some embodiments, the medicament is for treating cancer. In some embodiments, the medicament is for enhancing CD226 interactions with CD112.

In further aspects, the invention provides methods for treating diseases and/or disorders where blocking CD112R are desired. In some embodiments, methods for enhancing, increasing and/or sustaining an anti-tumor immune response in a subject having a tumor are provided comprising administering an anti-CD112R antibody as described herein. In some embodiments, the tumor is cancerous. In some embodiments, methods for treating cancer in a subject having cancer are provided comprising administering an anti-CD112R antibody as described herein. In some embodiments, methods for enhancing CD226 interactions with CD112 in a subject, optionally having cancer, are provided comprising administering an anti-CD112R antibody as described herein.

In some aspects, the invention provides a method for alleviating one or more symptoms of a CD112R protein associated disease or disorder; or an anti-CD112R antibody or a medicament comprising anti-CD112R antibody for alleviating one or more symptoms of a CD112R protein associated disease or disorder (such as any of the diseases or disorders described herein, for example, cancer). In some aspects, the invention provides a method for reducing the number of symptoms or the severity of one or more symptoms of a CD112R protein associated disease or disorder; or an anti-CD112R antibody or a medicament comprising anti-CD112R antibody for reducing the number of symptoms or the severity of one or more symptoms of a CD112R protein associated disease or disorder (such as any of the diseases or disorders described herein, for example, cancer). In a particular embodiment, the symptom of a CD112R protein associated disease or disorder is a tumor, and a reduction is a reduction in size of a tumor, the failure of the tumor to grow, or the elimination of the tumor.

The antibodies described herein may be used, for example, for treating cancer. In some embodiments, methods for treating cancer are provided, comprising administering an effective amount of an antibody described herein to a subject. In some embodiments, the antibodies may trigger or enhance an immune response in the subject, such as an antigen-specific immune response. In some embodiments, the antibodies may stimulate T cell activity. In some embodiments, the antibodies may inhibit the growth of at least one tumor in the subject.

Provided herein are methods for treating a subject having cancer, comprising administering to the subject a therapeutically effective amount of a CD112R antibody described herein, such that the subject is treated. A CD112R antibody can be used alone. Alternatively, a CD112R antibody can be used in conjunction with another agent, as described further below.

Cancers can be cancers with solid tumors or blood malignancies (e.g., liquid tumors).

Non-limiting examples of cancers for treatment include squamous cell carcinoma, small-cell lung cancer, non-small cell lung cancer, squamous non-small cell lung cancer (NSCLC), nonsquamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B cell lymphomas, T cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T cell lymphoma/leukemia, mantle cell lymphoma, angio immunoblastic T cell lymphoma, angiocentric lymphoma, intestinal T cell lymphoma, primary mediastinal B-cell lymphoma, precursor T-lymphoblastic lymphoma, T-lymphoblastic; and lymphoma/leukaemia (T-Lbly/T-ALL), peripheral T cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T cell and B cell tumors, including but not limited to T cell disorders such as T-prolymphocytic leukemia (T-PLL), including of the small cell and cerebriform cell type; large granular lymphocyte leukemia (LGL) of the T cell type; a/d T-NHL hepatosplenic lymphoma; peripheral/post-thymic T cell lymphoma (pleomorphic and immunoblastic subtypes); angiocentric (nasal) T cell lymphoma; cancer of the head or neck, renal cancer, rectal cancer, cancer of the thyroid gland; acute myeloid lymphoma, as well as any combinations of said cancers. The methods described herein can also be used for treatment of metastatic cancers, unresectable, refractory cancers (e.g., cancers refractory to previous immunotherapy, e.g., with a blocking CTLA-4 or PD-1 antibody), and/or recurrent cancers.

In certain embodiments, an antibody described herein is administered to subjects having a cancer that has exhibited an inadequate response to, or progressed on, a prior treatment, e.g., a prior treatment with an immuno-oncology or immunotherapy drug. In some embodiments, the cancer is refractory or resistant to a prior treatment, either intrinsically refractory or resistant (e.g., refractory to a PD-1 pathway antagonist), or a resistance or refractory state is acquired. For example, an antibody described herein may be administered to subjects who are not responsive or not sufficiently responsive to a first therapy or who have disease progression following treatment, e.g., anti-PD-1 pathway antagonist treatment, either alone or in combination with another therapy (e.g., with an anti-PD-1 pathway antagonist therapy). In other embodiments, an antibody described herein is administered to subjects who have not previously received (i.e., been treated with) an immuno-oncology agent, e.g., a PD-1 pathway antagonist.

F. Combinations

Antibodies of the invention can be used either alone or in combination with other agents in a therapy. For instance, an antibody of the invention may be co-administered with at least one additional therapeutic agent (e.g., further comprising administering a second therapy).

In some embodiments, targeting an additional independent inhibitory pathway or combinations thereof has the potential to lead to further enhanced immune cell activation beyond monotherapy.

In some embodiments, the additional therapeutic agent or second agent is a chemotherapeutic agent, an opsonizing agent, a regulatory T cell ("Treg") depleting agent, an antagonist of a target other than CD112R, or an agonist of a target other than CD112R. In certain embodiments, the second agent is a chemotherapeutic agent described herein or any known chemotherapeutic agent. In some embodiments, the second agent is an opsonizing agent, wherein the opsonizing agent is an antibody other than an anti-CD112R antibody that targets cancer or tumor cells. In some embodiments, the second agent is a Treg depleting agent described herein or any known Treg depleting agent. In some embodiments, the second agent is an antagonist of a target other than CD112R. In some embodiments, the second agent is an agonist of a target other than CD112R.

In some instances, the second agent targets an independent inhibitory pathway, such as, for example, a pathway involving PD-1, PD-L1, CTLA-4, Lag-3 or TIM-3. In some embodiments, the second agent antagonizes one or more of PD-1, PD-L1, CTLA-4, Lag-3 and TIM-3. Suitable antagonists for use in the combination therapy described herein, include, without limitation, ligands, antibodies (e.g., monoclonal antibodies and bispecific antibodies), and multivalent agents. In one embodiment, the antagonist is a fusion protein, e.g., an Fc fusion protein, such as AMP-244. In some embodiments, the PD-1 antagonist is an anti-PD-1 or anti-PD-L1 antibody.

An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD-1 antibody is MK-3475 (Lambrolizumab) described in WO2012/145493; AMP-514 described in WO 2012/145493; or PDR001. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 can also be used. An anti-PD-1 antibody that competes for binding with, and/or binds to the same epitope on PD-1 as, as one of these antibodies can also be used in combination treatments.

In some embodiments, the anti-PD-L1 antibody useful for the combination therapy is BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiment an anti-PD-L1 antibody is MEDI4736 (also known as durvalumab and Anti-B7-H1), MPDL3280A (also known as atezolizumab and RG7446), MSB0010718C (also known as avelumab; WO2013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 can also be used. Anti-PD-L1 antibodies that compete with and/or bind to the same epitope as that of any of these antibodies can also be used in combination treatments.

In certain embodiments, the CD112R antibody of the disclosure can be used with a CTLA-4 antagonist, e.g., an anti-CTLA-4 antibody. In one embodiment, an anti-CTLA-4 antibody is an antibody selected from the group of: Yervoy® (ipilimumab or antibody 10D1, described in PCT Publication WO 01/14424), tremelimumab (formerly ticilimumab, CP-675,206), monoclonal or an anti-CTLA-4 antibody described in any of the following publications: WO 98/42752; WO 00/37504; U.S. Pat. No. 6,207,156; Hurwitz et al. (1998) Pro. Natl. Acad. Sci. USA 95(17): 10067-10071; Camacho et al. (2004) J. Clin. Oncology 22(145): antibodiestract No. 2505 (antibody CP-675206); and Mokyr et al. (1998) Cancer Res. 58:5301-5304. Any of the anti-CTLA-4 antibodies disclosed in WO2013/173223 can also be used.

In some embodiments, a CD112R antibody of the disclosure is used in combination with a LAG-3 (also referred to herein and by others as LAGS) antagonist. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273. Anti-LAG-3 antibodies that compete with and/or bind to the same epitope as that of any of these antibodies can also be used in combination treatments.

In some embodiments, targeting two or more of TIGIT, CD96 and CD112R receptors simultaneously increases CD226 mediated signaling beyond the anti-CD112R monotherapy. Therefore, in some embodiments, the second agent is an antagonist of TIGIT and/or CD96. Suitable antagonists for use in the combination therapy described herein, include, without limitation, ligands, antibodies (e.g., monoclonal antibodies and bispecific antibodies), and multivalent agents.

In some embodiments, members of the PVR gene family are upregulated on tumor cells and can exhibit intrinsic tumor-promoting properties. Targeting additional members of the PVR gene family in combination with anti-CD112R antibodies leads to enhanced sensitivity to tumors beyond monotherapy. Therefore, in some embodiments, the second agent is selected from one or more of an antagonist of PVRL1, PVRL2, PVRL3, PVRL4, and CD155. Suitable antagonists for use in the combination therapy described herein, include, without limitation, ligands, antibodies (e.g., monoclonal antibodies and bispecific antibodies), and multivalent agents.

STING agonists induce innate immune cell activation resulting in increased T cell priming and recruitment of immune cells into the tumor microenvironment. Targeting STING agonists in combination with CD112R has the potential to lead to an even further increase in T cell and NK cell recruitment and activation.

Increased anti-CD47 antibody mediated phagocytosis can lead to an increase in the presentation of cancer derived antigens by macrophages to T cells. Combination treatment with an anti-CD47 antibody and an anti-CD112R antibody, such as an anti-CD112R antibody provided herein provides an opportunity to enhance cancer antigen specific T cell responses and is fully encompassed herein.

Adenosine, via adenosine receptors expressed on immune cells, inhibits T cell and NK cell activation. Anti-CD39 antibodies inhibit the generation of adenosine by preventing hydrolysis of adenosine triphosphate (ATP). Combination treatment with an anti-CD39 antibody and an anti-CD112R antibody, such as an anti-CD112R antibody provided herein, provides an opportunity to further enhance CD112R therapy by inhibiting adenosine mediated cell signaling in immune cells.

Cytokines can effectively modulate T cell and NK cell activation. IL-27 is an immunosuppressive cytokine that inhibits T cell and NK cell mediated responses. Anti-IL-27 antibodies provide an opportunity to enhance CD112R therapy by limiting immunosuppressive cytokine signaling in immune cells. Thus, combination treatment with an anti-IL-27 antibody and an anti-CD112R antibody, such as an anti-CD112R antibody provided herein, is provided.

The antibodies herein may also be provided before, substantially contemporaneous with, or after other modes of treatment, for example, surgery, chemotherapy, radiation therapy, or the administration of a biologic, such as another therapeutic antibody. In some embodiments, the cancer has recurred or progressed following a therapy selected from surgery, chemotherapy, and radiation therapy, or a combination thereof. For example, a CD112R antibody as described herein could be administered as adjunctive therapy when there is a risk that micrometastases can be present and/or in order to reduce the risk of a relapse.

For treatment of cancer, the combinations may be administered in conjunction with one or more additional anti-cancer agents, such as a chemotherapeutic agent, growth inhibitory agent, anti-cancer vaccine such as a gene therapy vaccine, anti-angiogenesis agent and/or anti-neoplastic composition.

In some embodiments, an anti-inflammatory drug may be administered with the combination, such as a steroid or a non-steroidal anti-inflammatory drug (NSAID). In cases where it is desirable to render aberrantly proliferative cells quiescent in conjunction with or prior to treatment with CD112R antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX®, can also be administered to the subject. When employing the methods or compositions described herein, other agents used in the modulation of tumor growth or metastasis in a clinical setting, such as antimimetics, can also be administered as desired.

Such combination therapies noted above encompass combined administration (where two or more therapeutic agents are included in the same or separate formulations or compositions), and separate administration, in which case, administration of the antibody of the invention can occur prior to, simultaneously, and/or following, administration of the additional therapeutic agent or agents. In some embodiments, administration of the anti-CD112R antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention can be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. As used herein, a "split dose" is the division of single unit dose or total daily dose into two or more doses, e.g., two or more administrations of the single unit dose. The antibody may be administered as "split dose."

The antibody need not be but is optionally formulated with one or more agents currently used to prevent or treat the disorder in question. The effective amount of such other agents depends on the amount of antibody present in the formulation or composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate. In some embodiments, the antibody is provided in a formulation for immediate release and the other agent is formulated for extended release or vice versa.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-CD112R antibody.

III. Examples

Example 1. Anti-CD112R Antibody Generation

Antigens were biotinylated using the EZ-Link Sulfo-NHS-Biotinylation Kit from Pierce. Goat F(ab')2 anti-human kappa-FITC (LC-FITC), ExtrAvidin-PE (EA-PE) and Streptavidin-AF633 (SA-633) were obtained from Southern Biotech, Sigma, and Molecular Probes, respectively. Streptavidin MicroBeads and MACS LC separation columns were purchased from Miltenyi Biotec. Goat anti-human IgG-PE (Human-PE) was obtained from Southern Biotech.

Primary Discovery.

Eight naïve human synthetic yeast libraries each of ~10⁹ diversity were propagated as previously described (see, e.g., Y. Xu et al, Addressing polyspecificity of antibodies selected from an in vitro yeast presentation system: a FACS-based, high-throughput selection and analytical tool. PEDS 26.10, 663-70 (2013); WO2009036379; WO2010105256; and WO2012009568.) For the first two rounds of selection, a magnetic bead sorting technique utilizing the Miltenyi MACS system was performed, as previously described (see, e.g., Siegel et al, High efficiency recovery and epitope-specific sorting of an scFv yeast display library." J Immunol Methods 286(1-2), 141-153 (2004).) Briefly, yeast cells (~10¹⁰ cells/library) were incubated with 1.5 ml of 10 nM biotinylated Fc-fusion antigen for 15 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidin MicroBeads (500 µl) were added to the yeast and incubated for 15 min at 4° C. Next, the yeast were pelleted, resuspended in 20 mL wash buffer, and loaded onto a Miltenyi LS column. After the 20 mL were loaded, the column was washed 3 times with 3 mL wash buffer. The column was then removed from the magnetic field, and the yeast were eluted with 5 mL of growth media and then grown overnight. The following rounds of selection were performed using flow cytometry. Approximately 2×10⁷ yeast were pelleted, washed three times with wash buffer, and incubated at 30° C. with either decreasing concentrations of biotinylated antigen (100 to 1 nM) under equilibrium conditions, or with a poly-specificity depletion reagent (PSR) to remove non-specific antibodies from the selection. For the PSR depletion, the libraries were incubated with a 1:10 dilution of biotinylated PSR reagent as previously described (see, e.g., Y. Xu et al, Addressing polyspecificity of antibodies selected from an in vitro yeast presentation system: a FACS-based, high-throughput selection and analytical tool. PEDS 26.10, 663-70 (2013).) Yeast were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Selections employing affinity pressure in order to select for and isolate higher affinity antibodies were performed by competing with cold (i.e., unlabeled) antigen.

Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Light Chain Batch Shuffle.

Light chain diversification protocol was used during the primary discovery phase for further discovery and improvement of antibodies.

Light chain batch diversification protocol: Heavy chains from a naïve selection output were extracted from the yeast via PCR and transformed into a light chain library with a diversity of 5×10⁶. Selections were performed with one round of MACS and three rounds of FACS as described in the naïve discovery. In the different FACS rounds the libraries were looked at for PSR binding, and affinity pressure by antigen titration down to 0.5 nM. Sorting was performed in order to obtain a population with the desired characteristics.

Antibody Optimization

Optimization of antibodies was performed by introducing diversities into the heavy chain variable regions as described below.

CDRH1 and CDRH2 selection: The CDRH3 of a single antibody was recombined into a premade library with CDRH1 and CDRH2 variants of a diversity of 1×10$^8$ and selections were performed with one round of MACS and three rounds of FACS as described in the naïve discovery. In the different FACS rounds the libraries were looked at for PSR binding, mouse cross-reactivity, and affinity pressure by titration or affinity pressure by pre-complexing the antigen with parental Fab or parental IgG to enrich for binders with higher affinity than the parental IgG. Sorting was performed in order to obtain a population with the desired characteristics.

Antibody Production and Purification

Yeast clones were grown to saturation and then induced for 48 hours at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio KD Measurements

ForteBio affinity measurements were performed on an Octet RED384 generally as previously described (see, e.g., Estep et al, High throughput solution-based measurement of antibody-antigen affinity and epitope binning. Mabs 5(2), 270-278 (2013)). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model.

ForteBio Epitope Binning/Ligand Blocking

Epitope binning/ligand blocking was performed using a standard sandwich format cross-blocking assay. Control anti-target IgG or receptor was loaded onto AHQ sensors and unoccupied Fc-binding sites on the sensor were blocked with an irrelevant (non-target) human IgG1 antibody. The sensors were then exposed to 100 nM target antigen followed by a second anti-target antibody. Additional binding by the second antibody after antigen association indicates an unoccupied epitope (non-competitor), while no binding indicates epitope blocking (competitor or ligand blocking).

Biacore Kintetic Assay

For the Biacore-based measurements, the antigen was covalently coupled to a anti mouse-Fc capture C1 chip using an amine-coupling kit (GE Healthcare BioSciences). Association between the antigen and a live-point three-fold titration of the antibody starting at 27 nM was measured for 300 sec. Subsequently, dissociation between the antigen and antibody was measured for 3600 sec. Kinetic data was analyzed and fitted globally using a 1:1 binding model.

Example 2. Anti-CD112R Antibodies Bind to CD112R

On Cell Binding Assay

The ability of anti-CD112R antibodies to bind to CD112R expressed on cells was evaluated. 1×10$^5$ Jurkat cells (acute T cell leukemia cell line, ATCC #TIB-152) that were either wild type or engineered to over-express human CD112R (Jurkat-CD112R OE) were added to each well of a 96-well V bottom plate and stained with either anti-CD112R antibodies or an IgG1 isotype control (0.63 µg/mL) for 1 hour at 4° C. Cells were washed twice with PBS +2% FCS and resuspended with Alexa Fluor® 647 anti-human IgG Fc antibody (Biolegend, Cat #409320) diluted 1:100 in PBS +2% FCS and incubated at 4° C. for 30 minutes. Cells were subsequently washed twice and resuspended in PBS +2% FCS. Cellular data was acquired using a LSRFortessa X-20 (BD Biosciences) and analyzed with FlowJo software (Tree Star).

Results are depicted in FIG. 1. Quantitation of antibody binding to Jurkat-CD112R OE cells was assessed by the geometric mean fluorescent intensity (gMFI) of the Alexa Fluor® 647 signal. These results demonstrate that anti-CD112R antibodies bind to cells that express CD112R. A summary of antibody binding is shown in Table 2.

Example 3. Anti-CD112R Antibodies Block CD112 from Binding to CD112R Expressing Cells On Cell Blocking Assay The ability of anti-CD112R antibodies to block CD112 binding to CD112R expressing cells was evaluated. 1×10$^5$ Jurkat cells (acute T cell leukemia cell line, ATCC #TIB-152) that were engineered to over-express human CD112R (Jurkat-CD112R OE) were added to each well of a 96-well V bottom plate and stained with serial dilutions of either anti-CD112R antibodies or an IgG1 isotype control (highest concentration, 10 µg/mL) for 1 hour at 4° C. Cells were washed twice with PBS +2% FCS and resuspended with biotinylated his-tagged human CD112 (3 µg/mL) (BPS Bioscience, #71234) and PE Streptavidin (5 µg/mL) (Biolegend, #405204) in PBS +2% FCS and incubated at 2 hours at 4° C. Cells were subsequently washed twice and resuspended in PBS +2% FCS. Cellular data was acquired using a LSRFortessa X-20 (BD Biosciences) and analyzed with FlowJo software (Tree Star).

Figure 2A:
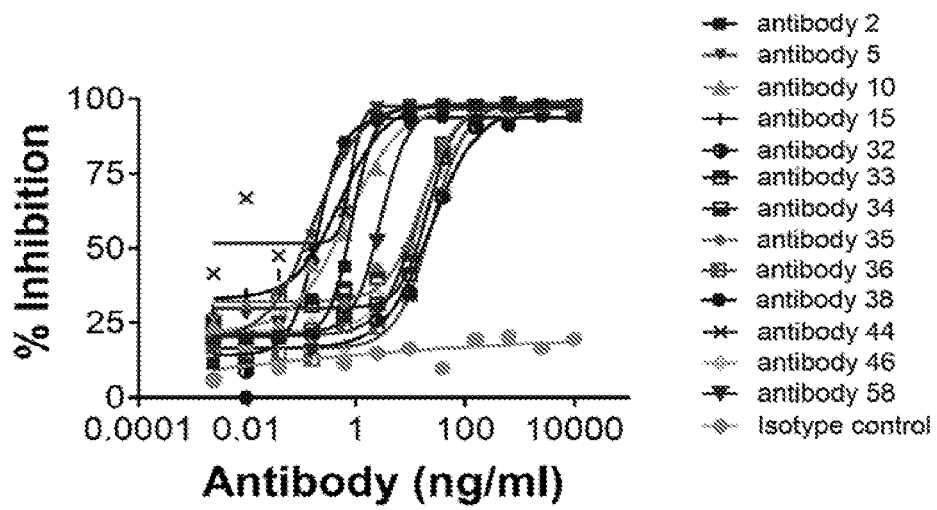
FIGS. 2A-2B depict the ability of anti-CD112R antibodies, as compared to an IgG1 isotype control antibody, to block the interaction of CD112R with CD112 on Jurkat cells engineered to overexpress human CD112R.

Results are depicted in FIG. 2A and Table 2. Quantitation of CD112 binding to cells was assessed by the geometric mean fluorescent intensity (gMFI) of the PE signal and displayed as percent inhibition. Percent inhibition was calculated as [100−((test sample MFI/Max MFI)*100%)] These results demonstrate that anti-CD112R antibodies inhibit the ability of CD112 to bind to CD112R expressing cells in a dose dependent fashion. A summary of antibody binding and blocking is shown in Table 2.

The ability of anti-CD112R antibodies to block human CD112R was also evaluated by ELISA. Briefly, 96 well Nunc Maxisorp plates were coated with 1 µg/mL of a CD112R-hIgG4 fusion protein in PBS overnight at 4° C. Plates were then washed 6× with PBS +0.01% Tween-20 (PBST) and subsequently blocked with 200 µl of PBS +1% BSA for 1.5 hours at room temperature. After blocking, plates were washed 6× with PBST. Next, 100 µl of anti-CD112R antibodies in PBS +1% BSA was added at a final starting concentration of 10 µg/mL, with 4-fold serial dilutions. Plates were incubated at room temperature for 1.5 hours. Next plates were washed 6× with PBST and then incubated with 1 µg/ml CD112 Fc protein (R&D Systems, Cat #9317-N2-050) that was biotinylated with a sulfo-NHS biotinylation kit (Thermo Fisher, Cat #21925) in 100 µl of PBS +1% BSA for 1 hour at room temperature. Plates were then washed 6× with PBST and subsequently incubated with streptavidin-HRP (Biolegend, Cat #405210) diluted in PBS +1% BSA according to the manufacturer recommendation for 1 hour at room temperature. Following this incubation, plates were then washed 6× with PBST and developed with TMB substrate (Life Technologies, Cat #002023). The reaction was stopped with an equal volume of stop solution (Life Technologies, Cat #SS04). Absorbance at 450 nm (O.D. 450) was measured on a SpectraMax plate reader.

Figure 2B:
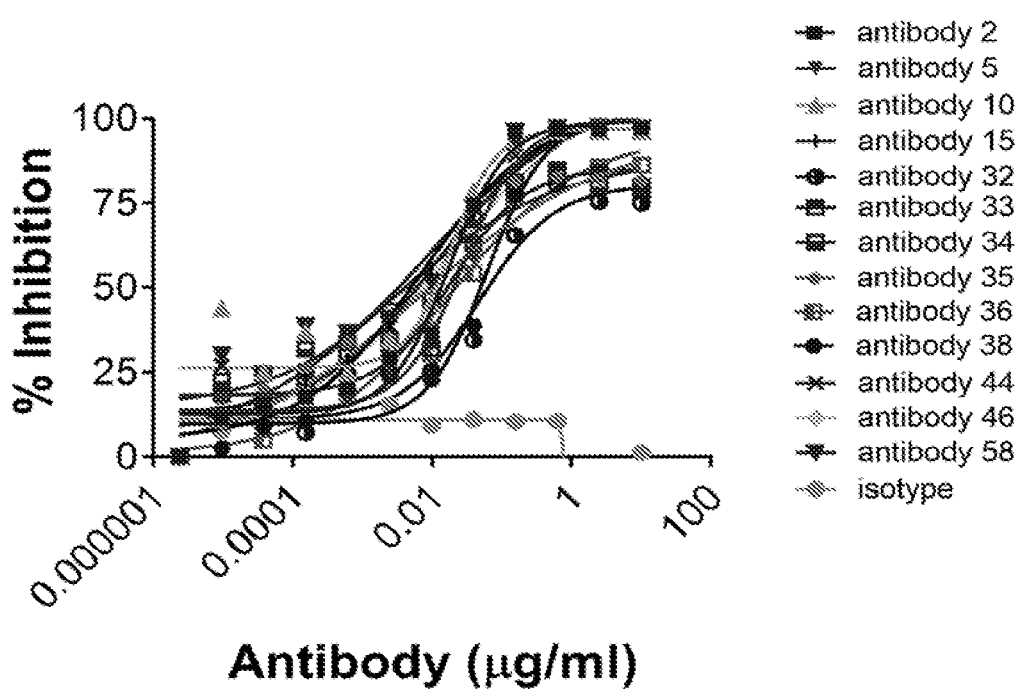

Results are depicted in FIG. 2B and Table 2. These results demonstrate that anti-CD112R antibodies block human CD112R from binding to human CD112. Percent inhibition was calculated as [100−((test sample O.D. 450/Max O.D. 450)*100%)] Max O.D. 450 was defined as absorbance at 450 nm in the absence of antibody.

TABLE 2

Summary of Antibody Binding and Blocking

| Antibody | Jurkat gMFI (fold increase over isotype) | Jurkat-CD112R over-expressed (OE) gMFI (fold increase over isotype) | CD112 blocking IC50 on Jurkat-CD112R OE (ng/mL) | CD112 blocking max inhibition on Jurkat-CD112R OE (%) | CD112 blocking max inhibition ELISA (%) |
|---|---|---|---|---|---|
| Antibody 2 | 4.7 | 63.9 | 0.83 | 94.1 | 97.0 |
| Antibody 5 | 3.8 | 63.3 | 0.17 | 97.0 | 97.4 |
| Antibody 10 | 4.6 | 55.7 | 0.69 | 96.8 | 96.3 |
| Antibody 15 | 4 | 53.2 | 0.51 | 97.9 | 97.0 |
| Antibody 32 | 2.5 | 27.9 | 23.57 | 96.0 | 75.1 |
| Antibody 33 | 3.4 | 34.2 | 21.89 | 97.4 | 78.8 |
| Antibody 34 | 3.8 | 33.8 | 13.22 | 96.9 | 80.0 |
| Antibody 35 | 3.3 | 32.1 | 16.19 | 97.4 | 81.7 |
| Antibody 36 | 3.5 | 31 | 24.37 | 97.5 | 86.2 |
| Antibody 38 | 3.8 | 51.7 | 0.19 | 95.5 | 97.2 |
| Antibody 44 | 4.8 | 46.9 | 0.81 | 97.7 | 96.8 |
| Antibody 46 | 4.2 | 23.8 | 16.22 | 95.5 | 97.6 |
| Antibody 58 | 4.5 | 37.3 | 2.8 | 96.3 | 97.3 |

Example 4. Anti-CD112R Antibodies Enhance NK Cell Mediated Killing

NK Cytotoxicity Assay

To determine the effect of anti-human CD112R antibodies on NK cell mediated cytotoxicity, human NK cells were cocultured with REH target cells (non-T/B cell acute lymphocytic leukemia cell line, ATCC #CRL-8286) in the presence of anti-CD112R antibody or isotype control.

Briefly, NK cells were isolated from the PBMCs of three healthy donors via negative selection (Easysep™ NK cell isolation kit, Stemcell #17955) and activated for 16 hours with IL-2 (10 units/mL) (Peprotech #200-02) and IL-12 (20 ng/mL (Peprotech #200-12) in RPMI+10% FBS+1% Penicillin-Streptomycin (R10) (ThermoFisher). REH cells were washed, resuspended in PBS (ThermoFisher) and labeled with CellTrace™ violet (CTV) (ThermoFisher #C34557) for 12 minutes at 37° C. Subsequently REH cells were washed with PBS +10% FBS and then resuspended in R10. Following activation, NK cells were washed and resuspended in R10. $2.5 \times 10^5$ NK cells and $5 \times 10^4$ REH cells were added to each well of a 96-well flat bottom plate for an effector-target cell ratio of 5:1. Anti-CD112R and an IgG$_1$ isotype antibody were diluted in R10 and also added to each well at a final concentration of 10 µg/mL. Each condition was run in duplicate. The plates were then incubated for 4 hours at 37° C. Cells were then washed and incubated at room temperature for 30 minutes in the dark with 7-AAD viability dye (1 µg/mL) (Biolegend #420404) to specifically label dead cells. Cell viability data was acquired using a LSRFortessa X-20 (BD Biosciences) and analyzed with FlowJo software (Tree Star). Dead REH cells were defined as CTV and 7-AAD double positive cells.

Figure 3:
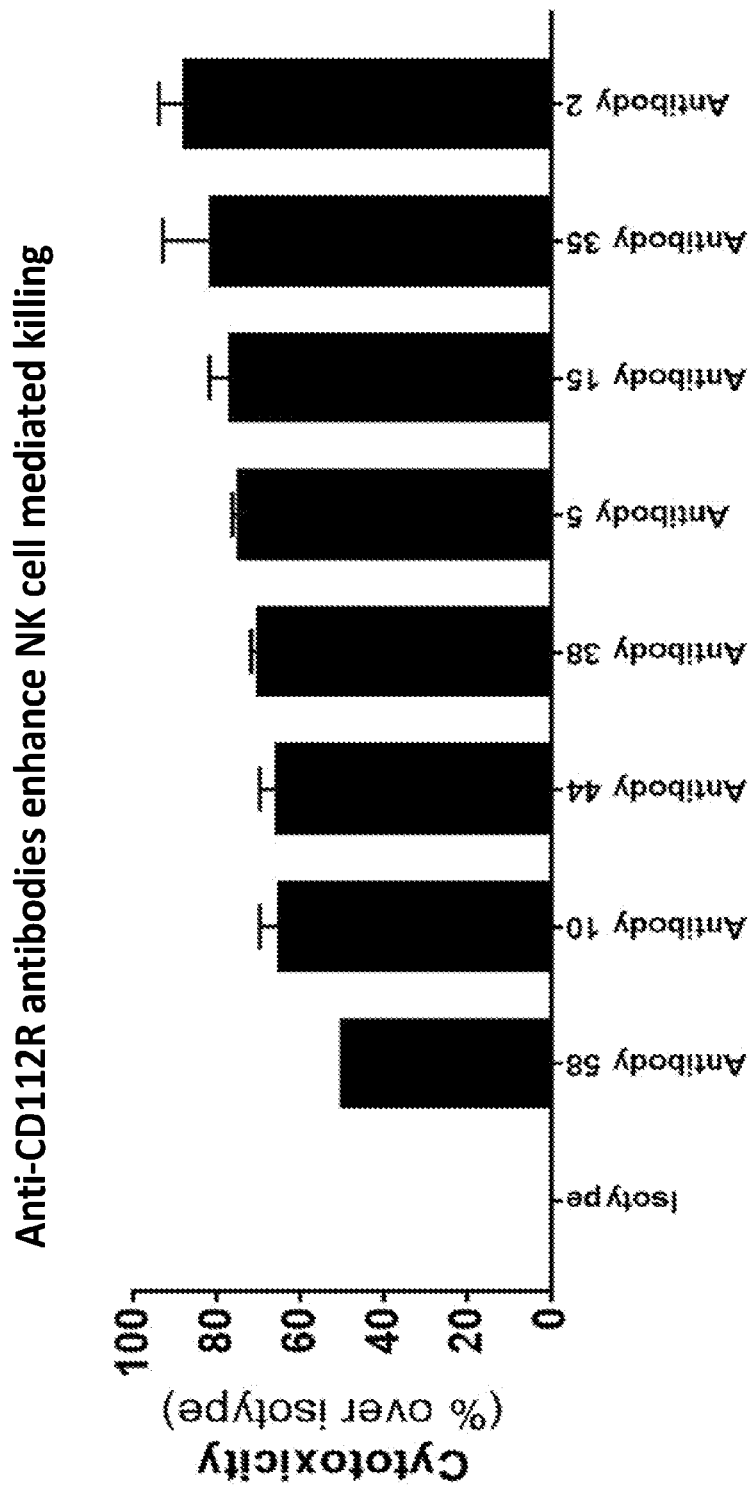
FIG. 3 shows enhanced human NK cell mediated cytotoxicity against REH cells (human leukemia cell line) in the presence of anti-CD112R antibodies as compared to an IgG1 isotype antibody. Activated NK cells and cellTrace violet labeled REH cells were co-cultured for four hours. After co-culture, the viability of REH cells was assessed by staining with 7-AAD. Cytotoxicity (percent over isotype) was calculated as ((test percent dead minus isotype percent dead) divided by isotype percent dead)×100.

Results are presented in FIG. 3. Cytotoxicity (percent-over isotype) was calculated as ((test percent dead minus isotype percent dead) divided by isotype percent dead)×100. Treatment of NK cells with each of the anti-CD112R antibodies described herein resulted in increased cell mediated cytotoxicity against REH cells compared with an isotype control. These results demonstrate that anti-CD112R antibodies enhance NK cell mediated killing.

Example 5. Anti-CD112R Antibodies Enhance Antigen Driven Activation of CD8+ T Cells Antigen Specific CD8+ T Cell Assay.

The effect of Anti-CD112R antibodies on antigen driven activation of CD8+ T cells was assessed. A primary HLA-A*0201 restricted cytomegalovirus (CMV) specific CD8+ T cell line (Astarte Biologics #1049, Lot #3782DE17) was incubated with peptide pulsed Colo205 cells (Colon Adenocarcinoma cell line, ATCC #CCL-222) in the presence of anti-CD112R antibody or isotype control.

Briefly, CMV specific T cells were thawed, washed and resuspended in X-VIVO 10 (ThermoFisher #BW04380Q). $2 \times 10^4$ CMV T cells were added to each well of a 96-well round bottom plate and rested for 4 hours at 37° C. After the initial rest period, $5 \times 10^4$ Colo 205 cells and CMV pp65 peptide (1 ng/mL) (Anaspec #AS-63937) were added to each well. Next, anti-CD112R and isotype antibodies were diluted in X-VIVO 10 and added to each well at a final concentration of 10 µg/mL. Each condition was run in duplicate. Plates were then incubated for 16 hours at 37° C. Supernatants from each well were harvested and subjected to one freeze/thaw cycle prior to cytokine evaluation. After thawing, assay supernatants were diluted 1:5 in X-VIVO 10 and interferon gamma (IFNg) was then measured in the assay supernatant by Luminex Human CD8+ T cell magnetic bead panel multiplex assay (Millipore Sigma #HCD8MAG-15K) and run on a Millipore FlexMap 3D.

Figure 4:
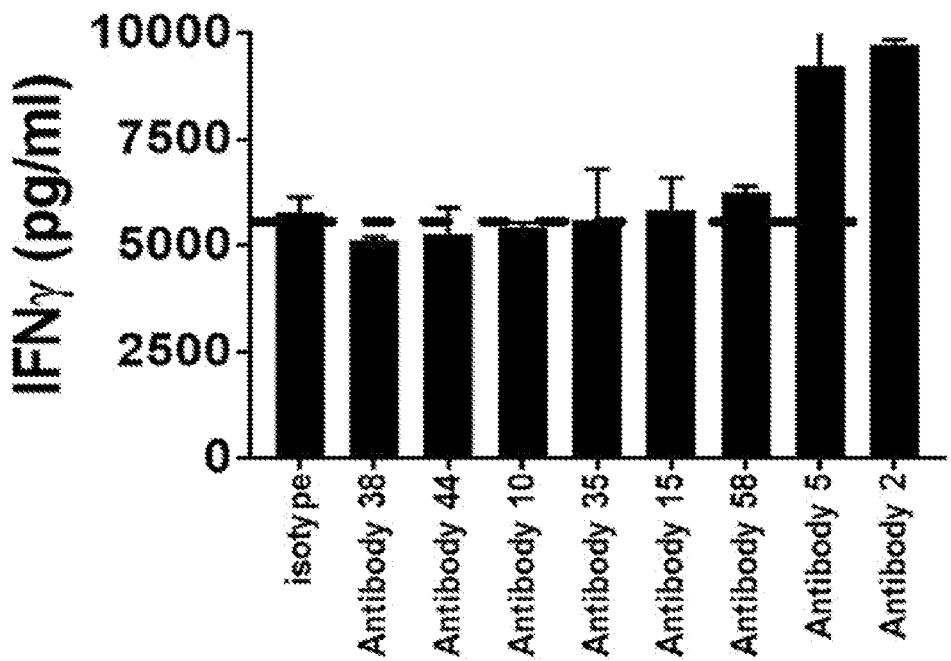
FIG. 4 shows enhanced antigen driven activation of CD8+ T cells, as measured by IFNγ secretion, in the presence of anti-CD112R antibodies, as compared to an IgG1 isotype control antibody. Colo205 cells were pulsed with pp65 peptide and co-cultured with human CMV specific T cells in the presence of anti-CD112R antibody or an IgG1 isotype control. IFNγ levels in the supernatants of cultured cells was measured by Luminex. CD8+ T cells treated with anti-CD112R antibodies 2 and 5 resulted in greater IFNγ secretion than observed with isotype control.

Results are presented in FIG. 4. Test condition IFNg levels were quantitated based on a standard curve generated with defined IFNg concentrations. CD8+ T cells treated with anti-CD112R antibodies 2 and 5 resulted in greater IFNg secretion than observed with isotype control. These results demonstrate that anti-CD112R antibodies enhance antigen driven CD8+ T cell activation.

Example 6. Combination of Anti-Mouse CD112R and Anti-Mouse TIGIT Antibodies has Therapeutic Effect in the Mouse CT-26 Tumor Model In Vivo Efficacy of CD112R and Tigit Combination Blockade Efficacy of CD112R and TIGIT blockade as single and combination agents was tested in a CT26 colon adenocarcinoma syngeneic mouse tumor model. Balb/c female mice of 7 weeks of age (Charles River Laboratories, #028) were implanted subcutaneously with $0.1 \times 10^6$ CT26.WT cells (ATCC #CRL-2638) in 0.1 mL 50% matrigel inoculation matrix. Mice were randomized into groups of 10 mice each (total of 40 mice) in a stratified manner at tumor volume range of 80-120 mm$^3$ and treated twice weekly for two weeks by intraperitoneal injection as in Table 3.

TABLE 3

Treatment group details

| Group | Treatment 1 | | Treatment 2 | |
| --- | --- | --- | --- | --- |
| | Antibody | Dose (µg/mouse) | Antibody | Dose (µg/mouse) |
| Isotype | Isotype 1 | 500 | Isotype 2 | 500 |
| CD112R | Isotype 1 | 500 | Anti-CD112R | 500 |
| TIGIT | Anti-TIGIT | 500 | Isotype 2 | 500 |
| CD112R + TIGIT | Anti-CD112R | 500 | Anti-TIGIT | 500 |

Tumor volumes were measured every 2-3 days until tumors reached IACUC limit size (<2000 mm$^3$).

TABLE 4

Antibody details

| Group | Clone |
| --- | --- |
| Isotype 1 | Clone C1.18.4, Mouse IgG2a Isotype Control |
| Isotype 2 | Polyclonal Human IgG Isotype control |
| Anti-Tigit | 10A7, mouse IgG2a |
| Anti-CD112R | Anti-CD112R human IgG4 |

Figure 5:
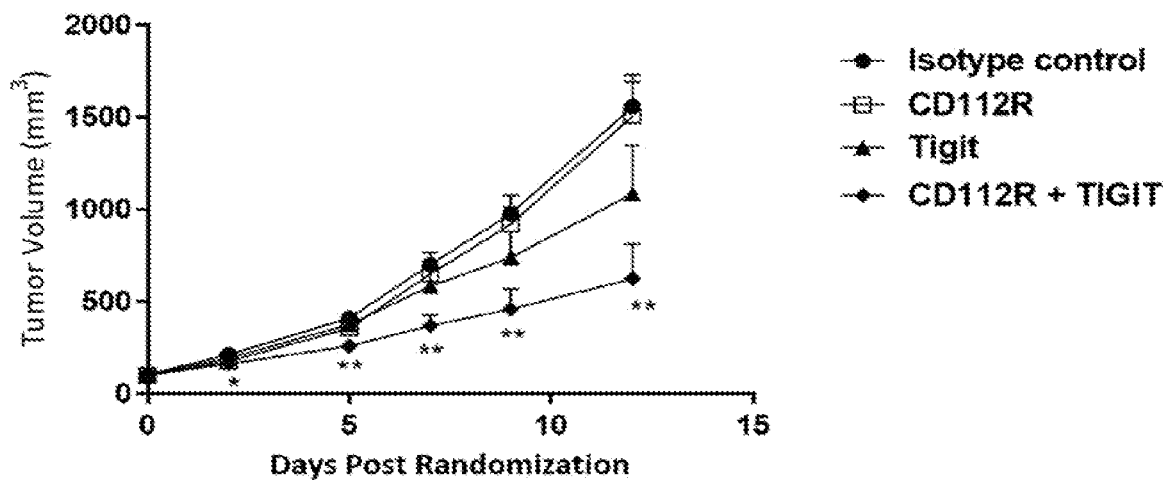
FIG. 5 is a graph depicting that a combination of murine anti-CD112R and murine anti-TIGIT antibodies has therapeutic effect in the mouse syngeneic CT-26 tumor model. Tumor-bearing mice were randomized into four groups and treated twice weekly for two weeks, by IP injection, with 1) isotype control antibody; 2) anti-TIGIT antibody; 3) anti-CD112R antibody; or 4) anti-TIGIT antibody combined with anti-CD112R antibody. Mean tumor volumes for each treatment group are depicted as a function of time. The results demonstrate that the combination of anti-CD112R with anti-TIGIT was effective at reducing tumor growth compared to isotype treated animals while anti-CD112R or anti-TIGIT monotherapies showed either no activity or only a modest effect on reducing tumor growth.

Results are presented in FIG. 5. Graph depicts mean tumor volumes for each treatment group as a function of time. The results demonstrate that the combination of anti-CD112R with anti-TIGIT was effective at reducing tumor growth compared to isotype treated animals while anti-CD112R or anti-TIGIT monotherapies showed either no activity or only a modest effect on reducing tumor growth. While anti-CD112R alone did not show activity in this assay, other experiments presented herein show benefit of anti-CD112R monotherapy. See, for example, FIG. 9.

Example 7. Increased Expression of CD112R in PBMC Following Anti-CD3 Activation CD112R is Upregulated in Activated PBMCs In Vitro To determine the effect of cellular activation on CD112R expression, human PBMCs were stimulated in vitro with anti-CD3 antibody. Peripheral blood mononuclear cells (PBMCs) from healthy donors were isolated from buffy coats (Research Blood Components). Individual buffy coats were processed separately. 15 mL of buffy coat was added to each 50 mL conical tubes (Corning #430290) and diluted with 15 mL PBS (Thermofisher #14190144)+2 mM EDTA (Fisher Scientific #BP2482-500) for a total volume of 30 mL each tube. Diluted buffy coats were underlain with 14 mL of Ficolpaque (GE Healthcare Life Science #17-544203) and centrifuged at 2000 RPM for 20 minutes at room temperature with the brake turned off. Gradient interphase was collected and washed twice with PBS +2 mM EDTA. Isolated cells were counted and resupended at 2.5–5×10$^7$ cell/mL in 10% DMSO (Sigma-Aldrich #472301)+90% heat-inactivated FBS (ThermoFisher #16140-071).

Frozen PBMCs were thawed quickly and resuspended in supplemented RPMI media, which contained RPMI+GlutaMax (1×) (ThermoFisher #61870-036), 10% heat-inactivated FBS, 1×MEM Non-essential amino acids solution (ThermoFisher #15140-122), 1 mM Sodium Pyruvate (ThermoFisher #11360070), 100 U/mL Pen/Strep (ThermoFisher #15140-122), 1×2-mercaptoethanol (ThermoFisher #21985023), 10 mM Hepes (ThermoFisher #15630-080). Isolated PBMCs were washed, counted and resuspended at concentration 0.5×10$^6$ cells/mL. 1×10$^6$ cells per well were placed in a 24-well flat-bottom plate (Corning #3526) and stimulated with 0.25 µg/mL of anti-CD3 antibody (clone UCHT1, Biolegend #300414). Cells were collected at the indicated time-points, washed in FACS buffer containing 1×PBS, 2% FBS and 2 mM EDTA, and transferred onto a 96-well V-bottom plate (Costar #3894) for antibody staining.

Cells were spun down at 1500 RPM for 3 minutes and the supernatant was removed by flicking. Cells were resuspended in FACS Buffer and incubated for 1 hour at 4° C. with primary antibodies in Table 5 as follows:

TABLE 5

| Antibody | Clone | Company |
| --- | --- | --- |
| CD3-A700 | SK7 | Biolegend # 344822 |
| CD8-FITC | RPA-T8 | Biolegend # 301006 |
| CD4-PEcy7 | RPA-T4 | Biolegend # 300511 |
| CD19-PEdazzle | HIB19 | Biolegend # 302251 |
| NKp46-PE | 9E2 | Biolegend # 331907 |
| CD11b-BV785 | ICRF44 | Biolegend # 301345 |
| PD1-BV421 | EH12.1 | Biolegend #565935 |
| CD226-BV711 | DX11 | BD Biosciences # 564796 |
| CD112R | Internal | Internal |
| Human IgG Fc | HP6017 | Biolegend # 409320 |

Cells were washed twice and incubated for 30 minutes at 4° C. with 1:100 diluted Alexa 647-conjugated anti-Human IgG antibody (clone HP6017, Biolegend #409320). Cells were washed once with FACS buffer and stained with 1:500 diluted Live/Dead Aqua viability dye in 1×PBS (Thermofisher #L34966) for 10 minutes at 4° C. Cells were washed once and acquired directly on flow cytometer X-20 Fortessa (BD Biosciences). Data was analyzed using Flowjo (TreeStar) and Graphpad prism (Graphpad Software).

Figure 6:
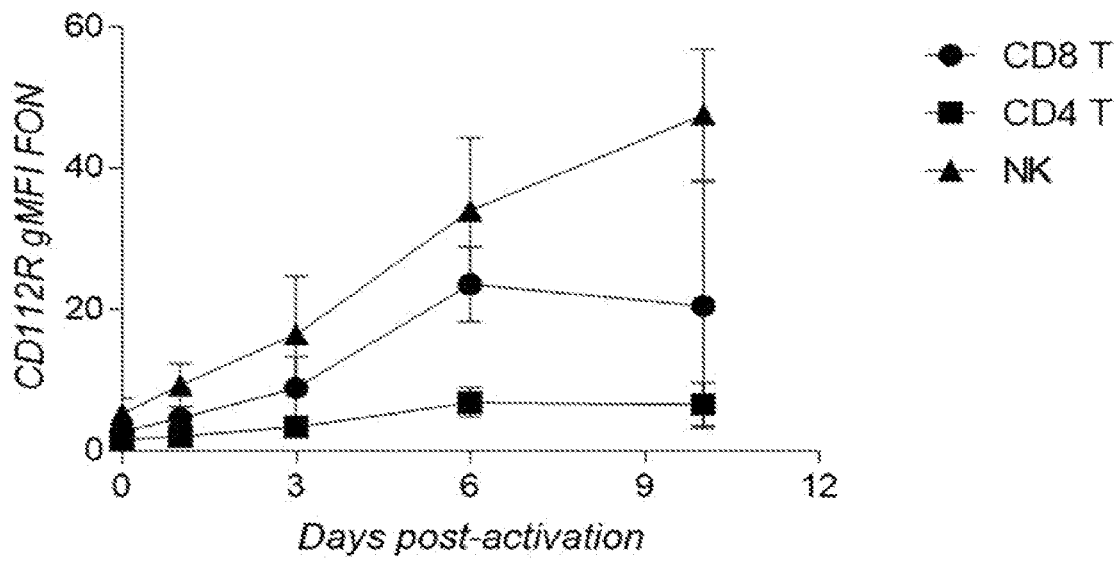
FIG. 6 is a graph depicting increased expression of CD112R in PBMCs following anti-CD3 activation. Human PBMCs were stimulated in vitro with anti-CD3 antibody and CD112R expression was assessed by flow cytometry. Quantitation of CD112R antibody binding was assessed by the geometric mean fluorescent intensity (gMFI) of the Alexa Fluor® 647 antibody label for the indicated cell type. CD112R is depicted as fold change over the negative control (FON, (CD112R gMFI divided by isotype gMFI)).

Results are depicted in FIG. 6. Quantitation of CD112R antibody binding was assessed by the geometric mean fluorescent intensity (gMFI) of the Alexa Fluor® 647 signal for the indicated cell type. Anti-CD112R binding is depicted as fold over negative (FON, (CD112R gMFI divided by isotype gMFI)). These results demonstrate that CD112R expression increases on NK cells and T cells following anti-CD3 activation.

Example 8. Anti-CD112R Antibodies Enhance NK Cell Degranulation in Tumor Cell CoCultures To determine the effect of anti-CD112R antibody on NK cell mediated degranulation, human NK cells were cocultured with Raji target cells (Burkitt lymphoma cell line, ATCC #CCL-86) that had been previously transduced with lentivirus to express CD112 (Origene, #RC213693L2), in the presence of antibodies 35, 38, 44 and isotype control.

Briefly, NK cells were isolated and pooled from the PBMCs of three healthy donors via negative selection (Easysep™ NK cell isolation kit, Stemcell #17955) and cultured for 16 hours in DMEM+10% FBS+1% Penicillin-Streptomycyin (D10) (ThermoFisher). Following overnight incubation at 37° C., NK cells were washed and resuspended in D10. Raji.CD112 cells were harvested, washed and then resuspended in D10. 1×10$^5$NK cells and 5×10$^4$ Raji.CD112 cells were added to each well of a 96-well flat bottom plate for an effector-target cell ratio of 2:1. Anti-CD112R antibodies and an IgG1 isotype control antibody were diluted in D10 and added to each well at starting concentration of 10

µg/mL, with 10-fold serial dilutions. Each condition was run in duplicate. PE anti-CD107a antibody (Biolegend, #328608) and Monensin (Biolegend, #420701) were also added to each well at the manufacturer's indicated concentrations. The final volume for each well was 200 µl. The plates were then incubated for 4 hours at 37° C. After 4 hours, Anti-CD3 FITC (Biolegend, #300306) and Anti-NKp46 APC (Biolegend #331914) antibodies were diluted in D10 and 50 µl was added to each well. The plates were then incubated for an additional 30 minutes at 4° C. to stain. Cells were then transferred to V bottom plates and washed twice and resuspended in PBS +2% FBS. Data was acquired using a LSRFortessa X-20 (BD Biosciences) flow cytometer and analyzed with FlowJo software (Tree Star). NK degranulation was defined as the frequency of CD107e cells within the CD3$^-$ NKp46$^+$ lymphocyte gate.

Figure 7:
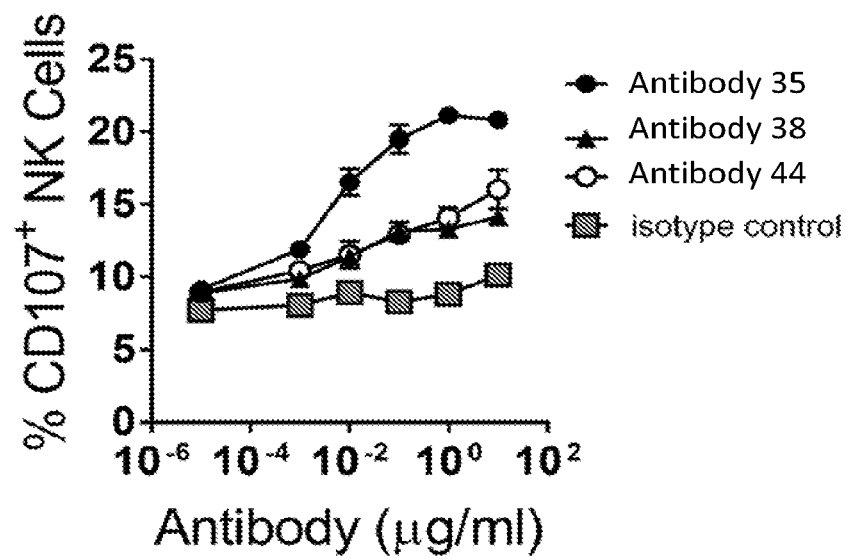
FIG. 7 shows enhanced NK cell mediated degranulation in response to tumor cells in the presence of CD112R antibodies with an IgG1 isotype. Human NK cells and Raji.CD112 cells were co-cultured for four hours with CD107a PE antibody in the presence of CD112R antibodies. After co-culture, NK cell degranulation was determined by frequency of NK cells that were CD107a positive.

Results are presented in FIG. 7. Treatment of NK cells with anti-CD112R antibodies described herein resulted in increased NK degranulation, as measured by CD107a staining, compared with an isotype control.

Example 9. Anti-CD112R Antibodies Increase NK Cell Activation in PBMC Tumor Cell Cocultures To assess the impact of CD112R antibodies on NK cell activation, several antibodies were evaluated in PBMC-tumor cell cocultures. Upregulation of CD137 (4-1BB), which has been previously established as a marker of NK cell activation (Baessler et al. (2010) Blood 115(15); André et al. (2018) Cell 175, 1731-1743) was measured on the NK cells from PBMCs cocultured with K562 target cells (chronic myelogenous leukemia cell line, ATCC #CCL-243) with anti-CD112R or isotype control antibodies.

Figure 8A:
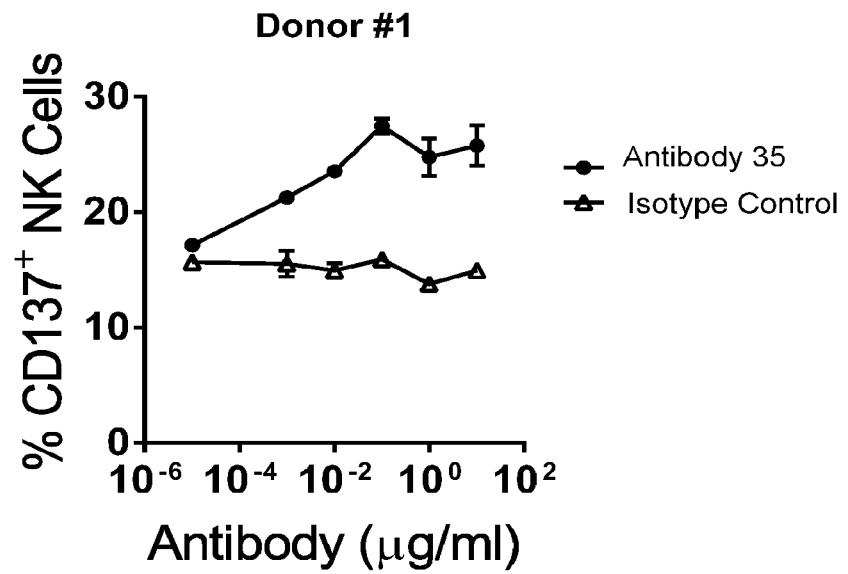
FIG. 8A-8D show enhanced NK cell activation in the presence of a CD112R antibody with an IgG1 isotype. Human PBMCs from 2 different donors and K562 cells were co-cultured for 16 hours in the presence of a CD112R antibody. After co-culture, NK cell activation was determined by the frequency of NK cells that were CD137 positive. The results for donor 1 and donor 2 in two independent assays are shown in FIGS. 8A-8D, respectively.
Figure 8B:
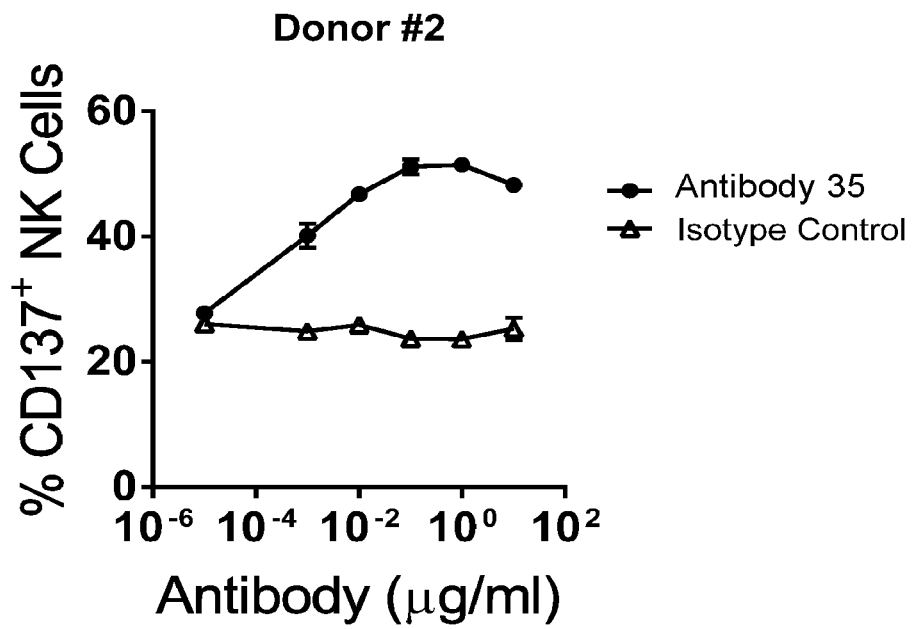
Figure 8C:
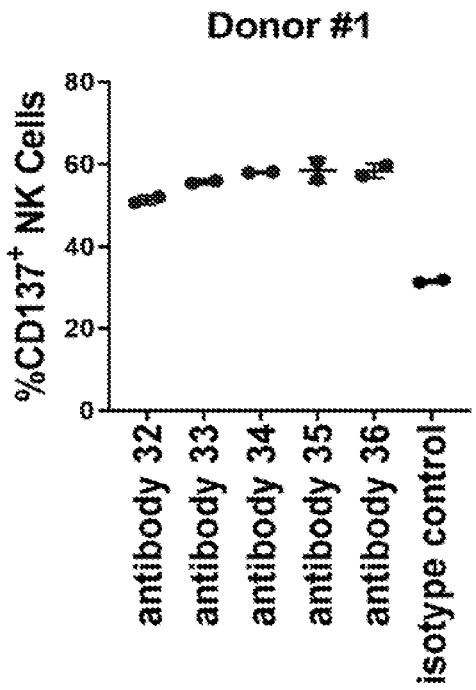
Figure 8D:
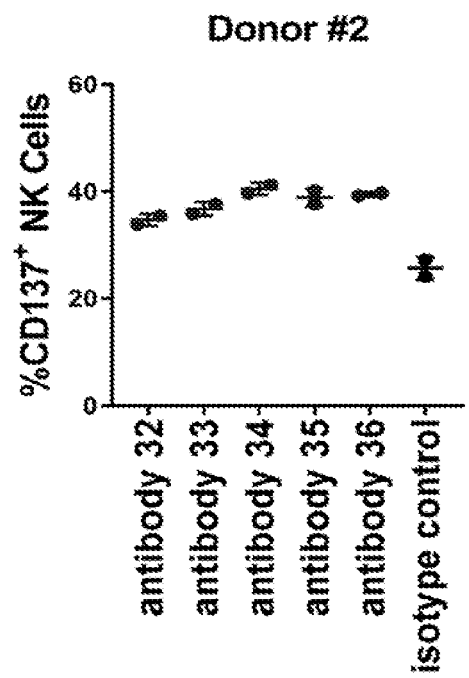

Briefly, frozen PBMCs isolated from the buffy coats of healthy donors were thawed, washed, resuspended in DMEM+10% FBS+1% Penicillin-Streptomycyin (D10) and plated into 96 well flat bottom plates at a concentration of $5 \times 10^5$ cells per well and rested for 4 hours at 37° C. prior to adding target cells and antibodies. Next, in a first experiment (FIG. 8A-8B) CD112R antibodies and an IgG1 isotype control antibody were diluted in D10 and added to each well at starting concentration of 10 µg/mL, with 10-fold serial dilutions. In a next experiment (FIG. 8C-8D) a single concentration (1 µg/mL) of anti-CD112R or IgG1 isotype control antibody was added to each well. For both experiments, each condition was run in duplicate. K562 cells were then harvested, washed and resuspended in D 10 and added to each well at a concentration of $5 \times 10^4$ cells per well. The final volume for each well was 200 µl. The plates were then incubated for 16 hours at 37° C. After 16 hours, cells were then transferred to V bottom plates and washed twice in PBS +2% FBS. Cells were stained with Anti-CD3 FITC (Biolegend, #300306), Anti-NKp46 BV421 (Biolegend #331914) and anti-CD137 APC (Biolegend, #309810) in PBS +2% FBS for 30 minutes at 4° C. Cells were subsequently washed twice and resuspended in PBS +2% FBS. Data was acquired using a LSRFortessa X-20 (BD Biosciences) flow cytometer and analyzed with FlowJo software (Tree Star). NK cell activation was defined as the frequency of CD137+ cells within the CD3− NKp46+ lymphocyte gate.

Results from two individual donors from two independent experiments are presented in FIG. 8A-8D. The addition of anti-CD112R antibody to PBMC-K562 cell cocultures resulted in significant activation of NK cells compared to isotype control, as measured by CD137 upregulation on NK cells.

Example 10. Anti-CD112R Decreases Tumor Growth in CT-26 Model

In vivo efficacy of CD112R blockade was evaluated in the CT26.WT colon adenocarcinoma syngeneic mouse tumor model. BALB/cAnNTac female mice of 7 weeks of age (Taconic Biosciences, Catalog #BALB-F) were implanted subcutaneously in the right flank with $0.2 \times 10^6$ CT26.WT (ATCC, Catalog #CRL-2638) in 0.1 mL 50% Geltrex (GIBCO, catalog #A1432-02) and 50% RPMI-1640 serum-free media (GIBCO, catalog #A10491-01). Mice with palpable tumors were randomized on day 4 post-implantation and treated intraperitoneally twice weekly for three weeks starting on the day of randomization as follows in Table 6.

TABLE 6

| Group | Treatment | Dose (µg/mouse) |
| --- | --- | --- |
| Isotype control | Mouse IgG2a isotype control | 500 |
| Antibody 46 | Anti-CD112R mouse IgG2a | 500 |

Tumor volumes were measured with a caliper every 2-3 days until tumors reached IACUC limit size (<2000 mm$^3$). Tumor volume (mm$^3$) was calculated as follows: width (mm)×[length (mm)]2×0.5.

Figure 9:
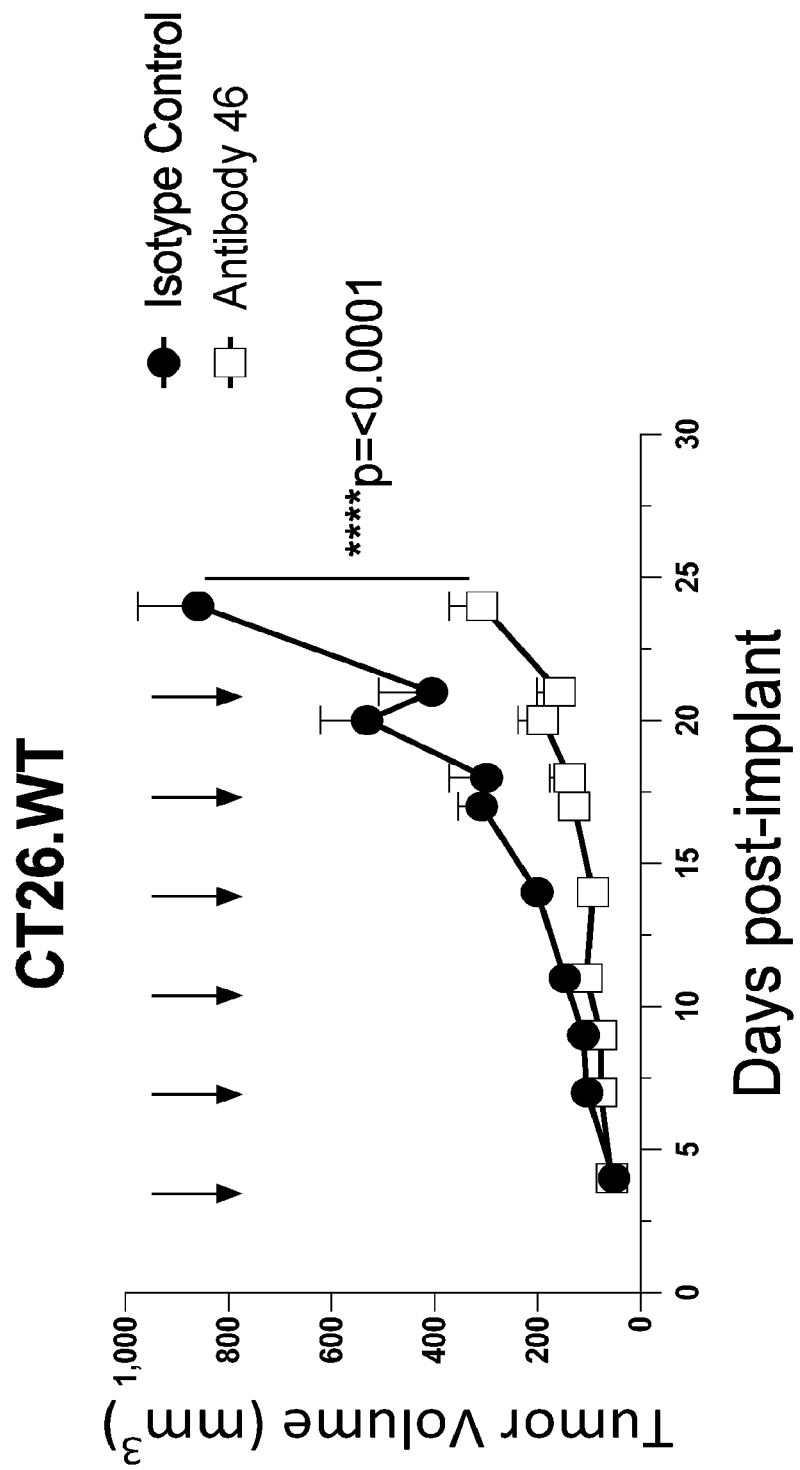
FIG. 9 shows tumor growth inhibition in mice treated with an anti-CD112R antibody. The figure shows a summary of 3 experiments, N=44-45 per group. Statistical analysis was performed by Mann-Whitney test on day 24 post implant.

Results are presented in FIG. 9. The graph depicts pooled data from three independent experiments showing mean tumor volumes for each treatment group as a function of time. These results demonstrate that the treatment of tumor bearing mice with CD112R antibody resulted in significant inhibition of tumor growth as measured on day 24 post-inoculation.

Example 11. CD112R Blockade Results in Anti-Tumor Immunity in Mice with Complete Tumor Rejection in the CT26 Model Anti-tumor immunity was evaluated in anti-CD112R treated mice that exhibited complete responses from primary CT26.WT tumor challenges. For the primary challenge, BALB/cAnNTac female mice of 7 weeks of age (Taconic Biosciences, Catalog #BALB-F) were implanted subcutaneously in the right flank with $0.2 \times 10^6$ CT26.WT (ATCC, Catalog #CRL-2638) in 0.1 mL 50% Geltrex (GIBCO, catalog #A1432-02) and 50% RPMI-1640 serum-free media (GIBCO, catalog #A10491-01). Mice with palpable tumors were randomized on day 4 post-implantation and treated intraperitoneally twice weekly for three weeks starting on the day of randomization as follows in Table 7.

TABLE 7

| Group | Treatment | Dose (µg/mouse) |
| --- | --- | --- |
| Isotype control | Mouse IgG2a isotype control | 500 |
| Antibody 46 | Anti-CD112R mouse IgG2a | 500 |

Tumor volumes were measured with a caliper every 2-3 days until tumors reached IACUC limit size (<2000 mm$^3$). Tumor volume (mm$^3$) was calculated as follows: width (mm)×[length (mm)]2×0.5.

All Surviving mice at day 50 post implantation that lacked any discernable tumors were considered to be survivors/complete responders. Complete responder mice (n=8) from the anti-CD112R treated group were re-challenged via inoculation in the left flank with 1×10⁶ CT26.WT cells (ATCC, Catalog #CRL-2638) in 0.1 mL 50% Geltrex (GIBCO, catalog #A1432-02) and 50% RPMI-1640 serum-free media (GIBCO, catalog #A10491-01), a five-fold increase from the primary inoculation dose. As a control, age-matched naïve Balb/c female mice (n=5) were also similarly inoculated in the left flank with 1×10⁶ CT26.WT cells in 0.1 mL 50% Geltrex and 50% RPMI-1640 serum-free media. Mice did not receive any further treatment. Tumor volumes were measured every 2-3 days until tumors reached IACUC limit size (<2000 mm³). Tumor volume (mm3) was calculated as follows: width (mm)×[length (mm)]2×0.5.

Figure 10A:
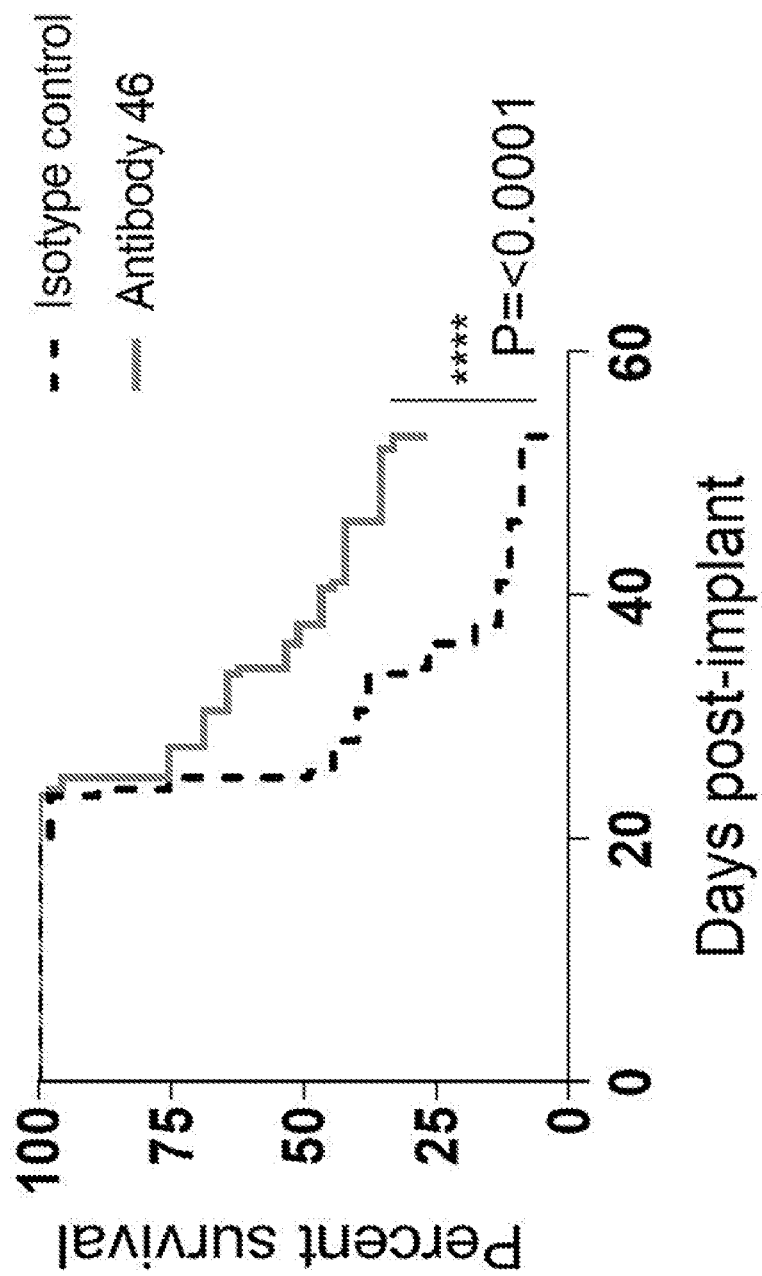
FIG. 10A-10B show that treatment with anti-CD112R antibody increases the overall survival of mice inoculated with CT-26 tumors and protects mice from tumor rechallenge.
Figure 10B:
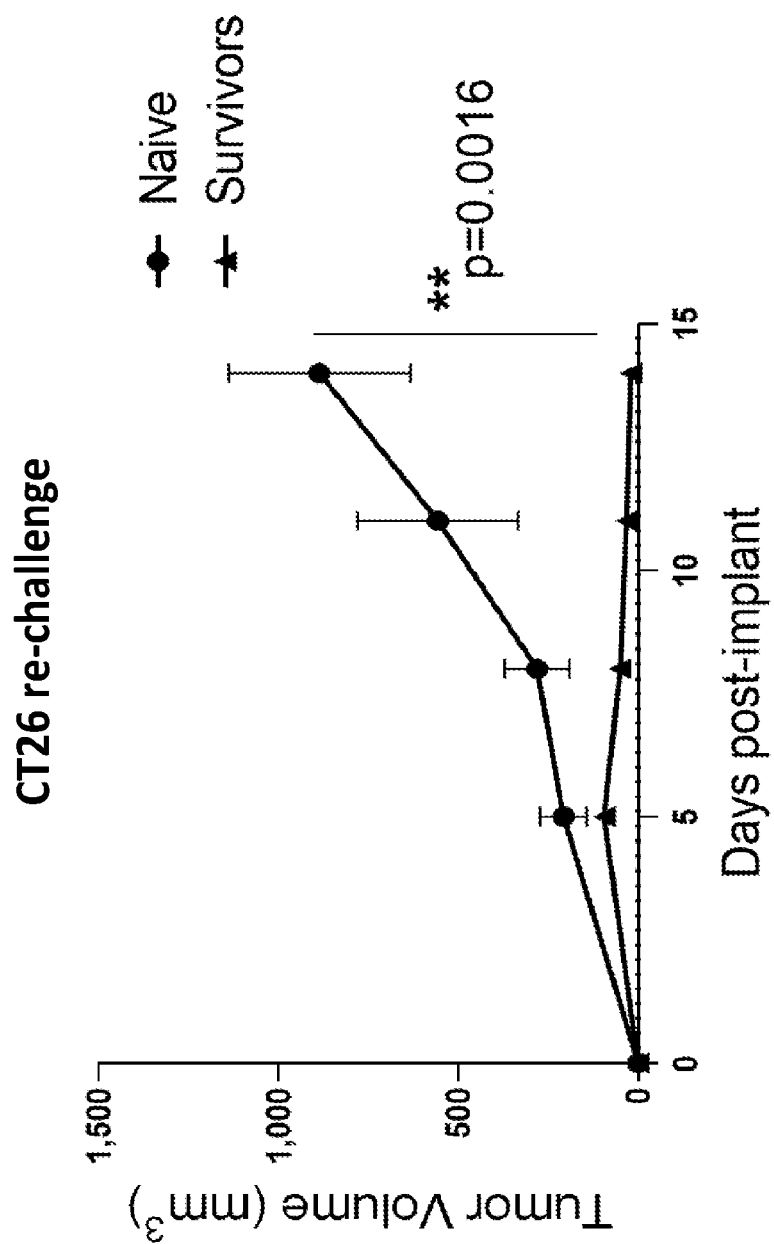

Results are presented in FIG. 10A-10B. FIG. 10A depicts pooled data from 3 independent experiments showing the survival frequency of mice implanted with CT26 primary tumors treated with anti-CD112R. FIG. 11B depicts mean tumor volumes for anti-CD112R treated complete responders following tumor re-challanged and naïve challenged controls as a function of time. Statistical analysis was performed by Mantel-Cox test on day 50 post implant (FIG. 10A) and by Mann-Whitney test on day 15 post implant (FIG. 10B). These results demonstrate that mice treated with anti-CD112R exhibited complete responses following primary tumor challenge and the subsequent rapid rejection upon tumor re-challenge in these mice also demonstrate that treatment with anti-CD112R antibody leads to the development of immunological memory and protective immunity.

Example 12. Both NK Cells and CD8 T Cells Contribute to Therapeutic Activity of Anti-CD112R in CT26 Tumor Challenge In vivo efficacy of CD112R blockade was evaluated in the CT26 syngeneic mouse tumor model following NK cell or CD8 T cell depletion. To deplete NK and CD8 T cells, mice were treated twice weekly for three weeks starting at randomization with Asialo-GM1 antibody ("asGM1" in FIG. 11; Biolegend; cat #146002; dose 100 uL/mouse; intraperitoneally) and anti-CD8a antibody (Bioxcell; cat #BE0085; 200 μg/mouse; intraperitoneally) respectively.

BALB/cAnNTac female mice of 7 weeks of age (Taconic Biosciences, Catalog #BALB-F) were implanted subcutaneously in the right flank with 0.2×10⁶ CT26.WT (ATCC, Catalog #CRL-2638) in 0.1 mL 50% Geltrex (GIBCO, catalog #A1432-02) and 50% RPMI-1640 serum-free media (GIBCO, catalog #A10491-01). Mice with palpable tumors were randomized on day 4 post-implantation and treated intraperitoneally twice weekly for three weeks starting on the day of randomization with antibody 46 (anti-CD112R mouse IgG2a; 12.5 mg/kg; intraperitoneally).

Tumor volumes were measured with a caliper every 2-3 days until tumors reached IACUC limit size (<2000 mm³). Tumor volume (mm³) was calculated as follows: width (mm)×[length (mm)]²×0.5.

Figure 11:
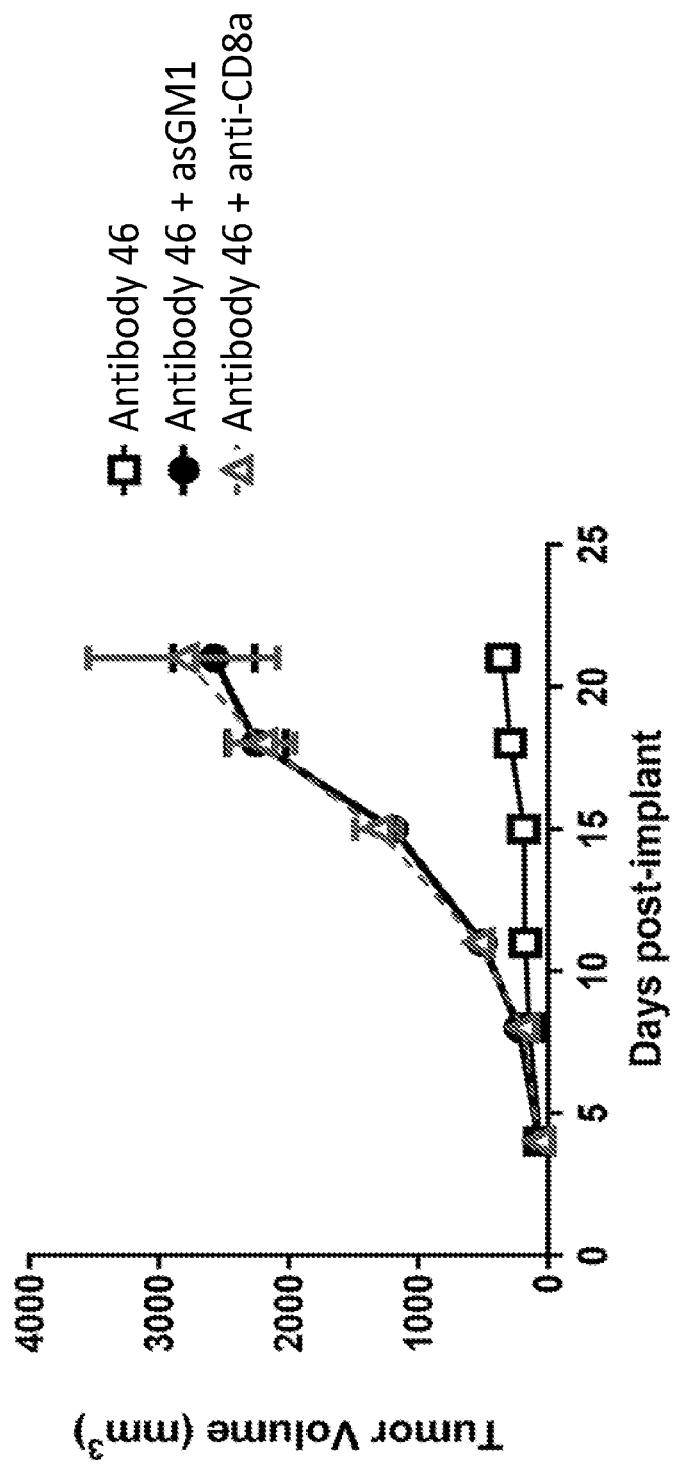
FIG. 11 shows the in vivo efficacy of CD112R blockade in a CT26 mouse tumor model is dependent on NK cells and CD8 T cells. The figure shows tumor growth inhibition of anti-CD112R treated mice simultaneously depleted of either NK cells or CD8 T cells.

Results are presented in FIG. 11. The graph depicts mean tumor volumes for each treatment group as a function of time. These results demonstrate that the therapeutic effect of anti-CD112R is significantly diminished following NK cell or CD8 T cell depletion. These results indicate that both CD8 T cells and NK cells are required for effective tumor growth inhibition mediated by anti-CD112R.

Example 13. CD112R Blockade Activates Tumor NK Cells In Vivo

Ex Vivo Assessment of NK Activation Markers after Dosing with Anti-CD112R Monotherapy.

To determine the effects of anti-CD112R antibody on NK cell activation in vivo, BALB/cAnNTac female mice of 7 weeks of age (Taconic Biosciences, Catalog #BALB-F) were implanted subcutaneously in the right flank with 0.2× 10⁶ CT26.WT (ATCC, Catalog #CRL-2638) in 0.1 mL 50% Geltrex (GIBCO, catalog #A1432-02). Mice with palpable tumors were randomized on day 4 post-implantation and administered with 500 μg of either isotype control antibody (clone C1.18.4, BioXcell, cat #0085) or antibody 46 (anti-CD112R mouse IgG2a). Both groups were also co-administered with 500 μg of an isotype control (clone MOPC-21, Bioxcell, cat #0083). Treatments were prepared in sterile 1×PBS (GIBCO cat #14190-136) and a total volume of 100 μL was injected intraperitoneally.

Tumor processing: Mice were euthanized and tumors were resected 24 hours post-treatment. Tumor were processed into single-cell suspensions by breaking tissue over a 440-micron mesh filter (Costar #3480) placed over a 50 mL centrifuge tube (Falcon #352350) using the rough end of a 3 mL syringe plunger (BD 301077) in FACS buffer (1×PBS, 2% heat-inactivated FBS, GIBCO cat #16140-071; 2 mM EDTA, Fisher Bioreagents, cat #BP2482-500). Dislodged tumors were filtered once more over a 70 micron strainer (Falcon cat #352350) and any remaining tissue was further broken down using a 3 mL syringe plunger. Cell were spun at 800 g for 10 minutes. Cell pellets were resuspended in FACS buffer.

Ex vivo re-stimulation: Roughly half of the single-cell suspension was transferred into a 96-well U-bottom polypropylene 2 mL deep plates (Thermofisher #AB-0932) and centrifuged at 1000 g for 5 minutes at 4° C. Cells were resuspended in pre-warmed 1×RPMI+Glutamax (GIBCO #61870-035) medium with 10% heat-inactivated FBS, containing 20 ng/mL PMA (Abcam #ab120297), 500 ng/mL Ionomycin Ca²⁺ salt (Abcam #ab120116), 5 μg/mL Brefeldin A (Biolegend #420601) and 2 μM Monensin (Biolegend #420701). Cells were incubated for 3.5 hours at 37° C., 5% CO₂. Cells were centrifuged again as described above.

Surface antigen antibody staining for FACS: Cell pellets were washed once with 500 μL of cold FACS buffer. Cells were resuspended in 100 μL of FACS buffer with TruStain fcX™ (anti-mouse CD16/32, at dilution indicated in Table 8. Cells were incubated on ice for 15 minutes. Surface antibody cocktail was prepared (see Table 8 for details) and added directly to pre-blocked cells. Cells were incubated for 1 hour on ice. Cells were then washed twice with 500 μL of FACS buffer.

Viability dyes staining: Cells stained with Live/Dead Aqua viability dye diluted 1:500 in 1×PBS (Thermofisher #L34966) for 10 minutes at 4° C.

Fixation: Cells were washed once and fixed with 200 μL of eBioscience Foxp3 Fixative/permeabilization buffer (Thermofisher #00-5523-00, using manufacturer's protocol for dilution guidelines) overnight at 4° C.

Intracellular antigen antibody staining for FACS: Cells were permeabilized by adding directly 200 μL of 1× eBioscience permeabilization buffer (see manufacturer's protocol for dilution guidelines). Cells were centrifuged at 1000 g for 5 minutes and stained with intracellular panel of antibodies at final dilution in 1× eBioscience permeabilization buffer. Cells were incubated for 1 hour at room temperature. Cells were washed twice with 500 μL of permeabilization buffer, resuspended in 150 μL of FACS buffer.

Cells were acquired on X-20 Fortessa flow cytometer (BD Biosciences). Data was analyzed using Flowjo (Flowjo, LLC) and Graphpad prism (Graphpad Software).

TABLE 8

Antibodies used in FIG. 12 A-B.

| Fluorophore | Antibody | Clone | Company | Catalog # | Dilution | Type of stain |
|---|---|---|---|---|---|---|
| N/A | FcBlock | 93 | Biolegend | 101320 | 1:100 | Fc block |
| Alexa700 | CD45 | I3/2.3 | Biolegend | 147716 | 1:100 | Surface |
| PEDazzle | NKp46 | 29A1.4 | Biolegend | 137630 | 1:100 | Surface |
| APC/Fire ™ | TCRbeta | H57-597 | Biolegend | 109246 | 1:100 | Surface |
| BV785 | CD69 | H1.2F3 | Biolegend | 101243 | 1:100 | Surface |
| BV510 | Live/Dead | | Thermofisher | L34966 | 1:500 | Viability |
| APC | Gzmb | NGZB | Thermofisher | 17-8898-82 | 1:100 | Intracellular |

Results are depicted in FIG. 12A-B. FIG. 12A shows the frequency of tumor infiltrating NK cells expressing CD69. FIG. 12B shows the frequency of tumor infiltrating NK cells expressing Granzyme B following ex vivo restimulation. NK cells were gated as follows: $CD45^|$, $CD45^|$ $SSC\text{-}A^{Low}$, Live, Singlets, $NKp46^|$ $TCRb^-$ population. Positive gate was set based on negative controls fluorescence-minus one (FMO). P-value was derived using unpaired t-test (*, $p<0.05$; , $p<0.01$; *, $p<0.001$). These results demonstrate that CD112R blockade significantly increases expression of the early activation marker CD69 and the cytotoxic granule protein, granzyme B, in intratumoral NK cells in CT-26 tumor model.

Example 14. Combination of Anti-CD112R and Anti-PD1 Antibodies has Therapeutic Effect and Increased Tumor-Free Survival in the Mouse CT-26 Tumor Model In Vivo Efficacy of CD112R and PD-1 Combination Blockade Efficacy of CD112R and PD-1 blockade as a monotherapy and as a combination therapy was tested in CT-26 colon adenocarcinoma syngeneic tumor model. BALB/cAnNTac female mice of 6 weeks of age (Taconic Biosciences, Balb-F) were implanted subcutaneously in the right flank with $0.2 \times 10^6$ CT26.WT (ATCC, Catalog #CRL-2638) in 0.1 mL 50% Geltrex (GIBCO, catalog #A1432-02) and 50% RPMI-1640 serum-free media (GIBCO, catalog #A10491-01). Mice were randomized into groups of 10 mice each with mean tumor volume of 90 mm$^3$ using the matched distribution randomization method. Mice were treated twice weekly for two weeks by intraperitoneal injection as in Table 9. Details about treatment agents are included in Table 10.

TABLE 9

Treatment group details

| | Treatment 1 | | Treatment 2 | |
|---|---|---|---|---|
| Group | Antibody | Dose (mg/kg) | Antibody | Dose (mg/kg) |
| Isotype | Isotype 1 | 12.5 | Isotype 2 | 10 |
| CD112R | Anti-CD112R | 12.5 | Isotype 2 | 10 |
| PD-1 | Isotype 1 | 12.5 | Anti-PD-1 | 10 |
| CD 112R + PD-1 | Anti-CD112R | 12.5 | Anti-PD-1 | 10 |

TABLE 10

Antibody details

| Group | Clone |
|---|---|
| Isotype 1 | Isotype Control Clone C1.18.4, Mouse IgG2a |
| Isotype 2 | Isotype Control Clone 2A3, Rat IgG2a |
| Anti-CD112R | Antibody 46, Mouse IgG2a |
| Anti-PD-1 | RMP1-14, Rat IgG2a |

Tumor volumes were measured twice weekly until tumors reached IACUC limit size (<2000 mm3). Tumor volume (mm3) was calculated as follows: width (mm)×[length (mm)]2×0.52.

Figure 13A:
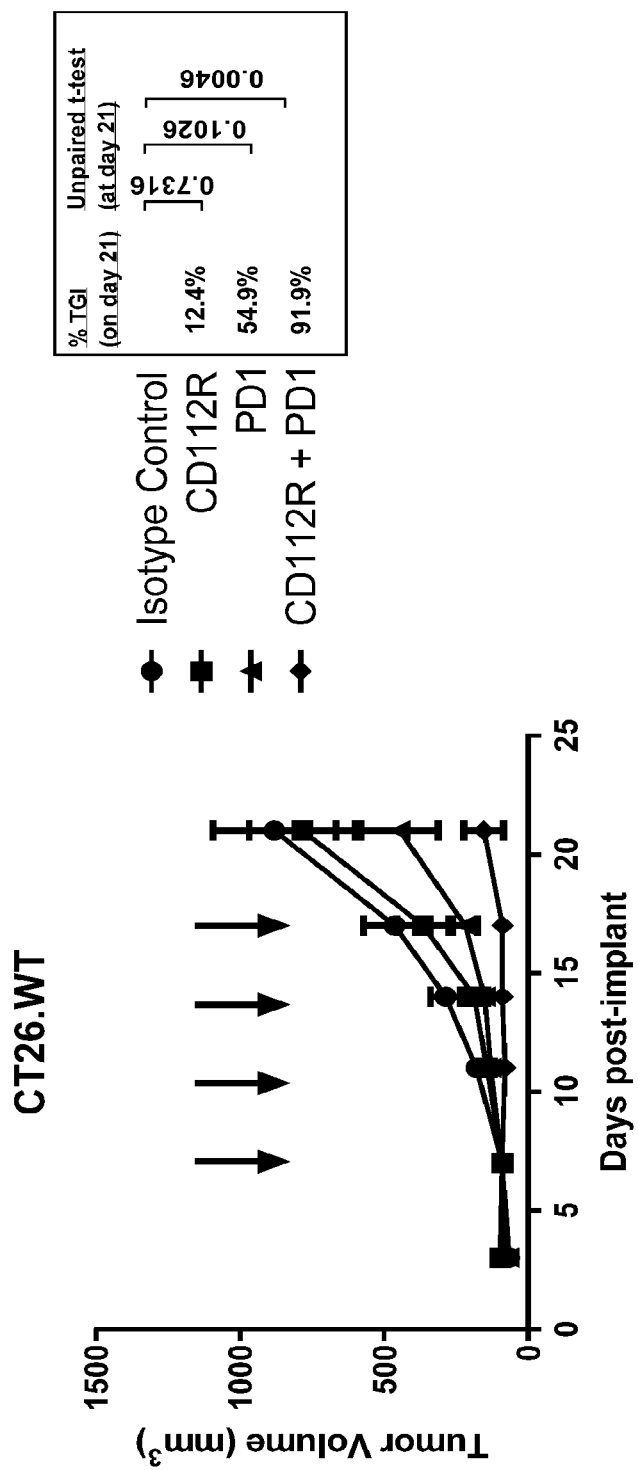
Figure 13C:
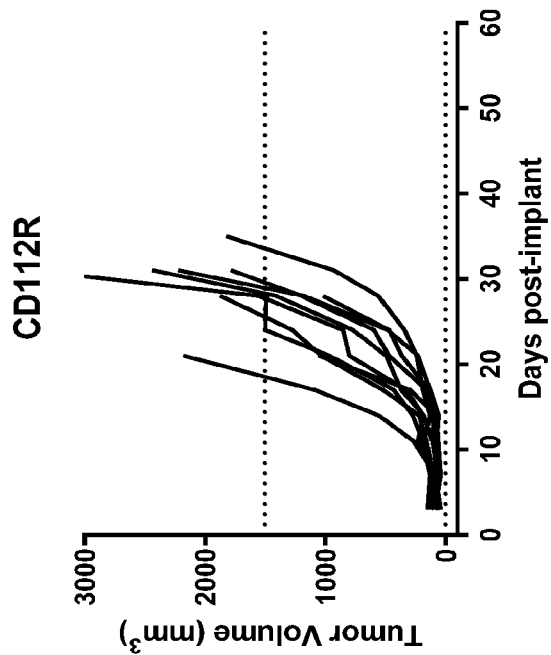
Figure 13B:
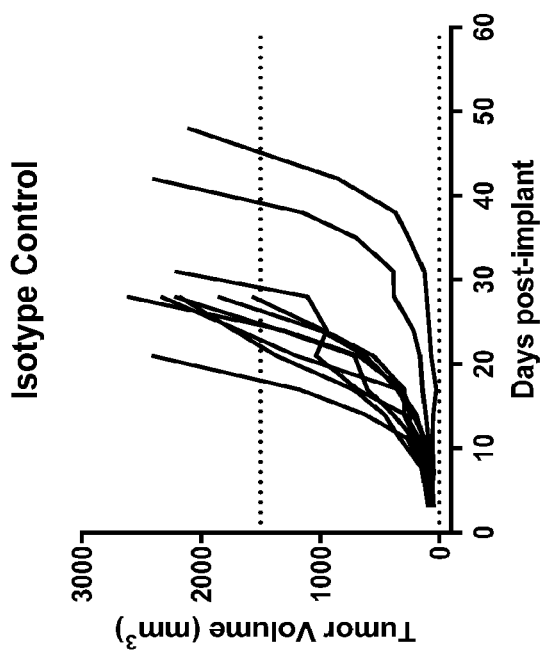
Figure 13E:
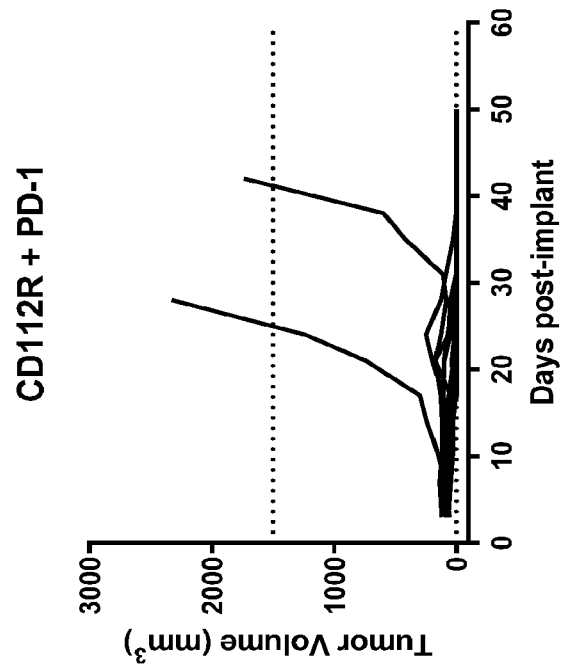
Figure 13D:
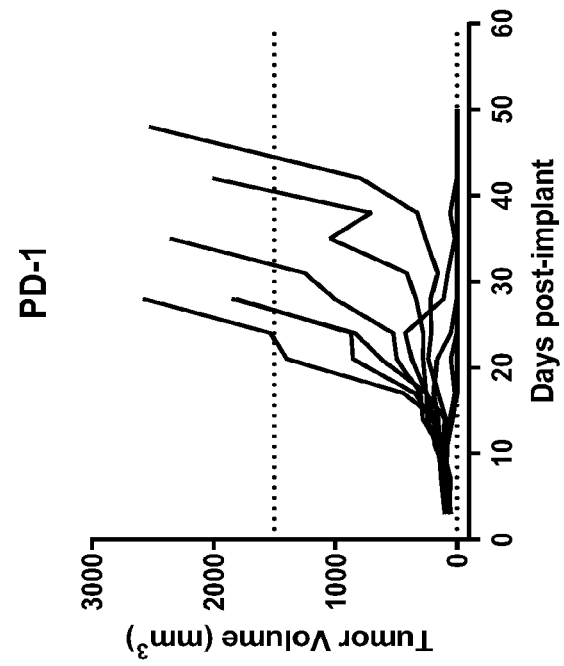

Results are presented in FIG. 13A-F. FIGS. 13A-E depict mean and individual tumor volume measurements respectively for each treatment group as a function of time. The results shown in FIG. 13A demonstrate that the combination of anti-CD112R with anti-PD-1 was effective and statistically significant (as measured on day 21 by unpaired t-test) at reducing tumor growth compared to isotype treated animals. Anti-CD112R or anti-PD-1 monotherapies also showed activity in reducing tumor growth. FIG. 13F depicts overall tumor-free survival on day 50 post-implantation indicated as fraction of tumor-free survivors per group after treatment as described above. These results demonstrate that the combination of anti-CD112R with anti-PD-1 confers higher tumor-free survival rate than isotype control or either monotherapeutic agent.

Example 15. Binding of Anti-CD112R Antibodies to Cells Expressing Murine CD112R

The ability of anti-CD112R antibodies to bind to mouse CD112R was evaluated on cells overexpressing mouse CD112R. $0.8 \times 10^5$ 293 T cells (ATCC CRL-3216) that were engineered to overexpress mouse CD112R (293T.mCD112R) were added to each well of a 96-well V bottom plate and stained with either anti-CD112R antibodies or an IgG1 isotype control at a starting concentration of 10 μg/mL, with 3-fold serial dilutions for 30 minutes at 4° C. Cells were washed twice with PBS +2% FCS and resuspended with Alexa Fluor® 647 anti-human IgG Fc antibody (Biolegend, Cat #409320) diluted 1:100 in PBS +2% FCS and incubated at 4° C. for 20 minutes. Cells were subsequently washed twice and resuspended in PBS +2% FCS. Cellular data was acquired using a LSRFortessa X-20 (BD Biosciences) and analyzed with FlowJo software (Tree Star).

Figure 17:
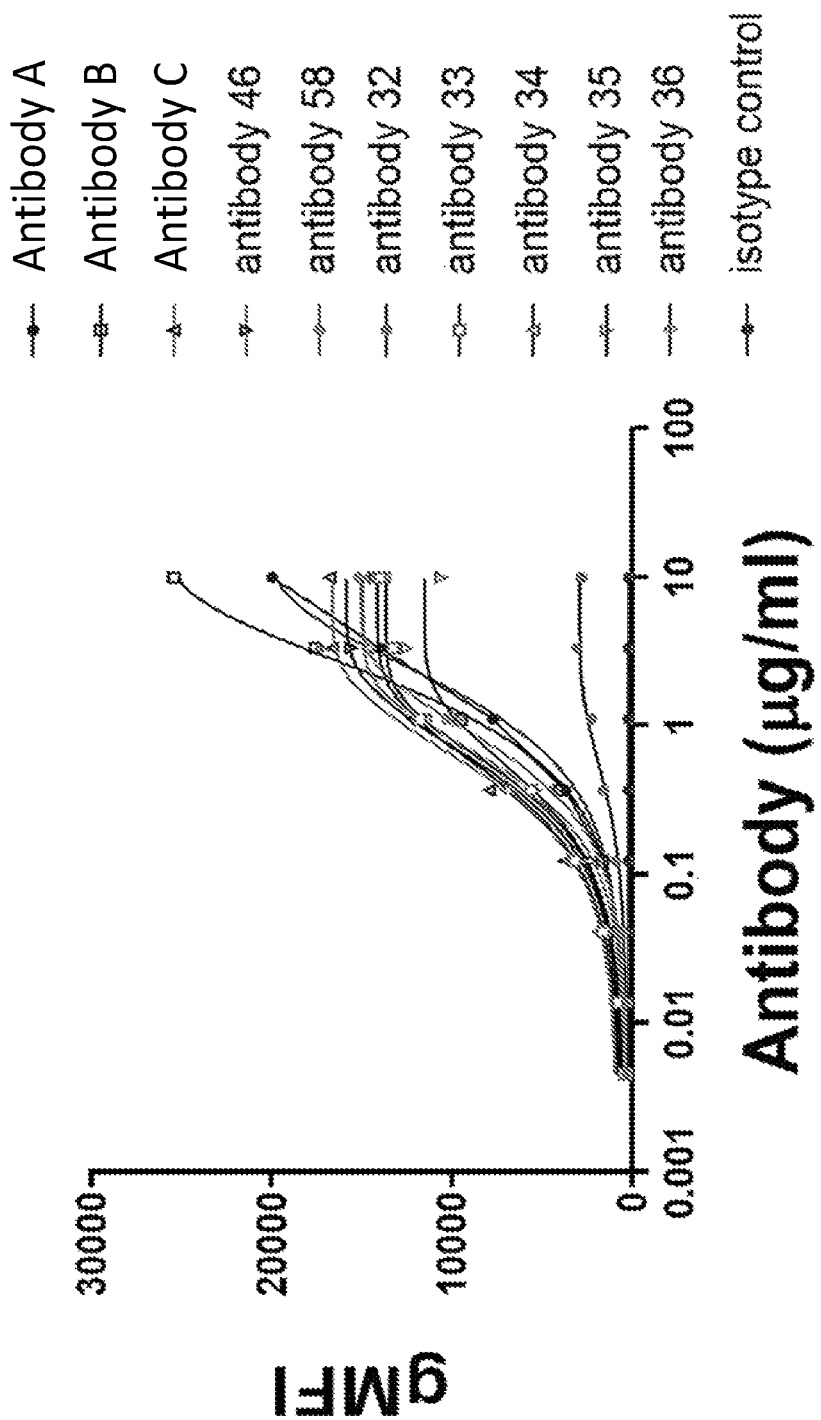
FIG. 17 shows extent of binding of anti-CD112R antibodies described herein and additional anti-CD112R antibodies (antibodies A, B, and C that bind human CD112R) to cells expressing mouse CD112R.

Results are depicted in FIG. 17 and Table 11. Quantitation of antibody binding to 293T.mCD112R cells was assessed by the geometric mean fluorescent intensity (gMFI) of the Alexa Fluor® 647 signal. These results demonstrate that several anti-CD112R antibodies bound to cells that expressed mouse CD112R.

Example 16. Binding of Anti-CD112R Antibodies to Soluble Murine CD112R

The ability of anti-CD112R antibodies to bind to soluble mouse CD112R was evaluated by ELISA. Briefly, 96 well Nunc Maxisorp plates were coated with 1 μg/mL of anti-CD112R antibodies or isotype control (Biolegend, Cat #403502) in PBS overnight at 4° C. Plates were then washed 6× with PBS +0.01% Tween-20 (PBST) and subsequently blocked with 200 μL of PBS +1% BSA for 1.5 hours at room temperature. After blocking, plates were washed 6× with PBST. Next, 100 μL of a mouse CD112R-hIgG4 fusion protein in PBS +1% BSA was added at a final starting concentration of 10 μg/mL, with 4-fold serial dilutions. Plates were incubated at room temperature for 1.5 hours. Next plates were washed 6× with PBST and then incubated with anti-IgG$_4$ HRP (Thermo Fisher, Cat #MA1-33437) in 100 μL for 1 hour at room temperature. Plates were then washed 6× with PBST and developed with TMB substrate (Life Technologies, Cat #002023). The reaction was stopped with an equal volume of stop solution (Life Technologies, Cat #SS04). Absorbance at 450 nm (O.D. 450) was measured on a SpectraMax plate reader.

Figure 18:
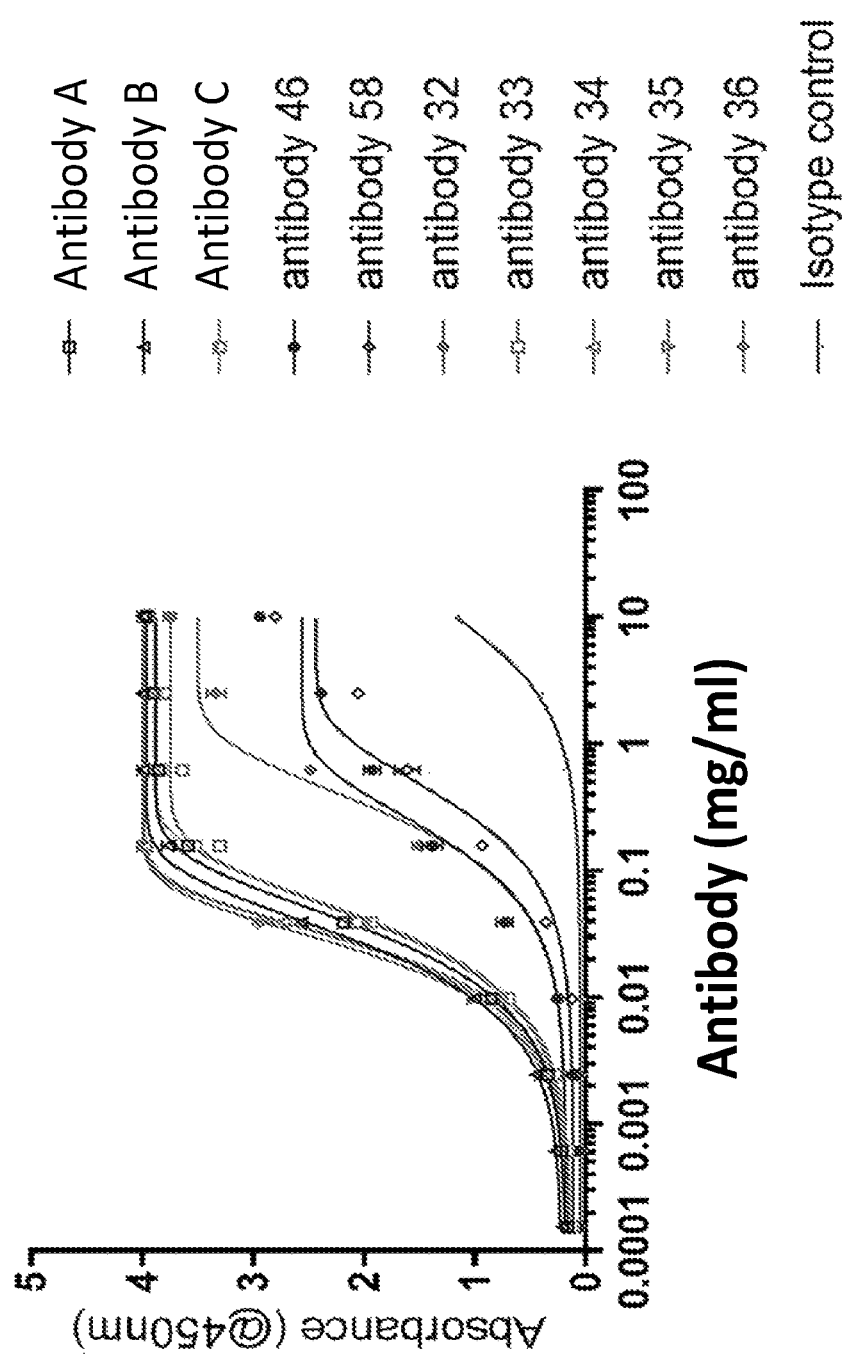
FIG. 18 shows extent of binding of anti-CD112R antibodies described herein and additional anti-CD112R antibodies (antibodies A, B, and C that bind human CD112R) to soluble mouse CD112R.

Results are depicted in FIG. 18 and Table 11. These results demonstrate that anti-CD112R antibodies bound to soluble mouse CD112R.

Example 17. Inhibition or Blocking of Murine CD112R Binding to CD112

The ability of species cross reactive anti-CD112R antibodies to block mouse CD112R binding to mouse CD112 was evaluated by ELISA. Briefly, 96 well Nunc Maxisorp plates were coated with 1 μg/mL of mouse CD112 (Sino Biological, Cat #50318-M08H) in PBS overnight at 4° C. Plates were then washed 6× with PBS +0.01% Tween-20 (PBST) and subsequently blocked with 200 μL of PBS +1% BSA for 1.5 hours at room temperature. After blocking, plates were washed 6× with PBST. Next, 50 μL of anti-CD112R antibodies or isotype control (Biolegend, Cat #403502) in PBS +1% BSA were added at a final starting concentration of 40 μg/mL, with 2-fold serial dilutions. 50 μL of a mouse CD112R-hIgG4 fusion protein was also added to each well at a final concentration of 2 μg/mL. Plates were incubated at room temperature for 1.5 hours. Next plates were washed 6× with PBST and then incubated with anti-IgG4 HRP (Thermo Fisher, Cat #MA1-33437) in 100 μL for 1 hour at room temperature. Plates were then washed 6× with PBST and developed with TMB substrate (Life Technologies, Cat #002023). The reaction was stopped with an equal volume of stop solution (Life Technologies, Cat #SS04). Absorbance at 450 nm (O.D. 450) was measured on a SpectraMax plate reader.

Figure 19:
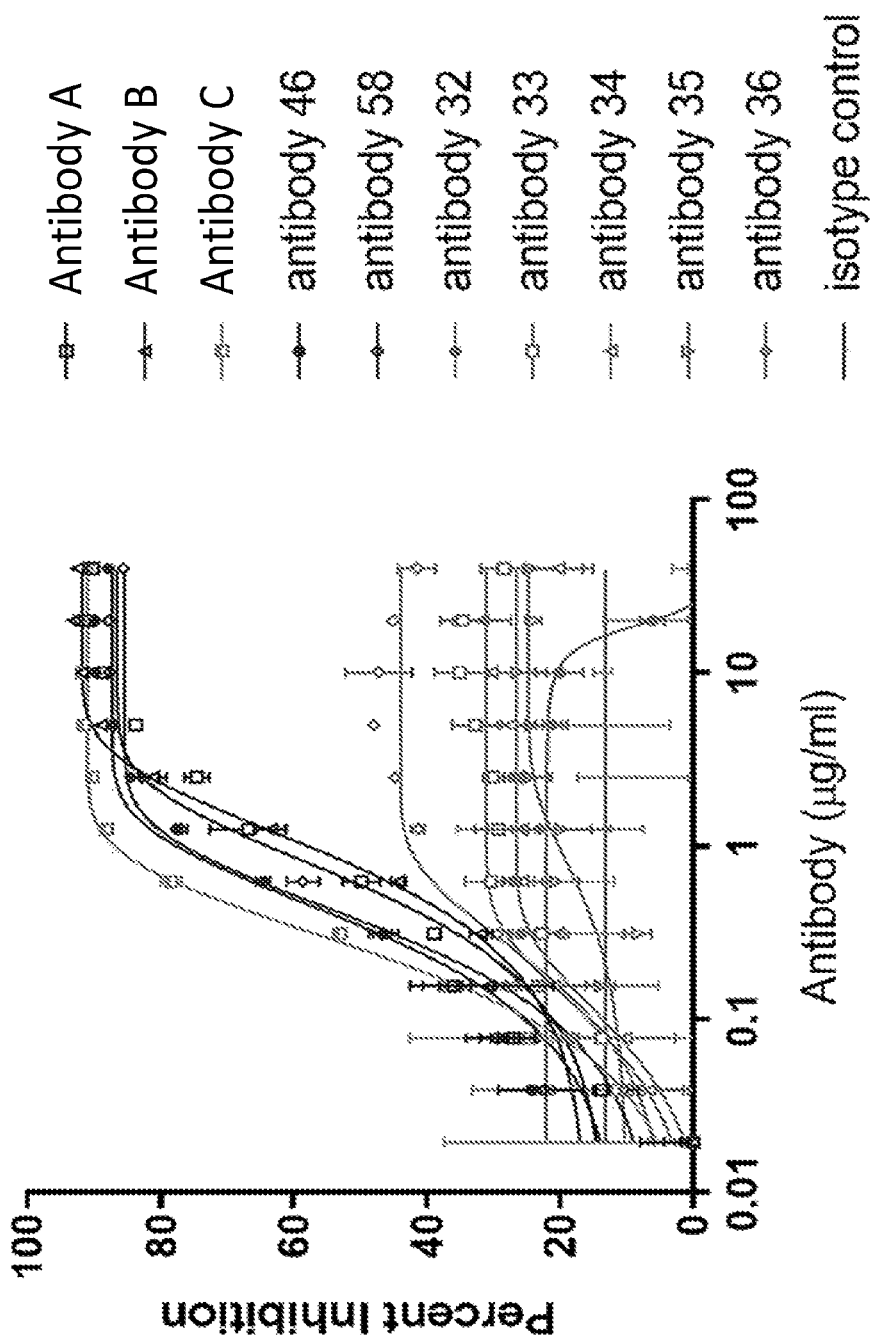
FIG. 19 shows percent inhibition of the interaction between mouse CD11R and mouse CD112 by anti-CD112R antibodies described herein and additional anti-CD112R antibodies (antibodies A, B, and C that bind human CD112R).

Results are depicted in FIG. 19 and Table 11. These results demonstrate that anti-CD112R antibodies inhibited mouse CD112R binding to mouse CD112 to varying degrees. Percent inhibition was calculated as [100−((test sample O.D. 450/Max O.D. 450)*100%)] Max O.D. 450 was defined as absorbance at 450 nm in the absence of antibody.

As shown in Table 11 and FIGS. 17-19, antibodies 32, 33, 34, 35 and 36 are capable of blocking the interaction of human CD112 to human CD112R, but according to the definition of blocking described herein, not capable of blocking the binding interaction between mouse CD112R and mouse CD112. See, e.g., the last two columns of Table 11 for antibodies 32, 33, 34, 35 and 36, showing % inhibition of the mouse interaction at 0, 28.3, 20.3, 24.2, and 41.6, respectively, as compared to the % inhibition of the human interaction at 75.1, 78.8, 80, 81.7, and 86.2, respectively. Antibodies not belonging to the exemplary class of antibodies related to antibody 32 do not exhibit such differential blocking.

TABLE 11

Summary of Antibody Binding and Blocking Antibody Details (mouse)

| Antibody | 293T-mouse CD112R gMFI (fold increase over isotype) | Mouse CD112R Binding ELISA EC50 (ng/ml) | mouse CD112/CD112R blocking ELISA max inhbition (%) | human CD112/CD112R blocking ELISA max inhibition (%) |
|---|---|---|---|---|
| Antibody A | 104.6 | 34.5 | 90.3 | 90.6 |
| Antibody B | 133.3 | 27.4 | 92.5 | 88.9 |
| Antibody C | 88.1 | 41.0 | 90.1 | 97.8 |
| Antibody 32 | 14.9 | 269.5 | 0.0 | 75.1 |
| Antibody 33 | 73.3 | 38.3 | 28.3 | 78.8 |
| Antibody 34 | 72.2 | 24.2 | 20.3 | 80.0 |
| Antibody 35 | 55.6 | 21.5 | 24.2 | 81.7 |
| Antibody 36 | 76.3 | 25.1 | 41.6 | 86.2 |
| Antibody 46 | 74.8 | 180.6 | 88.0 | 97.6 |
| Antibody 58 | 79.4 | 411.7 | 85.7 | 97.3 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Clone No | Description | Sequence |
|---|---|---|---|
| 1 | 2 | VH CDR1 | FTFSEYTMN |
| 2 | 2 | VH CDR2 | AIVGSGDSTYYADSVKG |
| 3 | 2 | VH CDR3 | AKDYSSGDWIDYGMDV |
| 4 | 2 | VL CDR1 | QASQDISNYLN |
| 5 | 2 | VL CDR2 | DASNLAT |

Table of Sequences

| SEQ ID NO | Clone No | Description | Sequence |
|---|---|---|---|
| 6 | 2 | VL CDR3 | QQFDLLPPT |
| 7 | 2 | VH FR1 | EVQLVESGGGLVKPGGSLRLSCAASG |
| 8 | 2 | VH FR2 | WVRQAPGKGLEWVS |
| 9 | 2 | VH FR3 | RFTISRDNSKNTLYLQMNSLRAEDTAVYYC |
| 10 | 2 | VH FR4 | WGQGTTVTVSS |
| 11 | 2 | VH DNA | GAGGTGCAGCTGGTGGAGTCTGGGGGAGGCCTGGTCAAGCCTG<br>GGGGGTCCCTGAGACTCTCCTGTGCAGCCTCTGGATTCACCTTC<br>AGTGAATATACCATGAACTGGGTCCGCCAGGCTCCAGGGAAGG<br>GGCTGGAGTGGGTCTCAGCTATTGTAGGTAGTGGTGACAGCAC<br>ATACTACGCAGACTCCGTGAAGGGCCGGTTCACCATCTCCAGA<br>GACAATTCCAAGAACACGCTGTATCTGCAAATGAACAGCCTGA<br>GAGCCGAGGACACGGCGGTGTACTACTGCGCCAAGGACTACAG<br>CTCCGGAGACTGGATCGATTATGGAATGGACGTATGGGGCCAG<br>GGAACAACTGTCACCGTCTCCTCA |
| 12 | 2 | VH Protein | EVQLVESGGGLVKPGGSLRLSCAASGFTFSEYTMNWVRQAPGKG<br>LEWVSAIVGSGDSTYYADSVKGRFTISRDNSKNTLYLQMNSLRAE<br>DTAVYYCAKDYSSGDWIDYGMDVWGQGTTVTVSS |
| 13 | 2 | VL FR1 | DIQMTQSPSSLSASVGDRVTITC |
| 14 | 2 | VL FR2 | WYQQKPGKAPKLLIY |
| 15 | 2 | VL FR3 | GVPSRFSGSGSGTDFTFTISSLQPEDIATYYC |
| 16 | 2 | VL FR4 | FGGGTKVEIK |
| 17 | 2 | VL DNA | GACATCCAGATGACCCAGTCTCCATCCTCCCTGTCTGCATCTGT<br>AGGAGACAGAGTCACCATCACTTGCCAGGCGAGTCAGGACATT<br>AGCAACTATTTAAATTGGTATCAGCAGAAACCAGGGAAAGCCC<br>CTAAGCTCCTGATCTACGATGCATCCAATTTGGCAACAGGGGTC<br>CCATCAAGGTTCAGTGGAAGTGGATCTGGGACAGATTTTACTTT<br>CACCATCAGCAGCCTGCAGCCTGAAGATATTGCAACATATTAC<br>TGTCAGCAGTTCGATCTCCTCCCTCCTACTTTTGGCGGAGGGAC<br>CAAGGTTGAGATCAAA |
| 18 | 2 | VL Protein | DIQMTQSPSSLSASVGDRVTITCQASQDISNYLNWYQQKPGKAPK<br>LLIYDASNLATGVPSRFSGSGSGTDFTFTISSLQPEDIATYYCQQFD<br>LLPPTFGGGTKVEIK |
| 19-100: Not used ||||
| 101 | 5 | VH CDR1 | FTFSDYAMI |
| 102 | 5 | VH CDR2 | AISGGGESTYYADSVKG |
| 103 | 5 | VH CDR3 | AKDYSSGDWIDYGMDV |
| 104 | 5 | VL CDR1 | QASQDISNYLN |
| 105 | 5 | VL CDR2 | DASNLAT |
| 106 | 5 | VL CDR3 | QQFDLLPPT |
| 107 | 5 | VH FR1 | EVQLLESGGGLVQPGGSLRLSCAASG |
| 108 | 5 | VH FR2 | WVRQAPGKGLEWVS |
| 109 | 5 | VH FR3 | RFTISRDNSKNTLYLQMNSLRAEDTAVYYC |
| 110 | 5 | VH FR4 | WGQGTTVTVSS |
| 111 | 5 | VH DNA | GAGGTGCAGCTGTTGGAGTCTGGGGGAGGCTTGGTACAGCCTG<br>GGGGGTCCCTGAGACTCTCCTGTGCAGCCTCTGGATTCACCTTT<br>AGCGACTATGCCATGATATGGGTCCGCCAGGCTCCAGGGAAGG<br>GGCTGGAGTGGGTCTCAGCTATTAGTGGTGGAGGTGAAAGCAC<br>ATACTACGCAGACTCCGTGAAGGGCCGGTTCACCATCTCCAGA |

-continued

Table of Sequences

| SEQ ID NO | Clone No | Description | Sequence |
|---|---|---|---|
| | | | GACAATTCCAAGAACACGCTGTATCTGCAAATGAACAGCCTGA GAGCCGAGGACACGGCGGTGTACTACTGCGCCAAGGACTACAG CTCCGGAGACTGGATCGATTATGGAATGGACGTATGGGGCCAG GGAACAACTGTCACCGTCTCCTCA |
| 112 | 5 | VH Protein | EVQLLESGGGLVQPGGSLRLSCAASGFTFSDYAMIWVRQAPGKGL EWVSAISGGGESTYYADSVKGRFTISRDNSKNTLYLQMNSLRAED TAVYYCAKDYSSGDWIDYGMDVWGQGTTVTVSS |
| 113 | 5 | VL FR1 | DIQMTQSPSSLSASVGDRVTITC |
| 114 | 5 | VL FR2 | WYQQKPGKAPKLLIY |
| 115 | 5 | VL FR3 | GVPSRFSGSGSGTDFTFTISSLQPEDIATYYC |
| 116 | 5 | VL FR4 | FGGGTKVEIK |
| 117 | 5 | VL DNA | GACATCCAGATGACCCAGTCTCCATCCTCCCTGTCTGCATCTGT AGGAGACAGAGTCACCATCACTTGCCAGGCGAGTCAGGACATT AGCAACTATTTAAATTGGTATCAGCAGAAACCAGGGAAAGCCC CTAAGCTCCTGATCTACGATGCATCCAATTTGGCAACAGGGGTC CCATCAAGGTTCAGTGGAAGTGGATCTGGGACAGATTTTACTTT CACCATCAGCAGCCTGCAGCCTGAAGATATTGCAACATATTAC TGTCAGCAGTTCGATCTCCTCCCTCCTACTTTTGGCGGAGGGAC CAAGGTTGAGATCAAA |
| 118 | 5 | VL Protein | DIQMTQSPSSLSASVGDRVTITCQASQDISNYLNWYQQKPGKAPK LLIYDASNLATGVPSRFSGSGSGTDFTFTISSLQPEDIATYYCQQFD LLPPTEGGGTKVEIK |
| | | 119-200: Not used | |
| 201 | 44 | VH CDR1 | GTFDNYYIS |
| 202 | 44 | VH CDR2 | GIFPIFGTANYAQKFQG |
| 203 | 44 | VH CDR3 | AREVGHYSGSPYYMDV |
| 204 | 44 | VL CDR1 | RASQSINSWLA |
| 205 | 44 | VL CDR2 | DASSLES |
| 206 | 44 | VL CDR3 | QQVGPYLT |
| 207 | 44 | VH FR1 | QVQLVQSGAEVKKPGSSVKVSCKASG |
| 208 | 44 | VH FR2 | WVRQAPGQGLEWMG |
| 209 | 44 | VH FR3 | RVTITADESTSTAYMELSSLRSEDTAVYYC |
| 210 | 44 | VH FR4 | WGKGTTVTVSS |
| 211 | 44 | VH DNA | CAGGTGCAGCTGGTGCAGTCTGGGGCTGAGGTGAAGAAGCCTG GGTCCTCGGTGAAGGTCTCCTGCAAGGCTTCTGGAGGCACCTTC GACAACTATTACATCAGCTGGGTGCGACAGGCCCCTGGACAAG GGCTTGAGTGGATGGGAGGGATCTTCCCTATCTTCGGTACCGCA AACTACGCACAGAAGTTCCAGGGCAGAGTCACGATTACCGCGG ACGAATCCACGAGCACAGCCTACATGGAGCTGAGCAGCCTGAG ATCTGAGGACACGGCGGTGTACTACTGCGCCAGAGAAGTCGGA CACTACTCCGGCAGCCCATACTACATGGACGTATGGGGCAAGG GTACAACTGTCACCGTCTCCTCA |
| 212 | 44 | VH Protein | QVQLVQSGAEVKKPGSSVKVSCKASGGTFDNYYISWVRQAPGQG LEWMGGIFPIFGTANYAQKFQGRVTITADESTSTAYMELSSLRSED TAVYYCAREVGHYSGSPYYMDVWGKGTTVTVSS |
| 213 | 44 | VL FR1 | DIQMTQSPSTLSASVGDRVTITC |
| 214 | 44 | VL FR2 | WYQQKPGKAPKLLIS |
| 215 | 44 | VL FR3 | GVPSRFSGSGSGTEFTLTTSSLQPDDFATYYC |
| 216 | 44 | VL FR4 | FGGGTKVEIK |

Table of Sequences

| SEQ ID NO | Clone No | Description | Sequence |
|---|---|---|---|
| 217 | 44 | VL DNA | GACATCCAGATGACCCAGTCTCCTTCCACCCTGTCTGCATCTGT AGGAGACAGAGTCACCATCACTTGCCGGGCCAGTCAGAGTATT AATAGCTGGTTGGCCTGGTATCAGCAGAAACCAGGGAAAGCCC CTAAGCTCCTGATCTCCGATGCCTCCAGTTTGGAAAGTGGGGTC CCATCAAGGTTCAGCGGCAGTGGATCTGGGACAGAATTCACTC TCACCATCAGCAGCCTGCAGCCTGATGATTTTGCAACTTATTAC TGCCAGCAGGTCGGCCCCTACCTCACTTTTGGCGGAGGGACCA AGGTTGAGATCAAA |
| 218 | 44 | VL Protein | DIQMTQSPSTLSASVGDRVTITCRASQSINSWLAWYQQKPGKAPK LLISDASSLESGVPSRFSGSGSGTEFTLTISSLQPDDFATYYCQQVG PYLTFGGGTKVEIK |
| | | 219-300: Not used | |
| 301 | 58 | VH CDR1 | FTFGDYAMS |
| 302 | 58 | VH CDR2 | FIGSKFYGGETEYTASVKG |
| 303 | 58 | VH CDR3 | ARGPRRYTYGMDV |
| 304 | 58 | VL CDR1 | RASQSISSYLN |
| 305 | 58 | VL CDR2 | AASSLQS |
| 306 | 58 | VL CDR3 | QQSSTPLT |
| 307 | 58 | VH FR1 | EVQLVESGGGLVQPGRSLRLSCTASG |
| 308 | 58 | VH FR2 | WFRQAPGKGLEWVG |
| 309 | 58 | VH FR3 | RFTISRDGSKSIAYLQMNSLKTEDTAVYYC |
| 310 | 58 | VH FR4 | WGQGTTVTVSS |
| 311 | 58 | VH DNA | GAGGTGCAGCTGGTGGAGTCTGGGGGAGGCTTGGTACAGCCAG GGCGGTCCCTGAGACTCTCCTGTACAGCTTCTGGATTCACCTTT GGTGATTATGCTATGAGCTGGTTCCGCCAGGCTCCAGGGAAGG GGCTGGAGTGGGTAGGTTTCATTGGAAGCAAATTCTATGGTGG GGAAACAGAATACACCGCGTCTGTGAAAGGCAGATTCACCATC TCAAGAGATGGTTCCAAAAGCATCGCCTATCTGCAAATGAACA GCCTGAAAACCGAGGACACGGCGGTGTACTACTGCGCCAGAGG ACCAAGACGCTACACATACGGAATGGACGTATGGGGCCAGGG AACAACTGTCACCGTCTCCTCA |
| 312 | 58 | VH Protein | EVQLVESGGGLVQPGRSLRLSCTASGFTFGDYAMSWFRQAPGKG LEWVGFIGSKFYGGETEYTASVKGRFTISRDGSKSIAYLQMNSLKT EDTAVYYCARGPRRYTYGMDVVVGQGTTVTVSS |
| 313 | 58 | VL FR1 | DIQMTQSPSSLSASVGDRVTITC |
| 314 | 58 | VL FR2 | WYQQKPGKAPKLLIY |
| 315 | 58 | VL FR3 | GVPSRFSGSGSGTDFTLTISSLQPEDFATYYC |
| 316 | 58 | VL FR4 | FGGGTKVEIK |
| 317 | 58 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC CTAAGCTCCTGATCTATGCTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAAGTTCCACCCCCCTCACTTTTGGCGGAGGGACCAA GGTTGAGATCAAA |
| 318 | 58 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSSTP LTFGGGTKVEIK |

-continued

| SEQ ID NO | Clone No | Description | Sequence |
|---|---|---|---|
| | 319-400: Not used |||
| 401 | 10 | VH CDR1 | FTFDDYAVH |
| 402 | 10 | VH CDR2 | GISWSSGLIGYADSVKG |
| 403 | 10 | VH CDR3 | AKGPPTYQDYFDL |
| 404 | 10 | VL CDR1 | RASQSVSRYLA |
| 405 | 10 | VL CDR2 | DASNRAT |
| 406 | 10 | VL CDR3 | QQVSFFPPIT |
| 407 | 10 | VH FR1 | EVQLVESGGGLVQPGRSLRLSCAASG |
| 408 | 10 | VH FR2 | WVRQAPGKGLEWVS |
| 409 | 10 | VH FR3 | RFTISRDNAKNSLYLQMNSLRAEDTAVYYC |
| 410 | 10 | VH FR4 | WGRGTLVTVSS |
| 411 | 10 | VH DNA | GAAGTGCAGCTGGTGGAGTCTGGGGGAGGCTTGGTACAGCCTG GCAGGTCCCTGAGACTCTCCTGTGCAGCCTCTGGATTCACCTTT GATGATTATGCCGTGCACTGGGTCCGGCAAGCTCCAGGGAAGG GCCTGGAGTGGGTCTCAGGTATTAGTTGGAGTAGTGGACTAAT AGGCTATGCGGACTCTGTGAAGGGCCGATTCACCATCTCCAGA GACAACGCCAAGAACTCCCTGTATCTGCAAATGAACAGTCTGA GAGCTGAGGACACGGCGGTGTACTACTGCGCCAAGGGCCCTCC TACCTACCAAGACTACTTCGACCTATGGGGGAGAGGTACCTTG GTCACCGTCTCCTCA |
| 412 | 10 | VH Protein | EVQLVESGGGLVQPGRSLRLSCAASGFTFDDYAVHWVRQAPGKG LEWVSGISWSSGLIGYADSVKGRFTISRDNAKNSLYLQMNSLRAE DTAVYYCAKGPPTYQDYFDLWGRGTLVTVSS |
| 413 | 10 | VL FR1 | EIVLTQSPATLSLSPGERATLSC |
| 414 | 10 | VL FR2 | WYQQKPGQAPRLLIY |
| 415 | 10 | VL FR3 | GIPARFSGSGSGTDFTLTISSLEPEDFAVYYC |
| 416 | 10 | VL FR4 | FGGGTKVEIK |
| 417 | 10 | VL DNA | GAAATTGTGTTGACACAGTCTCCAGCCACCCTGTCTTTGTCTCC AGGGGAAAGAGCCACCCTCTCCTGCAGGGCCAGTCAGAGTGTT AGCAGGTACTTAGCCTGGTACCAACAGAAACCTGGCCAGGCTC CCAGGCTCCTCATCTATGATGCATCCAACAGGGCCACTGGCATC CCAGCCAGGTTCAGTGGCAGTGGGTCTGGGACAGACTTCACTC TCACCATCAGCAGCCTAGAGCCTGAAGATTTTGCAGTTTATTAC TGTCAGCAGGTCAGTTTCTTCCCTCCTATCACTTTTGGCGGAGG GACCAAGGTTGAGATCAAA |
| 418 | 10 | VL Protein | EIVLTQSPATLSLSPGERATLSCRASQSVSRYLAWYQQKPGQAPRL LIYDASNRATGIPARFSGSGSGTDFTLTISSLEPEDFAVYYCQQVSF FPPITFGGGTKVEIK |
| | 419-500: Not used |||
| 501 | 38 | VH CDR1 | FTFSGHLMS |
| 502 | 38 | VH CDR2 | AISGSAGETYYADSVKG |
| 503 | 38 | VH CDR3 | ARDAYYDDWSGWADWYFDL |
| 504 | 38 | VL CDR1 | RASQSVSRYLA |
| 505 | 38 | VL CDR2 | DASNRAT |
| 506 | 38 | VL CDR3 | QQVSLLPPT |
| 507 | 38 | VH FR1 | EVQLLESGGGLVQPGGSLRLSCAASG |

Table of Sequences

| SEQ ID NO | Clone No | Description | Sequence |
|---|---|---|---|
| 508 | 38 | VH FR2 | WVRQAPGKGLEWVS |
| 509 | 38 | VH FR3 | RFTISRDNSKNTLYLQMNSLRAEDTAVYYC |
| 510 | 38 | VH FR4 | WGRGTLVTVSS |
| 511 | 38 | VH DNA | GAGGTGCAGCTGTTGGAGTCTGGGGGAGGCTTGGTACAGCCTG GGGGGTCCCTGAGACTCTCCTGTGCAGCCTCTGGATTCACCTTT AGCGGACACCTAATGAGCTGGGTCCGCCAGGCTCCAGGGAAGG GGCTGGAGTGGGTCTCAGCTATTAGTGGATCCGCAGGTGAAAC ATACTACGCAGACTCCGTGAAGGGCCGGTTCACCATCTCCAGA GACAATTCCAAGAACACGCTGTATCTGCAAATGAACAGCCTGA GAGCCGAGGACACGGCGGTGTACTACTGCGCCAGAGATGCTA CTACGACGACTGGAGCGGATGGGCCGATTGGTACTTCGATTTA TGGGGAGAGGTACCTTGGTCACCGTCTCCTCA |
| 512 | 38 | VH Protein | EVQLLESGGGLVQPGGSLRLSCAASGFTFSGHLMSWVRQAPGKG LEWVSATSGSAGETYVADSVKGRFTTSRDNSKNTLYLQMNSLRAE DTAVYYCARDAYYDDWSGWADWYFDLWGRGTLVTVSS |
| 513 | 38 | VL FR1 | EIVLTQSPATLSLSPGERATLSC |
| 514 | 38 | VL FR2 | WYQQKPGQAPRLLIY |
| 515 | 38 | VL FR3 | GIPARFSGSGSGTDFTLTISSLEPEDFAVYYC |
| 516 | 38 | VL FR4 | FGGGTKVEIK |
| 517 | 38 | VL DNA | GAAATTGTGTTGACACAGTCTCCAGCCACCCTGTCTTTGTCTCC AGGGGAAAGAGCCACCCTCTCCTGCAGGGCCAGTCAGAGTGTT AGCAGGTACTTAGCCTGGTACCAACAGAAACCTGGCCAGGCTC CCAGGCTCCTCATCTATGATGCATCCAACAGGGCCACTGGCATC CCAGCCAGGTTCAGTGGCAGTGGGTCTGGGACAGACTTCACTC TCACCATCAGCAGCCTAGAGCCTGAAGATTTTGCAGTTTATTAC TGTCAGCAGGTCAGTCTCCTCCCTCCTACTTTTGGCGGAGGGAC CAAGGTTGAGATCAAA |
| 518 | 38 | VL Protein | EIVLTQSPATLSLSPGERATLSCRASQSVSRYLAWYQQKPGQAPRL LIYDASNRATGIPARFSGSGSGTDFTLTISSLEPEDFAVYYCQQVSL LPPTFGGGTKVEIK |
| 519-600: Not used | | | |
| 601 | 15 | VH CDR1 | FTFGDVAMS |
| 602 | 15 | VH CDR2 | YIGSKAYGGETEYTASVKG |
| 603 | 15 | VH CDR3 | ARAGHSYGSIASNWFDP |
| 604 | 15 | VL CDR1 | RASQSISSYLN |
| 605 | 15 | VL CDR2 | GASSLQS |
| 606 | 15 | VL CDR3 | QQGFYTPWT |
| 607 | 15 | VH FR1 | EVQLVESGGGLVQPGRSLRLSCTASG |
| 608 | 15 | VH FR2 | WFRQAPGKGLEWVG |
| 609 | 15 | VH FR3 | RFTISRDGSKSIAYLQMNSLKTEDTAVYYC |
| 610 | 15 | VH FR4 | WGQGTLVTVSS |
| 611 | 15 | VH DNA | GAGGTGCAGCTGGTGGAGTCTGGGGGAGGCTTGGTACAGCCAG GGCGGTCCCTGAGACTCTCCTGTACAGCTTCTGGATTCACCTTT GGTGATGTCGCTATGTCCTGGTTCCGCCAGGCTCCAGGGAAGG GGCTGGAGTGGGTAGGTTACATTGGAAGCAAAGCTTATGGTGG GGAAACAGAATACACCGCGTCTGTGAAAGGCAGATTCACCATC TCAAGAGATGGTTCCAAAAGCATCGCCTATCTGCAAATGAACA GCCTGAAAACCGAGGACACGGCGGTGTACTACTGCGCCAGAGC TGGACACAGCTACGGATCCATCGCCAGCAACTGGTTCGACCCA TGGGGACAGGGTACATTGGTCACCGTCTCCTCA |

Table of Sequences

| SEQ ID NO | Clone No | Description | Sequence |
|---|---|---|---|
| 612 | 15 | VH Protein | EVQLVESGGGLVQPGRSLRLSCTASGFTFGDVAMSWFRQAPGKG LEWVGYIGSKAYGGETEYTASVKGRFTISRDGSKSIAYLQMNSLK TEDTAVYYCARAGHSYGSIASNWFDPWGQGTLVTVSS |
| 613 | 15 | VL FR1 | DIQMTQSPSSLSASVGDRVTITC |
| 614 | 15 | VL FR2 | WYQQKPGKAPKLLIY |
| 615 | 15 | VL FR3 | GVPSRFSGSGSGTDFTLTISSLQPEDFATYYC |
| 616 | 15 | VL FR4 | FGGGTKVEIK |
| 617 | 15 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC CTAAGCTCCTGATCTATGGTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAGGATTCTACACTCCTTGGACTTTTGGCGGAGGGAC CAAGGTTGAGATCAAA |
| 618 | 15 | VL Protein | DIQMTQSPSSLSASVGDRVTITCRASQSISSYLNWYQQKPGKAPKL LIYGASSLQSGVPSRFSGSGSGTDFTLTISSLQPEDFATYYCQQGFY TPWTFGGGTKVEIK |
| 619-700: Not used ||||
| 701 | 35 | VH CDR1 | GTFSSAAIS |
| 702 | 35 | VH CDR2 | NIIPIVGIANYAQKFQG |
| 703 | 35 | VH CDR3 | ARDTGRGYTRHFWFDP |
| 704 | 35 | VL CDR1 | RASQSISSYLN |
| 705 | 35 | VL CDR2 | AASSLQS |
| 706 | 35 | VL CDR3 | QQSDILYT |
| 707 | 35 | VH FR1 | QVQLVQSGAEVKKPGSSVKVSCKASG |
| 708 | 35 | VH FR2 | WVRQAPGQGLEWMG |
| 709 | 35 | VH FR3 | RVTITADESTSTAYMELSSLRSEDTAVYYC |
| 710 | 35 | VH FR4 | WGQGTLVTVSS |
| 711 | 35 | VH DNA | CAGGTGCAGCTGGTGCAGTCTGGGGCTGAGGTGAAGAAGCCTG GGTCCTCGGTGAAGGTCTCCTGCAAGGCTTCTGGAGGCACCTTC AGCTCCGCCGCTATCAGCTGGGTGCGACAGGCCCCTGGACAAG GGCTTGAGTGGATGGGAAACATCATCCCTATCGTAGGTATAGC AAACTACGCACAGAAGTTCCAGGGCAGAGTCACGATTACCGCG GACGAATCCACGAGCACAGCCTACATGGAGCTGAGCAGCCTGA GATCTGAGGACACGGCGGTGTACTACTGCGCCAGAGACACGGG ACGGGGATACACCAGACACTTCTGGTTTGACCCCTGGGGACAG GGTACATTGGTCACCGTCTCCTCA |
| 712 | 35 | VH Protein | QVQLVQSGAEVKKPGSSVKVSCKASGGTFSSAAISWVRQAPGQG LEWMGNIIPIVGIANYAQKFQGRVTITADESTSTAYMELSSLRSED TAVYYCARDTGRGYTRHFWFDPWGQGTLVTVSS |
| 713 | 35 | VL FR1 | DIQMTQSPSSLSASVGDRVTITC |
| 714 | 35 | VL FR2 | WYQQKPGKAPKLLIY |
| 715 | 35 | VL FR3 | GVPSRFSGSGSGTDFTLTISSLQPEDFATYYC |
| 716 | 35 | VL FR4 | FGGGTKVEIK |
| 717 | 35 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC |

-continued

Table of Sequences

| SEQ ID NO | Clone No | Description | Sequence |
|---|---|---|---|
| | | | CTAAGCTCCTGATCTATGCTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAAGCGACATCCTCTACACTTTTGGCGGAGGGACCAA GGTTGAGATCAAA |
| 718 | 35 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSDIL YTFGGGTKVEIK |
| | | 719-800: Not used | |
| 801 | 47 | VH CDR1 | GTFSNYAIS |
| 802 | 47 | VH CDR2 | GIIPIFGTANYAQKFQG |
| 803 | 47 | VH CDR3 | ARGRGALALVGPYYGMDV |
| 804 | 47 | VL CDR1 | RSSQSLLHSNGYNYLD |
| 805 | 47 | VL CDR2 | LGSHRAS |
| 806 | 47 | VL CDR3 | MQALRAPT |
| 807 | 47 | VH FR1 | EVQLVQSGAEVKKPGSSVKVSCKASG |
| 808 | 47 | VH FR2 | WVRQAPGQGLEWMG |
| 809 | 47 | VH FR3 | RVTITADESTSTAYMELSSLRSEDTAVYYC |
| 810 | 47 | VH FR4 | WGQGTTVTVSS |
| 811 | 47 | VH DNA | GAGGTGCAGCTGGTGCAGTCTGGGGCTGAGGTGAAGAAGCCTG GGTCCTCGGTGAAGGTCTCCTGCAAGGCTTCTGGAGGCACCTTC AGCAACTATGCTATCAGCTGGGTGCGACAGGCCCCTGGACAAG GGCTTGAGTGGATGGGAGGGATCATCCCTATCTTTGGTACAGC AAACTACGCACAGAAGTTCCAGGGCAGAGTCACGATTACCGCG GACGAATCCACGAGCACAGCCTACATGGAGCTGAGCAGCCTGA GATCTGAGGACACGGCGGTGTACTACTGCGCCAGAGGCAGAGG CGCTCTGGCACTCGTCGGACCATACTACGGAATGGACGTATGG GGCCAGGGAACAACTGTCACCGTCTCCTCA |
| 812 | 47 | VH Protein | EVQLVQSGAEVKKPGSSVKVSCKASGGTFSNYAISWVRQAPGQG LEWMGGIIPIFGTANYAQKFQGRVTITADESTSTAYMELSSLRSED TAVYYCARGRGALALVGPYYGMDVWGQGTTVTVSS |
| 813 | 47 | VL FR1 | DIVMTQSPLSLPVTPGEPASISC |
| 814 | 47 | VL FR2 | WYLQKPGQSPQLLIY |
| 815 | 47 | VL FR3 | GVPDRFSGSGSGTDFTLKISRVEAEDVGVYYC |
| 816 | 47 | VL FR4 | FGGGTKVEIK |
| 817 | 47 | VL DNA | GATATTGTGATGACTCAGTCTCCACTCTCCCTGCCCGTCACCCC TGGAGAGCCGGCCTCCATCTCCTGCAGGTCTAGTCAGAGCCTCC TGCATAGTAATGGATACAACTATTTGGATTGGTACCTGCAGAA GCCAGGGCAGTCTCCACAGCTCCTGATCTATTTGGGTTCTCATC GGGCCTCCGGGGTCCCTGACAGGTTCAGTGGCAGTGGATCAGG CACAGATTTTACACTGAAAATCAGCAGAGTGGAGGCTGAGGAT GTTGGGGTTTATTACTGCATGCAGGCACTCCGAGCCCCTACTTT TGGCGGAGGGACCAAGGTTGAGATCAAA |
| 818 | 47 | VL Protein | DIVMTQSPLSLPVTPGEPASISCRSSQSLLHSNGYNYLDWYLQKPG QSPQLLTYLGSHRASGVPDRFSGSGSGTDFTLKTSRVEAEDVGVYY CMQALRAPTFGGGTKVEIK |
| | | 819-900 not used | |
| 901 | 46 | VH CDR1 | FTFGDYAMS |
| 902 | 46 | VH CDR2 | FIGSKAYGGTTEYTASVKG |

Table of Sequences

| SEQ ID NO | Clone No | Description | Sequence |
|---|---|---|---|
| 903 | 46 | VH CDR3 | ARGPRRYTYGMDV |
| 904 | 46 | VL CDR1 | RASQSISSYLN |
| 905 | 46 | VL CDR2 | AASSLQS |
| 906 | 46 | VL CDR3 | QQSSTPLT |
| 907 | 46 | VH FR1 | EVQLVESGGGLVQPGRSLRLSCTASG |
| 908 | 46 | VH FR2 | WFRQAPGKGLEWVG |
| 909 | 46 | VH FR3 | RFTISRDGSKSIAYLQMNSLKTEDTAVYYC |
| 910 | 46 | VH FR4 | WGQGTTVTVSS |
| 911 | 46 | VH DNA | GAGGTGCAGCTGGTGGAGTCTGGGGGAGGCTTGGTACAGCCAG GGCGGTCCCTGAGACTCTCCTGTACAGCTTCTGGATTCACCTTT GGTGATTATGCTATGAGCTGGTTCCGCCAGGCTCCAGGGAAGG GGCTGGAGTGGGTAGGTTTTCATTGGAAGCAAAGCTTATGGTGG GACAACAGAATACACCGCGTCTGTGAAAGGCAGATTCACCATC TCAAGAGATGGTTCCAAAAGCATCGCCTATCTGCAAATGAACA GCCTGAAAACCGAGGACACGGCGGTGTACTACTGCGCCAGAGG ACCAAGACGCTACACATACGGAATGGACGTATGGGGCCAGGG AACAACTGTCACCGTCTCCTCA |
| 912 | 46 | VH Protein | EVQLVESGGGLVQPGRSLRLSCTASGFTFGDYAMSWFRQAPGKG LEWVGFIGSKAYGGTTEYTASVKGRFTISRDGSKSIAYLQMNSLKT EDTAVYYCARGPRRYTYGMDVWGQGTTVTVSS |
| 913 | 46 | VL FR1 | DIQMTQSPSSLSASVGDRVTITC |
| 914 | 46 | VL FR2 | WYQQKPGKAPKLLIY |
| 915 | 46 | VL FR3 | GVPSRFSGSGSGTDFTLTISSLQPEDFATYYC |
| 916 | 46 | VL FR4 | FGGGTKVEIK |
| 917 | 46 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC CTAAGCTCCTGATCTATGCTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAAGCTCCACCCCCCTCACTTTTGGCGGAGGGACCAA GGTTGAGATCAAA |
| 918 | 46 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSSTP LTFGGGTKVEIK |
| | | 919-1000 not used | |
| 1001 | 32 | VH CDR1 | GTFSSYAIS |
| 1002 | 32 | VH CDR2 | GIIPISGTANYAQKFQG |
| 1003 | 32 | VH CDR3 | ARDTGRGYTRHFWFDP |
| 1004 | 32 | VL CDR1 | RASQSISSYLN |
| 1005 | 32 | VL CDR2 | AASSLQS |
| 1006 | 32 | VL CDR3 | QQSDILYT |
| 1007 | 32 | VH FR1 | QVQLVQSGAEVKKPGSSVKVSCKASG |
| 1008 | 32 | VH FR2 | WVRQAPGQGLEWMG |
| 1009 | 32 | VH FR3 | RVTITADESTSTAYMELSSLRSEDTAVYYC |
| 1010 | 32 | VH FR4 | WGQGTLVTVSS |

-continued

Table of Sequences

| SEQ ID NO | Clone No | Description | Sequence |
|---|---|---|---|
| 1011 | 32 | VH DNA | CAGGTGCAGCTGGTGCAGTCTGGGGCTGAGGTGAAGAAGCCTG GGTCCTCGGTGAAGGTCTCCTGCAAGGCTTCTGGAGGCACCTTC AGCAGCTATGCTATCAGCTGGGTGCGACAGGCCCCTGGACAAG GGCTTGAGTGGATGGGAGGGATCATCCCTATCTCTGGTACAGC AAACTACGCACAGAAGTTCCAGGGCAGAGTCACGATTACCGCG GACGAATCCACGAGCACAGCCTACATGGAGCTGAGCAGCCTGA GATCTGAGGACACGGCGGTGTACTACTGCGCCAGAGACACGGG ACGGGGATACACCAGACACTTCTGGTTTGACCCCTGGGGACAG GGTACATTGGTCACCGTCTCCTCA |
| 1012 | 32 | VH Protein | QVQLVQSGAEVKKPGSSVKVSCKASGGTFSSYAISWVRQAPGQG LEWMGGIIPISGTANYAQKFQGRVTITADESTSTAYMELSSLRSED TAVYYCARDTGRGYTRHFWFDPWGQGTLVTVSS |
| 1013 | 32 | VL FR1 | DIQMTQSPSSLSASVGDRVTITC |
| 1014 | 32 | VL FR2 | WYQQKPGKAPKLLIY |
| 1015 | 32 | VL FR3 | GVPSRFSGSGSGTDFTLTISSLQPEDFATYYC |
| 1016 | 32 | VL FR4 | FGGGTKVEIK |
| 1017 | 32 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC CTAAGCTCCTGATCTATGCTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAAGCGACATCCTCTACACTTTTGGCGGAGGGACCAA GGTTGAGATCAAA |
| 1018 | 32 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSDIL YTFGGGTKVEIK |
| 1019-2000 not used | | | |
| 2001 | 33 | VH CDR1 | GTFGNYAIS |
| 2002 | 33 | VH CDR2 | GIIPIPGIANYAQKFQG |
| 2003 | 33 | VH CDR3 | ARDTGRGYTRHFWFDP |
| 2004 | 33 | VL CDR1 | RASQSISSYLN |
| 2005 | 33 | VL CDR2 | AASSLQS |
| 2006 | 33 | VL CDR3 | QQSDILYT |
| 2007 | 33 | VH FR1 | QVQLVQSGAEVKKPGSSVKVSCKASG |
| 2008 | 33 | VH FR2 | WVRQAPGQGLEWMG |
| 2009 | 33 | VH FR3 | RVTITADESTSTAYMELSSLRSEDTAVYYC |
| 2010 | 33 | VH FR4 | WGQGTLVTVSS |
| 2011 | 33 | VH DNA | CAGGTGCAGCTGGTGCAGTCTGGGGCTGAGGTGAAGAAGCCTG GGTCCTCGGTGAAGGTCTCCTGCAAGGCTTCTGGAGGCACCTTC GGAAACTATGCTATCAGCTGGGTGCGACAGGCCCCTGGACAAG GGCTTGAGTGGATGGGAGGGATCATCCCTATCCCAGGTATCGC AAACTACGCACAGAAGTTCCAGGGCAGAGTCACGATTACCGCG GACGAATCCACGAGCACAGCCTACATGGAGCTGAGCAGCCTGA GATCTGAGGACACGGCGGTGTACTACTGCGCCAGAGACACGGG ACGGGGATACACCAGACACTTCTGGTTTGACCCCTGGGGACAG GGTACATTGGTCACCGTCTCCTCA |
| 2012 | 33 | VH Protein | QVQLVQSGAEVKKPGSSVKVSCKASGGTFGNYAISWVRQAPGQG LEWMGGIIPIPGIANYAQKFQGRVTITADESTSTAYMELSSLRSEDT AVYYCARDTGRGYTRHFWFDPWGQGTLVTVSS |
| 2013 | 33 | VL FR1 | DIQMTQSPSSLSASVGDRVTITC |

-continued

Table of Sequences

| SEQ ID NO | Clone No | Description | Sequence |
|---|---|---|---|
| 2014 | 33 | VL FR2 | WYQQKPGKAPKLLIY |
| 2015 | 33 | VL FR3 | GVPSRFSGSGSGTDFTLTTSSLQPEDFATYYC |
| 2016 | 33 | VL FR4 | FGGGTKVEIK |
| 2017 | 33 | VL DNA | GACATCCAGATGACCCAGTCTCCATCCTCCCTGTCTGCATCTGT<br>AGGAGACAGAGTCACCATCACTTGCCGGGCAAGTCAGAGCATT<br>AGCAGCTATTTAAATTGGTATCAGCAGAAACCAGGGAAAGCCC<br>CTAAGCTCCTGATCTATGCTGCATCCAGTTTGCAAAGTGGGGTC<br>CCATCAAGGTTCAGTGGCAGTGGATCTGGGACAGATTTCACTCT<br>CACCATCAGCAGTCTGCAACCTGAAGATTTTGCAACTTACTACT<br>GTCAGCAAAGCGACATCCTCTACACTTTTGGCGGAGGGACCAA<br>GGTTGAGATCAAA |
| 2018 | 33 | VL Protein | DIQMTQSPSSLSASVGDRVTITCRASQSISSYLNWYQQKPGKAPKL<br>LIYAASSLQSGVPSRFSGSGSGTDFTLTISSLQPEDFATYYCQQSDIL<br>YTFGGGTKVEIK |

2019-3000 not used

| 3001 | 34 | VH CDR1 | GTFSSAAIS |
| 3002 | 34 | VH CDR2 | GIFPISGHANYAQKFQG |
| 3003 | 34 | VH CDR3 | ARDTGRGYTRHFWFDP |
| 3004 | 34 | VL CDR1 | RASQSISSYLN |
| 3005 | 34 | VL CDR2 | AASSLQS |
| 3006 | 34 | VL CDR3 | QQSDILYT |
| 3007 | 34 | VH FR1 | QVQLVQSGAEVKKPGSSVKVSCKASG |
| 3008 | 34 | VH FR2 | WVRQAPGQGLEWMG |
| 3009 | 34 | VH FR3 | RVTITADESTSTAYMELSSLRSEDTAVYYC |
| 3010 | 34 | VH FR4 | WGQGTLVTVSS |
| 3011 | 34 | VH DNA | CAGGTGCAGCTGGTGCAGTCTGGGGCTGAGGTGAAGAAGCCTG<br>GGTCCTCGGTGAAGGTCTCCTGCAAGGCTTCTGGAGGCACCTTC<br>AGCAGCGCCGCTATCAGCTGGGTGCGACAGGCCCCTGGACAAG<br>GGCTCGAGTGGATGGGAGGGATCTTCCCTATCTCCGGTCACGC<br>AAACTACGCACAGAAGTTCCAGGGCAGAGTCACGATTACCGCG<br>GACGAATCCACGAGCACAGCCTACATGGAGCTGAGCAGCCTGA<br>GATCTGAGGACACGGCGGTGTACTACTGCGCCAGAGACACGGG<br>ACGGGGATACACCAGACACTTCTGGTTTGACCCCTGGGGACAG<br>GGTACATTGGTCACCGTCTCCTCA |
| 3012 | 34 | VH Protein | QVQLVQSGAEVKKPGSSVKVSCKASGGTFSSAAISWVRQAPGQG<br>LEWMGGIFPISGHANYAQKFQGRVTITADESTSTAYMELSSLRSED<br>TAVYYCARDTGRGYTRHFWFDPWGQGTLVTVSS |
| 3013 | 34 | VL FR1 | DIQMTQSPSSLSASVGDRVTITC |
| 3014 | 34 | VL FR2 | WYQQKPGKAPKLLIY |
| 3015 | 34 | VL FR3 | GVPSRFSGSGSGTDFTLTISSLQPEDFATYYC |
| 3016 | 34 | VL FR4 | FGGGTKVEIK |
| 3017 | 34 | VL DNA | GACATCCAGATGACCCAGTCTCCATCCTCCCTGTCTGCATCTGT<br>AGGAGACAGAGTCACCATCACTTGCCGGGCAAGTCAGAGCATT<br>AGCAGCTATTTAAATTGGTATCAGCAGAAACCAGGGAAAGCCC<br>CTAAGCTCCTGATCTATGCTGCATCCAGTTTGCAAAGTGGGGTC<br>CCATCAAGGTTCAGTGGCAGTGGATCTGGGACAGATTTCACTCT<br>CACCATCAGCAGTCTGCAACCTGAAGATTTTGCAACTTACTACT<br>GTCAGCAAAGCGACATCCTCTACACTTTTGGCGGAGGGACCAA<br>GGTTGAGATCAAA |

-continued

Table of Sequences

| SEQ ID NO | Clone No | Description | Sequence |
|---|---|---|---|
| 3018 | 34 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSDIL YTFGGGTKVEIK |
| | | 3019-4000 not used | |
| 4001 | 36 | VH CDR1 | GTFATYAIS |
| 4002 | 36 | VH CDR2 | GIFPLSGTANYAQKFQG |
| 4003 | 36 | VH CDR3 | ARDTGRGYTRHFWFDP |
| 4004 | 36 | VL CDR1 | RASQSISSYLN |
| 4005 | 36 | VL CDR2 | AASSLQS |
| 4006 | 36 | VL CDR3 | QQSDILYT |
| 4007 | 36 | VH FR1 | QVQLVQSGAEVKKPGSSVKVSCKASG |
| 4008 | 36 | VH FR2 | WVRQAPGQGLEWMG |
| 4009 | 36 | VH FR3 | RVTITADESTSTAYMELSSLRSEDTAVYYC |
| 4010 | 36 | VH FR4 | WGQGTLVTVSS |
| 4011 | 36 | VH DNA | CAGGTGCAGCTGGTGCAGTCTGGGGCTGAGGTGAAGAAGCCTG GGTCCTCGGTGAAGGTCTCCTGCAAGGCTTCTGGAGGCACCTTC GCAACCTATGCTATCAGCTGGGTGCGACAGGCCCCTGGACAAG GGCTTGAGTGGATGGGAGGGATCTTCCCTCTCTCCGGTACAGC AAACTACGCACAGAAGTTCCAGGGCAGAGTCACGATTACCGCG GACGAATCCACGAGCACAGCCTACATGGAGCTGAGCAGCCTGA GATCTGAGGACACGGCGGTGTACTACTGCGCCAGAGACACGGG ACGGGGATACACCAGACACTTCTGGTTTGACCCCTGGGGACAG GGTACATTGGTCACCGTCTCCTCA |
| 4012 | 36 | VH Protein | QVQLVQSGAEVKKPGSSVKVSCKASGGTFATYAISWVRQAPGQG LEWMGGIFPLSGTANYAQKFQGRVTITADESTSTAYMELSSLRSE DTAVYYCARDTGRGYTRHFWFDPWGQGTLVTVSS |
| 4013 | 36 | VL FR1 | DIQMTQSPSSLSASVGDRVTITC |
| 4014 | 36 | VL FR2 | WYQQKPGKAPKLLIY |
| 4015 | 36 | VL FR3 | GVPSRFSGSGSGTDFTLTISSLQPEDFATYYC |
| 4016 | 36 | VL FR4 | FGGGTKVEIK |
| 4017 | 36 | VL DNA | GACATCCAGATGACCCAGTCTCCATCCTCCCTGTCTGCATCTGT AGGAGACAGAGTCACCATCACTTGCCGGGCAAGTCAGAGCATT AGCAGCTATTTAAATTGGTATCAGCAGAAACCAGGGAAAGCCC CTAAGCTCCTGATCTATGCTGCATCCAGTTTGCAAAGTGGGGTC CCATCAAGGTTCAGTGGCAGTGGATCTGGGACAGATTTCACTCT CACCATCAGCAGTCTGCAACCTGAAGATTTTGCAACTTACTACT GTCAGCAAAGCGACATCCTCTACACTTTTGGCGGAGGGACCAA GGTTGAGATCAAA |
| 4018 | 36 | VL Protein | DIQMTQSPSSLSASVGDRVTITCRASQSISSYLNWYQQKPGKAPKL LIYAASSLQSGVPSRFSGSGSGTDFTLTISSLQPEDFATYYCQQSDIL YTFGGGTKVEIK |

What is claimed is:

1. A method of treating a cancer in a subject in need thereof, the method comprising administering to the subject a therapeutically effective amount of an antibody or antigen binding portion thereof that binds to CD112R and comprises:

i) a heavy chain variable region CDR1 comprising the amino acid sequence of SEQ ID NO: 701;

ii) a heavy chain variable region CDR2 comprising the amino acid sequence of SEQ ID NO: 702;

iii) a heavy chain variable region CDR3 comprising the amino acid sequence of SEQ ID NO: 703;

iv) a light chain variable region CDR1 comprising the amino acid sequence of SEQ ID NO: 704;

v) a light chain variable region CDR2 comprising the amino acid sequence of SEQ ID NO: 705; and vi) a light chain variable region CDR3 comprising the amino acid sequence of SEQ ID NO: 706.

2. The method of claim 1, wherein the antibody or antigen binding portion thereof comprises a heavy chain variable region having a sequence at least 90% identical to the amino acid sequence of SEQ ID NO: 712 and a light chain variable region having a sequence at least 90% identical to the amino acid sequence of SEQ ID NO: 718.

3. The method of claim 2, wherein the antibody or antigen binding portion thereof comprises a heavy chain variable region comprising the amino acid sequence of SEQ ID NO: 712 and a light chain variable region comprising the amino acid sequence of SEQ ID NO: 718.

4. The method of claim 3, wherein the antibody is a monoclonal antibody.

5. The method of claim 3, wherein the antibody is fully human or humanized.

6. The method of claim 3, wherein the Fc region of the antibody comprises IgG1, IgG2, IgG3, or IgG4.

7. The method of claim 6, wherein the antibody comprises a human IgG1 heavy chain constant region.

8. The method of claim 6, wherein the antibody comprises a human IgG4 heavy chain constant region.

9. The method of claim 8, wherein the antibody comprises a mutant human IgG4 heavy chain constant region.

10. The method of claim 9, wherein the mutant IgG4 heavy chain constant region comprises a mutation selected from a substitution at Ser228, a substitution at Leu235, a substitution at Asn297, or a combination thereof, numbering according to EU numbering.

11. The method of claim 10, wherein the mutant IgG4 heavy chain constant region comprises an S228P substitution and an L235E substitution, numbering according to EU numbering.

12. The method of claim 1, wherein the CD112R is a human CD112R.

13. The method of claim 1, wherein the subject is a human subject.

14. The method of claim 13, wherein the cancer is carcinoma, lymphoma, blastoma, sarcoma, or leukemia.

15. The method of claim 13, wherein the cancer is squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or various types of head and neck cancer.

16. The method of claim 1, further comprising administering to the subject:
   i) an antagonist of PD-1, PD-L1, CTLA-4, Lag-3, TIM-3, TIGIT, CD96, PVRL1, PVRL2, PVRL3, PVRL4, CD155, CD47, CD39 or IL-27;
   ii) a STING agonist; or
   iii) a combination of (i) and (ii).

17. The method of claim 1, further comprising administering to the subject an antagonist of TIGIT, an antagonist of CD96, an antagonist of PD-1 or an antagonist of PD-L1.

18. The method of claim 1, further comprising administering to the subject a radiotherapy or surgery.

19. The method of claim 1, further comprising administering to the subject chemotherapy, an opsonizing agent, or a regulatory T cell depleting agent.

* * * * *